(12) United States Patent  (10) Patent No.: US 7,067,633 B2
Kumar et al.  (45) Date of Patent: Jun. 27, 2006

(54) TARGETING CELLULAR ENTRY, CELL SURVIVAL, AND PATHOGENICITY BY DYNEIN LIGHT CHAIN 1/PIN IN HUMAN CELLS

(75) Inventors: Rakesh Kumar, Houston, TX (US); Ratna Vadlamudi, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/787,603

(22) Filed: Feb. 26, 2004

(65) Prior Publication Data

US 2004/0208880 A1  Oct. 21, 2004

Related U.S. Application Data

(60) Provisional application No. 60/451,117, filed on Feb. 26, 2003.

(51) Int. Cl.
*C07K 1/00* (2006.01)
*C07K 14/00* (2006.01)
*C07K 17/00* (2006.01)

(52) U.S. Cl. ..................................... 530/350
(58) Field of Classification Search ............. 424/146.1; 530/350
See application file for complete search history.

(56) References Cited

OTHER PUBLICATIONS

Dharmawardhane, S., et al.; Regulation of Macropinocytosis by p21-activated Kinase-1, The American Society for Cell Biology (Oct. 2000) vol. 11, pp. 3341-3352.
Dharmawardhane, S., et al,; Localization of p21-Activated Kinase 1 (PAK1) to Pinocytic Vesicles and Cortical Actin Structures in Stimulated Cells, The Journal of Cell Biology, (Sep. 22, 1997), vol. 138, No. 6, pp. 1265-1278.
Hirokawa, N.; Kinesin and Dynein Superfamily Proteins and the Mechanism of Organelle Transport, (Jan. 23, 1998) Science, vol. 279, pp. 519-526.
Pazour, G., et al.; A Dynein Light Chain Is Essential for the Retrograde Particle Movement of Intraflagellar Transport (IFT), The Journal of Cell Biology, (May 18, 1998), vol. 141, No. 4, pp. 979-992.
Vallee, Richard B., et al.; Targeting of Motor Proteins, Science, (Mar. 15, 1996), vol. 271, pp. 1539-1544.
Vadlamudi, Ratna, K., et al.; Differential Regulation of Components of the Focal Adhesion Complex by Heregulin: Role of Phosphatase SHP-2, Journal of Cellular Physiology, (2002), vol. 190, pp. 189-199.
Vadlamudi, Ratna, K., et al.; Evidence of Rab3A Expression, Regulation of Vesicle Trafficking, and Cellular Secretion in Response to Heregulin in Mammary Epithelial Cells, American Society for Microbiology (Dec. 2000), vol. 20, No. 23, pp. 9092-9101.
Vadlamudi, Ratna, K., et al.; Regulatable Expression of p21-activated Kinase-1 Promotes Anchorage-independent Growth and Abnormal Organization of Mitotic Spindles in Human Epithelial Breast Cancer Cells, The Journal of Biological Chemistry, (Nov. 17, 2000), vol. 275, No. 46, pp. 36238-36244.
Vadlamudi, Ratna, K., et al.; Filamin is essential in actin cytoskeletal assembly mediated by p21-activated kinase 1, Nature Cell Biology (Sep. 2002), vol. 4, pp. 681-690.

*Primary Examiner*—Karen Cochrane Carlson
*Assistant Examiner*—Agnes Rooke
(74) *Attorney, Agent, or Firm*—Fulbright & Jaworski, LLP

(57) ABSTRACT

Methods of modulating macropinocytosis in cells of a target cell population by modulating the binding of Pak1 to DLC1/PIN are disclosed. In addition, the invention provides for methods of screening for modulators of macropinocytosis that involve determining whether a candidate substance inhibits or promotes the binding of Pak1 to DLC1/PIN. Also disclosed are methods of reducing cell proliferation in a target cell population, methods of inhibiting growth and survival of a cancer cell, methods of inhibiting the invasiveness of a cancer cell, and methods of treating viral infection using an agent that modifies the binding of Pak1 to DLC1/PIN.

6 Claims, 48 Drawing Sheets

B
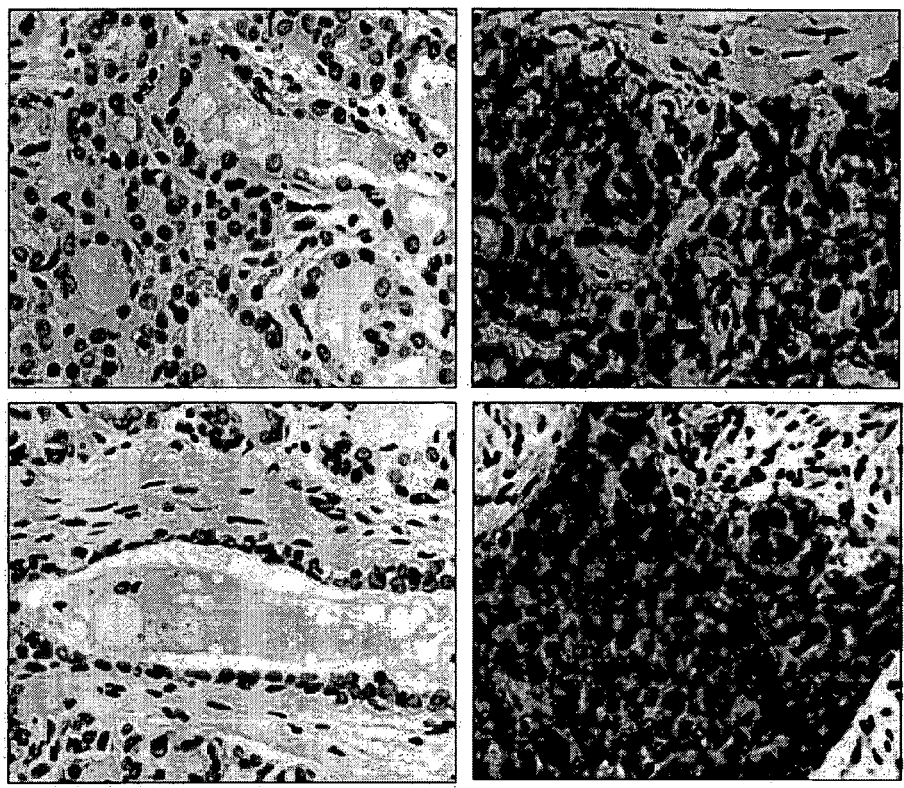
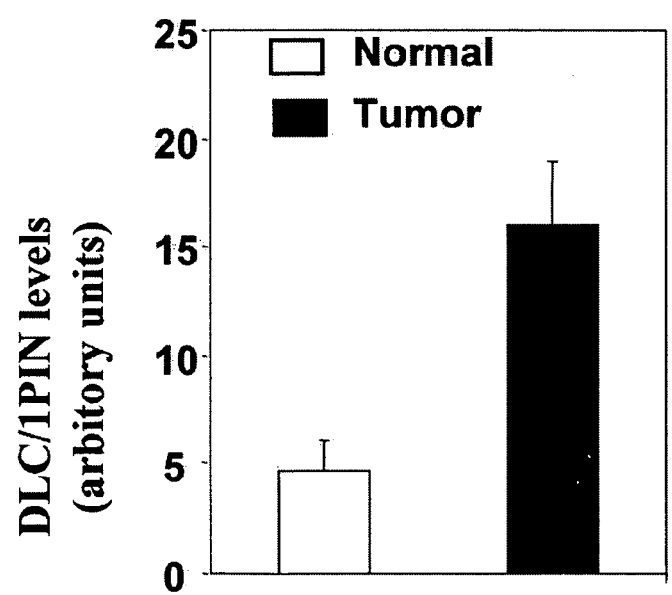

TARGETING CELLULAR ENTRY, CELL SURVIVAL, AND PATHOGENICITY BY DYNEIN LIGHT CHAIN 1/PIN IN HUMAN CELLS

This application claims priority to U.S. Provisional Patent Application Ser. No. 60/451,117, filed Feb. 26, 2003, which is incorporated by reference herein in its entirety.

The present invention was developed at least in part with funds from NIH Grant No. CA80066. The United States Government may have certain rights in the invention.

BACKGROUND OF THE INVENTION

1. Field of the Invention

The present invention relates generally to the fields of molecular biology, oncology and pharmacology. More particularly, it concerns methods for modulating macropinocytosis by modulating the binding of dynein light chain-1/ protein inhibitor of nitric oxide synthase (DLC1/PIN) to p21-activated protein kinase 1 (Pak1). It also concerns methods of screening for modulators of macropinocytosis by assessing the ability of candidate substances to modulate the binding of DLC1/PIN to Pak1. In addition, it concerns methods of treatment of cancer, viral infections, and other conditions associated with macropinocytosis wherein targeting DLC1/PIN and Pak1 interaction may be beneficial.

2. Description of Related Art

The p21-activated kinases (Paks), an evolutionarily conserved family of serine/threonine kinases, are important for a variety of cellular functions including cell morphogenesis, cell motility, cell survival, angiogenesis and mitosis (Kumar and Vadlamudi, 2002; Jaffer and Chernoff, 2002). At present, the Pak family consists of six members, Pak 1 through Pak 6. Paks are identified as one of the targets of the activated Rho GTPases Cdc42 and Rac1, which stimulate Pak autophosphorylation and activity (Manser et al., 1994). Stimulation of Pak activity results in several phenotypic changes reminiscent of those produced by Cdc42 and Rac1 (Sells et al., 1997). Overexpression of Paks in cancer cells increases cell migration potential and anchorage-independent growth and causes abnormalities in mitosis (Banerjee et al., 2002; Vadlamudi et al., 2000a; Li et al., 2002a; Thiel et al., 2002).

Paks are widely expressed in numerous tissues and are activated by a number of polypeptide factors and extracellular signals in both a GTPase-dependent (via Rac1 or Cdc42) and GTPase-independent manner via its localization to membrane/focal adhesion (Bokoch et al., 1996; Bagrodia and Cerione, 1999; Zhao et al., 2000). They are also activated by lipids (Bokoch et al., 1998), tyrosine kinases (McManus et al., 2000; Bagheri et al., 2001), novel substrates such as filamin (Vadlamudi et al., 2002b) and G-proteins (Lian et al., 2001). The activation of Pak1 by diverse signals leads to its autophosphorylation at multiple sites, including threonine 423 (T423), within the activation loop of the kinase (Daniels and Bokoch, 1999). Expression of an activated Pak1 mutant (T423E) triggers the dissolution of stress fibers and focal adhesion complexes, the formation of lamellipodia (Manser et al., 1997; Zhao et al., 1998), and reorganization of actin cytoskeleton. Some of the effects of Pak on the actin cytoskeleton appear to be independent of Pak1 kinase activity but dependent on protein-protein interactions (Turner et al., 1999; Sells et al., 1997). However, kinase activity is important for directional motility (Sells et al., 2000). Pak1 mutants with defective GTPase binding sites or kinase activity nonetheless still maintain the ability to induce the formation of membrane ruffles and filopodia (Frost et al., 1998; Sells et al., 1997). Pak1 also stimulates LIM kinase (LIMK) activity and, in turn, increases phosphorylation and inactivation of cofilin, leading to reducing the depolymerization of actin filaments (Edwards and Gill, 1999; Edwards et al., 1999, Jaffer and Chernoff, 2002; Bagheri et al., 2002). However, the molecular mechanism by which Pak1 induces rearrangement of the actin cytoskeleton and directional movement remains elusive.

Reorganization of the cytoskeleton not only affects cell motility but also plays an important role in pinocytosis, a process by which macromolecules and fluids are taken up into small invaginations in the cell membrane that eventually bud off into pinosomes (Swanson and Watts, 2002). Pinocytosis contributes to both the growth and motility processes of cells (Davies et al., 1980; Thompson and Bretscher, 2002). Recently, Pak1 was shown to localize to the areas of pinocytic vesicles and to contribute to the process of macropinocytosis (Dharmawardhane et al., 1997; West et al., 2000). Pak activity was also required for growth factor-induced macropinocytosis, and accordingly, catalytically activated Pak1 enhanced both the uptake and efflux of a 70-kDa dextran particle, suggesting that Pak1 activity modulates pinocytic vesicle cycling (Dharmawardhane et al., 2000). Furthermore, transient stimulation of macropinocytosis by growth factors has been also implicated in directed cell motility, as regulation of membrane flux via Pinocytosis could contribute to the membrane flow generating force for cell locomotion (Thompson and Bretscher, 2002; Bretscher and Aguado, 1998; Dharmawardhane et al., 2000). Although Pak1 has been shown to regulate macropinocytosis, the nature of the responsive molecular mechanism remains unknown.

Cytoskeleton remodeling-dependent cellular processes, such as vesicle transport and membrane transport are also influenced by dynein, a multi protein complex originally shown to regulate the movement of chromosomes, assembly and orientation of mitotic spindles and nuclear migration (Holzbaur and Vallee, 1994; Hayden, 1988; Steuer et al., 1990; Vaisberg et al., 1993; Beckwith et al., 1998). Dynein light chain-1 (DLC1/PIN), an 8-kDa component of the cytoplasmic dynein complex, is a minus end-directed microtubule-based motor that transports cargo along microtubules (Hirokawa, 1998). DLC1/PIN is highly conserved among species and widely expressed in a number of tissues; it is localized predominantly in the cytoplasm. In addition to playing an essential role in dynein motor function, DLC1/ PIN interacts with a number of proteins and has diverse functions. For example, DLC1/PIN associates with neuronal nitric oxide synthase (nNOS) and inhibits its activity and proapoptotic function (Jaffrey and Snyder, 1996). DLC1/ PIN also interacts and interferes with the proapoptotic Bcl-2 family protein Bim (Puthalakath et al., 1999). Although the functional role of DLC1/PIN in vesicle trafficking and cell survival has been observed, no function of DLC1/PIN has been associated with its phosphorylation. In addition, no upstream signaling kinase have been shown to phosphorylate DLC1/PIN and influence these functional outcomes.

Macropinocytosis, a cytoskeleton remodeling-dependent cellular process, plays a central role in cellular uptake of nutrients and macromolecules, and membrane flux (Haigler et al., 1979). In addition, regulated cycling of plasma membrane via macropinocytosis has been proposed to have a role in directed cell movement (Bretscher and Aguado, 1998; Dharmawardhane et al., 2000; Thompson and Bretscher, 2002). Macropinocytosis is considered to generally be a nonspecific mechanism for internalization of extracellular material by a cell, in that it is not reliant on ligand binding to a specific receptor (reviewed in Sieczkarski and Whittaker, 2002). Instead, formation of endocytic vesicles occurs as a cell type-specific response to cell stimulation, resulting in the closure of lamellipodia at the sites of membrane ruffling to form the large (0.2 to 3 μm), irregular vesicles known as macroPinosomes (Lanzavecchia, 1996). Membrane ruffling is primarily actin-driven and macropinocytosis is, in terms of mechanics, similar to the process of phagocytosis that occurs in specialized immune system cells such as neutrophils and macrophages.

Macropinocytosis also plays an important role in the uptake of macromolecules in epithelial cells, neutrophils and macrophages (Aderem and Underhill, 1999), in taking up extracellular antigens into antigen-presenting dendritic cells (West et al., 2000), and the entering of human immunodeficiency Type 1 virus (HIV) in macrophages (Marechal et al., 2001) and endothelial cells (Hirokawa, 1998).

The process of macropinocytosis requires the small GTPases and p21-activated kinase 1 (Pak1) (West, 2000; Dharmawardhane et al., 2000). Pak1, an effector of Cdc42/Rac1, specifically regulates macropinocytosis, but not clathrin- or receptor-mediated endocytosis (Dharmawardhane et al., 1997). Even though the mechanism by which Pak1 regulates macropinocytosis is not known the results of earlier studies suggest that Pak1 activity plays an essential role (Dharmawardhane et al., 2000).

Furthermore, intracellular vesicle transport is also regulated by microtubule-based DLC1/PIN, a component of dynein complex originally shown to regulate the movement of chromosomes and orientation of spindles (Hirokawa, 1998; Vallee and Sheetz, 1996; Pazour et al., 1998). DLC1/PIN has also been shown to promote cell survival (Vadlamudi et al., 2000; Vadlamudi et al., 2002). However, no function of DLC1/PIN has been associated with its phosphorylation by upstream signaling kinase and whether such changes might control macropinocytosis in mammalian cells.

The inventors have identified DLC1/PIN as a Pak1-interacting protein and have shown that DLC1/PIN is a physiological interacting substrate of Pak1. The Pak1-DLC1/PIN interactions play an essential role for the macropinocytosis and cell-survival functions of Pak1 and also DLC1/PIN. The inventors have found that the underlying mechanism involves the phosphorylation of serine 88 of DLC1/PIN by Pak1 because mutation of this serine residue to alanine abolishes the ability of DLC1/PIN to support macropinocytosis and cell survival. Unexpectedly, the inventors have found that DLC1/PIN expression is elevated in human breast tumors, and deregulation of DLC1/PIN but not DLC1/PIN mutant lacking serine 88 promotes the tumorigenic potential of breast cancer cells.

Thus, the regulation of macropinocytosis, cell survival and tumorigenic functions by interaction between DLC1/PIN and Pak1 represents a novel mechanism by which a signaling kinase might control these essential processes in cells.

SUMMARY OF THE INVENTION

In certain embodiments, the present invention is concerned generally with methods of modulating macropinocytosis in cells of a target cell population, which is achieved by modulating the binding of Pak1 to DLC1/PIN in the cells. This invention arises out of the inventors' discovery that cellular macropinocytosis, including macropinocytosis in human cells, is modulated by the binding of p21-activated kinase (Pak1), to dynein light chain-1/protein inhibitor of nitric oxide synthase (DLC1/PIN), an 8-kDa component of the cytoplasmic dynein complex which is also known as dynein light chain 8 (DLC1/PIN) and protein inhibitor of nitric oxide synthase (DLC1/PIN). The inventors discovered that DLC1/PIN interacts with Pak1 via Pak1's C-terminal region amino acids 132–270 while the Pak1 binding site in DLC1/PIN is localized within the C-terminal 19 amino acids of DLC1/PIN. The inventors also discovered that macropinocytosis is dependent on Pak1's phosphorylation of serine 88 of DLC1/PIN and the C-terminal 19 amino acids. In addition, they found that both proteins colocalize in pinocytic vesicles upon growth factor stimulation of human cells, and that interference with the binding of Pak1 to DLC1/PIN or interference with the phosphorylation of serine 88 of DLC1/PIN by Pak1 results in inhibition of macropinocytosis. Thus, macropinocytosis may be upregulated by means of agents that will promote or mimic the binding of Pak1 to DLC1/PIN, and may conversely be downregulated by means of agents that will interfere with the binding of DLC1/PIN to Pak1. Because macropinocytosis is involved in fundamental cellular processes such as directional motility, cellular internalization of exogenous material, and cell survival, modulators of macropinocytosis will be useful in the treatment of diseases such as cancer and viral infections.

The mRNA sequence of human DLC1/PIN is disclosed in Genbank accession number U32944 (herein SEQ ID NO:1). The amino acid sequence of human DLC1/PIN is disclosed in Genbank accession number AAB04149 (herein SEQ ID NO:2). The mRNA sequence of human Pak1 is disclosed in Genbank accession number U24152 (herein SEQ ID NO: 7). The amino acid sequence of human Pak is disclosed in Genbank accession number AAA65441 (herein SEQ ID NO: 8).

In certain other embodiments, the invention is concerned with methods of modulating macropinocytosis by modulating the binding of Pak1 to DLC1/PIN. Modulation of the binding of Pak1 to DLC1/PIN can be accomplished by either inhibiting or promoting the binding of Pak1 to DLC1/PIN. The inhibition of binding of Pak1 to DLC1/PIN can further be accomplished by inhibiting the phosphorylation of DLC1/PIN by Pak1 in the cells. In a specific embodiment, the phosphorylation of serine 88 of DLC1/PIN by Pak1 is inhibited. In a specific embodiment, modulating the binding of Pak1 to DLC1/PIN, such as by inhibiting the binding of Pak1 to DLC1/PIN, may be further defined as administering at least one mutant DLC1/PIN polypeptide to a cell comprising the Pak1 and DLC1/PIN molecules.

In certain embodiments, there is a method of modulating macropinocytosis in cells of a target cell population comprising administering to said cells an agent that modulates the binding of Pak1 to DLC1/PIN in the cells. In specific embodiments, the agent inhibits the binding of Pak1 to DLC1/PIN, the agent promotes the binding of Pak1 to DLC1/PIN, the agent inhibits the phosphorylation of DLC1/PIN by Pak1 in the cells, or the agent inhibits the phosphorylation of DLC1/PIN by Pak1 in the cells.

DLC1 is important for macropinocytosis function of both normal and cancer cells, for example. Macropinocytosis is important for motility, cell growth and for uptake of particles or medium by cells. The molecules for uptake may be, for example, a virus, pathogen, or any other type of molecule (including, for example, low density lipoprotein cholesterol, LDL).

The cells of the target cell population can be of any cell type. In a preferred embodiment, the cells of the target cell population are cancer cells. For example, the cancer cells can be breast cancer cells, lung cancer cells, prostate cancer cells, ovarian cancer cells, brain cancer cells, liver cancer cells, prostate cancer cells, cervical cancer cells, colon cancer cells, renal cancer cells, skin cancer cells, head and neck cancer cells, bone cancer cells, esophageal cancer cells, bladder cancer cells, uterine cancer cells, lymphatic cancer cells, stomach cancer cells, pancreatic cancer cells, testicular cancer cells, or leukemic cells. In another preferred embodiment, the cells are infected with a virus. Although any virus is contemplated by the invention, in certain embodiments the virus is HIV, neurotropic virus, adenovirus, foot and mouth disease virus, or respiratory syncytial virus. In other embodiments, the cells of the target cell population are macrophages, foam cells, neuronal cells, or dendritic cells.

The cells may or may not be located in a subject. In a preferred embodiment, the cells of the target cell population are located in a patient. For example, the cells can be cancer cells located in a patient. In another example, the cells are infected with a virus. The cells can also be uninfected bystander cells located in a patient with HIV. In another embodiment, the cells undergo reduction in directed cell motility as a result of modulation of macropinocytosis.

Another embodiment of the invention provides for a method of screening for modulators of macropinocytosis that is achieved by: (a) obtaining a candidate substance suspected of modulating macropinocytosis; (2) contacting the candidate substance with Pak1 and DLC1/PIN; and (c) detecting inhibition or promotion of binding between Pak1 and DLC1/PIN. In one embodiment, the candidate substance suspected of modulating macropinocytosis is a candidate substance suspected of effecting a modulation of the binding between DLC1/PIN and Pak1. The candidate substance suspected of effecting a modulation of the binding between DLC1/PIN and Pak1 can be a candidate substance suspected of inhibiting the binding between DLC1/PIN and Pak1 or a candidate substance suspected of promoting the binding between DLC1/PIN and Pak1. In yet another embodiment, the candidate substance suspected of effecting a modulation of the binding between DLC1/PIN and Pak1 is a candidate substance suspected of modulating the phosphorylation of DLC1/PIN by Pak1. For example, the candidate substance can be a substance suspected of promoting the phosphorylation of DLC1/PIN by Pak1. In a particular embodiment, the candidate substance suspected of promoting the phosphorylation of DLC1/PIN by Pak1 is a candidate substance suspected of promoting the phosphorylation of serine 88 of DLC1/PIN by Pak1. In yet another embodiment, the candidate substance suspected of modulating the phosphorylation of DLC1/PIN by Pak1 pertains to a candidate substance suspected of inhibiting the phosphorylation of DLC1/PIN by Pak1. For example, the candidate substance can be a substance suspected of inhibiting the phosphorylation of serine 88 of DLC1/PIN by Pak1.

Another embodiment of the invention provides for a method of screening for modulators of macropinocytosis that is achieved by: (a) obtaining a candidate substance suspected of modulating macropinocytosis; and (b) determining whether said candidate substance inhibits or promotes the binding of Pak1 and DLC1/PIN. In certain aspects of the invention, the method further comprises providing in a pharmaceutical composition the candidate substance determined to have such activity. In other aspects, the pharmaceutical composition comprising the candidate substance is administered to a cell, such as one in a patient, such as a cancer or virus-infected patient.

The candidate substance can be any type of substance that is suspected of modulating macropinocytosis. However, in a certain embodiment, the candidate substance is a small molecule. Although any small molecule is contemplated, in a preferred embodiment the candidate substance can be a small molecule that modulates the binding of Pak1 to DLC1/PIN. The modulation of the binding of Pak1 to DLC1/PIN can be accomplished by either inhibiting or promoting the binding of Pak1 to DLC1/PIN.

The candidate substance can also be a peptide or a polypeptide. In a certain embodiment, the polypeptide is a DLC1/PIN polypeptide. For example, the DLC1/PIN polypeptide can be a mutant DLC1/PIN polypeptide. Examples of such mutant polypeptides include a DLC1/PIN polypeptide lacking the C-terminal 19 amino acids (SEQ ID NO: 3). Another example of a mutant DLC1/PIN polypeptide is a DLC1/PIN polypeptide lacking serine 88, the phosphorylation site of Pak1 (SEQ ID NO: 4). An additional example of a mutant DLC1/PIN polypeptide is a mutant DLC1/PIN polypeptide composed of only the C-terminal 19 amino acids of DLC1/PIN (SEQ ID NO:5). Another mutant DLC1/PIN polypeptide is a modified version of SEQ ID NO:5 which includes additional amino acids to enable entry into cells (SEQ ID NO:6). The DLC1/PIN polypeptide can be a DLC1/PIN polypeptide that includes the C-terminal 19 amino acids of DLC1/PIN. In yet another embodiment, the polypeptide is a polypeptide capable of being phosphorylated by Pak1. In other embodiments, the candidate substance can be an antibody or a polynucleotide.

The method of screening for modulators of macropinocytosis may or may not involve the use of cells. In a preferred embodiment, the method of screening for modulators of macropinocytosis includes contacting the candidate substance with a cell. In another embodiment, the candidate substance is a composition including an expression cassette that includes a promoter, active in the cell, operably linked to a polynucleotide encoding a polypeptide. In a preferred embodiment, the expression cassette is carried in a vector. Although one of skill in the art would understand that any type of vector is contemplated by the invention, in a specific embodiment the vector is a viral vector. For example, the viral vector can be an adenovirus vector, retrovirus vector, adeno-associated virus vector, herpesvirus vector, vaccinia virus vector or polyoma virus vector. Alternatively, the vector can be a nonviral vector. In a specific embodiment, the nonviral vector is a lipid. One of skill in the art would understand that the expression cassette includes any type of promoter that is active in the cell. In particular, the promoter may be a constitutive or inducible promoter.

Although the invention contemplates that the expression cassette can include any polynucleotide that encodes a polypeptide, in a preferred embodiment the polypeptide is a DLC1/PIN polypeptide. Although the invention contemplates any DLC1/PIN polypeptide, in a certain embodiment the polypeptide is a mutant DLC1/PIN polypeptide. For example, the mutant DLC1/PIN polypeptide can be a polypeptide that lacks the C-terminal 19 amino acids of DLC1/PIN or a DLC1/PIN polypeptide can include the C-terminal 19 amino acids of DLC1/PIN. The mutant DLC1/PIN polypeptide can also be a DLC1/PIN polypeptide that lacks serine 88 of DLC1/PIN. The mutant can also be the DLC1-66 peptide sequence (SEQ ID NO:11), such as wherein the polypeptide lacks the C-terminal 23 amino acids.

In a still further embodiment, the expression cassette can include a polynucleotide that hybridizes to a DLC1/PIN-encoding polynucleotide, resulting in inhibition of the expression of DLC1/PIN. Alternatively, the expression cassette can include a polynucleotide that hybridizes to a Pak1-encoding polynucleotide, resulting in inhibition of the expression of Pak1. A polynucleotide of any length is contemplated, as long as that polynucleotide is capable of hybridizing to the targeted Pak1- or DLC1/PIN-encoding polynucleotide. In a preferred embodiment, the polynucleotide is an oligonucleotide having a length of 8–50 bases. However, oligonucleotides of fewer than 8 bases or more than 50 bases is also contemplated, as long as the oligonucleotide is capable of hybridizing to the targeted Pak1- or DLC1/PIN-encoding polynucleotide.

The candidate substance suspected of modulating macropinocytosis can include, for example, a candidate substance capable of binding to Pak1. Although any method of measuring binding to Pak1 is contemplated, in one embodiment the binding to Pak1 is measured in an assay using the Pak1 N-terminal amino acids 1–270 as bait.

Although the method of screening for modulators of macropinocytosis involving contacting the candidate substance with a cell contemplates use of any type of cell, in a preferred embodiment the cell is a cancer cell. For instance, the cancer cell can be a breast cancer cell, lung cancer cell, prostate cancer cell, ovarian cancer cell, brain cancer cell, liver cancer cell, prostate cancer cell, cervical cancer cell, colon cancer cell, renal cancer cell, skin cancer cell, head and neck cancer cell, bone cancer cell, esophageal cancer cell, bladder cancer cell, uterine cancer cell, lymphatic cancer cell, stomach cancer cell, pancreatic cancer cell, testicular cancer cell, an endometrial cancer cell, or leukemic cell. In another embodiment, cell is infected with a virus. For example, the virus can be HIV, neurotropic virus, adenovirus, foot and mouth disease virus, or respiratory syncytial virus. Alternatively, the cell can be a dendritic cell, macrophage, foam cell, or a neuronal cell.

In another embodiment, the method of screening for modulators of macropinocytosis involves determining whether the candidate substance has an effect on macropinocytosis of the cell. For example, the effect on macropinocytosis can include either an inhibition or promotion of macropinocytosis. One of skill in the art would understand that any means for measuring macropinocytosis in a cell is contemplated by the invention. However, in a preferred embodiment the effect on macropinocytosis is measured by determining whether there is a modulation of binding between DLC1/PIN and Pak1. Modulation of binding between DLC1/PIN and Pak1 can include either an increased binding between DLC1/PIN and Pak1 or an inhibition of binding between DLC1/PIN and Pak1. The effect on macropinocytosis can be measured using any experimental technique known to one of skill in the art. However, immunofluorescence and confocal microscopy are used in preferred embodiments. A dextran bead and labeled bioparticle uptake assays are examples of techniques that can be used in determining whether the candidate substance has an effect on macropinocytosis. The cell that is assessed for macropinocytosis can be any type of cell. However, in a preferred embodiment the cell is a stimulated cell. In a still preferred embodiment, the cell is stimulated with heregulin (HRG). In yet another embodiment, the cell is stimulated with a growth factor, such as epidermal growth factor (EGF).

In yet another embodiment, the method of screening for modulators of macropinocytosis involves a determination of whether the candidate substance modulates the phosphorylation of DLC1/PIN by Pak1. The modulation of phosphorylation can include either an inhibition or promotion of phosphorylation of DLC1/PIN by Pak1. Although the invention contemplates using any method to measure phosphorylation, in a preferred embodiment the phosphorylation can be determined by an in vitro kinase assay. In yet another embodiment, the phosphorylation is measured in vivo. In a preferred embodiment, the inhibition of phosphorylation of serine 88 of DLC1/PIN is measured.

A further embodiment provides for a method of modulating macropinocytosis in cells of a target cell population in a subject that is accomplished by administering to the subject a pharmacologically effective amount of a modulator of macropinocytosis identified by the method of screening for modulators of macropinocytosis that has been previously described. In a preferred embodiment, the cells are cancer cells. For example, the cells can be breast cancer cells, lung cancer cells, prostate cancer cells, ovarian cancer cells, brain cancer cells liver cancer cells, prostate cancer cells, cervical cancer cells, colon cancer cells, renal cancer cells, skin cancer cells, head and neck cancer cells, bone cancer cells, esophageal cancer cells, bladder cancer cells, uterine cancer cells, lymphatic cancer cells, stomach cancer cells, pancreatic cancer cells, testicular cancer cells, or leukemic cells. In another embodiment, the cells are infected with a virus. For example, the virus can be HIV, neurotropic virus, adenovirus, foot and mouth disease virus, or respiratory syncytial virus. There is evidence that macropinocytosis is involved in atherosclerosis, Alzheimer disease, immune response regulation, and antigen presentation by dendritic cells. Therefore, in yet other embodiments, the cells are macrophages, foam cells, neuronal cells, or dendritic cells. In a preferred embodiment, the cells of the target cell population are located in a patient. For example, the cells can be normal bystander cells located in a patient with HIV. In another embodiment, the cells can undergo a reduction in directed cell motility.

In a preferred embodiment, the method involves use of a human subject. In yet another specific embodiment, the human subject is a subject with cancer. The human subject with cancer may have undergone secondary antihyperproliferative treatment. The secondary antihyperplastic treatment can include chemotherapy, radiation therapy, surgical therapy, immunotherapy, gene therapy, or any other secondary antihyperproliferative therapy. In another embodiment, the human subject is a subject with atherosclerosis. In yet another embodiment, the human subject is a subject in need of a vaccine. The vaccine can be a DC vaccine. The subject can also be a subject with an immune disorder, such as an immune disorder associated with excess antigen presentation by dendritic cells. Because DLC1/PIN is implicated in modulating mannose receptor-mediated cellular functions such as endocytosis, the target cell population can undergo modulation of mannose receptor-mediated endocytosis. The modulation can be an inhibition or promotion of mannose receptor-mediated endocytosis.

A specific embodiment provides for a method of modulating macropinocytosis in a target cell population in a subject that is accomplished by administering to the target cell population a pharmacologically effective amount of a composition composed of an expression cassette including a promoter, active in the target cell population, operably linked to a polynucleotide encoding a DLC1/PIN polypeptide lacking the C-terminal 19 amino acids of DLC1/PIN. In yet another specific embodiment, there is provided a method of modulating macropinocytosis in a target cell population in a subject that is achieved by administering to the target cell population a pharmacologically effective amount of a composition composed of an expression cassette that includes a promoter, active in the target cell population, operably linked to a polynucleotide encoding a DLC1/PIN polypeptide lacking serine 88 of DLC1/PIN. An additional specific embodiment includes a method of modulating macropinocytosis in a target cell population in a subject that is achieved by administering to the target cell population a pharmacologically effective amount of a composition composed of an expression cassette including a promoter, active in the target cell population, operably linked to a polynucleotide encoding the C-terminal 19 amino acids of DLC1/PIN.

Certain other embodiments provide for methods of reducing cell proliferation in a cell population that is achieved by administering to the cell population a pharmacologically effective amount of an agent that inhibits the binding of Pak1 to DLC1/PIN. Reducing cell proliferation includes any reduction in the growth of the cells in the cell population or any reduction in the ability of the cells of the cell population to increase in number. In a preferred embodiment, the agent is a modulator of macropinocytosis identified by any of the methods of screening for modulators of macropinocytosis that have been previously described. A specific embodiment provides for a method of reducing cell proliferation in a target cell population in a subject by administering to the target cell population a pharmacologically effective amount of a composition composed of an expression cassette including a promoter, active in the target cell population, operably linked to a polynucleotide encoding a DLC1/PIN polypeptide lacking the C-terminal 19 amino acids of DLC1/PIN. Another specific embodiment provides a method of reducing cell proliferation in a target cell population in a subject by administering to the target cell population a pharmacologically effective amount of a composition that includes an expression cassette further including a promoter, active in the target cell population, operably linked to a polynucleotide encoding a DLC1/PIN polypeptide lacking serine 88 of DLC1/PIN, a polynucleotide encoding a DLC1/PIN polypeptide lacking one or more of the C-terminal 23 amino acids, or a polynucleotide encoding a DLC1/PIN polypeptide lacking one or more of the C-terminal 19 amino acids.

A certain embodiment of the invention provides for a method for inhibiting the growth and survival of a cancer cell that is achieved by inhibiting the binding of DLC1/PIN to Pak1 in the cancer cell. Inhibition of the growth and survival of the cancer cell can be manifested in various ways. For example, the cancer cell can be killed or can undergo apoptotic cell death. In a preferred embodiment, the cancer cell is in a human subject. The human subject can be a subject receiving secondary anti-proliferative therapy. Examples of secondary anti-proliferative therapy can include chemotherapy, radiation therapy, surgical therapy, immunotherapy or gene therapy. In another embodiment, there is provided a method for inhibiting the growth and survival of a cancer cell wherein the binding is inhibited by administering to the target cell population a pharmacologically effective amount of a modulator of macropinocytosis that has been identified by any of the screening methods previously disclosed. A specific embodiment of the invention provides for a method of inhibiting the growth and survival of a cancer cell in a subject that is accomplished by administering to the cancer cell a pharmacologically effective amount of a composition including an expression cassette that includes a promoter, active in the cancer cell, operably linked to a polynucleotide encoding a DLC1/PIN polypeptide lacking the C-terminal 19 amino acids of DLC1/PIN. An additional specific embodiment of the invention provides for a method of inhibiting the growth and survival of a cancer cell in a subject that is accomplished by administering to the cancer cell a pharmacologically effective amount of a composition that is composed of an expression cassette including a promoter, active in the cancer cell, operably linked to a polynucleotide encoding a DLC1/PIN polypeptide lacking serine 88 of DLC1/PIN.

Another embodiment of the invention provides for a method of inhibiting the invasiveness of a cancer cell that is achieved by inhibiting the binding of DLC1/PIN to Pak1 in the cancer cell. In a preferred embodiment, the cancer cell is in a human subject. For example, the binding of DLC1/PIN to Pak1 can be inhibited by administering a pharmacologically effective amount of a modulator of macropinocytosis identified by any of the methods of screening for modulators of macropinocytosis that have been previously described. One example of inhibition of invasiveness of a cancer cell is failure of the cell to metastasize. Examples of cancer cells include a breast cancer cell, lung cancer cell, prostate cancer cell, ovarian cancer cell, brain cancer cell, liver cancer cell, prostate cancer cell, cervical cancer cell, colon cancer cell, renal cancer cell, skin cancer cell, head and neck cancer cell, bone cancer cell, esophageal cancer cell, bladder cancer cell, uterine cancer cell, lymphatic cancer cell, stomach cancer cell, pancreatic cancer cell, testicular cancer cell, or leukemic cell. A specific embodiment of the invention provides for a method of inhibiting the invasiveness of a cancer cell in a subject that involves administering to the cancer cell a pharmacologically effective amount of a composition including an expression cassette that includes a promoter, active in the cancer cell, operably linked to a polynucleotide encoding a DLC1/PIN polypeptide lacking the C-terminal 19 amino acids of DLC1/PIN or a polynucleotide encoding a DLC1/PIN polypeptide lacking the C-terminal 23 amino acids of DLC1/PIN. Another specific embodiment provides for a method of inhibiting the invasiveness of a cancer cell in a subject which is achieved by administering to the cancer cell a pharmacologically effective amount of a composition including an expression cassette with a promoter, active in the cancer cell, operably linked to a polynucleotide encoding a DLC1/PIN polypeptide lacking serine 88 of DLC1/PIN.

An additional embodiment of the invention provides for a method of treating cancer in a human subject, which is achieved by administering to the subject a pharmacologically effective amount of an antibody directed against a modulator of binding between DLC1/PIN and Pak1. In a specific embodiment, the modulator is a modulator of macropinocytosis identified by one of the methods of screening for modulators of macropinocytosis that have been previously described. Although the cancer can be of any type, in a preferred embodiment the cancer is breast cancer. In another preferred embodiment, the antibody is directed against a DLC1/PIN polypeptide. For example, the antibody can be directed against a mutant DLC1/PIN polypeptide, such as a DLC1/PIN polypeptide lacking the C-terminal 19 amino acids of DLC1/PIN.

Yet an additional embodiment provides for a method of treating a viral infection in a patient comprising administering to the patient a pharmacologically effective amount of a modulator of macropinocytosis identified by any of the previously described methods of screening for modulators of macropinocytosis. Studies have demonstrated that one of the mechanisms by which virus particles gain access to cells is by macropinocytosis. Therefore, inhibiting the process of macropinocytosis through modulation of the binding of Pak1 to DLC1/PIN can provide a novel mechanism of treating viral infection in a subject.

Although the invention contemplates treatment of any type of viral infection, in a preferred embodiment, the viral infection is HIV. In a specific embodiment, the method of treating a viral infection in cells of a human subject is achieved by administering to the cells of a subject a pharmacologically effective amount of a composition that is composed of an expression cassette including a promoter, active in the cells, operably linked to a polynucleotide encoding a DLC1/PIN polypeptide lacking the C-terminal 19 amino acids of DLC1/PIN. Yet another preferred embodiment provides for a method of treating a viral infection in cells of a human subject that is accomplished by administering to the subject a pharmacologically effective amount of a composition that includes an expression cassette including a promoter, active in the cells, operably linked to a polynucleotide encoding a DLC1/PIN polypeptide lacking serine 88 of DLC1/PIN as well as the C-terminal 19 amino acids.

An additional embodiment provides for a method of treating Alzheimer disease in a patient comprising administering to the patient a pharmacologically effective amount of a modulator of macropinocytosis identified by the method of screening for modulators of macropinocytosis that have been previously described. It has been shown that there is increased neuronal endocytosis and protease delivery to early endosomes in Alzheimer disease. Modulation of macropinocytosis can thus be used as a therapeutic strategy to treat Alzheimer disease. A certain embodiment provides for a method of treating Alzheimer disease in cells of a human subject which is achieved by administering to the cells a pharmacologically effective amount of a composition including an expression cassette comprising a promoter, active in the cells, operably linked to a polynucleotide encoding a DLC1/PIN polypeptide lacking the C-terminal 19 amino acids of DLC1/PIN. Another embodiment provides for a method of treating Alzheimer disease in cells of a human subject comprising administering to the cells a pharmacologically effective amount of a composition including an expression cassette which includes a promoter, active in the cells, operably linked to a polynucleotide encoding a DLC1/PIN polypeptide lacking serine 88 of DLC1/PIN.

The inventors have also discovered that a modification of the C-terminal amino acids of DLC1/PIN wherein the peptide is 31 amino acids and includes 12 extra amino acid polybasic sequences from the HIV tat protein results in facilitated entry of the peptide into cells. Therefore, certain embodiments of the invention pertain to methods of modulating macropinocytosis in a target cell population in a subject including administering to said target cell population a pharmacologically effective amount of a composition that includes an expression cassette comprising a promoter, active in the target cell population, operably linked to a polynucleotide encoding the amino acid sequence of SEQ ID NO:6. SEQ ID NO:6 is the amino acid sequence of the modified C-terminal 19 amino acids of DLC1/PIN, disclosed herein. Other embodiments include methods of reducing cell proliferation in a target cell population in a subject including administering to said target cell population a pharmacologically effective amount of a composition including an expression cassette that includes a promoter, active in the target cell population, operably linked to a polynucleotide encoding the amino acid sequence of SEQ ID NO:6. Other embodiments of the invention include methods of inhibiting the growth and survival of a cancer cell in a subject by administering to the cancer cell a pharmacologically effective amount of a composition including an expression cassette that includes a promoter, active in the cancer cell, operably linked to a polynucleotide encoding a polypeptide having the amino acid sequence of SEQ ID NO:6. In addition, other embodiments include methods of treating a viral infection in cells of a human subject which is accomplished by administering to said cells a pharmacologically effective amount of a composition including an expression cassette that includes a promoter, active in the cells, operably linked to a polynucleotide encoding a polypeptide having the amino acid sequence of SEQ ID NO:6.

In other embodiments of the present invention, there is a method of treating a hormonal resistant cancer in a human subject by administering a pharmacologically effective amount of a composition comprising an expression cassette having a promoter, active in a cancer cell of the subject, that is operably linked to a polynucleotide encoding a mutant DLC1/PIN polypeptide, such as a DLC1/PIN polypeptide lacking serine 88 or a DLC1/PIN polypeptide lacking one or more of the C-terminal 23 amino acids of DLC1/PIN polypeptide. The hormonal resistant cancer may be estrogen receptor (ER)-positive breast cancer or endometrial cancer, for example, and the hormonal resistant cancer may also be resistant to one or more particular cancer therapies, such as a chemotherapeutic, such as tamoxifen. In a specific embodiment, the mutant DLC1/PIN1 polypeptide interferes with interaction between estrogen receptor and DLC1.

In an additional embodiment of the present invention, there is a method of inducing apoptosis in a cell, such as a cancer cell, by delivering to the cell a pharmacologically effective amount of a DLC1/PIN mutant polypeptide. The DLC1/PIN mutant polypeptide may interfere with a Pak1-associated pathway in the cell. Examples of mutant DLC1/PIN polypeptides include those that lack serine 88 and/or that lack one or more of the C-terminal 23 amino acids of DLC1/PIN polypeptide.

In particular methods, the cell is a cancer cell comprised in a human subject, and the human subject may be being administered or will be administered an additional cancer therapy, such as chemotherapy, radiotherapy, immunotherapy, surgery, gene therapy, or a combination thereof. In other particular methods, the cell is a viral-infected cell, a pathogen-infected cell, and so on.

In one particular method of the present invention, there is inhibition of growth and survival of a cancer cell in a subject by administering to the cancer cell a pharmacologically effective amount of a composition comprising an expression cassette comprising a promoter, active in the cancer cell, operably linked to a polynucleotide encoding a DLC1/PIN polypeptide lacking serine 88 of DLC1/PIN, a polynucleotide encoding a DLC1/PIN polypeptide lacking the C-terminal 19 amino acids of DLC1/PIN, a polynucleotide encoding a DLC1/PIN polypeptide lacking the C-terminal 23 amino acids of DLC1/PIN, or a mixture thereof. In one particular aspect of the method, the cancer cell is resistant to treatment of any kind. The cancer cell may be resistant to treatment such as chemotherapy, hormonal therapy, gene therapy, surgery, radiation, immunotherapy, or a combination thereof, for example. In a specific embodiment of the present invention, the chemotherapy comprises tamoxifen and the cell is resistant thereto.

In another aspect of the invention there is a method of modulating estrogen receptor (ER) function by inhibiting the interaction of DLC1 with ER, by inhibiting the interaction of Pak1 with ER, or by inhibiting the interaction of both DLC1 and Pak1 with ER. That is, in specific embodiments there is a method of modulating ER function in a cell by administering to the cell an agent that inhibits the interaction of DLC1 with ER, by administering an agent that inhibits the interaction of Pak1 with ER, or an agent that inhibits the interaction of both DLC1 and Pak1 with ER. This arises out of the inventors discovery that Pak1 and DLC1 are molecular targets of tamoxifen and also of ER-interacting proteins in tamoxifen-resistant breast and endometrial cancer cells. In addition, DLC1 overexpression in specific embodiments is sufficient to confer estrogen hypersensitivity and tamoxifen resistance. The underlying mechanism involves the DLC1-mediated regulation of ER accumulation in the nucleus, DLC1 recruitment to the ER target gene chromatin, and the AF1 function of ER. Because these phenotypic changes could be reversed by the downregulation of DLC1, this indicates a novel target for therapy to control tamoxifen resistance and the hormone independence of hormone-responsive cancers. The ER function being modulated may be in a cell, such as a cancer cell. In a specific embodiment, the cancer cell is resistant to treatment, such as chemotherapy, hormonal therapy, or both. In a further specific embodiment, the chemotherapy comprises tamoxifen.

In another aspect of the invention, there is a method of treating cardiovascular disease in an individual by inhibiting low-density lipoprotein (LDL) cholesterol-induced macropinocytosis in the individual through administration of a DLC1/PIN peptide. In another particular aspect, a mutant DLC1/PIN peptide, polypeptide, or protein is administered to the individual.

In an additional embodiment of the present invention, there is a method of determining resistance of a cancer cell to a hormonal therapy by identifying a change in expression level in the cell of DLC1/PIN, Pak1, or both DLC1/PIN and Pak1. The identification of the change in expression level may be detected in any manner, yet in a particular aspect the identification comprises immunohistochemical staining with antibodies to said DLC1/PIN, Pak1, or both.

In a particular aspect of the invention, there is a composition comprising a mutant DLC1/PIN polypeptide, wherein said mutant polypeptide comprises activity that inhibits binding of DLC1/PIN to Pak1. The mutant polypeptide may comprise a DLC1/PIN polypeptide lacking serine 88 of DLC1/PIN, a DLC1/PIN polypeptide lacking the C-terminal 19 amino acids of DLC1/PIN, a DLC1/PIN polypeptide lacking the C-terminal 23 amino acids of DLC1/PIN, or a mixture thereof. The composition may be further defined as a pharmaceutical composition. In a particular embodiment, the composition is dispersed in a pharmaceutically acceptable excipient.

In another particular aspect of the invention, there is a composition comprising a polynucleotide that encodes a mutant DLC1/PIN polypeptide, wherein said mutant polypeptide comprises activity that inhibits binding of DLC1/PIN to Pak1. The mutant polypeptide may comprise a DLC1/PIN polypeptide lacking serine 88 of DLC1/PIN, a DLC1/PIN polypeptide lacking the C-terminal 19 amino acids of DLC1/PIN, a DLC1/PIN polypeptide lacking the C-terminal 23 amino acids of DLC1/PIN, or a mixture thereof. The polynucleotide may be comprised in an expression cassette in a vector, and the cassette may comprise a promoter active in a cell, such as active in a cancer cell, a cell infected with a virus, a macrophage, a foam cell, a neuronal cell, or a dendritic cell. The promoter may also be a constitutive promoter or an inducible promoter.

In specific embodiments, the composition is comprised in a vector, such as a viral vector or a non-viral vector. The viral vector may be an adenoviral vector, a retroviral vector, an adeno-associated viral vector, a herpesvirus vector, a vaccinia virus vector or a polyoma virus vector. Exemplary nonviral vectors include a plasmid or a lipid. The composition may be further defined as a pharmaceutical composition, which may be dispersed in a pharmaceutically acceptable excipient.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A: Yeast cells were cotransfected with control GAD vector or GAD-DLC1/PIN, GAD-Rac1 along with GBD vector or GBD-Pak1 (amino acids 1–270) or GBD-Pak1 (amino acids 270–570). Cotransformants were plated on selection plates lacking leucine and tryptophan (LT) or adenine, histidine, leucine, and tryptophan (AHLT). Growth was recorded after 72 h. For beta-galactosidase assay, filter lift assays were performed (middle panel). Blue color indicates specific interaction of two proteins. Rac1 was used as a positive control. FIG. 1B: Pak1 and DLC1/PIN interaction in the GST pull-down assays. DLC1/PIN or Pak1 cDNAs were translated in vitro and $^{35}$S-labeled proteins were incubated with either GST-Pak1 or GST-DLC1/PIN, and analyzed by SDS-PAGE and autoradiography. FIG. 1C: In vivo interaction of Pak1 with endogenous DLC1/PIN. MCF-7 cells were serum starved for 48 hour, treated with EGF for 30 min and cell lysates were immunoprecipitated with Pak1 antibody and DLC1/PIN association was analyzed by Western blotting with DLC1 antibody. FIG. 1D: Activated Pak1 interacts with DLC1/PIN. Tet on-vector or Tet on-HA-Pak1-T423E expressing MCF-7 cells grown in 10% serum were lysed, and lysates containing equal amounts of protein were immunoprecipitated with HA antibody and immunoblotted with antibodies against DLC1/PIN and Pak1. FIG. 1E: Colocalization of Pak1 and DLC1/PIN on vesicles by physiologic signals. MDA-231 cells were serum-starved for 48 h, treated with EGF or HRG (1 nM) for 20 min and then fixed and co-stained for DLC1/PIN (blue), Pak1 (green), and F-actin (red). Merged images are presented in the right panels, and dual color images (Pak1 and DLC1/PIN) are represented in the middle and left panels. Insert in HRG-treated cells is enlarged and presented in a dotted box and shown in the upper row. The level of vesicle in unstimulated control cells was very low, but in the EGF and HRG-treated cells, significant formation of intracytoplasmic vesicular structures can be observed.

FIG. 2A: Identification of Pak1 domains that interact with DLC1/PIN. GST-Pak1 fusion proteins containing wild-type (amino acids 1–545), kinase domain (amino acids 270–545), N-terminal domain (amino acids 1–132), PIX binding domain (amino acids 132–270), Nck-binding domain (amino acids 1–75), Cdc42/Rac-interacting (CRIB) domain (amino acids 52–132), and auto-inhibitory domain (amino acids 75–149) were incubated with in vitro translated DLC1/PIN (amino acids 1–89), and binding was analyzed by GST pull-down assay. FIG. 2B: Identification of the DLC1/PIN region that is involved in the binding of Pak1. GST-fusions of various lengths of DLC1/PIN were used in the GST pull-down assay using $^{35}$S-labelled Pak1 (amino acids 1–545). FIGS. 2C–2G—Pak1 phosphorylation of DLC1/PIN. FIG. 2C: In vitro kinase assay using GST-DLC1/PIN as a substrate and purified bacterially expressed Pak1 as an enzyme. MBP was used as a positive control. FIG. 2D: ZR75R cells stably expressing T7-DLC1/PIN were labeled in vivo with $^{32}$P-orthophosphate, serum starved, treated with EGF or HRG, and immunoprecipitated and phosphorylation status of DLC1/PIN was visualized by autoradiography. FIG. 2E: MCF-7 cells were cotransfected with T7 tagged DLC1/PIN along with or without Pak1 autoinhibitory domain (Pak1 amino acids 83–149). Cells were metabolically labeled with $^{32}$P orthophosphate, treated with or without EGF (1 nM) and phosphorylation of T7-DLC1/PIN was analyzed by immunoprecipitation. FIG. 2F: MCF-7 cells were cotransfected with wild-type T7 tagged DLC1/PIN and constitutively active (T423E) Pak1. DLC1/PIN was immunoprecipitated and phosphorylation status was visualized by autoradiography. FIG. 2G: In vitro Pak1 kinase assay using GST fusion of DLC1/PIN fragments containing the indicated serial deletions.

FIG. 4A: expression of DLC1/PIN in a number of normal and breast cancer cells analyzed by western blot analysis. FIG. 4B: Expression of T7-DLC1/PIN in stable clones analyzed by western blot analysis. FIG. 4C: Effect DLC1/PIN expression on the motility. Migratory potential of DLC1/PIN wild type or DLC1/PIN$^{del88-89}$ mutant expressing clones was measured by Boyden chamber assay using NIH3T3 conditioned medium as chemoattractant. Migrated cells were recorded by microscopy. Representative data of three replicate experiments is shown. FIG. 4D: ZR75/RFP-DLC1 cells which stably expressing wild type red florescent-tagged DLC1/PIN protein (RFPDLC1/PIN) was incubated with FITC-dextran beads. After twenty minutes, cells were fixed with methanol and stained for endogenous Pak1 (blue), RFPDLC1/PIN (red) and FITC-dextran (green). An inset containing the cytoplasmic region was blown up to visualize the colocalization of Pak1 and DLC1/PIN on dextran beads. Merged images are presented in the upper right panel, and colocalization of Pak1 with DLC1/PIN can be visualized as white vesicles due to colocalization of pixels from Pak1 (blue), DLC1/PIN (red) and FITC dextran (green). FIG. 4E: ZR75/RFP-DLC1/PIN were transfected with a dominant negative mutant of Pak1 K299RLL (a myc-tagged kinase dead and GTPase binding defective construct of Pak1). After 24 h cells were incubated with FITC-dextran beads for 20 min and cells were fixed in methanol and stained for myc-tagged Pak1 or Pak1K299RLL (blue), DLC1/PIN (red) and FITC-dextran (green).

FIG. 5A: Equal number of cells ZR75R stable cells expressing DLC1/PIN wild type or DLC1/PIN$^{del88-89}$ mutant were plated and cell proliferation was determined by trypsinizing and counting cells using a coulter counter. Each colne was plated in triplicate and experiment was repeated twice with similar results. FIG. 5B: Cell cycle progression of DLC1/PIN wild type or mutant clones was analyzed by FACS analysis. FIG. 5C: Immunofluorescence staining of NIH3T3 cells cotransfected with various combinations of DLC1/PIN wild type or DLC1/PIN S88A mutant and various Pak1 constructs, exposed to UV radiation 100 mJ/s and after 10 h. costained for myc-tag (for Pak1 constructs, blue), RFP-DLC1/PIN wild type or mutants (DLC1/PIN constructs, red) and for Lamin A/C (green). Cells expressing the transfected plasmid(s) were identified using appropriate filter settings, and then characterized for their nuclear integrity using morphologic features identified by Lamin A/C staining. For example, a smooth nuclear membrane was scored as non-apoptotic, as opposed to membrane blebbing or rupture, which was scored as apoptotic. Nuclei committed to enter mitosis were not scored in either of these groups because they were easily identified for their specific "pulverized" pattern of Lamin A/C staining. Ten randomly selected fields were analyzed for each condition. The experiment was repeated twice with similar results.

FIG. 6A: Effect DLC1/PIN expression on anchorage-independent growth of ZR75 cells. The anchorage-independent growth potential of DLC1/PIN-expressing clones was measured by the ability of the cells to form colonies on soft agar. Similar results were seen in three independent experiments. Error bars represent standard error of mean. FIG. 6B: Western blot analysis of the expression of DLC1/PIN and Pak1 in lysates from cells derived from MCF10AT model system. MCF 10A, non-malignant human breast cancer cells; MCF10AT, weakly tumorigenic; MCF10DCIS, Comedo-type DCIS, highly proliferative, aggressive, invasive; MCF10CA, undifferentiated carcinomas, metastatic. FIG. 6C: Nude mice were injected with 5×10$^6$ cells stably expressing pcDNA or wild type DLC1/PIN (clone#2) or mutant DLC1/PIN$^{del88-89}$ and tumor growth was measured at weekly intervals. FIG. 6D: A representative picture of DLC1/PIN induced tumor in nude mice. Tumor growth was only observed in cells expressing wild type DLC1/PIN but not detected in mutant expressing cells. FIG. 6E: Morphology of tumor and expression of T7-DLC1/PIN in DLC1/PIN-induced tumors as measured by H&E and anti T7 staining respectively.

FIG. 7A: DLC1/PIN levels in normal and breast tumors pairs. Breast tumor lysates were analyzed by Western blot analysis for Pak1 expression (upper panel) and subsequently reprobed with a vinculin antibody as a loading control (middle panel). FIG. 7B: Immunohistochemical analysis of DLC1/PIN in breast tissue samples. Two left panels are normal mammary gland tissue and four right panels represent tumors from the same patient. All tumors show very strong positivity for DLC1/PIN. FIG. 7C: Quantitation of DLC1/PIN expression in normal and tumor samples.

FIG. 8A: Delivery of the DLC1 peptide via liposomal formulation. To visualize entry, the DLC1 peptide was labeled with biotin (red). Actin staining was used as a marker of cell morphology (green). FIG. 8B: Efficacy of DLC1 in liposomal formulation to block entry of HIV virus via macropinocytosis.

FIGS. 9A, 9B: Western blot analysis of Pak1 expression and DLC1 expression in normal and endometrial tumors. FIG. 9C: Immunohistochemcial analysis and localization of Pak1 and DLC1 in endometrioid adenocarcinoma sections. FIG. 9D: Immunohistochemcial analysis and localization of Pak1 and DLC1 in normal and endometrial tumor sections of breast cancer patients exposed to tamoxifen.

FIG. 10A: Breast tumor lysates were analyzed by Western blot analysis for DLC1 expression (upper panel) and subsequently reprobed with a vinculin antibody as a loading control (middle panel). FIG. 10B: Quantitation of DLC1 expression in normal and tumor samples. FIG. 10C: Immunohistochemical analysis of DLC1 in breast tissue samples. The left panel are normal mammary gland tissue and the right panel represent tumors from the same patient. All tumors show very strong DLC1 immunoreactivity. FIG. 10D: Quantitation of DLC1 expression in breast tumor array.

FIG. 12A: DLC1 upregulation potentiates growth stimulation by E2 in a Tam-insensitive manner. MCF-7/DLC1 cells were treated with or without Dox and then with E2 ($10^{-9}$M) or Tam ($10^{-8}$M) for 5 days, and the cell number was determined. FIG. 12B: DLC1 upregulation promotes anchorage independence. MCF-7/DLC1 cells were plated in soft-agar, treated with or without Dox for 24 h and then with E2 ($10^{-9}$M) or Tam ($10^{-9}$M) for 21 days, and the colonies were counted. FIG. 12C: DLC1 expression supports optimum growth of Tam-resistant cells. Ishikawa and MCF-7/TAMR1 cells were transfected with control or DLC siRNA for 48 h and then treated with or without Tam ($10^{-9}$M) for 96 h, and the cell number was determined. FIG. 12D: DLC1-mediated potentiation of ER transactivation depends on the Pak1 status in Ishikawa and MCF-7/TAMR1 cell lines. Ishikawa and MCF-7/TAMR1 cells were transfected with control or Pak1 siRNA for 48 h and then with ERE-luc for 24 h and treated with E2 ($10^{-9}$M) for 24 h and ERE-luc activity was measured. FIG. 12E: Pak1 expression level influences the growth of Tam resistant cells. Ishikawa and MCF-7/TAMR1 cells were treated with control or Pak1 siRNA for 48 h and treated with or without Tam ($10^{-8}$M) for 4 days, and cell number was determined. FIG. 12F: Co-downregulation of Pak1 and DLC1 in Tam-resistant cells restores Tam-sensitivity. Ishikawa cells were treated with control or and Pak1 and DLC siRNA for 48 h and then transfected with ERE-luc and treated with Tam ($10^{-8}$M) for 24 h and ERE-luc activity was measured.

FIG. 13A: Interaction of DLC1 with ERá. In vitro-translated $^{35}$ER were incubated with GST-DLC1, and analyzed by SDS-PAGE and autoradiography. FIG. 13B: Identification of ER domains that interact with DLC1. GST-ER fusion proteins containing different deletion constructs were incubated with in vitro-translated 35S-DLC1 (aa 1-89), and binding was analyzed by GST pull-down assay. FIG. 13C: Mapping of the ER-binding region in DLC1. GST-fusions of various DLC1 deletion constructs were incubated with in vitro-translated $^{35}$S-ER, and binding was analyzed by GST pull-down assay. FIG. 13D: Endogenous DLC1 and ER interaction. Cell lysates from Ishikawa cells was immunoprecipitated (IP) with anti-ERá mAb and immunoblotted with anti-DLC1 or ER Abs. FIG. 13E: Tam increases DLC1-ER interaction in Tam-resistant cells. Cell lysates from MCF-7/TAM-sen or Ishikawa cells were treated with Tam ($10^{-9}$M) for 24 h, and IP with anti-ERá mAb and immunoblotted with anti-DLC1 or ER Abs. FIG. 13F: DLC1 deregulation increases DLC1-ER interaction. MCF-7/DLC1 cells were treated with or without Dox for 24 h and then treated with E2 ($10^{-9}$M) or Tam ($10^{-8}$M) for 24 h, and IP with anti-ERá mAb and immunoblotted with anti-DLC1 or ER Abs. FIG. 13G: Characterization of MCF-7 cells expressing T7-DLC1-Ser88A mutant under a tetracycline-inducible promoter. Time and dose-dependent Dox-mediated upregulation of T7-DLC1-Ser88A expression. FIG. 13H: Deregulation of DLC1 but not DLC1-Ser88A increases DLC1-ER interaction. MCF-7/DLC1 and MCF-7/DLC1-Ser88A cells were treated with or without Dox for 24 h and cell lysates were IP with anti-ERá mAb and blotted with anti-DLC1, ERá and T7 Abs.

FIG. 14A: Characterization of MCF-7 cells expressing T7-DLC1 under a tet-inducible promoter. Time and dose dependent upregulation of Dox-mediated T7-DLC1 expression. FIG. 14B: DLC1 deregulation potentiates stimulation of Bcl-2 by E2 and by Tam. MCF-7/DLC1 cells were treated with or without Dox (1 µg/ml) for 24 h and treated with E2 or Tam for 24 h and cell lysates were immunoblotted with the indicated antibodies. FIG. 14C: DLC1 upregulation suppress Tam ability to inhibit E2-mediated ER transactivation. MCF-7/DLC1 cells were transfected with ERE-luc. After 24 h, the cells were treated with or without Dox for 24 h and then treated with E2 ($10^{-9}$M) or Tam ($10^{-8}$M), and ERE-luc activity was measured after 24 h. FIG. 14D: DLC1 deregulation potentiated E2-mediated stimulation of ERE-luc activity in Ishikawa and MCF-7/TAMR1 cells. Ishikawa and MCF-7/TAMR1 cells were transfected with ERE-luc and then treated with E2 ($10^{-9}$M) for 24 h and luc activity was measured. FIG. 14E: Recruitment of DLC1 and ERá to the pS2 promoter chromatin. MCF-7/DLC1 cells were treated with or without Dox for 24 and then with E2 ($10^{-9}$M) for 1 h. Chromatin lysates were immunoprecipitated with anti-ER-á or anti-T7 (to detect T7-DLC1) antibodies. Upper panels show the PCR analysis of 304 bp pS2 promoter fragment associated with ER or T7-DLC1. The lower panel shows the PCR analysis of the input DNA.

FIG. 17A: Effect of Pak1 phosphorylation on the binding of DLC1 with BimL. GST-DLC1 was phosphorylated with Pak1 enzyme, and GST pull down assay was performed using phosphorylated GST-DLC1 or wild type GST-DLC1. Autoradiogram showing the phosphorylation of DLC1 is shown in the right panel. FIG. 17B: Ability of DLC1-Ser88A or DLC1-Ser88E mutants to interact with BimL in GST-pull down assay. FIG. 17C: Ability of GST-DLC1-(aa 1-87) to interact with BimL was analyzed by GST pull down assay. FIG. 17D: Ability of Pak1 to interact with DLC1-BimL dimers 35S-labeled DLC1 and BimL were incubated with GST-Pak1 and GST pull down assay was performed. FIG. 17E: MCF-7 cells were labeled with $^{32}$P-orthophosphoric acid and cells were treated with UV or pretreated with EGF (100 ng/ml) followed by UV treatment. Cell lysates were immunoprecipitated with antibodies against DLC1 or BimL, and the phosphorylation status of proteins was analyzed by autoradiography. FIG. 17F: Phosphorylation of GST-BimL by Pak1 in in vitro kinase assay. FIG. 17G: GST-BimL was incubated with purified beads bound GST-DLC1 along with or with GST-dynein intermediate chain. After 60 min of incubation, dimeric and trimeric complexes were purified by GST-DLC1 pull down and used as a substrate in vitro Pak1 kinase assay. FIG. 17H: Downregulation of BimL levels by constitutively active Pak1. MCF-7 cells expressing T423E-Pak1 under the control of Tet-regulated promoter were treated with doxycycline for 12 or 24 h. Expression of BimL, cyclin D1, and HA-tagged T423E Pak1 was analyzed by western blotting. FIG. 17I: Model for Pak1 regulation of DLC1 and BimL functions. Under physiological conditions, DLC1 sequesters BimL to the microtubules. Under apoptotic conditions, DLC1-BimL dimers are released and interact with Bcl-2. Survival factors activate Pak1, which in-turn phosphorylates DLC1-BimL dimers and, thus, prevents BimL interaction with Bcl-2.

FIG. 18A: MCF-7 cells were transfected with DLC-specific or control siRNA. After 48 hours, total cellular lysate was analyzed by western blotting using DLC1 antibody. Actin was used as a loading control. FIG. 18B: MCF-7 cells were transfected with control or DLC specific siRNA. After 72 h, cells were trypsinized and counted using a coulter counter. FIG. 18C: MCF-7 cells were serum starved and transfected with DLC siRNA and treated with or without EGF (100 ng/ml). After 72 hours, cells were trypsinized and counted using coulter counter. FIG. 18D: MCF-7 cells were transfected with DLC-specific, Pak1-specific or control siRNA. Cells were serum starved for 24 h and pretreated for 30 min with EGF or with out EGF. Cells were then exposed to UV 100 J/m$^2$. After 12 h, cell morphology was documented using phase contrast microscope (10×).

FIGS. 19A–19C show immunohistochemical analysis and localization of Pak1. Expression pattern of Cyclin D1 in breast tumor arrays is demonstrated in FIGS. 19E–19G. Correlation between Pak1 (FIGS. 19I and 19K) and Cyclin D1 expression (FIGS. 19J and 19L) is provided. In FIGS. 19D and 19H, negative controls are stained with corresponding IgG in place of the primary antibody.

FIG. 20A: Pak1 activation promoted ER-transactivation function. MCF-7 cells were transiently transfected with ERE-luc and wtPak1, and treated with or without tamoxifen (Tam) (10$^{-8}$M) and luc activity was measured after 24 h. FIG. 20B: Conditional expression of Pak1 enhanced E2-responsiveness and tamoxifen resistant. MCF-7/DA-Pak1 cells were transfected with ERE-luc, treated with or without Dox for 24 h and then with or without E2 (10$^{-9}$M) and/or Tam (10$^{-8}$M) for 24 h, and ERE-luc activity was measured. FIG. 20C: Characterization of MCF-7/TAM-Sen and MCF-7/TAMR1 cells. MCF-7/TAM-Sen and MCF-7/TAMR1 cells were treated with or without Tam (10$^{-8}$M) for 72 h, and the cell number was determined. FIG. 20D: MCF-7/TAM-Sen and MCF-7/TAMR1 cells were transfected with ERE-luc and treated with E2 or Tam for 24 h and ERE-luc activity was measured. FIG. 20E: Upregulation of Pak1 protein in MCF-7/TAMR1 cells. Cell lysates from exponentially growing cells were immunoblotted with anti-Pak1 antibody. FIG. 20F: Upregulation of Pak1 activity in MCF-7/TAMR1 cells. Cell lysates from exponentially growing cells were assayed for Pak1 activity. FIG. 20G: Tam potentiated Pak1 regulation of ER-transactivation in Ishikawa cell line. FIG. 20H: Tamoxifen potentiated activated Cdc42 mediated ERE-luc activity in Ishikawa cells. FIG. 20I: Upregulation of Pak1 activity in Ishikawa cells by Tam and E2. FIG. 20J: Upregulation of Pak1 expression and activity in Ishikawa cells by Tam. FIG. 20K: Tam enhanced Pak1-ER interaction in Tam-resistant cells. Cells were treated with or without Tam (10$^{-8}$M) for 24 h and immunoprecipitated with anti-Pak1 Ab and immunoblotted with ERα or Pak1 Abs. FIG. 20L: Ishikawa cells were cotransfected with Pak1 siRNA control or Pak1 siRNA wt and treated with or without Tam (10$^{-8}$M) for 24 h and ERE-luc activity was measured.

FIG. 21A: DLC1 upregulation by E2 or Tam. MCF-7/Tam-sen, MCF-7/TAMR1 and Ishikawa cells were treated with E2 (10$^{-9}$M) or Tam (10$^{-9}$M) for 24 h, and cell lysates were assayed for DLC1 and Pak1 protein expression. FIG. 21B: Upregulation of DLC1 mRNA in MCF-7 cells treated with different doses of E2 for 24 h. FIG. 21C: Effect of different periods of E2 treatment and cycloheximide (CHX) and Actinomycin D (ACTD) treatment on the ability of E2 to upregulate DLC1 mRNA in MCF-7 cells. FIG. 21D: DLC1 mRNA and protein levels in MCF-7/DA-Pak1 cells by Northern and Western blotting. FIG. 21E: DLC1 mRNA and protein levels in MCF-7/DN-Pak1 cells by Northern and Western blotting. FIG. 21F: Downregulation of DLC1 protein expression in MCF-7 cells treated with Pak1-siRNA for 24 h. FIG. 21G: Modulation of DLC1 promoter (1245 bp) luc activity by the expression of wtPak1 or DN-Pak1. MCF-7 cells were transfected with DLC1-luc and transfected with either wtPak1 or Pak1 inhibitor 83-149 and luc activity was measured after 24 h. FIG. 21H: Upregulation of DLC1 promoter luc activity following pak1 induction in MCF-7/DA-Pak 1 cells. FIG. 21I: Downegulation of DLC1 promoter luc activity in MCF-7/DN-pak1 cells. FIG. 21J: Upregulation of DLC1 promoter activity in Ishikawa cells treated with different concentrations of E2 (10$^{-8}$ and 10$^{-9}$M or Tam (10$^{-8}$ and 10$^{-9}$M) for 24 h.

FIG. 22A: DLC1 upregulation potentiates growth stimulation by E2 in a Tam-insensitive manner. MCF-7/DLC1 cells were treated with or without Dox and then with E2 (10$^{-9}$M) or Tam (10$^{-8}$M) for 5 days, and the cell number was determined. FIG. 22B: DLC1 upregulation promotes anchorage independence. MCF-7/DLC1 cells were plated in soft-agar, treated with or without Dox for 24 h and then with E2 (10$^{-9}$M) or Tam (10$^{-8}$M) for 21 days, and the colonies were counted. FIG. 22C: DLC1 expression supports optimum growth of Tam-resistant cells. Ishikawa and MCF-7/TAMR1 cells were transfected with control or DLC siRNA for 48 h and then treated with or without Tam (10$^{-8}$M) for 96 h, and the cell number was determined. FIG. 22D: DLC1-mediated potentiation of ER transactivation depends on the Pak1 status in Ishikawa and MCF-7/TAMR1 cell lines. Ishikawa and MCF-7/TAMR1 cells were transfected with control or Pak1 siRNA for 48 h and then with ERE-luc for 24 h and treated with E2 ($10^{-9}$M) for 24 h and ERE-luc activity was measured. FIG. 22E: Pak1 expression level influences the growth of Tam resistant cells. Ishikawa and MCF-7/TAMR1 cells were treated with control or Pak1 siRNA for 48 h and treated with or without Tam ($10^{-8}$M) for 4 days, and cell number was determined. FIG. 22F: Co-downregulation of Pak1 and DLC1 in Tam-resistant cells restores Tam-sensitivity. Ishikawa cells were treated with control or and Pak1 and DLC siRNA for 48 h and then transfected with ERE-luc and treated with Tam ($10^{-8}$M) for 24 h and ERE-luc activity was measured.

DESCRIPTION OF ILLUSTRATIVE EMBODIMENTS

Figure 1:
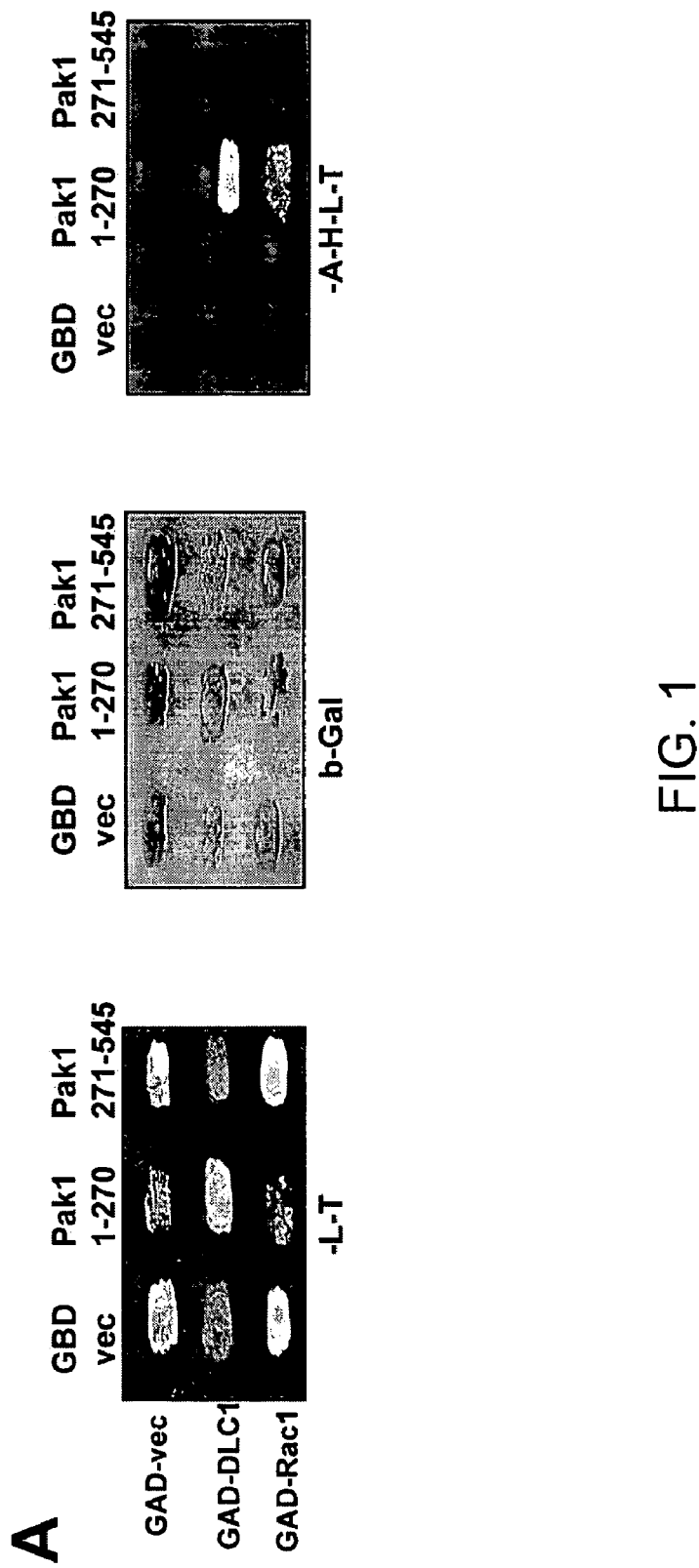
FIGS. 1A–1E.—Identification of DLC1/PIN as a Pak1-binding protein.
Figure 1:
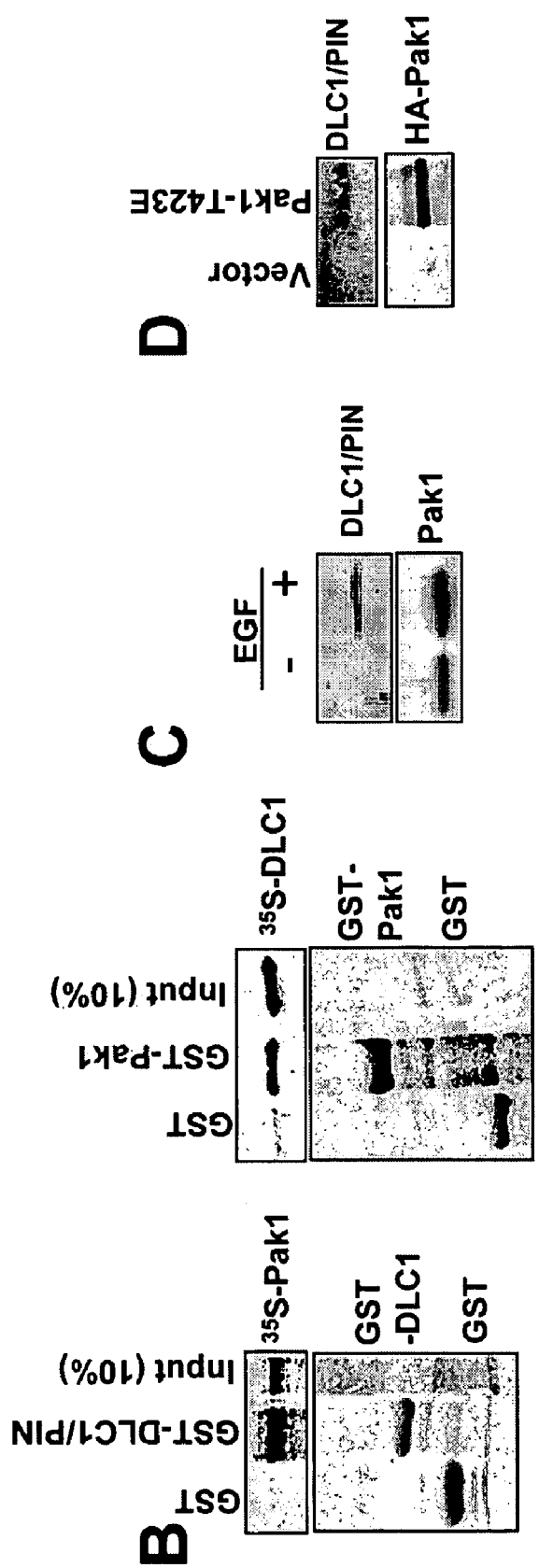
Figure 1:
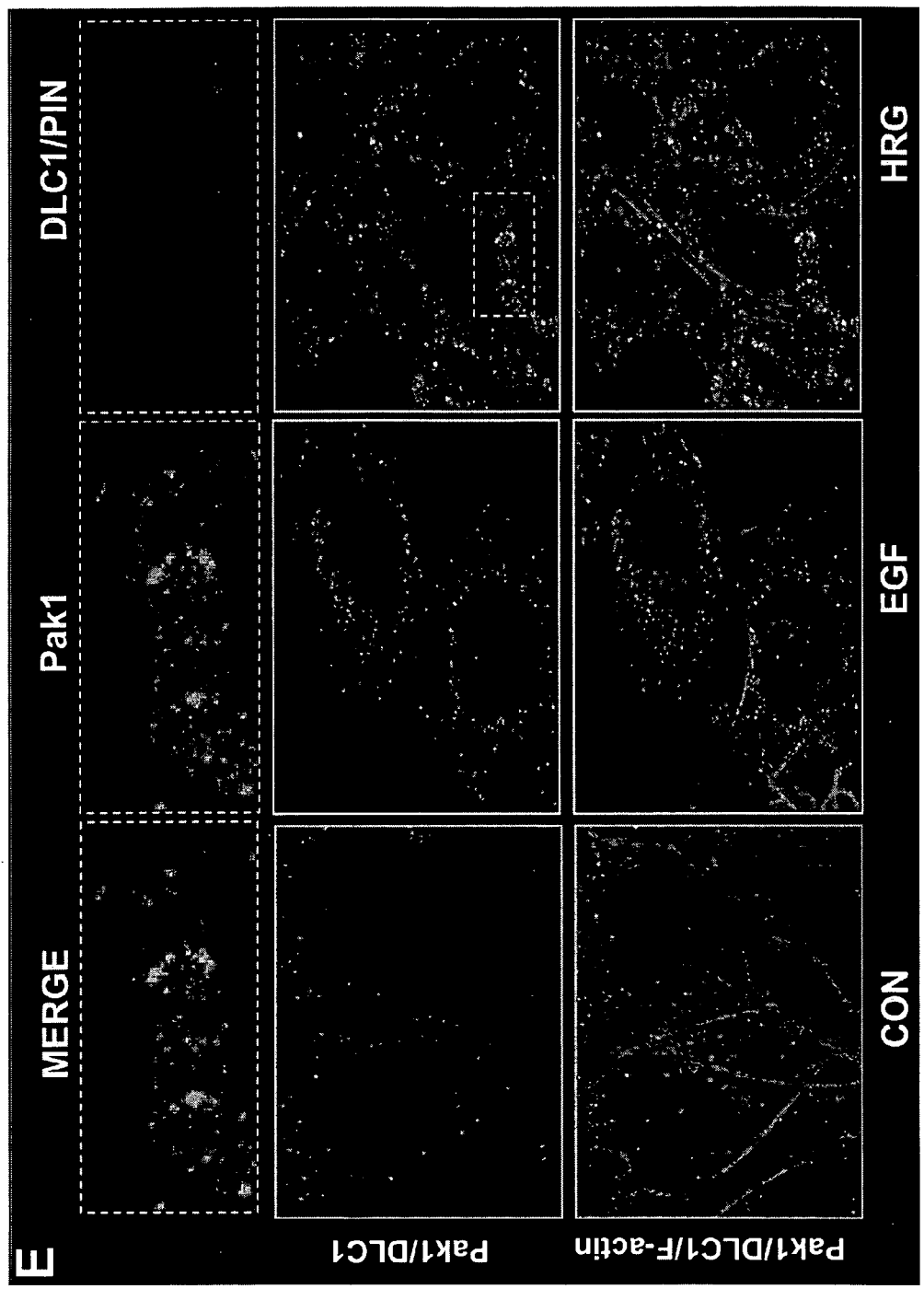

Cytoskeleton remodeling-dependent cellular processes, such as macropinocytosis and vesicle transport and cell survival, are influenced by evolutionarily conserved DLC1/PIN, a component of microtubule-associated dynein motor complex. DLC1/PIN was initially identified as a subunit of dynein. Dyneins are molecular motors that provide the driving force for microtubule-based retrograde transport (Holzbaur and Vallee, 1994; Hirokawa, 1998). Later studies showed that DLC1/PIN is also a subunit of the ubiquitously expressed family of actin-based molecular motors Myosin V (Espindola et al., 2000), suggesting that actin-based and microtubule-based motors share a common subunit, DLC1/PIN.

DLC1/PIN is ubiquitously expressed in different cell types and highly conserved throughout the evolution. DLC1/PIN not only is associated with myosin V and dynein motors, but also binds to neuronal nitric-oxide synthase (Jaffrey and Snyder, 1996; Fan et al., 1998), proapoptotic Bcl-2 family protein Bim (Puthalakath et al., 1999), *Drosophila* mRNA localization protein Swallow (Schnorrer et al., 2000), transcriptional regulator IkB (Crepieux et al., 1997) and postsynaptic scaffold protein GKAP (Naisbitt et al., 2000), suggesting that DLC1/PIN is a multifunctional regulatory protein. Structural studies show that DLC1/PIN exists as a dimer and contains two identical target-binding grooves on the opposite faces of the protein dimer interface (Fan et al., 2001). It has been suggested that DLC1/PIN may function as a linker protein by binding two different proteins (Liang et al., 1999).

Paks are implicated in both actin-mediated and microtubule-dependent changes in the cytoskeleton, changes induced by the ability of Pak1 to phosphorylate myosin light chain kinase, LIMK, and Stathmin (Kumar and Vadlamudi, 2002). Paks are activated by a number of signals that promote cell survival. Pak1 is involved in the cell survival pathway by phosphorylating and inactivating the proapoptotic functions of Bad (Schurmann et al., 2000). Overexpression of a constitutively active T423E Pak1 mutant promotes the survival of NIH 3T3 murine fibroblasts. Similarly, *Drosophila* DLC1/PIN plays a role in the inhibition of apoptosis (Dick et al., 1996). DLC1/PIN interacts with Bim and promotes cell survival by inhibiting its proapoptotic activity (Puthalakath et al., 1999). In addition, cyclooxygenase 2 promotes cell survival by stimulating DLC1/PIN expression and inhibiting the neuronal nitric oxide pathway (Chang et al., 2000).

Using a yeast two-hybrid screen, the inventors have identified DLC1/PIN as a Pak1-binding protein and showed that DLC1/PIN is a physiological interacting substrate of Pak1, and both proteins colocalized in pinocytic vesicles upon growth factor stimulation of human cells. DLC1/PIN interacted with Pak1 via its C-terminal region amino acids 132–270 while the Pak1 binding site in DLC1/PIN was localized within the C-terminal 19 amino acids. The Pak1-DLC1/PIN interactions played an essential role for the macropinocytosis, directional motility and cell-survival functions of both Pak1 and DLC1/PIN, and these phenotypic changes were dependent on Pak1's phosphorylation of DLC1/PIN on Ser88. Deregulation of DLC1/PIN alone but not its serine 88 to alanine mutant promoted anchorage-independence and the tumorigenic potential of breast cancer cells. Furthermore, DLC1/PIN expression was elevated in 14 out of 15 of human breast tumors specimens examined.

The regulation of pinocytosis-linked motility and cell survival functions by Pak1-DLC1/PIN interaction represents a novel mechanism by which a signaling kinase might regulate these fundamental processes in cells. In addition, DLC1/PIN deregulation might contribute towards malignant phenotypes in cancer. The present invention seeks to exploit the inventors' discovery by modulating the interaction of DLC1/PIN and Pak1 in various therapeutic contexts. For instance, inhibiting the ability of a cell to undergo macropinocytosis can be used in the treatment of cancer and viral disease. In addition, screening for agents that promote or inhibit the binding of DLC1/PIN to Pak1 may prove useful in the therapy of diseases associated with macropinocytosis, such as cancer. These agents can also be used to reduce cancer invasiveness and to modulate immune function. These and other embodiments are discussed in detail below.

A. DLC1/PIN

In certain embodiments, the present invention concerns methods utilizing a DLC1/PIN polypeptide as described herein. Other terms used in the scientific literature to refer to DLC1/PIN and which are synonymous with DLC1/PIN include dynein light chain 1 (DLC1) and protein inhibitor of nitric acid synthase (DLC1/PIN). However, throughout this application the term DLC1/PIN will be used.

The complete mRNA sequence of DLC1/PIN is identified in Genbank accession number U32944 (herein identified as SEQ ID NO:1). DLC1/PIN encodes an 8-kDa component of the cytoplasmic dynein complex which is a minus end-directed microtubule-based motor that transports cargo along microtubules (Hirokawa, 1998; Vallee and Sheetz, 1996; Pazour et al., 1996). The complete amino acid sequence of DLC1/PIN is identified in Genbank accession number AAB04149 (herein identified as SEQ ID NO:2).

Other embodiments of the present invention pertain to methods utilizing mutants of DLC1/PIN. "Mutant DLC1/PIN" refers to a change in the sequence of a nucleic acid or its encoded protein, polypeptide or peptide that is the result of the hand of man. SEQ ID NO:3 is the amino acid sequence of a DLC1/PIN mutant that lacks the C-terminal 19 amino acids of DLC1/PIN. SEQ ID NO:4 is the amino acid sequence of a DLC1/PIN mutant that lacks serine 88. SEQ ID NO:5 pertains to the amino acid sequence of the C-terminal 19 amino acids of DLC1/PIN. SEQ ID NO:6 pertains to a modified version of SEQ ID NO:5 designed to facilitate its entry into cells. SEQ ID NO:11 is the amino acid sequence of a DLC1/PIN mutant that lacks the C-terminal 23 amino acids of DLC1/PIN polypeptide. In a particular embodiment, the SEQ ID NO:11 mutant consists essentially of amino acids 1–66 of the DLC1/PIN polypeptide.

1. DLC1/PIN Polypeptides

The present invention may utilize DLC1/PIN protein purified from a natural source or from recombinantly-produced material. This material may use the 20 common amino acids in naturally synthesized proteins, or one or more modified or unusual amino acids.

In certain embodiments, the DLC1/PIN protein may be purified. Generally, "purified" will refer to a DLC1/PIN composition that has been subjected to fractionation to remove various other proteins, polypeptides, or peptides, and which composition substantially retains its activity. Purification may be substantial, in which the DLC1/PIN polypeptide is the predominant species, or to homogeneity, which purification level would permit accurate degradative sequencing.

Throughout this application, the term "DLC1/PIN" is intended to refer to the exemplified DLC1/PIN molecules as well as all DLC1/PIN homologues from other species. "Wild-type" and "mutant" DLC1/PIN refer, respectively, to a DLC1/PIN gene expressing normal DLC1/PIN activity and to a DLC1/PIN gene lacking or having reduced DLC1/PIN activity. Thus, "mutant" DLC1/PIN are not merely sequence variants but rather, are those variants showing altered functional profiles.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity, i.e., ability of DLC1/PIN to bind to Pak1. Biologically functional equivalent polypeptides are thus defined herein as those polypeptides in which certain, not most or all, of the amino acids may be substituted. Of course, a plurality of distinct proteins/polypeptides/peptides with different substitutions may easily be made and used in accordance with the invention.

Amino acid sequence variants of DLC1/PIN also are encompassed by the present invention. Amino acid sequence variants of the polypeptide can be substitutional mutants or insertional mutants. Insertional mutants typically involve the addition of material at a non-terminal point in the peptide. This may include the insertion of a few residues; an immunoreactive epitope; or simply a single residue. The added material may be modified, such as by methylation, acetylation, and the like. Alternatively, additional residues may be added to the N-terminal or C-terminal ends of the peptide.

Amino acid substitutions are generally based on the relative similarity of the amino acid side-chain substituents, or example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

2. DLC1/PIN-Encoding Polynucleotides

The polynucleotides according to the present invention may encode an entire DLC1/PIN sequence (for example, the amino acid sequence of SEQ ID NO:2), a functional DLC1/PIN protein domain, or any DLC1/PIN polypeptide. The polynucleotides may be derived from genomic DNA, i.e., cloned directly from the genome of a particular organism. In other embodiments, however, the polynucleotides may be complementary DNA (cDNA). cDNA is DNA prepared using messenger RNA (mRNA) as a template. Thus, a cDNA does not contain any interrupted coding sequences and usually contains almost exclusively the coding region(s) for the corresponding protein. In other embodiments, the polynucleotide may be produced synthetically.

It may be advantageous to combine portions of the genomic DNA with cDNA or synthetic sequences to generate specific constructs. For example, where an intron is desired in the ultimate construct, a genomic clone will need to be used. Introns may be derived from other genes in addition to DLC1/PIN. The cDNA or a synthesized polynucleotide may provide more convenient restriction sites for the remaining portion of the construct and, therefore, would be used for the rest of the sequence.

The present invention is not limited to human DLC1/PIN, but includes use of any naturally-occurring variants. The present invention also encompasses chemically synthesized mutants of these sequences.

Another kind of sequence variant results from codon variation. Because there are several codons for most of the 20 normal amino acids, many different DNAs can encode the DLC1/PIN. Reference to the following table will allow such variants to be identified.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAG AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Allowing for the degeneracy of the genetic code, sequences that have between about 50% and about 75%, or between about 76% and about 99% of nucleotides that are identical to the nucleotides disclosed herein will be preferred. Sequences that are within the scope of "a polynucleotide encoding a DLC1/PIN polypeptide" or "a polynucleotide encoding a mutant DLC1/PIN polypeptide" are those that are capable of base-pairing with a polynucleotide segment set forth above under intracellular conditions.

As stated above, the DLC1/PIN encoding sequences may be full length genomic or cDNA copies, or large fragments thereof. The present invention also may employ shorter oligonucleotides of DLC1/PIN. Sequences of 17 bases long should occur only once in the human genome and, therefore, suffice to specify a unique target sequence. Although shorter oligomers are easier to make and increase in vivo accessibility, numerous other factors are involved in determining the specificity of base-pairing. Both binding affinity and sequence specificity of an oligonucleotide to its complementary target increases with increasing length. It is contemplated that oligonucleotides of 8, 9, 10, 11, 12, 13, 14, 15, 16, 17, 18, 19 or 20 base pairs will be used, for example, in the preparation of DLC1/PIN mutants and in PCR reactions.

Any sequence of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length.

In certain embodiments, one may wish to employ constructs which include other elements, for example, those which include C-5 propyne pyrimidines. Oligonucleotides which contain C-5 propyne analogues of uridine and cytidine have been shown to bind RNA with high affinity (Wagner et al., 1993).

B. Pak1

In certain embodiments, the present invention concerns methods utilizing a Pak1 polypeptide as described herein. Pak1 is a member of the Pak family of p21-activated kinases. The complete mRNA sequence of human Pak1, herein incorporated by reference, is shown in Genbank accession number U24152 (herein further identified as SEQ ID NO:7). The amino acid sequence of human Pak1 is the amino acid sequence shown in Genbank accession number AAA65441 (herein further identified as SEQ ID NO:8). Paks are an evolutionarily-conserved family of serine-threonine kinases which are important for a variety of cellular functions including cell morphogenesis, cell motility, cell survival, angiogenesis and mitosis (Kumar and Vadlamudi, 2002; Jaffer and Chernoff, 2002). Recently, Pak1 was shown to localize to the areas of pinocytotic vesicles and to contribute to the process of macropinocytosis (Dharmawardhane et al., 2000; West et al., 2000).

1. Pak1 Polypeptides

The present invention may utilize Pak1 protein purified from a natural source or from recombinantly-produced material. This material may use the 20 common amino acids in naturally synthesized proteins, or one or more modified or unusual amino acids, including but not limited to those shown on Table 1 shown above.

In certain embodiments, the Pak1 protein may be purified. Generally, "purified" will refer to a Pak1 composition that has been subjected to fractionation to remove various other proteins, polypeptides, or peptides, and which composition substantially retains its activity. Purification may be substantial, in which the DLC1/PIN polypeptide is the predominant species, or to homogeneity, which purification level would permit accurate degradative sequencing.

Throughout this application, the term "Pak1" is intended to refer to the exemplified Pak1 molecule (i.e., the amino acid sequence of SEQ ID NO:8) as well as all Pak1 homologues from other species. "Wild-type" and "mutant" Pak1 refer, respectively, to a Pak1 gene expressing normal Pak1 activity and to a Pak1 gene lacking or having reduced Pak1 activity. Thus "mutant" Pak1 are not merely sequence variants but rather, are those variants showing altered functional profiles.

It is also well understood by the skilled artisan that, inherent in the definition of a biologically functional equivalent protein, peptide, or polypeptide is the concept that there is a limit to the number of changes that may be made within a defined portion of the molecule and still result in a molecule with an acceptable level of equivalent biological activity, i.e., ability of Pak1 to bind to DLC1/PIN. Biologically functional equivalent polypeptides are thus defined herein as those polypeptides in which certain, not most or all, of the amino acids may be substituted. Of course, a plurality of distinct proteins/polypeptides/peptides with different substitutions may easily be made and used in accordance with the invention.

Amino acid sequence variants of Pak1 also are encompassed by the present invention. Amino acid sequence mutants of the polypeptide can be substitutional mutants or insertional mutants. Insertional mutants typically involve the addition of material at a non-terminal point in the peptide. This may include the insertion of a few residues; an immunoreactive epitope; or simply a single residue. The added material may be modified, such as by methylation, acetylation, and the like. Alternatively, additional residues may be added to the N-terminal or C-terminal ends of the peptide.

Amino acid substitutions are generally based on the relative similarity of the amino acid side-chain substituents, or example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

C. Screening Methods

The present invention includes embodiments that provide for methods of screening for modulators of macropinocytosis. These assays may comprise random screening of large libraries of candidate substances; alternatively, the assays may be used to focus on particular classes of compounds selected with an eye towards structural attributes that are believed to make them more likely to modulate the function of this molecule. By function, it is meant that one may assay for affects on macropinocytosis. For example, a stimulated cell can be analyzed for its ability to undergo macropinocytosis following contact of the cell with a candidate substance using techniques such as confocal scanning microscopy and immunohistochemistry.

A modulator of macropinocytosis is any substance that can inhibit or promote macropinocytosis. The method of screening modulators of macropinocytosis generally comprises:

(a) obtaining a candidate substance suspected of modulating macropinocytosis;

(b) contacting the candidate substance with Pak1 and DLC1/PIN; and (c) detecting inhibition or promotion of binding between Pak1 and DLC1/PIN.

The candidate substance can be a candidate substance suspected of either inhibiting or promoting macropinocytosis. For example, candidate substance suspected of inhibiting macropinocytosis can be a substance that is capable of inhibiting the phosphorylation of DLC1/PIN by Pak1. Examples of other candidate substances include DLC1/PIN polypeptides and mutant DLC1/PIN polypeptides.

It will, of course, be understood that all the screening methods of the present invention are useful in themselves notwithstanding the fact that effective candidates may not be found. The invention provides methods for screening for such candidates, not solely methods of finding them.

1. Modulators

As used herein the term "candidate substance" refers to any molecule that may potentially inhibit or enhance macropinocytosis. The candidate substance may be a protein or fragment thereof, a small molecule, an antibody, or even a polynucleotide. It may prove to be the case that the most useful pharmacological compounds will be compounds that are structurally related to DLC1/PIN or Pak1, i.e., mimics. Using lead compounds to help develop improved compounds is known as "rational drug design" and includes not only comparisons with known inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single-chain antibodies or expression constructs coding thereof), each of which would be specific for a given target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An modulator (i.e., inhibitor or activator) according to the present invention may be one which exerts its inhibitory or activating effect upstream, downstream or directly on the binding of DLC1/PIN and Pak1. Regardless of the type of inhibitor or activator identified by the present screening methods, the effect of the inhibition or activator by such a compound results in an alteration binding between DLC1/PIN and Pak1 as compared to that observed in the absence of the added candidate substance.

In specific embodiments, the candidate substance is a DLC1/PIN peptide or polypeptide, a DLC1 peptide or polypeptide, including mutants described herein, or an agent identified by, for example, direct binding assays, such as two-hybrid assays described herein.

2. In Vitro Assays

A quick, inexpensive and easy assay to run is an in vitro assay. Such assays can be run quickly and in large numbers, thereby increasing the amount of information obtainable in a short period of time. A variety of vessels may be used to run the assays, including test tubes, plates, dishes and other surfaces such as dipsticks or beads. One example of a cell free assay is a binding assay. While not directly addressing function, the ability of a modulator to modulate the binding of DLC1/PIN and Pak1 is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic DLC1/PINs or some other surface. Bound polypeptide is detected by various methods.

Another example of an in vitro assay is an assay to measure the phosphorylation of DLC1/PIN by Pak1. A description of this assay is presented below in the examples. One of skill in the art would understand that there may be other types of in vitro assays that may be beneficial in measuring the binding of Pak1 to DLC1/PIN.

3. In cyto Assays

In certain embodiments of the present invention, there are provided methods of screening for modulators of macropinocytosis wherein the candidate substance is contacted with a cell. The cell can then be assayed for various parameters associated with binding of Pak1 and DLC1/PIN. For instance, the cells can be directly assayed for binding between DLC1/PIN and Pak1. Immunohistochemical techniques, confocal techniques, or other techniques to assess binding are well known to those of skill in the art. In other embodiments, the cell is assayed for phosphorylation of DLC1/PIN by Pak1. In still other embodiments, the cell is assayed for macropinocytosis or functions associated with macropinocytosis such as cell motility or growth. Various cell lines can be utilized for such screening assays, including cells specifically engineered for this purpose. Examples of cells used in the screening assays include cancer cells, cells infected with a virus, foam cells, macrophages, neuronal cells or dendritic cells. The cell may be a stimulated cell, such as a cell stimulated with a growth factor. One of skill in the art would understand that the invention disclosed herein contemplates a wide variety of in cyto assays for measuring parameters that correlate with the binding of Pak1 to DLC1/PIN.

Depending on the assay, culture may be required. The cell may be examined using any of a number of different physiologic assays, as discussed above for binding between DLC1/PIN and Pak1. Alternatively, molecular analysis may be performed, for example, looking at protein expression, mRNA expression (including differential display of whole cell or polyA RNA) and others.

4. In vivo Assays

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to the functions associated with macropinocytosis (e.g., cell growth and survival, invasiveness of a cancer cell), or instead a broader indication such as immune response.

The present invention provides methods of screening for a candidate substance that can modulate macropinocytosis in cells. Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal. inhalation or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

D. Nucleic Acid Compositions

Certain embodiments of the present invention pertain to nucleic acid compositions. For instance, certain embodiments provide for methods of screening for modulators of macropinocytosis comprising (a) obtaining a candidate substance suspected of modulating macropinocytosis; (b) contacting the candidate substance with Pak1 1 and DLC1/PIN; and (c) detecting inhibition or promotion of binding between Pak1 and DLC1/PIN. In some embodiments of the invention, the candidate substance is a polynucleotide. In other embodiments, the candidate substance is contacted with a cell. When contacted with a cell, the candidate substance in some embodiments is a composition comprising an expression cassette comprising a promoter, active in the cell, operably linked to a polynucleotide encoding a polypeptide. In certain embodiments, the polynucleotide comprises a polynucleotide that hybridizes to a DLC1/PIN-encoding polynucleotide or a Pak1-encoding polynucleotide. Other embodiments involve use of these polynucleotides and expression cassettes in methods to modulate macropinocytosis in a target cell population, methods of reducing cell proliferation in a target cell population, methods of inhibiting the growth and survival of a cancer cell, methods of inhibiting the invasiveness of a cancer cell, methods of treating a viral infection in a human subject, and methods of treating Alzheimer disease.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 50 nucleobases in length. The term "polynucleotide" refers to at least one molecule of greater than about 50 nucleobases in length.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss," a double stranded nucleic acid by the prefix "ds," and a triple stranded nucleic acid by the prefix "ts."

1. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moiety. Preferred alkyl (e.g., alkyl, caboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like.

A nucleobase may be comprised in a nucleoside or nucleotide, using any chemical or natural synthesis method described herein or known to one of ordinary skill in the art.

2. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

3. Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

4. Nucleic Acid Analogs

A nucleic acid such as a polynucleotide may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as fluorescent nucleic acids probes; U.S. Pat. No. 5,614,617 which describes oligonucleotide analogs with substitutions on pyrimidine rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446,137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' internucleotide linkages and ribonucleotides with 2'-5' internucleotide linkages; U.S. Pat. No. 5,714,606 which describes a modified internucleotide linkage wherein a 3'-position oxygen of the internucleotide linkage is replaced by a carbon to enhance the nuclease resistance of nucleic acids; U.S. Pat. No. 5,672,697 which describes oligonucleotides containing one or more 5' methylene phosphonate internucleotide linkages that enhance nuclease resistance; U.S. Pat. Nos. 5,466,786 and 5,792,847 which describe the linkage of a substituent moiety which may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967 which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240 which describe oligonucleotides with three or four atom linker moiety replacing phosphodiester backbone moiety used for improved nuclease resistance, cellular uptake and regulating RNA expression; U.S. Pat. No. 5,858,988 which describes hydrophobic carrier agent attached to the 2'-O position of oligonucleotides to enhanced their membrane permeability and stability; U.S. Pat. No. 5,214,136 which describes oligonucleotides conjugated to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154 which describes RNA linked to a DNA to form a DNA-RNA hybrid.

In a non-limiting example, one or more nucleic acid analogs may be prepared containing about 3, about 5, about 8, about 10 to about 14, or about 15, about 20, about 30, about 40, about 50, about 100, about 200, about 500, about 1,000, about 2,000, about 3,000, about 5,000, about 10,000, about 15,000, about 20,000, about 30,000, about 50,000, about 100,000, about 250,000, about 500,000, about 750,000, to about 1,000,000 nucleotides in length, as well as constructs of greater size, up to and including chromosomal sizes (including all intermediate lengths and intermediate ranges).

5. Polyether and Peptide Nucleic Acids

In certain embodiments, it is contemplated that a nucleic acid comprising a derivative or analog of a nucleoside or nucleotide may be used in the methods and compositions of the invention. For instance, such a derivative can be a candidate substance suspected of modulating the binding of DLC1/PIN to Pak1. A non-limiting example is a "polyether nucleic acid", described in U.S. Pat. No. 5,908,845, incorporated herein by reference. In a polyether nucleic acid, one or more nucleobases are linked to chiral carbon atoms in a polyether backbone.

Another non-limiting example is a "peptide nucleic acid", also known as a "PNA", "peptide-based nucleic acid analog" or "PENAM", described in U.S. Pat. Nos. 5,786,461, 5891,625, 5,773,571, 5,766,855, 5,736,336, 5,719,262, 5,714,331, 5,539,082, and WO 92/20702, each of which is incorporated herein by reference. Peptide nucleic acids generally have enhanced sequence specificity, binding properties, and resistance to enzymatic degradation in comparison to molecules such as DNA and RNA (Egholm et al., 1993; PCT/EP/01219). A peptide nucleic acid generally comprises one or more nucleotides or nucleosides that comprise a nucleobase moiety, a nucleobase linker moiety that is not a 5-carbon sugar, and/or a backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

In certain embodiments, a nucleic acid analogue such as a peptide nucleic acid may be used to inhibit nucleic acid amplification, such as in PCR, to reduce false positives and discriminate between single base mutants, as described in U.S. Pat. No. 5,891,625. Other modifications and uses of nucleic acid analogs are known in the art, and are encompassed by the nucleic acids encoding for DLC1/PIN or Pak1. In a non-limiting example, U.S. Pat. No. 5,786,461 describes PNAs with amino acid side chains attached to the PNA backbone to enhance solubility of the molecule. In another example, the cellular uptake property of PNAs is increased by attachment of a lipophilic group. U.S. application Ser. No. 117,363 describes several alkylamino moieties used to enhance cellular uptake of a PNA. Another example is described in U.S. Pat. Nos. 5,766,855, 5,719,262, 5,714,331 and 5,736,336, which describe PNAs comprising naturally and non-naturally occurring nucleobases and alkylamine side chains that provide improvements in sequence specificity, solubility and/or binding affinity relative to a naturally occurring nucleic acid.

6. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

7. Purification of Nucleic Acids

A nucleic acid may be purified on polyacrylamide gels, cesium chloride centrifugation gradients, or by any other means known to one of ordinary skill in the art (see for example, Sambrook et al., 2001, incorporated herein by reference).

In certain aspect, the present invention concerns a nucleic acid that is an isolated nucleic acid, such as a candidate substance that is a polynucleotide As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

8. Nucleic Acid Complements

In particular embodiments the invention encompasses a nucleic acid or a nucleic acid segment complementary to all or a portion of the sequence of DLC1/PIN or Pak1. Modulators of the binding between DLC1/PIN and Pak1 include molecules that directly affect RNA transcripts encoding DLC1/PIN or Pak1 polypeptides. Antisense molecules target a particular sequence to achieve a reduction or elimination of a particular polypeptide, such as DLC1/PIN polypeptide. Thus, it is contemplated that nucleic acid molecules that are identical or complementary to all or part of the sequence of DLC1/PIN and Pak1 are included as part of the invention.

A nucleic acid is "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule.

As used herein, the term "complementary" or "complement(s)" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

In certain embodiments, a "partly complementary" nucleic acid comprises a sequence that may hybridize in low stringency conditions to a single or double stranded nucleic acid, or contains a sequence in which less than about 70% of the nucleobase sequence is capable of base-pairing with a single or double stranded nucleic acid molecule during hybridization.

9. Hybridization

The present invention also encompasses a polynucleotide or oligonucleotide that is hybridizes to a polynucleotide encoding a DLC1/PIN or Pak1 polypeptide. As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)." As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

As used herein "wild-type" refers to the naturally occurring sequence of a nucleic acid at a genetic locus in the genome of an organism, or a sequence transcribed or translated from such a nucleic acid. Thus, the term "wild-type" also may refer to an amino acid sequence encoded by a nucleic acid. As a genetic locus may have more than one sequence or alleles in a population of individuals, the term "wild-type" encompasses all such naturally occurring allele(s). As used herein the term "polymorphic" means that variation exists (i.e., two or more alleles exist) at a genetic locus in the individuals of a population. As used herein "mutant" refers to a change in the sequence of a nucleic acid or its encoded protein, polypeptide or peptide that is the result of the hand of man. Thus, "mutant DLC1/PIN" refers to a change in the sequence of a nucleic acid or its encoded protein, polypeptide or peptide that is the result of the hand of man.

E. Expression Cassettes

1. Overview

Certain embodiments of the invention pertain to methods utilizing compositions that include an expression cassette. Throughout this application, the term "expression cassette" is meant to include any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a mRNA into a polypeptide.

2. Promoters and Enhancers

In order for the expression cassette to effect expression of a polypeptide, the polynucleotide encoding the polynucleotide will be under the transcriptional control of a promoter. A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

The promoter will be one which is active in the target cell. For instance, where the cell in the specific embodiment is a breast cancer cell, the promoter will be one which has activity in the breast cancer cell.

A promoter may be one naturally associated with a gene or sequence, as may be obtained by isolating the 5'-non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202 and U.S. Pat. No. 5,928,906, each incorporated herein by reference). Furthermore, it is contemplated the control sequences that direct transcription and/or expression of sequences within non-nuclear organelles such as mitochondria, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (2001), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The particular promoter that is employed to control the expression of a polynucleotide is not believed to be critical, so long as it is capable of expressing the polynucleotide in the targeted cell at sufficient levels. Thus, where a human cell is targeted, it is preferable to position the polynucleotide coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high level expression of the polynucleotide. The use of other viral or mammalian cellular or bacterial phage promoters which are well-known in the art to achieve expression of polynucleotides is contemplated as well, provided that the levels of expression are sufficient to produce a growth inhibitory effect.

By employing a promoter with well-known properties, the level and pattern of expression of a polynucleotide following transfection can be optimized. For example, selection of a promoter which is active in specific cells, such as tyrosine (melanoma), alpha-fetoprotein and albumin (liver tumors), CC10 (lung tumors) and prostate-specific antigen (prostate tumor) will permit tissue-specific expression of polynucleotides. Table 2 lists several promoters/elements which may be employed, in the context of the present invention, to regulate the expression of polypeptide. This list is not intended to be exhaustive of all the possible elements but, merely, to be exemplary thereof.

TABLE 2

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α$_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., |

TABLE 2-continued

| Promoter/Enhancer | References |
| --- | --- |
| | 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have very similar modular organization.

Additionally, any promoter/enhancer combination (as per the Eukaryotic Promoter Data Base EPDB) could also be used to drive expression of the polynucleotide. Use of a T3, T7, or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional expression vector.

Further selection of a promoter that is regulated in response to specific physiologic signals can permit inducible expression of the expression cassette. For example, with the polynucleotide under the control of the human PAI-1 promoter, expression is inducible by tumor necrosis factor. Table 3 provides examples of inducible elements, which are regions of a nucleic acid sequence that can be activated in response to a specific stimulus.

TABLE 3

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |

TABLE 3-continued

| Element | Inducer | References |
| --- | --- | --- |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2 κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

3. Markers

In certain embodiments of the invention, the delivery of an expression cassette in a cell may be identified in vitro or in vivo by including a marker in the expression vector. The marker would result in an identifiable change to the transfected cell permitting easy identification of expression. Usually the inclusion of a drug selection marker aids in cloning and in the selection of transformants. Alternatively, enzymes such as herpes simplex virus thymidine kinase (tk) (eukaryotic) or chloramphenical acetyltransferase (CAT) (prokaryotic) may be employed. Immunologic markers can also be employed. The selectable marker employed is not believed to be important, so long as it is capable of being expressed along with the polynucleotide of the expression cassette. Further examples of selectable markers are well known to one of skill in the art.

4. Initiation Signals

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

5. IRES

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819).

6. Multiple Cloning Sites

Expression cassettes can include a multiple cloning site (MCS), which is a nucleic acid region that contains multiple restriction enzyme sites, any of which can be used in conjunction with standard recombinant technology to digest the vector. See Carbonelli et al. (1999); Levenson et al. (1998); Cocea (1997). "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see Chandler et al., 1997).

7. Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

8. Other Expression Cassette Components

In preferred embodiments of the present invention, the expression cassette comprises a virus or engineered construct derived from a viral genome. The ability of certain viruses to enter cells via receptor-mediated endocytosis and, in some cases, integrate into the host cell chromosomes, have made them attractive candidates for gene transfer in to mammalian cells. However, because it has been demonstrated that direct uptake of naked DNA, as well as receptor-mediated uptake of DNA complexes, expression vectors need not be viral but, instead, may be any plasmid, cosmid or phage construct that is capable of supporting expression of encoded genes in mammalian cells, such as pUC or Bluescript™ plasmid series.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

In certain embodiments of the invention, a treated cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

F. Gene Transfer

1. Viral Vectors

A "viral vector" is meant to include those constructs containing viral sequences sufficient to (a) support packaging of the expression cassette and (b) to ultimately express a recombinant gene construct that has been cloned therein.

a. Adenoviral Vectors

One method for delivery of the recombinant DNA involves the use of an adenovirus expression vector. Although adenovirus vectors are known to have a low capacity for integration into genomic DNA, this feature is counterbalanced by the high efficiency of gene transfer afforded by these vectors.

Adenoviruses are currently the most commonly used vector for gene transfer in clinical settings. Among the advantages of these viruses is that they are efficient at gene delivery to both nondividing an dividing cells and can be produced in large quantities. In many of the clinical trials for cancer, local intratumor injections have been used to introduce the vectors into sites of disease because current vectors do not have a mechanism for preferential delivery to tumor.

The vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP (located at 16.8 m.u.), is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) have disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

The adenovirus vector may be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Animal studies have suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

b. Retroviral Vectors

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, packaging cell lines are available that should greatly decrease the likelihood of recombination (Markowitz et al., 1988; Hersdorffer et al., 1990).

c. AAV Vectors

Adeno-associated virus (AAV) is an attractive vector system for use in the present invention as it has a high frequency of integration and it can infect nondividing cells, thus making it useful for delivery of genes into mammalian cells in tissue culture (Muzyczka, 1992). AAV has a broad host range for infectivity (Tratschin, et al., 1984; Laughlin, et al., 1986; Lebkowski, et al., 1988; McLaughlin, et al., 1988), which means it is applicable for use with the present invention. Details concerning the generation and use of rAAV vectors are described in U.S. Pat. No. 5,139,941 and U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt et al., 1994; Lebkowski et al., 1988; Samulski et al., 1989; Shelling and Smith, 1994; Yoder et al., 1994; Zhou et al., 1994; Hermonat and Muzyczka, 1984; Tratschin et al., 1985; McLaughlin et al., 1988) and genes involved in human diseases (Flotte et al., 1992; Ohi et al., 1990; Walsh et al., 1994; Wei et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild-type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild-type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994a; Clark et al., 1995). Cell lines carrying the rAAV DNA as an integrated provirus can also be used (Flotte et al., 1995).

d. Herpesvirus Vectors

Herpes simplex virus (HSV) has generated considerable interest in treating nervous system disorders due to its tropism for neuronal cells, but this vector also can be exploited for other tissues given its wide host range. Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al. (1995).

HSV, designated with subtypes 1 and 2, are enveloped viruses that are among the most common infectious agents encountered by humans, infecting millions of human subjects worldwide. The large, complex, double-stranded DNA genome encodes for dozens of different gene products, some of which derive from spliced transcripts. In addition to virion and envelope structural components, the virus encodes numerous other proteins including a protease, a ribonucleotides reductase, a DNA polymerase, a ssDNA binding protein, a helicase/primase, a DNA dependent ATPase, a dUTPase and others.

HSV genes form several groups whose expression is coordinately regulated and sequentially ordered in a cascade fashion (Hones and Roizman, 1974; Hones and Roizman 1975). The expression of α genes, the first set of genes to be expressed after infection, is enhanced by the virion protein number 16, or α-transinducing factor (Post et al, 1981; Batterson and Roizman, 1983). The expression of β genes requires functional α gene products, most notably ICP4, which is encoded by the α4 gene (DeLuca et al., 1985). γ genes, a heterogeneous group of genes encoding largely virion structural proteins, require the onset of viral DNA synthesis for optimal expression (Holland and Holland, 1980).

In line with the complexity of the genome, the life cycle of HSV is quite involved. In addition to the lytic cycle, which results in synthesis of virus particles and, eventually, cell death, the virus has the capability to enter a latent state in which the genome is maintained in neural ganglia until some as of yet undefined signal triggers a recurrence of the lytic cycle. Avirulent variants of HSV have been developed and are readily available for use in gene therapy contexts (U.S. Pat. No. 5,672,344).

e. Vaccinia Virus Vectors

Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome. The majority of essential genes appear to map within the central region, which is most highly conserved among poxviruses. Estimated open reading frames in vaccinia virus number from 150 to 200. Although both strands are coding, extensive overlap of reading frames is not common.

At least 25 kb can be inserted into the vaccinia virus genome (Smith and Moss, 1983). Prototypical vaccinia vectors contain transgenes inserted into the viral thymidine kinase gene via homologous recombination. Vectors are selected on the basis of a tk-phenotype. Inclusion of the untranslated leader sequence of encephalomyocarditis virus, the level of expression is higher than that of conventional vectors, with the transgenes accumulating at 10% or more of the infected cell's protein in 24 h (Elroy-Stein et al., 1989).

f. Other Viral Vectors

Other viral vectors may be employed as constructs in the present invention. Vectors derived from viruses such as poxvirus may be employed. A molecularly cloned strain of Venezuelan equine encephalitis (VEE) virus has been genetically refined as a replication competent vaccine vector for the expression of heterologous viral proteins (Davis et al., 1996). Studies have demonstrated that VEE infection stimulates potent CTL responses and has been suggested that VEE may be an extremely useful vector for immunizations (Caley et al., 1997). It is contemplated in the present invention, that VEE virus may be useful in targeting dendritic cells.

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

g. Gene Delivery Using Modified Viruses

A polynucleotide may be housed within a viral vector that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

2. Nonviral Vectors a. Examples of Non-Viral Vectors

Several non-viral methods for the transfer of expression vectors into cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and liofectamine-DNA complexe, cell sonication (Fechheimer et al., 1987), gene bombardment using high velocity microprojectiles (Yang et al., 1990), polycations (Boussif et al., 1995) and receptor-mediated transfection (Wu and Wu, 1987; Wu and Wu, 1988). Some of these techniques may be successfully adapted for in vivo or ex vivo use.

In one embodiment of the invention, the adenoviral expression cassette may simply consist of naked recombinant vector. Transfer of the construct may be performed by any of the methods mentioned above which physiclaly or chemically permeabilize the cell membrane. For example, Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a polypeptide may also be transferred in a similar manner in vivo.

Another embodiment of the invention for transferring a naked DNA expression vector into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990). This may require surgical exposure of the tissue or cells, to eliminate any intervening tissue between the gun and the target organ. DNA encoding polypeptide may be delivered via this method.

In other embodiments of the present invention, the transgenic construct is introduced to the cells using calcium phosphate co-precipitation. Mouse primordial germ cells have been transfected with the SV40 large T antigen, with excellent results (Watanabe et al., 1997). Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

In another embodiment, the expression construct is delivered into the cell using DEAE-dextran followed by polyethylene glycol. In this manner, reporter plasmids were introduced into mouse myeloma and erythroleukemia cells (Gopal, 1985).

Further embodiments of the present invention include the introduction of the nucleic acid construct by direct microinjection or sonication loading. Direct microinjection has been used to introduce nucleic acid constructs into *Xenopus oocytes* (Harland and Weintraub, 1985), and LTK$^-$ fibroblasts have been transfected with the thymidine kinase gene by sonication loading (Fechheimer et al., 1987).

b. Lipid and Liposome Non-Viral Vectors

In a further embodiment of the invention, the expression cassette may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL).

Lipid-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of lipid-mediated delivery and expression of foreign DNA in cultured chick embryo, HeLa and hepatoma cells.

Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in liposome stability in the presence and absence of serum proteins. The interaction between liposomes and serum proteins has a dramatic impact on the stability characteristics of liposomes (Yang and Huang, 1997). Cationic liposomes attract and bind negatively charged serum proteins. Liposomes coated by serum proteins are either dissolved or taken up by macrophages leading to their removal from circulation. Current in vivo liposomal delivery methods use subcutaneous, intradermal, intratumoral, or intracranial injection to avoid the toxicity and stability problems associated with cationic lipids in the circulation. The interaction of liposomes and plasma proteins is responsible for the disparity between the efficiency of in vitro (Felgner et al., 1987) and in vivo gene transfer (Zhu et al., 1993; Solodin et al., 1995; Thierry et al., 1995; Tsukamoto et al., 1995; Aksentijevich et al., 1996).

Recent advances in liposome formulations have improved the efficiency of gene transfer in vivo (WO 98/07408). A novel liposomal formulation composed of an equimolar ratio of 1,2-bis(oleoyloxy)-3-(trimethyl ammonio)propane (DOTAP) and cholesterol significantly enhances systemic in vivo gene transfer, approximately 150 fold. The DOTAP: cholesterol lipid formulation is said to form a unique structure termed a "sandwich liposome". This formulation is reported to "sandwich" DNA between an invaginated bi-layer or 'vase' structure. Beneficial characteristics of these liposomes include a positive ρ, colloidal stabilization by cholesterol, two dimensional DNA packing and increased serum stability.

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Liposomal encapsulation has resulted in a lower toxicity and a longer serum half-life for such compounds (Gabizon et al., 1990). Numerous disease treatments are using lipid based gene transfer strategies to enhance conventional or establish novel therapies, in particular therapies for treating hyperproliferative diseases.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1.

G. Immunological Reagents

In certain aspects of the invention, the candidate substance suspected of modulating macropinocytosis may be an antibody. In other aspects of the invention, there is provided a method of treating cancer in a human subject that comprises adinistering to the subject a pharmacologically effective amount of an antibody directed against a modulator of binding between DLC1/PIN and Pak1. For example, the antibody may be directed against a DLC1/PIN polypeptide, a mutant DLC1/PIN polypeptide, or the C-terminal 19 amino acids of DLC1/PIN. These antibodies may be used in various diagnostic or therapeutic applications, described herein below.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

However, "humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's dental disease are likewise known and such custom-tailored antibodies are also contemplated.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia op synthetic compositions.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m$^2$) (Johnson/Mead, NJ), cytokines such as γ-interferon, IL-2, or IL-12 or genes encoding proteins involved in immune helper functions, such as B-7.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

It is also contemplated that a molecular cloning approach may be used to generate monoclonals. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies. In another example, LEEs or CEEs can be used to produce antigens in vitro with a cell free system. These can be used as targets for scanning single chain antibody libraries. This would enable many different antibodies to be identified very quickly without the use of animals.

Alternatively, monoclonal antibody fragments encompassed by the present invention can be synthesized using an automated peptide synthesizer, or by expression of full-length gene or of gene fragments in E. coli.

H. Antibody Conjugates

The present invention also provides for antibodies in which the antibody is linked to at least one agent to form an antibody conjugate. In order to increase the efficacy of antibody molecules as therapeutic agents or as candidate substances capable of modulating macropinocytosis, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993). In addition, the variable domain is involved in antibody self-binding (Kang et al., 1988), and contains epitopes (idiotopes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti-cellular agent, and may be termed "immunotoxins".

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody-directed imaging".

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850, 752; 3,939,350; 3,996,345; 4,277,437; 4,275,149 and 4,366, 241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens and Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

I. Immunodetection Methods

In still further embodiments, the present invention concerns immunodetection methods for screening for modulators of macropinocytosis. For instance, these methods may be used to detect modulation of binding between Pak1 and DLC1/PIN. Some immunodetection methods include enzyme linked immunosorbent assay (ELISA), radioimmunoassay (RIA), immunoradiometric assay, immunohistochemistry, fluoroimmunoassay, chemiluminescent assay, bioluminescent assay, and Western blot to mention a few. The steps of various useful immunodetection methods have been described in the scientific literature, such as, e.g., Doolittle and Ben-Zeev, 1999; Gulbis and Galand, 1993; De Jager et al., 1993; Nakamura et al., 1987, each incorporated herein by reference.

In general, the immunobinding methods include obtaining a candidate substance suspected of modulating macropinocytosis and contacting the substance with a first anti-DLC1/PIN and/or anti-Pak1 message in accordance with the present invention, as the case may be, under conditions effective to allow the formation of immunocomplexes. Alternatively, the candidate substance may be contacted with an anti-DLC1/PIN translated product antibody and/or an anti-Pak1 translated product antibody under conditions effective to allow the formation of immunocomplexes.

These methods include methods for purifying a DLC1/PIN and/or Pak1 message, protein, polypeptide and/or peptide from organelle, cell, tissue or organism's samples. In these instances, the antibody removes the antigenic DLC1/PIN or Pak1 message, protein, polypeptide and/or peptide component from a sample. The antibody will preferably be linked to a solid support, such as in the form of a column matrix, and the sample suspected of containing the message, protein, polypeptide and/or peptide antigenic component will be applied to the immobilized antibody. The unwanted components will be washed from the column, leaving the antigen immunocomplexed to the immobilized antibody to be eluted.

The immunobinding methods also include methods for detecting and quantifying the amount of an antigen component in a sample and the detection and quantification of any immune complexes formed during the binding process. Here, one would obtain a sample suspected of containing an antigen, and contact the sample with an antibody against the DLC1/PIN or Pak1 antigen, and then detect and quantify the amount of immune complexes formed under the specific conditions.

In terms of antigen detection, the biological sample analyzed may be any sample that is suspected of containing an antigen, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum, although tissue samples or extracts are preferred.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any DLC1/PIN or Pak1 antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The DLC1/PIN or Pak1 antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

1. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, the anti-DLC1/PIN or anti-Pak1 message and/or anti-DLC1/PIN or anti-Pak1 translated product antibodies of the invention are immobilized onto a selected surface exhibiting protein affinity, such as a well in a polystyrene microtiter plate. Then, a test composition suspected of containing the antigen, such as a clinical sample, is added to the wells. After binding and/or washing to remove non-specifically bound immune complexes, the bound antigen may be detected. Detection is generally achieved by the addition of another anti-DLC1/PIN or anti-Pak1 message and/or anti-DLC1/PIN or anti-Pak1 translated product antibody that is linked to a detectable label. This type of ELISA is a simple "sandwich ELISA". Detection may also be achieved by the addition of a second anti-DLC1/PIN or anti-Pak1 message and/or anti-DLC1/PIN or anti-Pak1 translated product antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with the anti-DLC1/PIN or anti-Pak1 message and/or anti-DLC1/PIN or anti-Pak1 translated product antibodies of the invention. After binding and/or washing to remove non-specifically bound immune complexes, the message and/or anti-translated product antibodies are detected. Where the initial anti-DLC1/PIN or anti-Pak1 message and/or anti-DLC1/PIN or anti-Pak1 translated product antibodies are linked to a detectable label, the immune complexes may be detected directly. Again, the immune complexes may be detected using a second antibody that has binding affinity for the first anti-DLC1/PIN or anti-Pak1 message and/or anti-DLC1/PIN or anti-Pak1 translated product antibody, with the second antibody being linked to a detectable label.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

2. Immunohistochemistry

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1999; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25–50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

J. Targeted Diseases and Conditions

1. Overview

The present invention is concerned generally with methods of modulating macropinocytosis in cells of a target cell population, which is achieved by modulating the binding of Pak1 to DLC1/PIN in the cells. This invention arises out of the inventors' discovery that cellular macropinocytosis, including macropinocytosis in human cells, is modulated by the binding of Pak1 to DLC1/PIN. Because Pinocytosis contributes to both the growth and motility processes of cells, the invention can be aimed at selective modification of macropinocytosis in conditions wherein modification of growth and motility of cells is desired.

2. Cancer and Other Proliferative Lesions

The inventors have discovered that deregulation of DLC1/PIN alone but not its Pak1 phosphorylation site promoted anchorage-independent and the tumorigenic potential of breast cancer cells. In addition, other studies have demonstrated that (a) macropinocytosis provides the force for directed cell locomotion; (2) Pak1 is required for directional cell motility; and (c) DLC1/PIN mutants can block macropinocytosis (Thompson and Bretscher, 2002; Sells et al., 1997). Thus there is a rationale that inhibitors of DLC1/PIN-Pak1 interactions can inhibit tumor cell motility. Therefore, an embodiment of this invention is directed to methods of modulating macropinocytosis in cancer cells. In addition, the invention includes methods to reduce growth and survival of a cancer cell by modulating the binding of Pak1 to DLC1/PIN.

The invention also includes methods to decrease the invasiveness of a cancer cell by inhibiting the binding of DLC1/PIN to Pak1 in the cancer cell. In addition, another embodiment of the invention includes use of antibodies to modulate the binding of DLC1/PIN to Pak1. In a preferred embodiment, the antibody is directed to the C-terminal 19 amino acids of DLC1/PIN. This is based on the inventors' discovery that DLC1/PIN is frequently overexpressed in breast tumors, and that overexpression of DLC1/PIN promotes tumorigenesis and anchorage independent growth of cancer cells.

DLC1/PIN has been shown to interact with proapoptotic protein Bim and thus promote cell survival and inhibit nitric oxide synthase activity (Puthalakath et al., 1999; Chang et al., 2000; Jakobi et al., 2001). In view of the inventors' finding that DLC1/PIN promotes tumorigenesis in nude mice, another aspect of this invention is the induction of apoptosis by interfering with the binding domain of DLC1/PIN.

The cancer cells can be any type of cancer cells. Examples include breast cancer, lung cancer, prostate cancer, ovarian cancer, brain cancer, liver cancer, prostate cancer, cervical cancer, colon cancer, renal cancer, skin cancer, head & neck cancer, bone cancer, esophageal cancer, bladder cancer, uterine cancer, lymphatic cancer, stomach cancer, pancreatic cancer, testicular cancer, or leukemia. The subject may or may not have undergone secondary antihyperplastic therapy. Examples of such secondary hyperplastic therapy include chemotherapy, radiation therapy, surgical therapy, immunotherapy, and gene therapy.

Other embodiments of this invention pertain to methods of reducing cell proliferation in a target cell population by administering a pharmacologically effective amount of an agent that inhibits the binding of Pak1 to DLC1/PIN. Although the cell proliferation can be related to cancer, the invention contemplates any proliferative lesion wherein there is abnormal or excessive cell growth and/or increase in cell numbers. Thus, cells in both benign and premalignant lesions are contemplated as targets of the claimed invention.

3. Breast Cancer

Breast cancer is one of the most common malignancies in the United States, affecting one in nine women. The molecular mechanisms underlying the progression of breast cancer to more malignant behavior are not completely understood at the present time and are believed to involve deregulation of signaling pathways activated by growth factors and their receptors. For example, overexpression or overactivation of the human epidermal growth factor receptors by EGF family of ligands is frequently associated with an aggressive clinical course, decreased disease-free survival, and metastasis in human breast cancer (Muss et al., 1994; Borg et al., 1994; Norton, 1997; Kumar and Mendelsohn, 1991; Wright et al., 1992, Slamon et al., 1994). Despite the remarkable growth of information about growth factors and its receptors, the progress in understanding the mechanism by which downstream target(s) of these cell surface-initiated signaling pathways regulate breast cancer progression remains elusive.

a. Physiology of Human Epidermal Growth Factor Receptors (HER) Family Members Over the years, numerous studies have shown a role for alterations in EGFR and HER2 signaling pathways in the development of human epithelial cancers such as breast cancer (Chang et al., 2000; Derynck, 1992; Riechmann, 1994). Ligand binding to the EGFR induces receptor dimerization and activation of the intrinsic EGFR tyrosine kinase domain, with subsequent autophosphorylation of key tyrosines in the C-terminal region of EGFR (Lemmon and Schlessinger, 1994; Earp et al., 1995). Phosphorylated specific tyrosine residues act as a docking site for proteins containing Src-homology 2 domains (SH2) such as Grb2, Shc, and PLC-gamma, and these events, in-turn, activate complex downstream signaling cascades leading to distinct phenotypic changes. In addition, accumulating evidence suggests that the progression of human breast cancer cells may be regulated by EGF and by the combinatorial ligand heregulin (HRG), a ligand for HER3 and HER4 (Peles et al., 1992; Wen et al., 1992). Recently, others and the inventors have demonstrated that the HRG promotes cell motility, invasiveness and the development of more aggressive phenotype in mammary cancer cells (Ullrich and Schlessinger, 1990; Menard et al., 2000; Dowsett, 2001a; Dowsett et al., 2001b; Mazumdar et al., 2001a; Benz et al., 1992; Pietras et al., 1995; Kumar et al., 1995; Tang et al., 1996; Kurokawa et al., 2000; Mazumdar et al, 2001b; Jordan, 1992; Wright et al., 1992; Kumar et al., 1996). Of the HER family of receptors, the HER2/HER3 dimer has been shown to elicit the most potent mitogenic signals (Horan et al., 1995). HRG stimulation of breast cancer cells enhances Shc phosphorylation and its association with phosphorylated HER3, association of P13K with HER2/HER3 heterodimers, and activation of MAP kinase and p70/p85 S6 kinase (Carraway et al., 1995; Kramarski et al., 1996; Soltoff et al., 1994; Marte et al., 1995). In brief, much has been learned about the physiology of HERs themselves, but the roles of key downstream target(s) of HER in promoting breast cancer cells tumorigenecity remains to be fully understood.

b. Cytoskeletal Reorganization and Breast Cancer

Localized breast cancer prior to metastasis can be cured by surgery. The high mortality rate associated with breast cancer, however, is related to its ability to metastasize beyond the mammary gland and invade distant sites while the primary tumor remains small and undetected. Thus, tumor cell migration is an important factor in the formation of solid tumors and necessary for their spread to distinct organs. The process of breast cancer metastasis requires, among other steps, changes in cytoskeleton signaling pathways, increased directional motility, and enhanced cell survival. The exposure of cells to growth factors causes cytoskeletal reorganization, the formation of lamellipodia, membrane ruffling, and changes in cell morphology; accordingly, such exposure is implicated in stimulating cell migration and invasion (Ben-Ze'ev, 1997; Lauffenburger and Horwitz, 1996). Most eukaryotic cells are able to move over or through a substrate, and cell migration plays key roles in both normal physiologic processes and in the biology of invasion and metastasis (Mitchison and Cramer, 1973). In many epithelial cells, the motility function is normally repressed, but can be activated by appropriate stimuli (i.e., growth factors) and/or oncogenic transformation. It is increasingly accepted that alterations in the reorganization and stability of actin filaments contribute to increased cell migration and to cell transformation, anchorage-independent growth, and invasiveness. Since both EGF and HRG have been shown to be involved in breast cancer invasion, it will be important to understand the role of downstream targets of cytoskeleton signaling that are responsive to the action of growth factors in breast cancer cells.

c. P21-Activated Kinase-1 (Pak1) and Breast Cancer

The small GTPases, including Cdc42, Rac1, and RhoA, have been implicated in the regulation of mammalian cell morphology and motility (Medina, 1973). More specifically, Rac1 induces cortical actin polymerization seen as membrane ruffling and lamellipodia, and Cdc42 induces the formation of peripheral actin microspikes and filopodia (Naruiya et al., 1997; Ridley and Hall, 1992; Kozma et al., 1995; Nobles and Hall, 1995). The small GTPases regulate the formation of cytoskeletal structures via a family of serine/threonine kinases known as Pak1 (Kumar and Vadlamudi, 2002). Pak1 is activated by a number of extracellular growth factors and signals, including tyrosine kinases, novel substrate such as filamin, and G-proteins (reviewed in Kumar and Vadlamudi, 2002). Overexpression of dominant-active Pak1 mutants causes the accumulation of F-actin and the formation of lamellipodia and filopodia. In addition to its cytoskeleton effects, Pak1 are also activates JNK and ERK kinases, and thus influences nuclear signaling (Ullrich and Schlessinger, 1990; Menard et al., 2000; Dowsett, 2001a; Dowsett et al., 2001b; Mazumdar et al., 2001). Polypeptide growth factors including, HRG and EGF are potent inducer of Pak1 activity (Ullrich and Schlessinger, 1990; Nobles and Hall, 1995). Activation of Pak1 is accompanied by the disassembly of stress fibers and focal adhesion complexes (Zhao et al., 1998) as well as in maintaining the integrity of motile leading edge (Vadlamudi et al., 2002), a process necessary for increased motility, which itself is a fundamental requirement for a productive invasion.

In addition to cell motility, several recent studies have suggested that Pak1 is involved in breast cancer. Adam et al. (2001a; 2001b) have shown a mechanistic role for Pak1 activation in the increased cell invasion of breast cancer cells by HRG (Ullrich and Schlesinger, 1990). Furthermore, expression of a kinase-dead Pak1 mutant in the highly invasive breast cancer cell lines MDA-MBA-435 and MDA-231 led to stabilization of stress fibers, enhanced cell spreading, reduction in JNK/AP1 pathway, and reduction in invasiveness (Menard et al., 2000). Conversely, conditional expression of kinase-active T423E Pak1 in the non-invasive breast cancer cell line MCF-7 promoted cell migration and anchorage-independent growth. Increased Pak1 activity correlates well with the invasiveness of human breast cancer cells and tumors (Dowsett, 2001a; 2001b). Pak1 signaling is required for vascular endothelial growth factor (VEGF) expression and, consequently VEGF function and angiogenesis (Yarmond et al., 2000). Pak1 activation also promotes cell survival by inactivating the pro-apoptotic protein Bad (Liana et al., 2001), suggesting that Pak1 may be involved in cancer progression. In addition, recent kinase-active T423E Pak1 transgenic mouse studies have established a role of Pak1 signaling in the development of hyperplasia in mammary epithelium, and underlying mechanism involved direct phosphorylation and transactivation of ER at Ser305 (Wang et al., 2002). Emerging studies have also shown the presence of Pak1 in the nuclear compartment with a putative role in the chromatin remodeling (Li et al., 2002). In spite of the widely acknowledged role of Pak1 in cell motility and breast cancer, the potential involvement of a specific downstream physiologic target of Pak1 as a critical mediator of the Pak1 (and its upstream activators) in the development of breast cancer and normal mammary development remains unknown.

d. Pak1 and Pinocytosis

Reorganization of the cytoskeleton not only affects cell motility but also plays an important role in macropinocytosis, a process by which exogenous macromolecules (0.2 to 3 μm) and fluids are taken up into small invaginations in the cell membrane that eventually bud off into Pinosomes (Lanzavecchia, 1996; Sieczkarski and Whittaker, 2002). Activated Pak1 has been shown to induce the extension of circular dorsal ruffles and colocalizes with actin in these structures (West et al., 2000; Dharmawardhane et al., 2000; Edwards et al., 1999). It is widely believed that such actin-rich circular ruffles eventually contract to form macroPinosomes (West et al., 2000). Pinocytosis contributes to both the growth and motility processes of cells (Bretscher, 1996; Bretscher and Aguado-Velasco, 1998). Recently, Pak1 has been shown to localize to the areas of Pinocytic vesicles and to contribute to the process of macropinocytosis (Dharmawardhane et al., 2000). Pak1 activity is also required for growth factor-induced macropinocytosis, and accordingly, catalytically activated Pak1 enhanced both the uptake and efflux of a 70-kDa-dextran particle, suggesting that Pak1 activity modulates Pinocytic vesicle cycling (Dharmawardhane et al., 2000). Furthermore, transient stimulation of macropinocytosis by growth factors has been also implicated in directed as motility, as regulation of membrane flux via Pinocytosis could contribute to the membrane flow generating force for cell locomotion (Bretscher, 1996; Bretscher and Aguado-Velasco, 1998). Although Pak1 has been shown to regulate macropinocytosis, the nature of the responsive molecular mechanism remains unknown.

e. Emerging Role of DLC1/PIN in Breast Cancer

To identify novel Pak1-interacting proteins, the inventors conducted a yeast two-hybrid screening of the mammary gland cDNA expression library using the Pak1 N-terminal amino acids 1–270 as bait. Sequence analysis of several isolates from one of the novel interacting clones was identical to that of DLC1/PIN. Following this unexpected finding, the inventors discovered that DLC1/PIN is a physiological substrate of Pak1 in growth factor activated cells.

Cytoskeleton remodeling-dependent cellular processes, such as vesicle transport and membrane transport are influenced by dynein, a multi protein complex originally shown to regulate the movement of chromosomes, assembly and orientation of mitotic spindles and nuclear migration (Holzbaur and Vallee, 1994; Hayden, 1988; Steuer et al., 1990; Vaisberg et al., 1993; Beckwith et al., 1998). DLC1/PIN is a minus end-directed microtubule-based motor that transports cargo along microtubules (Hirokawa, 1998; Vallee and Sheetz, 1996; Pazour et al., 1998). DLC1/PIN is highly conserved among species and widely expressed in a number of tissues; it is localized predominantly in the cytoplasm.

In addition to playing an essential role in dynein motor function, DLC1/PIN interacts with a number of proteins and has diverse functions. For example, DLC1/PIN associates with neuronal nitric oxide synthase (nNOS) and inhibits its activity and proapoptotic function; hence, named as Protein Inhibitor of NOS (DLC1/PIN) (Jaffery and Snyder, 1996). Furthermore, DLC1/PIN has also been shown to regulate the proapoptotic activity of the Bcl-2 family protein Bim-L (Puthalakath et al., 1999). Normally in healthy cells, Bim-L is bound to DLC1/PIN and sequestered to the microtubule-associated dynein motor complex. However, upon apoptotic stimuli, Bim-L is released from the DLC1/PIN/dynein complex and freed Bim-L translocates to Bcl-2 and neutralizes its antiapoptotic activity (Puthalakath et al., 1999). Collectively, these findings provide clues about a potential role of DLC1/PIN in human cancers, at-least, in part, by conferring the cell survival function. Although the functional roles of DLC1/PIN in vesicle trafficking and cell survival have been observed, no function of DLC1/PIN has been associated with its phosphorylation, and no upstream signaling kinase has been shown to phosphorylate DLC1/PIN and influence these functional outcomes. Furthermore, until the present studies of the inventors, DLC1/PIN has not been directly implicated in human cancers.

4. Viral Infections and Prevention of Infection in Uninfected Bystander Cells

The present invention contemplates methods to modulate macropinocytosis by modulating the binding of Pak1 to DLC1/PIN in cells that are infected with a virus. In addition, the present invention includes methods of treating a viral infection in a human subject comprising administering to the subject a pharmacologically effective amount of a modulator of macropinocytosis identified in the methods of screening for modulators of macropinocytosis disclosed herein. In certain embodiments, the modulator of macropinocytosis is a pharmacologically effective amount of an expression cassette comprising a promoter, active in the cells of the subject, operably linked to a polynucleotide encoding a DLC1/PIN polypeptide lacking the C-terminal 19 amino acids of DLC1/PIN or a DLC1/PIN polypeptide lacking serine 88 of DLC1/PIN.

Studies have shown that a number of viruses utilize endocytosis and macropinocytosis to infect host cells mediating their internalization and trafficking (Sieczkarski and Whittaker, 2002; Marechal et al., 2001; Meir et al., 2002; Rigden et al., 2002). Since the inventors have shown that binding of DLC1/PIN and Pak1 is associated with macropinocytosis, inhibitors of the DLC1/PIN-Pak1 interaction can be used to inhibit and disrupt the uptake of viruses or pathogens into cells. The invention contemplates use of inhibitors of Pak1-DLC1/PIN binding against any type of viral infection that can infect a cell. However, in preferred embodiments the virus is HIV, a neurotropic virus, adenovirus, foot and mouth disease virus, or respiratory syncytial virus.

In addition, inhibitors of the binding of Pak1 to DLC1/PIN can be used to prevent infection of uninfected bystander cells near cells infected with HIV. It has been shown that the HIV tat protein is secreted from HIV-infected cells and enters uninfected bystander cells via endocytosis, resulting in apoptosis of the bystander cell (Chen et al., 2002; Mann et al., 1991). Inhibition of the DLC1/PIN-Pak1 interaction as a strategy to inhibit macropinocytosis is contempleted by the invention disclosed herein in an effort to prevent infection of normal bystander cells.

5. Alzheimer Disease

Increased neuronal endocytosis and protease delivery to early endosomes in sporadic Alzheimer disease has been described (Cataldo et al., 2001). Since Pak1 is highly expressed in heuronal cells, inhibition of Pak1-DLC1/PIN interactions can be targeted to inhibited endocytosis in Alzheimer disease.

6. Atherogenesis

Modified low density proteins (LDL) such as acetylated LDL and oxidized LDL activate macropinocytosis and use macropinocytosis to enter cells. This process is implicated in foam cell formation (Zwaka et al., 2001; Jones et al., 2000). Thus, targeting inhibition of macropinocytosis in macrophages and foam cells can be used as a means to prevent or treat atherogenesis.

7. LDL Uptake/Cardiovascular Disease

Modified LDLs are internalized by macrophages in part via macropinocytosis (Jones and Willingham, 1999). Given that LDL addition increased ruffling activity, an indicator of increased macropinocytosis, the present inventors show herein that DLC/PIN peptide-treated cells have very little ruffling activity. This indicates that at least DLC/PIN peptide can interfere with LDL-induced macropinocytosis. Since LDL mediated macropinocytosis is implicated in foam cell formation and macrophage cholesterol accumulation in atherosclerosis (Zwaka et al., 2001), DLC1/PIN peptide is useful for treating foam cell and atherosclerosis diseases, such as cardiovascular disease.

8. Regulation of Immune Responses or Antigen Presentation Capabilities

Dendritic cells use macropinocytosis to sample soluble antigens and also to concentrate macromolecules in the histocomplex class II compartment (Nobes and Marsh, 2000; West et al., 2000). Therefore, the invention contemplates modulation of macropinocytosis in an effort to increase or decrease immune functions, immune response, and antigen presentation. In addition, the invention contemplates modulation of DLC1/PIN-Pak1 interaction to modulate the process of antigen presentation and treat diseases associated with antigen processing. Another embodiment of the invention is interference with DLC1/PIN-Pak1 interactions to modulate the ability of dendritic cells to process antigens, including the ability of antigen processing in DC (dendritic cell) vaccines, as well as modulation of mannose receptor-mediated cellular functions.

K. Therapeutic Methods

1. Overview

The present invention contemplates methods to modulate macropinocytosis in a subject comprising administering to the subject a pharmacologically effective amount of a modulator of macropinocytosis identified by any of the methods of screening for modulators of macropinocytosis disclosed herein. In particular embodiments, the modulator of macropinocytosis is a DLC1/PIN polypeptide lacking the C-terminal 19 amino acids of DLC1/PIN, a DLC1/PIN polypeptide lacking the C-terminal 23 amino acids of DLC1/PIN, or a DLC1/PIN polypeptide lacking serine 88 of DLC1/PIN. The invention also contemplates methods of reducing cell proliferation in a cell population comprising administering to the cell population a pharmacologically effective amount of an agent that inhibits the binding of Pak1 to DLC1/PIN. The invention also contemplates methods to inhibit the growth and survival of a cancer cell, or the invasiveness of a cancer cell, by administering to the cells pharmacologically effective amounts of modulators of macropinocytosis identified by the methods disclosed in the invention herein. Thus, in various forms, this invention contemplates administration of pharmacologically effective amounts of substances or agents.

2 Pharmaceutically Acceptable Carriers

Aqueous compositions of the present invention comprise an effective amount of a modulator of macropinocytosis, agent that inhibits the binding of Pak1 to DLC1/PIN, expression cassette encoding a polynucleotide encoding a mutant DLC1/PIN polypeptide, and the like, dissolved or dispersed in a pharmaceutically acceptable carrier or aqueous medium. Aqueous compositions of gene therapy vectors expressing any of the foregoing are also contemplated. The phrases "pharmaceutically" or "pharmacologically effective" of "pharmaceutically acceptable" refer to molecular entities and compositions that do not produce an adverse, allergic or other untoward reaction when administered to an animal, or a human, as appropriate.

As used herein, "pharmacologically effective amount" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes. The preparation of an aqueous composition containing an active agent of the invention disclosed herein as a component or active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An agent or substance of the present invention can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. In terms of using peptide therapeutics as active ingredients, the technology of U.S. Pat. Nos. 4,608,251; 4,601,903; 4,599,231; 4,599,230; 4,596,792; and 4,578,770, each incorporated herein by reference, may be used.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

The active agents disclosed herein may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

One may also use nasal solutions or sprays, aerosols or inhalants in the present invention. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Additional formulations which are suitable for other modes of administration include vaginal suppositories and pessaries. A rectal pessary or suppository may also be used. Suppositories are solid dosage forms of various weights and shapes, usually medicated, for insertion into the rectum, vagina or the urethra. After insertion, suppositories soften, melt or dissolve in the cavity fluids. In general, for suppositories, traditional binders and carriers may include, for example, polyalkylene glycols or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25–60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

3 Liposomes and Nanoparticles

The use of liposomes and/or nanoparticles is also contemplated for the introduction of the modulator of macropinocytosis or gene therapy vectors into host cells. The formation and use of liposomes is generally known to those of skill in the art, and is also described below.

Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

The following information may also be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

4 Dosage

An effective amount of the therapeutic or preventive agent is determined based on the intended goal, for example (i) inhibition of macropinocytosis or (II) inhibition of growth and survival of cancer in a human subject. The quantity to be administered, both according to number of treatments and dose, depends on the subject to be treated, the state of the subject and the protection desired. Precise amounts of the therapeutic composition also depend on the judgment of the practitioner and are peculiar to each individual.

In certain embodiments, it may be desirable to provide a continuous supply of the therapeutic compositions to the patient. For topical administrations, repeated application would be employed. For various approaches, delayed release formulations could be used that provide limited but constant amounts of the therapeutic agent over an extended period of time. For internal application, continuous perfusion of the region of interest may be preferred. This could be accomplished by catheterization, post-operatively in some cases, followed by continuous administration of the therapeutic agent. The time period for perfusion would be selected by the clinician for the particular patient and situation, but times could range from about 1–2 hours, to 2–6 hours, to about 6–10 hours, to about 10–24 hours, to about 1–2 days, to about 1–2 weeks or longer. Generally, the dose of the therapeutic composition via continuous perfusion will be equivalent to that given by single or multiple injections, adjusted for the period of time over which the doses are administered.

Those of skill in the art are well aware of how to apply gene delivery to in vivo and ex vivo situations. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times^{12}$ infectious particles to the patient. Similar figures may be extrapolated for liposomal or other non-viral formulations by comparing relative uptake efficiencies. Formulation as a pharmaceutically acceptable composition is discussed below.

5. Treatment of Artificial and Natural Body Cavities

One of the prime sources of recurrent cancer is the residual, microscopic disease that remains at the primary tumor site, as well as locally and regionally, following tumor excision. In addition, there are analogous situations where natural body cavities are seeded by microscopic tumor cells. The effective treatment of such microscopic disease would present a significant advance in therapeutic regimens.

Thus, in certain embodiments, a cancer may be removed by surgical excision, creating a "cavity." Both at the time of surgery and thereafter (periodically or continuously), the therapeutic composition of the present invention is administered to the body cavity. The volume of the composition should be sufficient to ensure that the entire surface of the cavity is contacted by the expression cassette.

In one embodiment, administration simply will entail injection of the therapeutic composition into the cavity formed by the tumor excision. In another embodiment, mechanical application via a sponge, swab or other device may be desired. Either of these approaches can be used subsequent to the tumor removal as well as during the initial surgery. In still another embodiment, a catheter is inserted into the cavity prior to closure of the surgical entry site. The cavity may then be continuously perfused for a desired period of time.

6. Tracers to Monitor Gene Expression Following Administration

Because destruction of microscopic tumor cells cannot be observed, it is important to determine whether the target site has been effectively contacted with the expression cassette. This may be accomplished by identifying cells in which the expression construct is actively producing the desired polypeptide product. It is important, however, to be able to distinguish between the exogenous polypeptide and that present in tumor and nontumor cells in the treatment area. Tagging of the exogenous polypeptide with a tracer element would provide definitive evidence for expression of that molecule and not an endogenous version thereof. Thus, the methods and compositions of the claimed invention may involve tagging of the polypeptide encoded by the expression cassette with a tracer element.

One such tracer is provided by the FLAG biosystem (Hopp et al., 1988). The FLAG polypeptide is an octapeptide (AspTyrLysAspAspAspAspLys) and its small size does not disrupt the expression of the delivered gene therapy protein. The coexpression of FLAG and the protein of interest is traced through the use of antibodies raised against FLAG protein.

Other immunologic marker systems, such as the 6XHis system (Qiagen) also may be employed. For that matter, any linear epitope could be used to generate a fusion protein with the desired polypeptide so long as (i) the immunologic integrity of the epitope is not compromised by the fusion and (ii) the functional integrity of the desired polypeptide is not compromised by the fusion.

7. Secondary Treatment a. General

Certain embodiments of the claimed invention provide for a method of modulating macropinocytosis in a subject with cancer. Other embodiments provide for methods of inhibiting the growth and survival of a cancer cell in a human subject by inhibiting the binding of DLC1/PIN and Pak1. In each of these embodiments, the subject may be receiving secondary antihyperplastic therapy. Examples of secondary antihyperplastic therapy include chemotherapy, radiotherapy, immunotherapy, phototherapy, cryotherapy, toxin therapy, hormonal therapy or surgery. Thus, the claimed invention contemplates use of the claimed methods and compositions in conjunction with standard anti-cancer therapies. The patient to be treated may be an infant, child, adolescent or adult.

A wide variety of cancer therapies, known to one of skill in the art, may be used in combination with the compositions of the claimed invention. Some of the existing cancer therapies and chemotherapeutic agents are described below. One of skill in the art will recognize the presence and development of other anticancer therapies which can be used in conjugation with the compositions comprising expression cassettes and will further recognize that the use of the secondary therapy of the claimed invention will not be restricted to the agents described below.

In order to increase the effectiveness of a an expression construct encoding a polypeptide that modulates macropinocytosis, it may be desirable to combine these compositions with other agents effective in the treatment of hyperproliferative disease. These compositions would be provided in a combined amount effective to kill or inhibit proliferation of the cell. This process may involve contacting the cells with the expression construct and the agent(s) or second factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent.

Alternatively, the gene therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12–24 h of each other and, more preferably, within about 6–12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed. For example, the inhibitor of macropinocytosis is therapy is "A" and the secondary agent, such as radio- or chemotherapy, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

b. Radiotherapy

Radiotherapy include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

In the context of the present invention radiotherapy may be used in addition to using the tumor cell specific-peptide of the invention to achieve cell-specific cancer therapy.

c. Surgery

Surgical treatment for removal of the cancerous growth is generally a standard procedure for the treatment of tumors and cancers. This attempts to remove the entire cancerous growth. However, surgery is generally combined with chemotherapy and/or radiotherapy to ensure the destruction of any remaining neoplastic or malignant cells. Thus, in the context of the present invention surgery may be used in addition to using the tumor cell specific-peptide of the invention to achieve cell-specific cancer therapy.

In the case of surgical intervention, the compositions of the present invention may be used preoperatively, to render an inoperable tumor subject to resection. Alternatively, the present invention may be used at the time of surgery, and/or thereafter, to treat residual or metastatic disease. For example, a resected tumor bed may be injected or perfused with a formulation comprising an expression construct. The perfusion may be continued post-resection, for example, by leaving a catheter implanted at the site of the surgery. Periodic post-surgical treatment also is envisioned.

In certain embodiments, the tumor being treated may not, at least initially, be resectable. Treatments with therapeutic viral constructs may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two-week period. The two-week regimen may be repeated one, two, three, four, five, six or more times. During a course of treatment, the need to complete the planned dosings may be re-evaluated.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently may be described in terms of plaque forming units (pfu) for a viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher.

d. Chemotherapeutic Agents

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate or any analog or derivative variant thereof. The term "chemotherapy" as used herein is defined as use of a drug, toxin, compound, composition or biological entity which is used as treatment for cancer. These can be, for example, agents that directly cross-link DNA, agents that intercalate into DNA, and agents that lead to chromosomal and mitotic aberrations by affecting nucleic acid synthesis.

Agents that directly cross-link nucleic acids, specifically DNA, are envisaged and are shown herein, to eventuate DNA damage leading to a synergistic antineoplastic combination. Agents such as cisplatin, and other DNA alkylating agents may be used.

Agents that damage DNA also include compounds that interfere with DNA replication, mitosis, and chromosomal segregation. Examples of these compounds include adriamycin (also known as doxorubicin), VP-16 (also known as etoposide), verapamil, podophyllotoxin, and the like. Widely used in clinical setting for the treatment of neoplasms, these compounds are administered through bolus injections intravenously at doses ranging from 25–75 mg/m$^2$ at 21 day intervals for adriamycin, to 35–100 mg/m$^2$ for etoposide intravenously or orally.

e. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with the expression cassette. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

f. Genes

In yet another embodiment, the secondary treatment is a gene therapy in which a different expression cassette than the one disclosed herein is administered before, after, or at the same time as the expression cassette of the claimed invention. Delivery may comprise use of a vector encoding polypeptide of the claimed invention in conjunction with a second vector encoding an additional gene product such as p53. Alternatively, a single vector encoding both genes may be used. A variety of secondary gene therapy proteins are envisioned within the invention.

g. Other Cancer Therapies

Examples of other cancer therapies include phototherapy, cryotherapy, toxin therapy, or hormonal therapy. One of skill in the art would know that this list is not exhaustive of the types of treatment modalities available for cancer and other hyperplastic lesions.

L. Vaccines

For an antigenic composition to be useful as a vaccine, an antigenic composition must induce an immune response to the antigen in a cell, tissue or animal (e.g., a human). As used herein, an "antigenic composition" may comprise an antigen (e.g., a peptide or polypepide), a nucleic acid encoding an antigen (e.g., an antigen expression vector), or a cell expressing or presenting an antigen. In particular embodiments the antigenic composition comprises or encodes all or part of the sequence of DLC1/PIN, or an immunologically functional equivalent thereof. In another particular embodiment, the antigenic composition comprises or encodes all or part of the C-terminal 19 amino acids of DLC1/PIN. In other embodiments, the antigenic composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In certain embodiments, an antigenic composition or immunologically functional equivalent, may be used as an effective vaccine in inducing an anti-DLC1/PIN humoral and/or cell-mediated immune response in an animal. The present invention contemplates one or more antigenic compositions or vaccines for use in both active and passive immunization embodiments.

A vaccine of the present invention may vary in its composition of proteinaceous, nucleic acid and/or cellular components. In a non-limiting example, a nucleic encoding an antigen might also be formulated with a proteinaceous adjuvant. Of course, it will be understood that various compositions described herein may further comprise additional components. For example, one or more vaccine components may be comprised in a lipid or liposome. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

In one embodiment of this invention, the vaccine is a DC (dendritic cell) vaccine. Dendritic cells derived from multiple myeloma patients have been shown to efficiently internalize different classes of myeloma protein (Butch et al., 2001). This internalization is via endocytosis. Therefore, modulation of macropinocytosis may be useful in producing DC vaccines.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Materials and Methods

Cell cultures, reagents, transfection, and cell extracts. MCF-7 breast cancer cells (Vadlamudi et al., 2000a) were maintained in Dulbecco's modified Eagle's medium (DMEM)-F12 (1:1) supplemented with 10% fetal calf serum. Antibodies against Pak1 were purchased from Santa Cruz Inc. (Santa Cruz, Calif.) and Zymed Inc. (San Francisco, Calif.). Antibody against T7 was purchased from Novagen (Milwaukee, Wis.). Transient transfection studies were performed using a Fugene-6 kit (Roche Biochemicals, Indianapolis, Ind.) in accordance with the manufacturer's instructions. Cell lysates were prepared as described (Vadlamudi et al., 2000b) and were resolved on an 8% sodium dodecyl sulfate (SDS)-polyacrylamide gel, transferred to nitrocellulose, and probed with the appropriate antibodies. ZR75 breast cancer cells (obtained from ATCC) were transfected with pcDNA3.1, pcDNA.T7-DLC1/PIN, or dsREDGFP-DLC1/PIN by using the calcium phosphate method. Forty-eight hours after transfection, cells were selected in medium containing 1000 μg/ml G418.

Two-hybrid library screening. Pak1 baits were constructed by amplifying amino acids 1–270 and amino acids 270–545 by polymerase chain reaction (PCR), and then subcloned into Gal4-binding domain vector pGBD vector (Clontech, Palo Alto, Calif.). The primers used were, forward-5'-CTGCTGGTGGAATTCCAATGTCAAATAAC-3' (SEQ ID NO:9); reverse-5'-TCCAATCTTCTCGAGCCGT-GTATA-3' (SEQ ID NO:10). A mammary gland cDNA library fused to Gal4 activation domain was purchased from Clontech (Palo Alto, Calif.) and screened using N-Terminal Pak 1 (1-270 aa) as a bait in accordance with the manufacturer's instructions. A total of $2\times10^6$ clones were screened. Plasmids from positive interactors were isolated and sequenced at the University of Texas M. D. Anderson Cancer Center core sequencing facility. Positive interactors were verified by one-on-one transformations followed by selection of agar plates lacking Adeosine, histidine, tryptophan, leucine (AHTL) and also by β-galactosidase assay.

Pak kinase assay. In vitro kinase assays using myelin basic protein (MBP) or glutathione-S-transferase (GST)-DLC1/PIN protein (4 μg each) were performed in HEPES buffer (50 mM HEPES, 10 mM $MgCl_2$, 2 mM $MnCl_2$, 0.2 mM DTT) containing 1 μg of purified bacterially expressed GST-Pak1 enzyme, 10 μCi of $\gamma$-$^{32}$P-ATP and 25 μM cold ATP.

GST pull-down assay. In vitro transcription and translation of the Pak1 and DLC1/PIN proteins were performed using the TNT transcription-translation system (Promega, Madison, Wis.) as previously described (Bagheri et al. 2002).

Cell proliferation, soft-agar, and tumorigenicity assays. Soft-agar colony growth assays were performed as previously described (Vadlamudi et al., 2000a; 2002b). Briefly, 1 ml of 0.6% DIFCO agar in DMEM supplemented with 10% fetal bovine serum and insulin was layered onto tissue culture plates. Test cells ($10^4$) mixed with 1 ml of 0.36% bactoagar solution in DMEM were layered on top of the 0.6% bactoagar layer. The plates were incubated at 37° C. in 5% $CO_2$ for 21 days. For xenograft studies, $5\times10^6$ cells were implanted subcutaneously into mammary fat-pads of 10 nude mice, as previously described (Bagheri et al., 2001), and allowed to grow for 20 weeks; tumor size was then measured.

Human samples. Tissue samples from patients who had undergone routine surgery for breast cancer were snap frozen in liquid nitrogen and stored at −80° C. by the M. D. Anderson Breast Core Pathology laboratory and were described previously (Kumar et al., 2002).

Immunofluorescence and confocal studies. The cellular location of proteins was determined using indirect immunofluorescence, as described previously (Vadlamudi et al., 2002a; 2002b). Briefly, cells grown on glass cover slips were fixed in methanol at −20° C. for 6 min. Cells were incubated with primary antibodies for 2 h, washed three times in PBS and then incubated with 546-Alexa-(red), 633-Alexa-(blue), or 488-Alexa (green)-labeled secondary antibodies (Molecular Probes). The DNA dye Topro-3 was used to co-stain the DNA, which gives an emission in the far-red segment of the light spectrum and color-coded in blue (Molecular Probes, Orlando, Fla.). Confocal analysis was performed using a Zeiss laser-scanning confocal microscope with established methods, involving processing of the same section for each detector (the two excitations corresponding to 546 and 488, or 633 nm) and comparing pixel by pixel.

Cell migration assays. For cell migration assays cells ($10^5$) were added to the upper chamber in serum free medium in the presence or absence of EGF (50 ng/ml) as previously described (Bagheri et al., 2001). Similar results were obtained from 4 independent experiments.

Cell cultures, reagents, transfection, and cell extracts. MCF-7 and ZR75 breast cancer cells were maintained in Dulbecco's modified Eagle's medium (DMEM)-F12 (1:1) supplemented with 10% fetal calf serum. Antibodies against Pak1 were purchased from Santa Cruz Inc. (Santa Cruz, Calif.) and Zymed Inc. (San Fransisco, Calif.). Antibody against T7 was purchased from Novagen (Milwaukee, Wis.). Transient transfection studies were performed using a Fugene-6 kit (Roche Biochemical, Palo Alto, Calif.) in accordance with the manufacturer's instructions. Dextran beads were obtained from Sigma.

EXAMPLE 2

Results

Pak1 Interacts with DLC1/PIN. To identify novel Pak1-interacting proteins, a yeast two-hybrid screening of the mammary gland cDNA expression library was performed using the Pak1 N-terminal amino acids 1–270 as bait. This bait contains several protein-binding motifs that differ between different Pak family members. This analysis resulted in the identification of a substantial number of known Pak1-binding proteins (i.e., Cdc42, Rac1, Pix, and Nck) and several new Pak1-interacting proteins. Sequence analysis of several isolates from one of the novel interacting clone was identical to that of DLC1/PIN (Genbank accession number NM_003746). The specificity of the Pak1-DLC1/PIN interactions was verified by one-on-one transformation of the yeast cells (FIG. 1A). Cotransfection of DLC1/PIN with Pak1 N terminal amino acids 1–270 but not control vectors enabled the transformed colonies to grow in medium lacking adenosine, histidine, tryptophan, and leucine (AHTL) and reacted positively in beta-galacosidase assay (FIG. 1A).

To verify the specificity of the Pak1-DLC1/PIN interaction, the inventors next evaluated the ability of in vitro-translated Pak1 protein to bind with the DLC1/PIN-GST fusion protein. The DLC1/PIN-GST-fusion protein but not GST efficiently interacted with $^{35}$S-labeled full-length Pak1 protein (FIG. 1B, left panel). Conversely, in vitro-translated DLC1/PIN protein specifically interacted with the GST-Pak1 (FIG. 1B, right panel). The in vivo interaction of endogenous DLC1/PIN with Pak1 was confirmed by immunoprecipitation of Pak1 using lysates from MCF-7 cells treated with or with out EGF and results show that Pak1 interacted with DLC1/PIN upon ligand stimulation (FIG. 1C). Similarly, immunoprecipitation of catalytically active Pak1 (HA-tagged T423E Pak1) also immunoprecipitated DLC1/PIN further confirming that activated Pak1 interacts with DLC1/PIN in vivo (FIG. 1D).

Because Pak1 and DLC1/PIN have been implicated in macropinocytosis and endocytic vesicle trafficking, respectively, and because DLC1/PIN interacts with Pak1 (FIGS. 1A–1D), the inventors next investigated whether the Pak1 interacts with DLC1/PIN in endocytic vesicles in cells stimulated with known physiologic Pak1 activators: heregulin (HRG) and epidermal growth factor (EGF). Unstimulated control MDA-MB231 cells exhibited no or low levels of vesicle, and cortical ruffling. In contrast, EGF— and HRG-treated cells showed a substantial enhancement of vesicle-like structures, with co localization of DLC1/PIN and Pak1 (FIG. 1E), in addition to expected formation of motile structures, such as lamellae and membrane ruffles.

Figure 2:
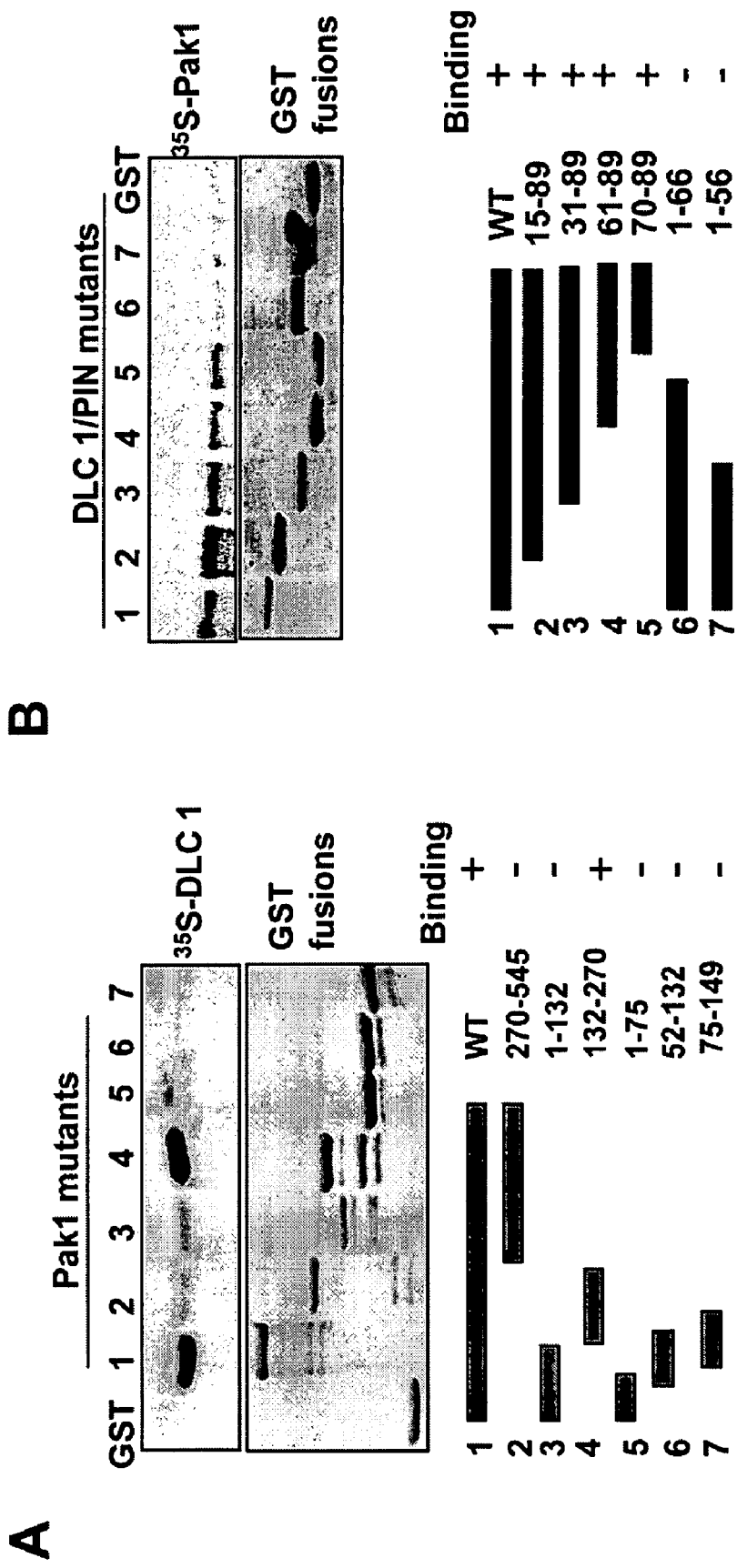
FIGS. 2A–2G—MapDLC1/PINg of interaction domains of Pak1 and DLC1/PIN.
Figure 2:
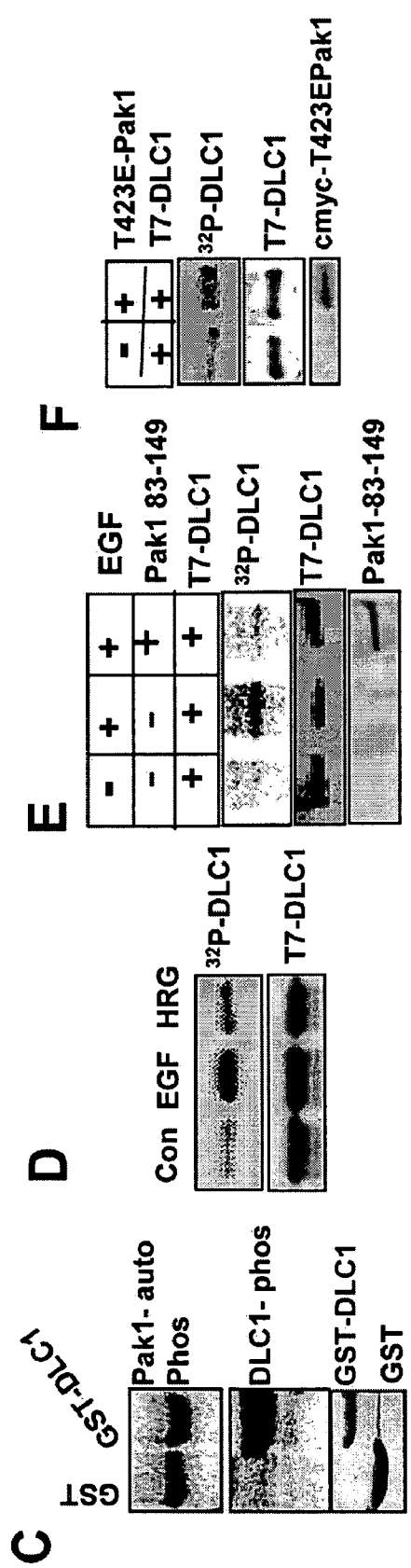
Figure 2:
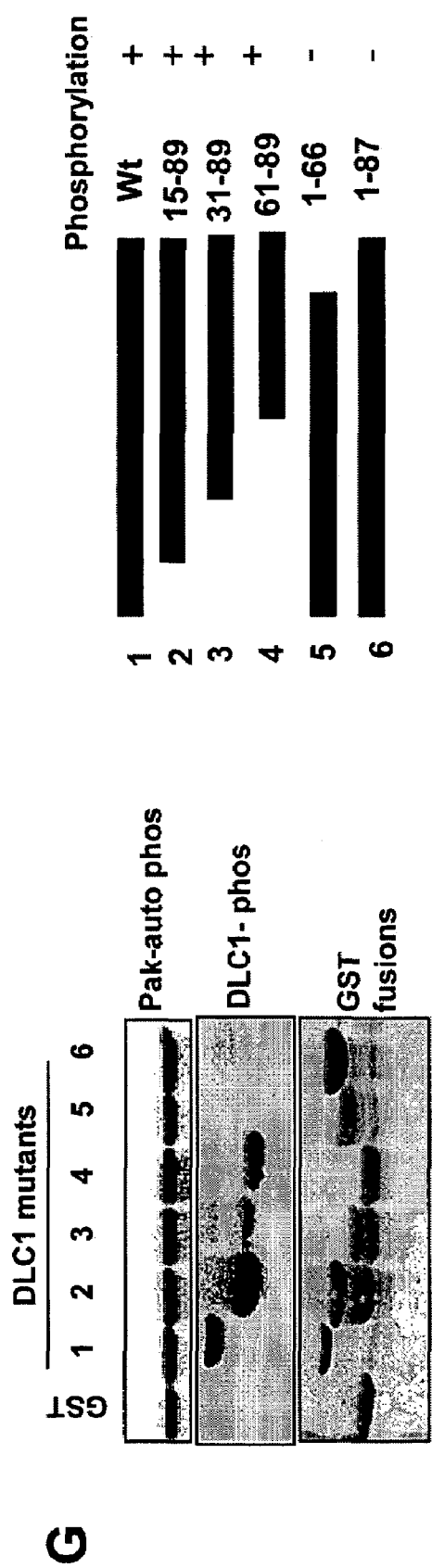

DLC1/PIN interacts with Pak1 via its C-terminal region. The inventors next mapped the DLC1/PIN binding site of Pak1 using GST fusion of various domains of Pak1 (FIG. 2A). Results showed that the Pak1 region consisting of amino acids 132–270 but not amino acids 1–132 efficiently interacted with DLC1/PIN. Furthermore, the Cdc42/Rac-interacting (CRIB) domain (amino acids 75–149) and Pak1 auto inhibitory domain (amino acids 53–132) did not interact with DLC1/PIN, suggesting that the binding site for DLC1/PIN is localized to amino acids 150–270 of Pak1. To identify the minimal region of DLC1/PIN required for its interaction with Pak1, the inventors generated a series of DLC1/PIN deletion mutant constructs. As illustrated in FIG. 2B, the Pak1 binding site in DLC1/PIN was localized within the C-terminal 19 amino acids.

DLC1/PIN is a physiologic substrate of Pak1. To determine whether DLC1/PIN is a substrate of Pak1, the inventors next performed in vitro kinase assays using GST-DLC1/PIN and purified Pak1 enzyme. The Pak1 enzyme efficiently phosphorylated DLC1/PIN (FIG. 2C). To next examine the possibility that DLC1/PIN could be phosphorylated in vivo by physiological signals, which activate Pak1. Since commercially available DLC1/PIN antibodies are not suitable for immunoprecipitation, the inventors have used ZR75 clones stably expressing T7 tagged DLC1/PIN. Cells were serum starved, metabolically labeled with 32P-orthophosphate and treated with EGF or HRG and T7-DLC1/PIN was immunoprecipitated. Autoradiogram showed substantial increase in the level of phosphorylation of DLC1/PIN in growth factor treated cells (FIG. 2D). To examine the role of Pak1 in growth factor mediated phosphorylation of DLC1/PIN, the inventors have used Pak1 auto inhibitory fragment as an inhibitor (Pak1 amino acids 83–149). Results show that EGF treatment stimulated DLC1/PIN phosphorylation in a Pak1-sensitive manner as it was completely blocked by coexpression of Pak1 autoinhibitory fragment amino acids 83–189 (FIG. 2E). The inventors next examined if expression of constitutively actvated Pak1 (PakT423E) into cells mimic growth factor mediated phosphorylation of DLC1/PIN. MCF-7 cells were cotransfected with the T7-tagged DLC1/PIN and myc-tagged constitutively active T423E Pak1, and then the cells were labeled with 32P-orthophoric acid. Immunoprecipitation of DLC1/PIN with an anti-T7 monoclonal antibody showed increased phosphorylation of DLC1/PIN in cells expressing T423E Pak1 (FIG. 2F). To map the phopshorylation site of Pak1 kinase in DLC1/PIN, the inventors performed in vitro kinase assays using a number of DLC1/PIN deletions. GST fusion containing the C-terminal 19 amino acids of DLC1/PIN was efficiently phosphorylated by Pak1, suggesting a putative site in the C-terminal region. Analysis of the C-terminal 19 amino acids sequence revealed one serine at amino acid 88. Deletion of Ser88 of DLC1/PIN completely abolished the ability of the Pak1 to phosphorylate DLC1/PIN (FIG. 2G).

Together, these results suggest that Pak1 can phosphorylate DLC1/PIN on Ser 88 and that DLC1/PIN is a physiologic substrate of Pak1.

Figure 3:
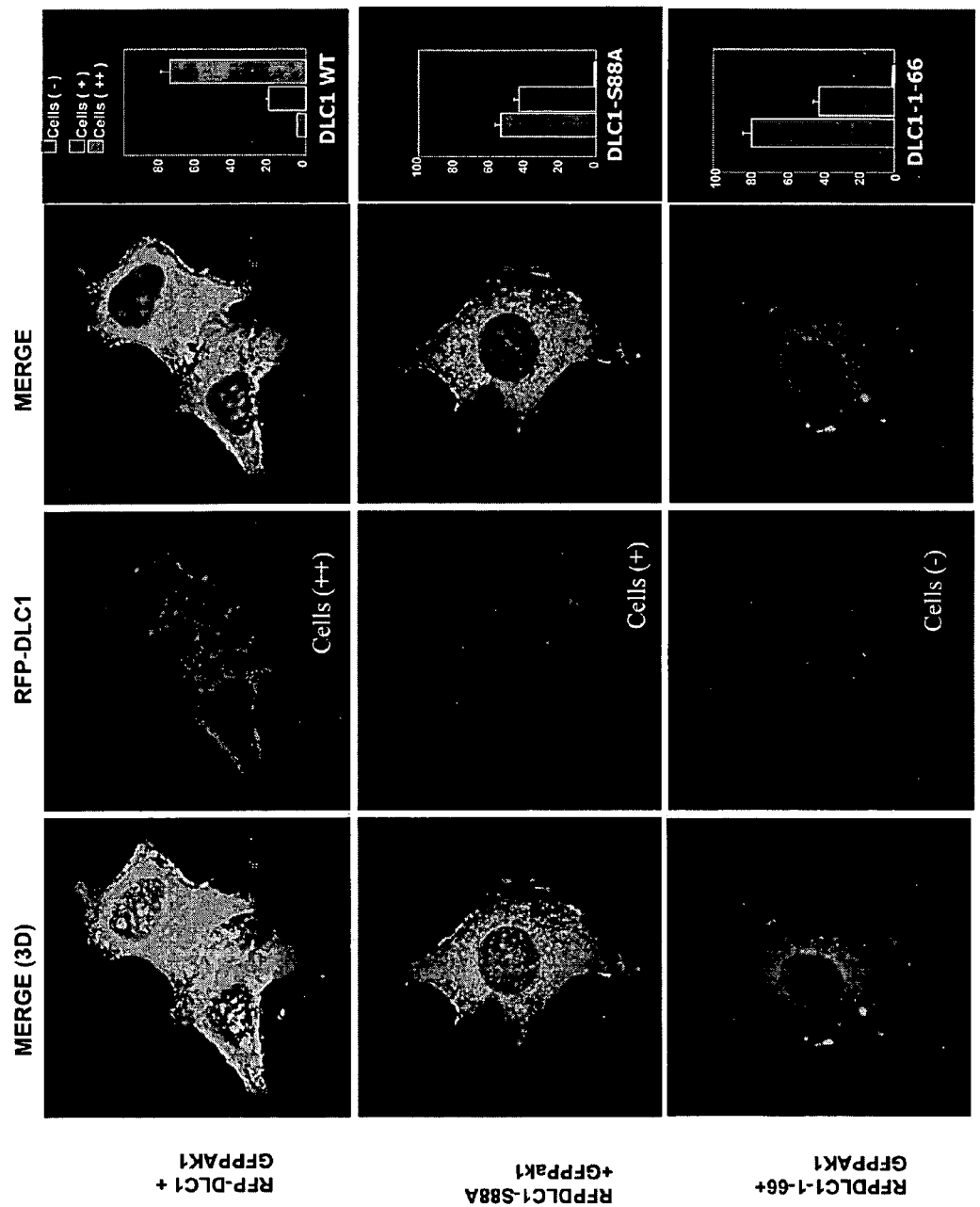
FIG. 3—Requirement of DLC1/PIN in Pak1 mediated macropinocytosis. SKBR-3 cells were cotransfected with RFP-DLC1/PIN and GFP-Pak1 (upper panel), RFP-DLC1/PIN-S88A, and GFP-Pak1 (middle panel) and RFP-DLC1-1-66, and GFP-Pak1 (lower panel). Vesicle formation and localization of GFP and RFP proteins were analyzed by confocal microscopy. Ten randomly selected fields were analyzed for each condition. The experiment was repeated twice with similar results. Quantitation of vesicles formation was done using the following scoring system. −, cells containing 0–9 vesicles; +, cells containing 10–20 vesicles; and ++, cells containing >20 vesicles.

Requirement of DLC1/PIN in Pak1 mediated macropinocytosis. Earlier studies suggested involvement of Pak1 in macropinocytosis (Dharmawardhane et al., 2000), to understand the significance of the noticed Pak1-DLC1/PIN interaction on Pak1 mediated macropinocytosis; the inventors next explored the potential involvement of DLC1/PIN in Pak-mediated macropinocytosis usining DLC1/PIN mutants. The inventors have used the fluorescein isothiocyanate (FITC)-labeled Dextran as a marker of endocytosis using a well-established dextran beads uptake assay (Dharmawardhane et al., 2000). Coexpression of GFP-tagged Pak1 and RFP-tagged DLC1/PIN in SKBR3 cells resulted in a profound stimulation of the vesicular structures containing GFP-Pak1 (green) and RFP-DLC1/PIN (red) at the cell periphery (FIG. 3, reconstructed confocal images in the left panel). To investigate the contribution of Pak1 phosphorylation of Ser 88 on DLC1/PIN, these studies were repeated with RFP-tagged DLC1/PIN mutants lacking either Pak1-phosphorylation site Ser88 (FIG. 3, middle panel), Pak1-binding site or both (FIG. 3, lower panel). Results showed that the DLC1/PIN lacking the phosphorylation site substantially interfered with Pak1-induced vesicle formation and that DLC1/PIN lacking both the phosphorylation and binding sites for Pak1 completely blocked the formation of vesicles in SKBR-3 cells in more than 80% of the transfected cells. These findings suggested that Pak1 phosphorylation of and interaction with DLC1/PIN plays an essential role in macropinocytosis.

Figure 4:
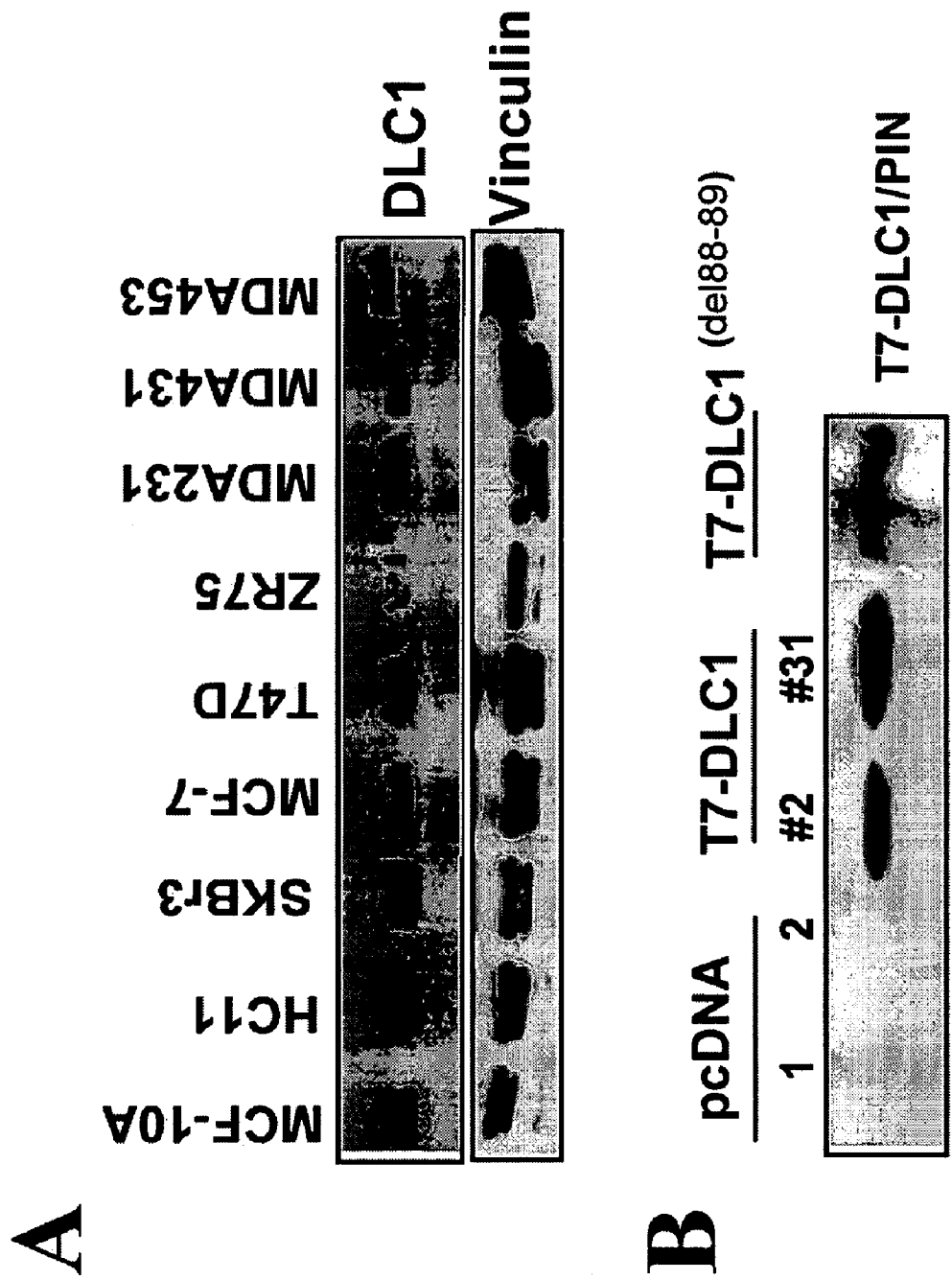
FIGS. 4A–4E—Effect of DLC1/PIN expression on cell motility.
Figure 4:
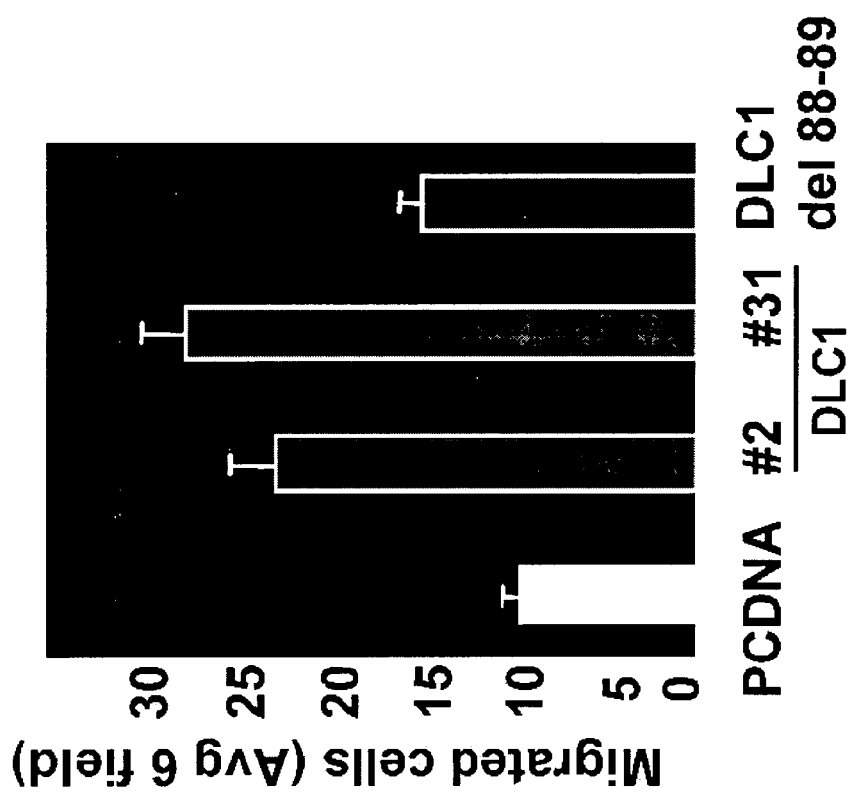
Figure 4:
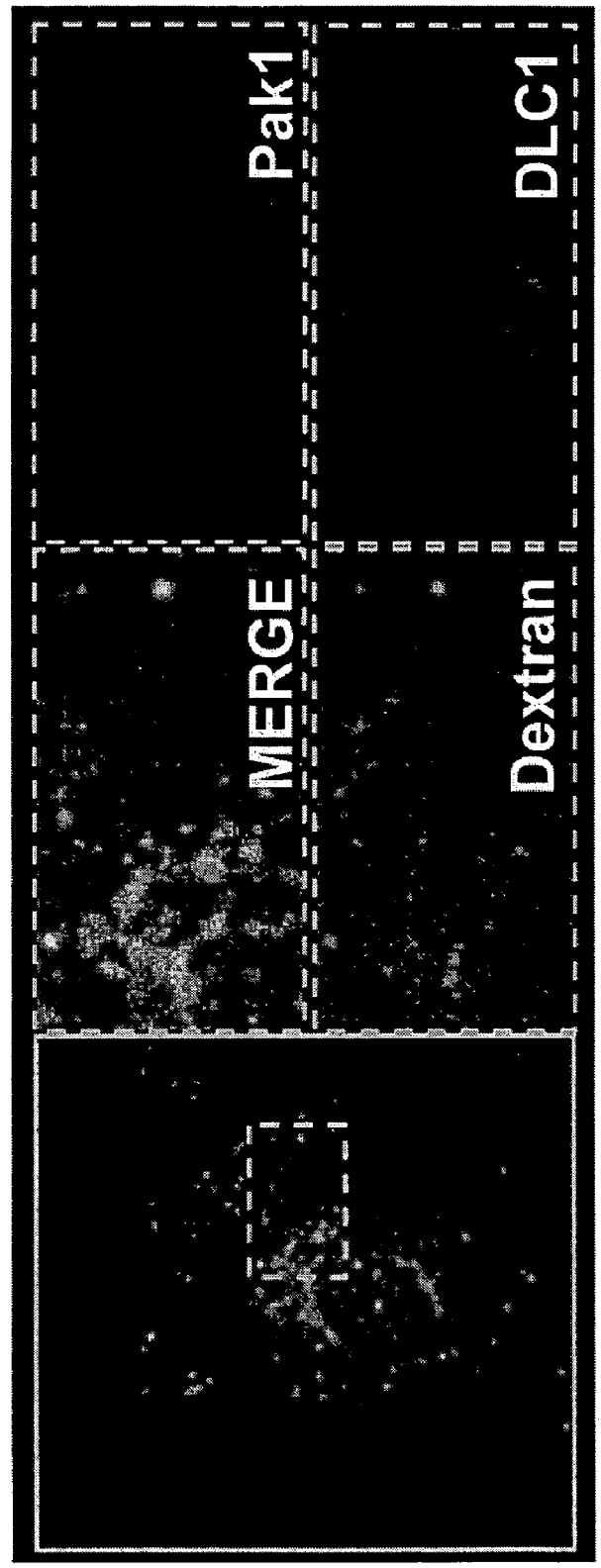
Figure 4:
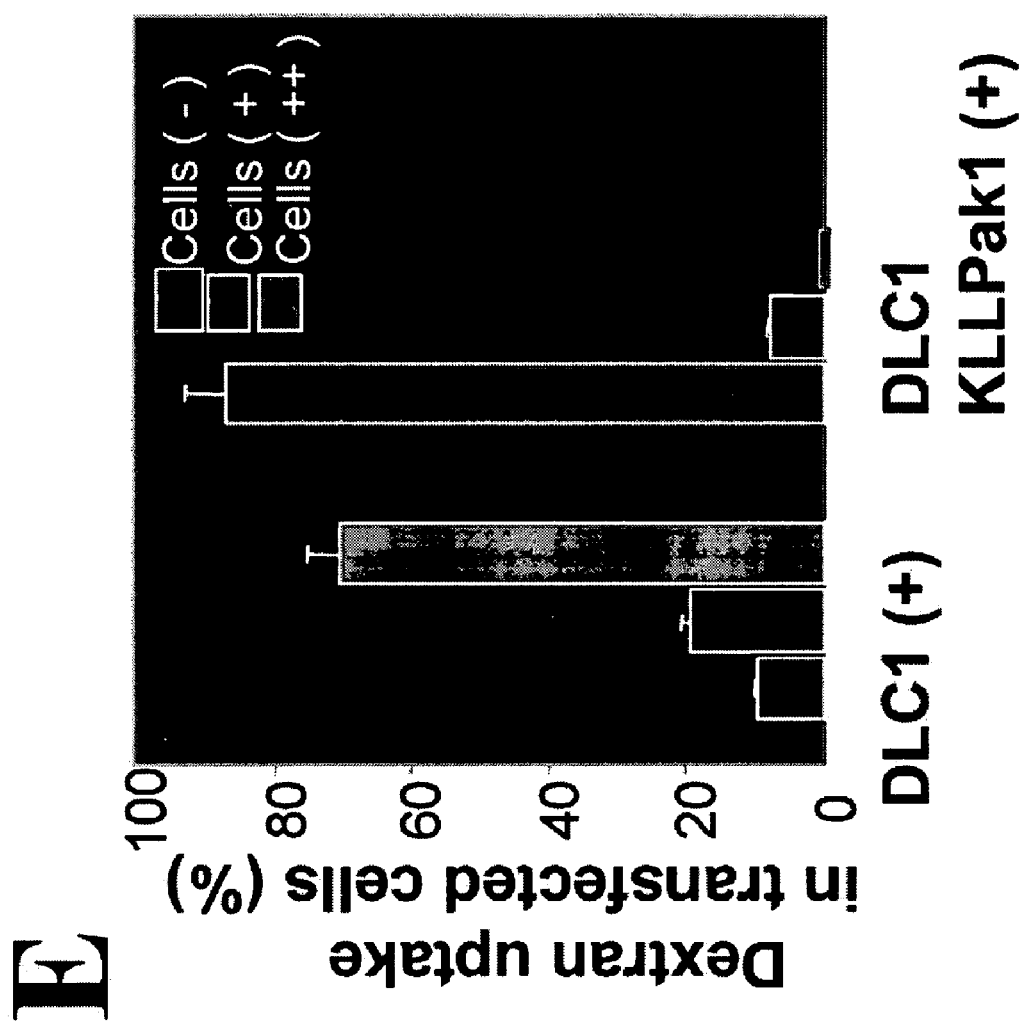

DLC1/PIN regulation of cell motility. To further delineate the potential effects of DLC1/PIN on the biology of breast cancer cells, the inventors examined the status of DLC1/PIN expression in a number of breast cancer cell lines. Breast cancer cells exhibited higher levels of DLC1/PIN than did non-tumorigenic breast cell lines, such as MCF10A and HC11 (FIG. 4A). Since the ZR75 showed low levels of DLC1/PIN expression than did other breast cancer cell lines, the inventors next established stable ZR75 clones expressing T7-tagged wild type DLC1/PIN or mutant DLC1/PIN$^{del\ 88-89}$ or control vector (FIG. 4B). These clones expressed DLC1/PIN levels two to three-fold than the endogenous level of DLC1/PIN. Transient stimulation of macropinocytosis by growth factors has been implicated to have a role in directional motility via flow generating force for cell locomotion (Thompson and Bretscher, 2002; Bretscher and Aguado, 1998). Earlier studies have also shown that Pak1 affects cell motility and its kinase activity is important for directional motility (Sells et al., 2000). Since Pak phosphorylated DLC1/PIN, the inventors next assayed the migratory potential of ZR 75 cells expressing DLC1/PIN wild type or DLC1/PIN$^{(del\ 88-89)}$ mutants using Boyden Chamber assays using NIH3T3 conditioned medium as a stimulus for directional migration (Bagheri et al., 2001). Breast cancer cells expressing wild type DLC1/PIN exhibited increased migratory potential, while deletion of Pak1 phosphorylation site in DLC1/PIN (DLC1/PIN$^{del\ 88-89}$) abolished DLC1/PIN mediated increase in the migratory potential (FIG. 4C).

Since DLC1/PIN is an integral part of dynein motor which is shown to have an important role in endocytosis, the inventors next examined role of Pak1 in DLC1/PIN mediated enodocytosis using FITC dextran bead assay. ZR75/RFP-DLC1 cells which stably expressing wild type red florescent tagged DLC1/PIN protein (RFP-DLC1/PIN) were incubated with FITC-dextran beads. After twenty minutes, cells were fixed with methanol and stained for endogenous Pak1 (blue), RFPDLC1/PIN (red) and FITC-dextran (green). One reproducible representative example is shown as a merged image in FIG. 4D, left panel. An inset corresponding to the cytoplasmic region toward the periphery of the cell also shows the partial colocalization of the three colors as white vesicles (due to co localization of pixels from Pak1 [blue], DLC1/PIN [red] and dextran [green]. To determine whether the noticed endocytosis of dextran beads is dependent on the Pak1 activation, the inventors expressed kinase-dead K299RLL-Pak1 into ZR75/FP-DLC1/PIN cells and then added FITC-detxtran particles to the cultures. The cells were stained for myc-tagged-K299LLPak1 and analyzed by confocal microscopy. The results showed that inhibition of the Pak1 pathway completely blocked the internalization of FITC dextran particles (green) as well as REP-DLC1/PIN-mediated vesicle formation in more than 90% of the cells expressing myc-K299RLL (blue) (FIG. 4E).

Figure 5:
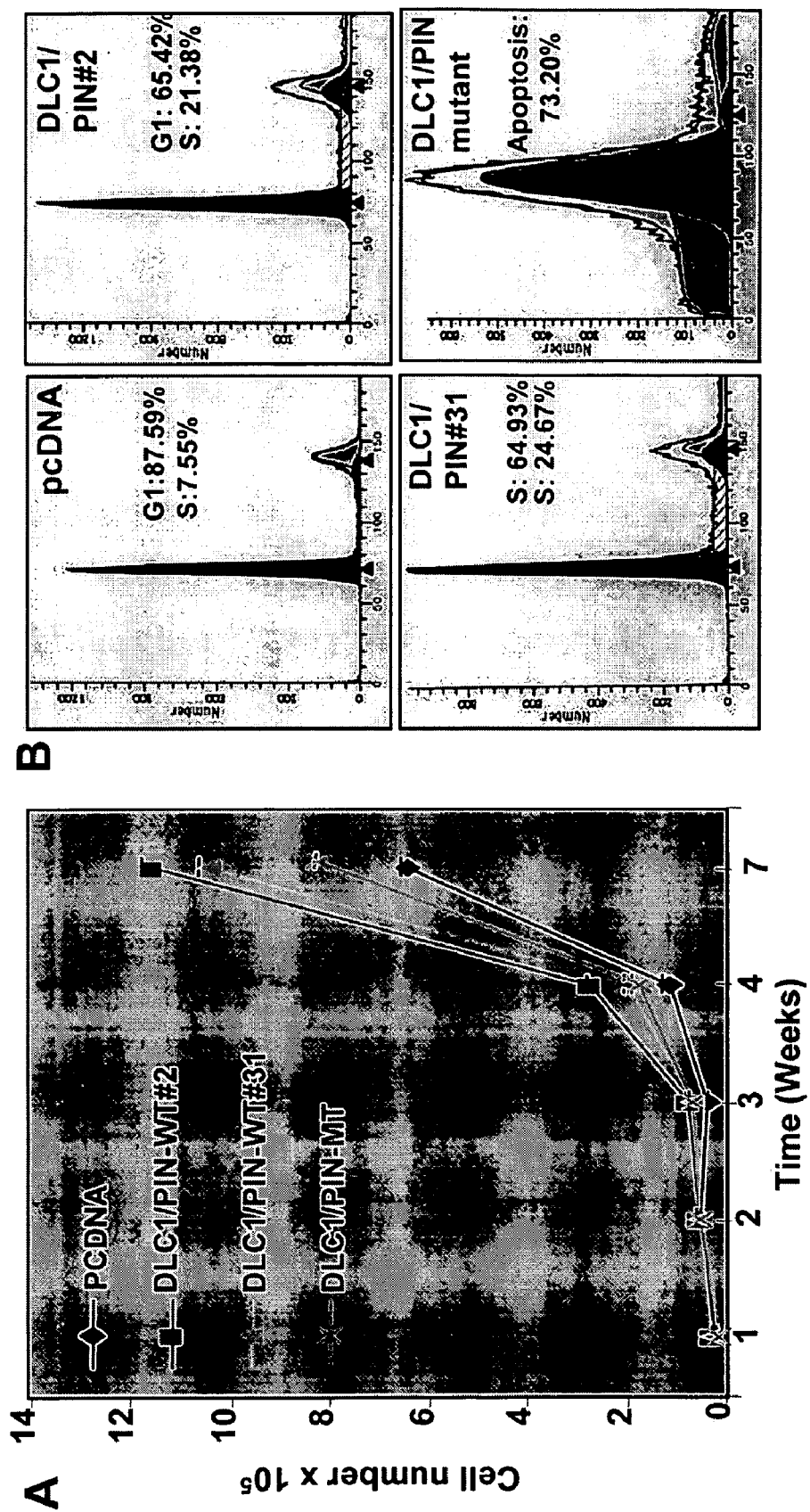
FIGS. 5A–5C—Requirement of DLC1/PIN and Pak1 interaction in cell proliferation and survival.
Figure 5:
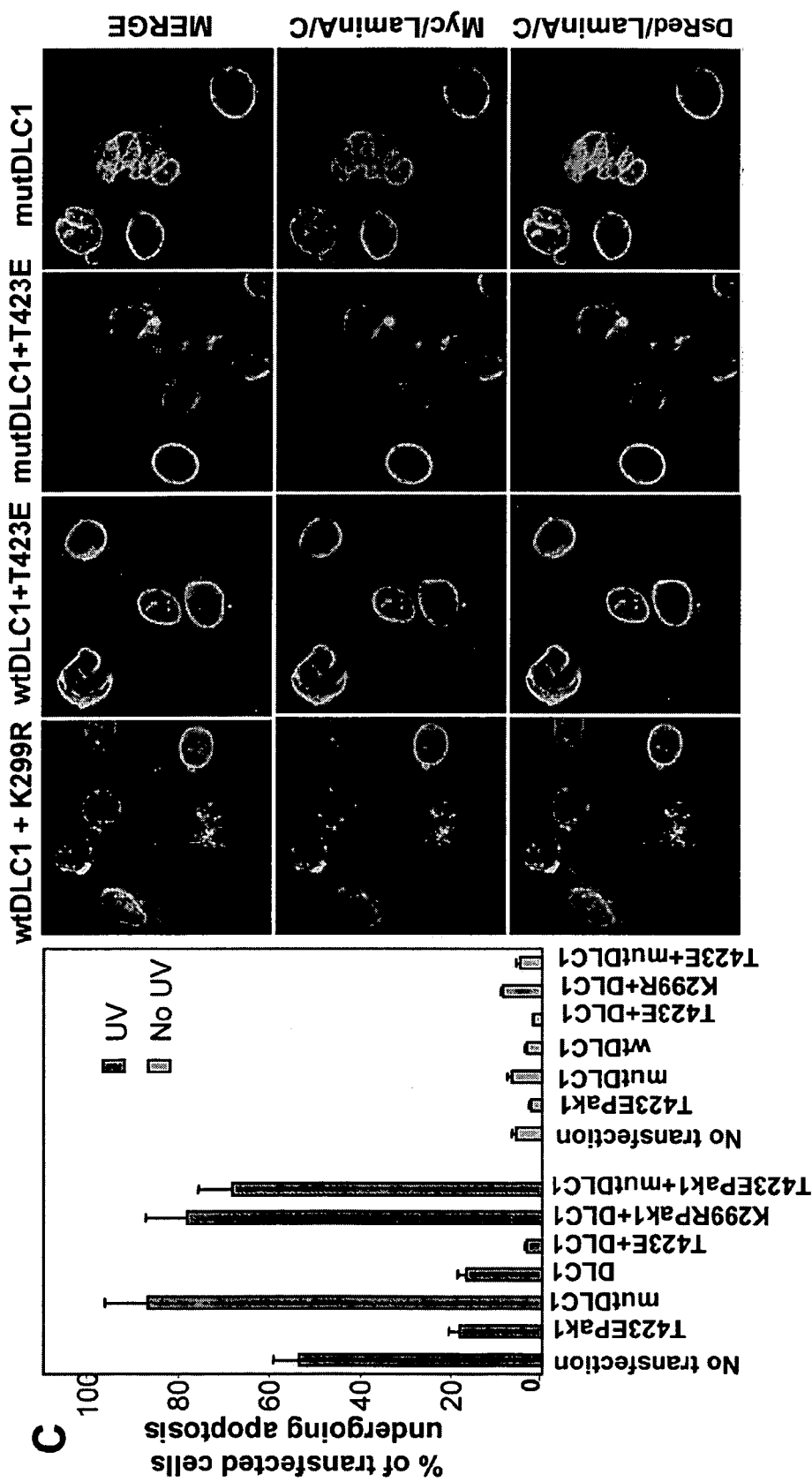

DLC1/PIN regulation of cell growth and survival. In addition to cell motility, Pak1 is also shown to have a role in cell growth and survival (Schurmann et al., 2000; Vadlamudi et al., 2000). DLC1/DLC1/PIN has also been shown to promote cell survival (Puthalakath et al., 1999; Chang et al., 2000). The inventors therefore examined if Pak1 and DLC1/PIN interaction have a role in cell growth and cell survival pathways. Interestingly, enhanced DLC1/PIN expression increased the proliferation rate of the ZR75 cells (FIG. 5A). The increased proliferation of the ZR75 cells could have reflected either an increased proliferation rate or protection of the cells from apoptosis. FACS analysis of serum-starved ZR75 clones revealed that deregulation of wild type DLC1/PIN but not mutant DLC1/PIN$^{(del\ 88-89)}$ was accompanied by increased G1-S progression of breast cancer cells. Interestingly, ZR75 cells expressing DLC1/PIN$^{(del\ 88-89)}$ exhibited a significant increase in the cells in pre-Go phase of the cell cycle. (FIG. 5C). These findings provided clues about a potential role of Pak1-mediated DLC1/PIN phosphorylation in optimal cell survival, and interference with this Pak1-DLC1/PIN pathway might trigger spontaneous apoptosis. Earlier studies have shown that Pak family kinases protects murine NIH3T3 cells from UV-induced apoptosis (Roig and Traugh, 1999; Jakobi et al., 2001). Using this well-established model system, the inventors next investigated the potential role of Pak1-DLC1/PIN interaction in protecting NIH3T3 cells against UV-induced apoptosis. NIH3T3 cells were co-transfected with RFP-tagged DLC or DLC1/PIN T88A mutant and catalytically active Pak1 (T7-T423E Pak1) or kinase-dead Pak1 (T7-K299LL Pak1), and cells were exposed to UV-irradiation. After 10 h, apoptosis was quantitated by scoring the integrity of the nuclear membrane in cells expressing both RFP and myc tags to detect DLC/DLC1/PIN and Pak1 respectively (FIG. 5D). Our results indicated that UV-induced apoptosis was substantially reduced in cells expressing DLC1/PIN or catalytically active Pak1 but not S88A DLC1/PIN or kinase-dead Pak1 and their combination (FIG. 5D). Interestingly, overexpression of active Pak1 was unable to protect the cells transfected with the mutant T88A DLC1/PIN. Similarly, overexpression of DLC1/PIN also failed to protect the NIH3T3 cells overexpressing the kinase-dead Pak1 from UV-induced apoptosis (FIG. 5D). Since DLC1/PIN is known to interact and sequester proapoptotic BimL in the cytoplasm (Puthalakath et al., 1999), and because the inventors have now demonstrated that Pak1 phosphorylates DLC1/PIN in the interacting region, these findings suggest a mechanistic role of DLC1/PIN Ser 88 phosphorylation in conferring a survival advantage to the cells. In brief, these findings suggested that DLC1/PIN and Pak1 cooperates in enhanced cell survival and consequently, increased growth-rate.

Figure 6:
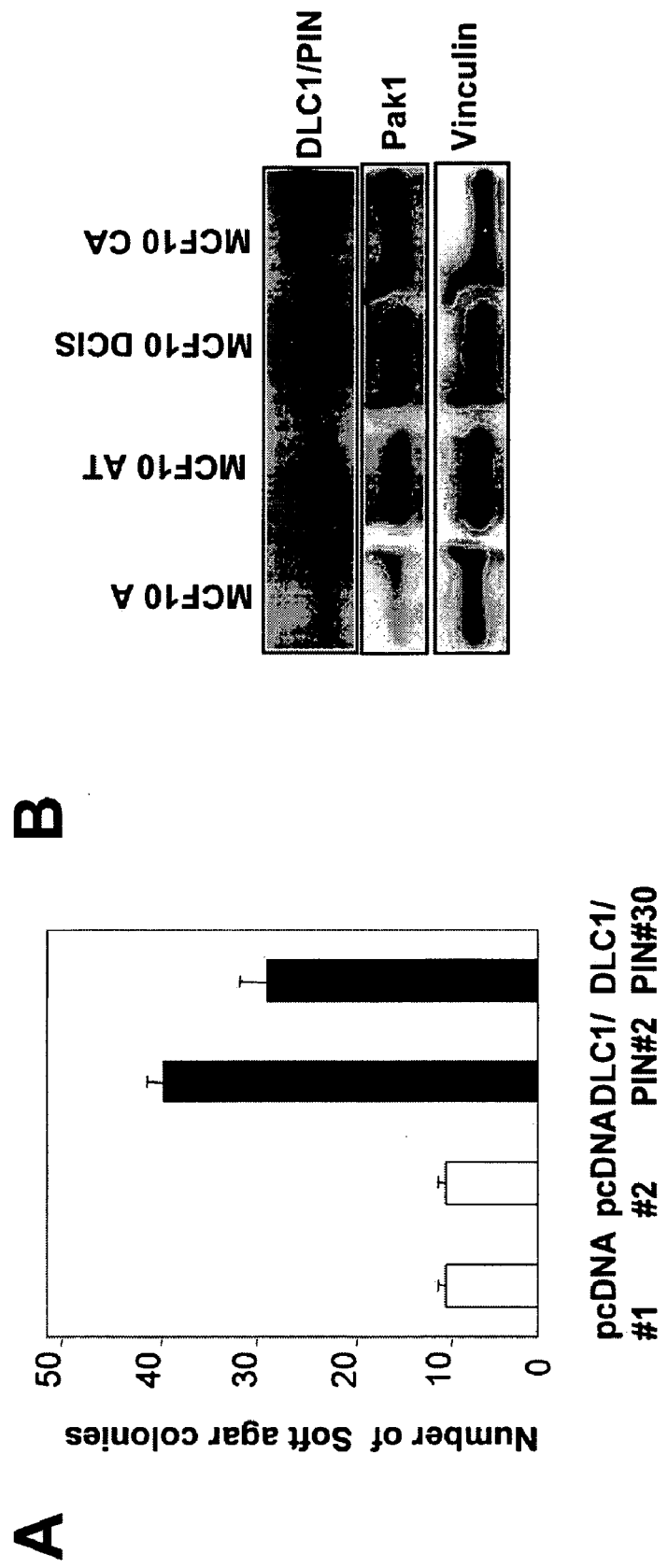
FIGS. 6A–6E—DLC1/PIN overexpression potentiates anchorage-independent growth and promotes tumorigenesis.
Figure 6:
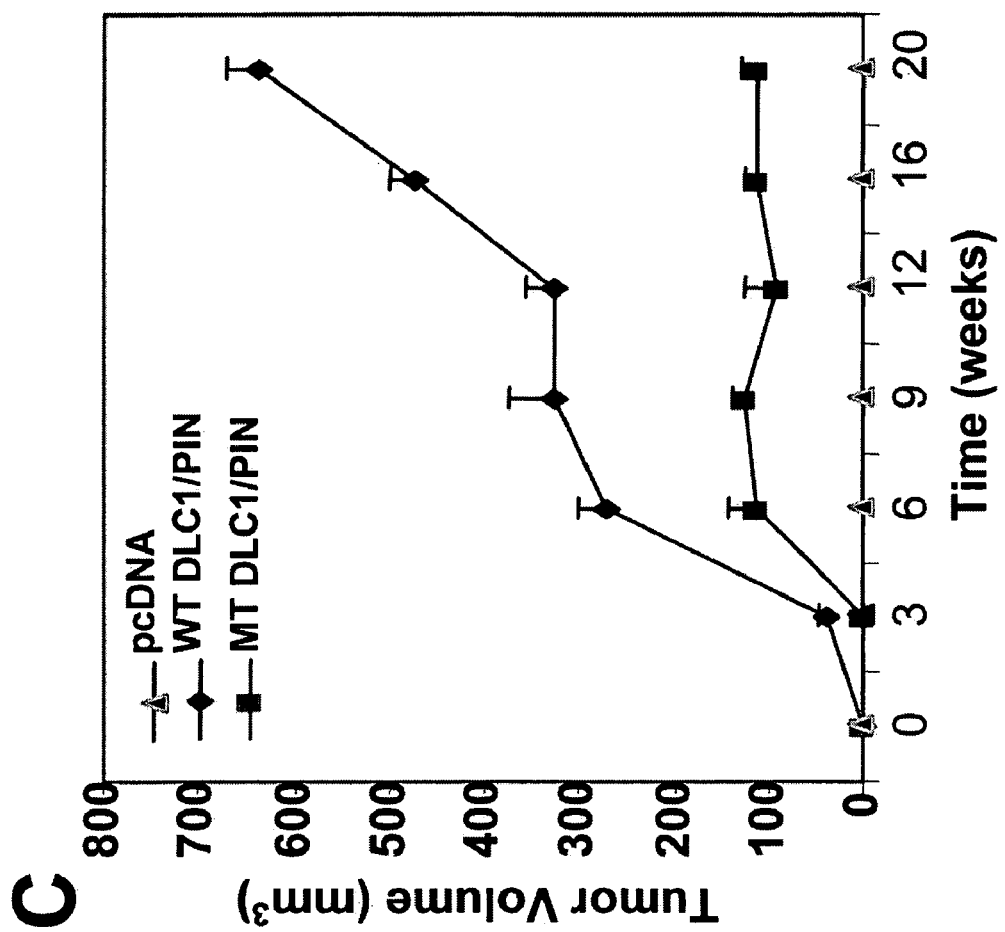
Figure 6:
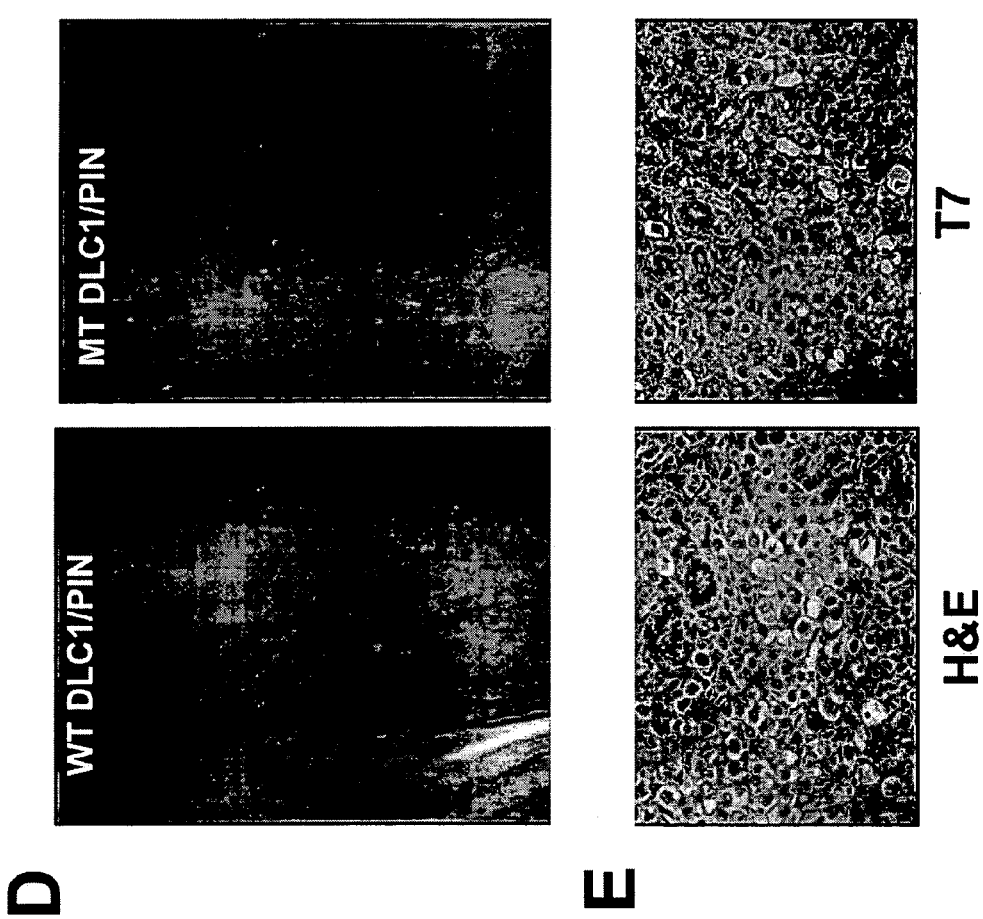

DLC1/PIN overexpression promotes tumorigenesis. Because DLC1/PIN expression promotes enhanced G1-S transition as well as cell survival (FIGS. 6A and 6B) and because Pak1 overexpression is known to support the anchorage independent growth of breast cancer cells (Vadlamudi et al., 2000a; 2000b), the inventors examined the ability of the ZR75-DLC1/PIN1 cells to grow in an anchorage-independent manner. DLC1/PIN expression substantially enhanced the number of colonies in soft agar (FIG. 6A).

To examine the potential correlation of DLC1/PIN deregulation with the progression of breast cancer to more invasiveness, the inventors have analyzed the DLC1/PIN expression in lysates from exponentially growing cell lines derived from MCF10AT model system. This model contains a spectrum of cell lines, which allows examining the expression of genes during the progression of breast malignancy (Santner et al., 2001; Heppner et al., 2000). The results in FIG. 6B shows a clear progressive upregulation of DLC1/PIN expression as a function of tumorigenesis. As expected from earlier studies, Pak1 expression was also deregulated in MCF10A malignant cells compared to control MCF10A cells. Consistent with the aggressive growth characteristics of the DLC1/PIN-expressing breast cancer cells, the ZR/DLC1/PIN cells (clones #2) exhibited increased tumorigenic potential in nude mice in the absence of any exogenous estradiol treatment (FIG. 6C). Interestingly, DLC1/PIN mutant lacking Pak1 phosphorylation site did not exhibited any tumorigenic potential in nude mice (FIG. 6C). The DLC1/PIN clonal cell origin of tumors was confirmed by staining the cells with an anti-T7 monoclonal antibody (FIG. 6D). These findings suggested the existence of a close relationship between DLC1/PIN deregulation, and phosphorylation and tumorigenesis.

Figure 7:
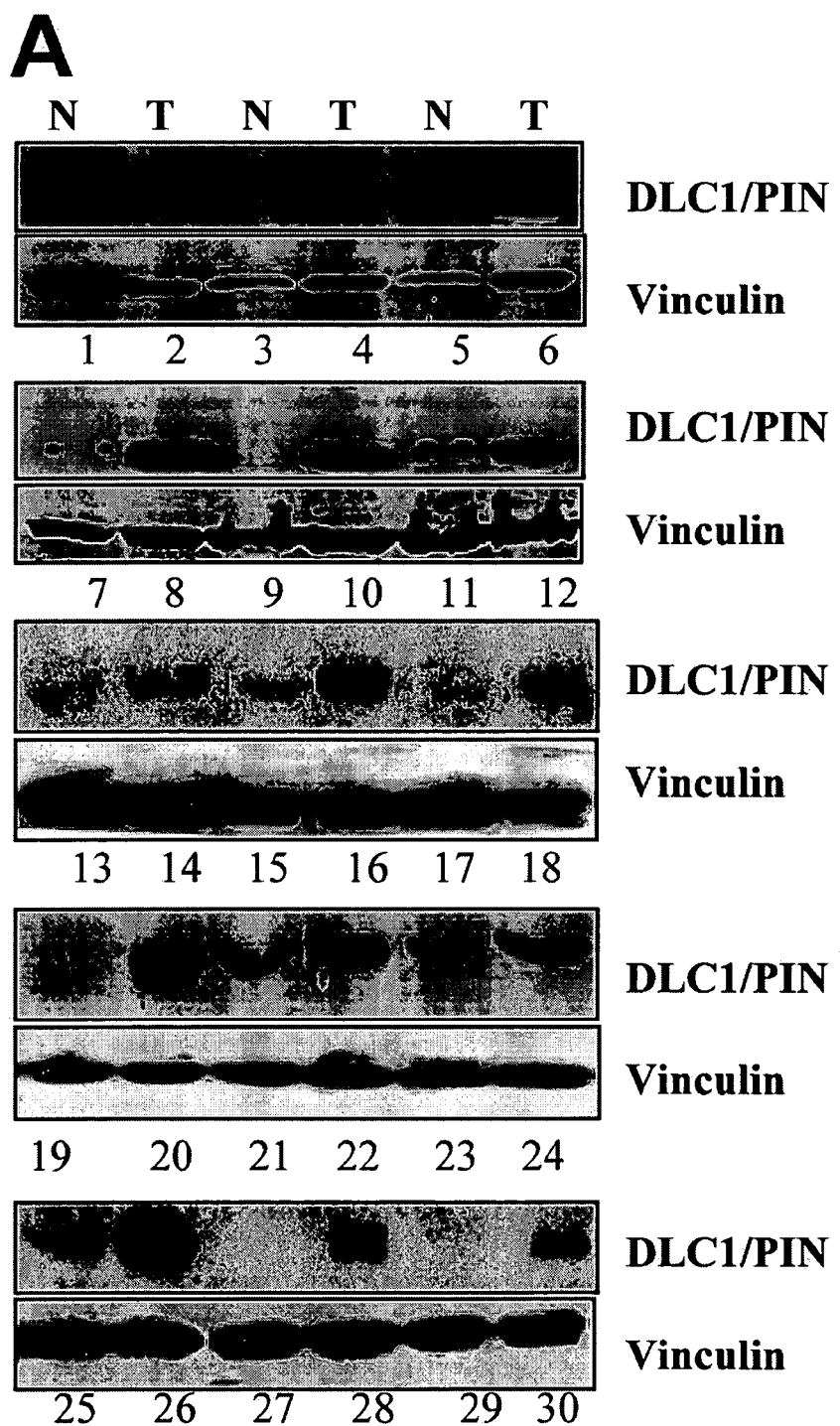
FIGS. 7A–7C—DLC1/PIN expression is deregulated in breast tumors.

The inventors next examined the level of DLC1/PIN in 15-paired samples of human breast tumors and adjacent normal-appearing tissues. The status of DLC1/PIN expression was considerably higher in 14 of 15 breast tumor specimens than it was in adjacent normal tissues (FIGS. 7A and 7B). The anti–DLC1/PIN antibody used here also works well in formalin-fixed paraffin-embedded human breast tissues, as shown in a representative DLC1/PIN immunohistochemical in FIG. 7B. Together, results from FIGS. 6–7 suggested that deregulation of DLC1/PIN and Pak1 may be a common event in breast cancer progression, and that these molecules may be involved in the development and/or maintenance of the malignant phenotypes in breast tumors.

Thus, the inventors have shown herein that Pak1 interacts with DLC1/PIN and that such interactions are essential for cell cycle progression and survival functions. Accordingly, overexpression of DLC1/PIN substantially increases the growth potential of the breast cancer cells, allowing the cells to survive in an anchorage-independent manner, thus increasing the tumorigenic potential of breast cancer cells. DLC1/PIN expression levels were also higher in breast tumors than in normal control specimens, suggesting that DLC1/PIN has a role in tumorigenesis. Therefore, DLC1/PIN is an interacting substrate of Pak1, DLC1/PIN is overexpressed in human breast cancers, and Pak1 phosphorylation of DLC1/PIN on Ser 88 plays a critical role in tumorigenic phenotypes of DLC1/PIN in breast cancer cells.

Identification of DLC1-interaction Proteins. To identify novel proteins that interact with DLC1 in the presence or in the absence of Pak1 phosphorylation, the present inventors utilized three exemplary but distinct DLC1 baits to pull down binding proteins.

(a) WT DLC1-wild type natural DLC1;

(b) DLC1S88A-DLC1 mutant which can be phosphorylated by Pak1; and (C) DLC1S88E, Dlc1 mutant which mimics Pak1 phosphorylated form of DLC1.

Table 4 demonstrates those proteins or fragments thereof that interact with DLC1 in the presence or absence of Pak1 phosphorylation. DLC1/PIN may have a therapeutic role in interfering with the function of the known and novel proteins in Table 4, particularly whose functions occurs via their interactions with DLC.

TABLE 4

List of DLC1-Binding proteins identified by GST-pull down and Mass Spec analysis

| GenBank # | Name of the bait used | Name of the gene |
| --- | --- | --- |
| BC045609 | WT DLC1 | New gene/hypothetical protein FLJ20294 |
| CAA71668 | WT DLC1 | Nuclear DNA Helicase II |
| AAH53558 | WT DLC1/DLC1 S88A | Myosin 1B |
| Q8IX03 | WT DLC1 | KIBRA |
| O14974 | WT DLC1 | Myosin phosphatase target subunit 1 |
| Q86TA0 | WT DLC1 | New gene |
| T00259 | WT DLC1 | New gene/hypothetical protein KIAA0477 |
| AAF23231 | WT DLC1/DLC1 S88A | NP-94/Ciz1 |
| Q9H4E9 | WT DLC1 | Gephyrin |
| Q9H3U1 | WT DLC1 | SMAP-1b |
| EF2_HUMAN | WT DLC1 | Elongation Factor 2 |
| Q8WXE4 | WT DLC1 | LIP1 |
| HS9B_HUMAN | WT DLC1 | HSP90-beta (HSP 84) |
| HS9A_HUMAN | WT DLC1 | HSP90-alpha (HSP 86) |
| RS9_HUMAN | WT DLC1 | Ribosomal protein 9 |
| S55916 | WT DLC1 | Ribosomal protein 5 |
| R3RT7 | WT DLC1 | Ribosomal protein 7 |
| H12_HUMAN | WT DLC1 | Histone H1.2 |
| H13_HUMAN | WT DLC1 | Histone H1.3 |
| AAH00452 | WT DLC1 | Peroxiredoxin 2, isoform a |
| Q9BTS0 | WT DLC1 | RAP2C |
| R5RT11 | DLC1 S88A | Ribosomal protein L11 |

TABLE 4-continued

List of DLC1-Binding proteins identified by GST-pull down and Mass Spec analysis

| GenBank # | Name of the bait used | Name of the gene |
|---|---|---|
| EF1B_HUMAN | DLC1 S88A/S88E | Elongation factor 1-beta |
| Q9BVK5 | DLC1 S88A | Cyclophilin B |
| A29132 | DLC1 S88E | ADP,ATP carrier protein T2 |
| S03894 | DLC1 S88E | ADP,ATP carrier protein T3 |
| AAA36597 | DLC1 S88E | Scar protein |
| AAA61223 | DLC1 S88E | ADP,ATP carrier protein |
| G01789 | DLC1 S88E | Citrate transporter protein |
| CAA65633 | DLC1 S88E | Citrate transporter protein |
| R5HU7 | DLC1 S88E | Ribosomal protein L7 |
| DHCA_HUMAN | DLC1 S88E | NADPH-dependent Carbonyl Reductase 1 |

Use of DLC1-Liposomal formulation as an anti-HIV agent. Since DLC1 peptide is 67% hydrophobic, the present inventors developed an effective liposomal formulation that allows the easy delivery of the DLC1 peptide to cells without solubility problems. A DLC1 liposomal formulation can be used to reduce, inhibit, or block some or all of the functions, known or unknown, described herein.

Figure 8:
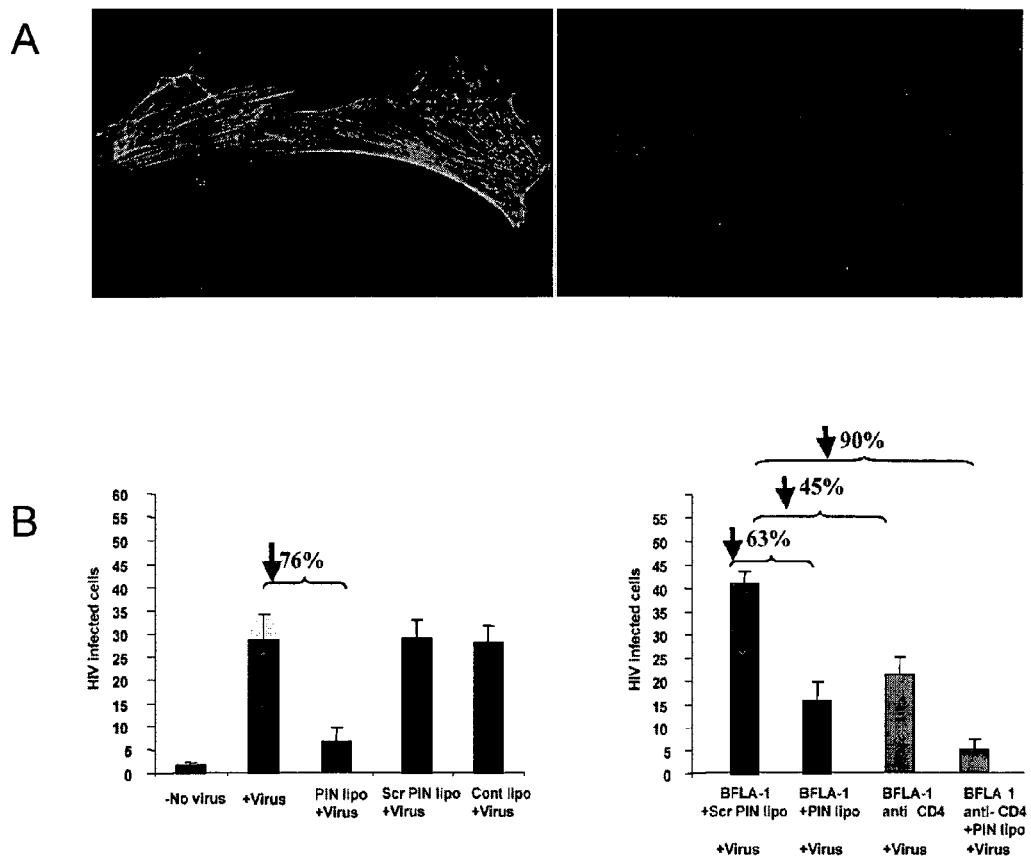
FIGS. 8A–8B—Functionality of DLC1-liposomal formulation and its effectiveness in blocking HIV infection.

The present inventors established that liposomal-DLC1 is effective in delivering DLC1 peptide in the cultured cancer cells, as measured by the monitoring of the intracellular biotin-staining (FIGS. 8A and 8B). In subsequent studies, this peptide was tested for its expected effectiveness in blocking HIV infection of HeLa/Magi cells. As a control, a scrambled DLC1-liposomal formulation and liposomal alone was utilized. Results indicated a clear inhibitory effect of liposomal-DLC1 peptide upon HIV infection. In FIG. 8A, there is delivery of the DLC1 peptide via liposomal formulation. To visualize the entry, the DLC1 peptide was labeled with biotin (red color). Actin staining was used as a marker of cell morphology (green color). FIG. 8B shows efficacy of DLC1-liposomal formulation to block entry of HIV virus via macropinocytosis.

Figure 9:
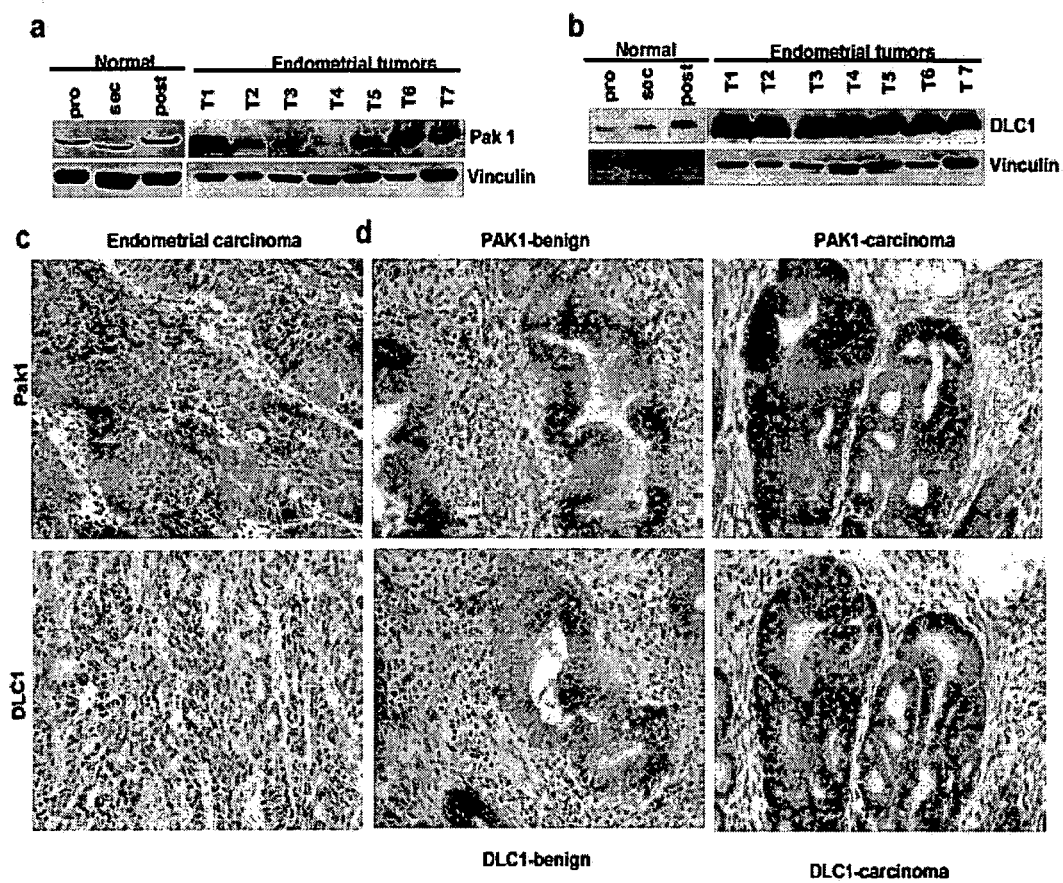
FIGS. 9A–9D—Expression of DLC1 and Pak1 in human endometrial tumors.

DLC1 deregulation promotes E2-induced tumorigenic phenotypes. FIGS. 9A and 9B illustrate expression of DLC1 and Pak1 in human endometrial tumors through western blot analysis. FIG. 9C provides immunohistochemical analysis and localization of Pak1 and DLC1 in endometrioid adenocarcinoma sections, whereas FIG. 9D shows immunohistochemical analysis and localization of Pak1 and DLC1 in normal and endometrial tumor sections of breast cancer patients exposed to tamoxifen.

Figure 10:
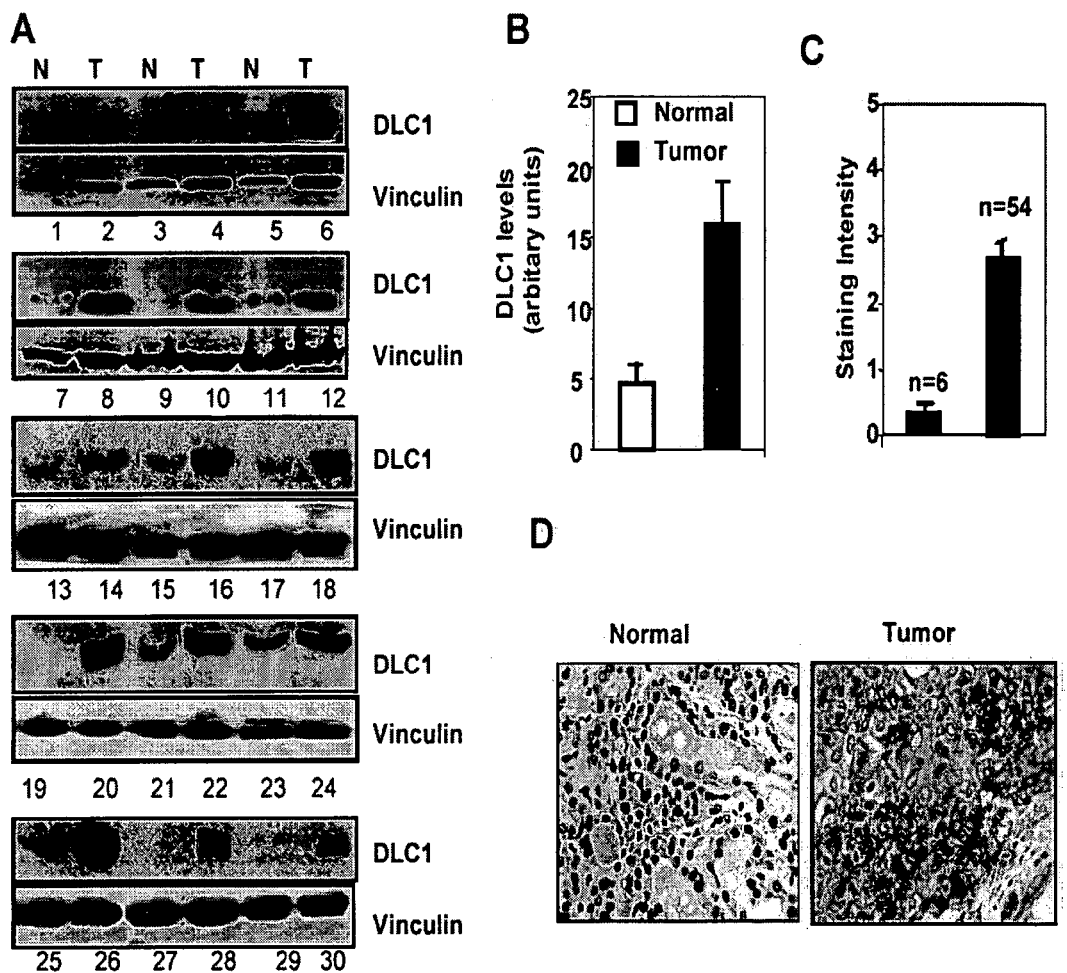
FIGS. 10A–10D—DLC1 deregulation in human breast tumors.

FIG. 10 demonstrates DLC1 deregulation in human breast tumors. In FIG. 10A, breast tumor lysates were analyzed by Western blot analysis for DLC1 expression (upper panel) and subsequently reprobed with a vinculin antibody as a loading control (middle panel). FIG. 10B provides quantitation of DLC1 expression in normal and tumor samples, and FIG. 10C shows immunohistochemical analysis of DLC1 in breast tissue samples. The left panel is normal mammary gland tissue, and the right panel represents tumors from the same patient. All tumors show very strong DLC1 immunoreactivity. FIG. 10D demonstrates quantitation of DLC1 expression in breast tumor array.

Figure 11:
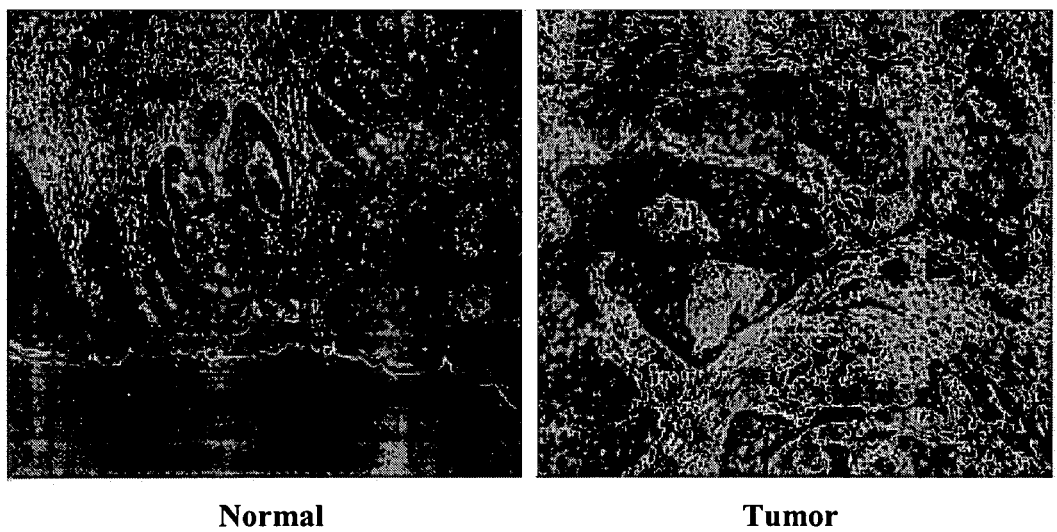
FIG. 11—Expression of DLC1 in normal tissue and cancers of head and neck.

Finally, FIG. 11 shows expression of DLC1 in normal tissue and cancers of head and neck.

Thus, the expression of DLC1 and Pak1 was widely increased in sporadic endometrial cancer, in endometrial tissue from breast cancer patients treated with tamoxifen, and in tamoxifen resistant breast cancer, ovarian and head and neck cancers. These findings reveal a previously unrecognized role of the Pak1-DLC1 pathway in the action of tamoxifen.

Therefore, in a specific embodiment, DLC1 or fragments or derivatives thereof, DLC1 peptide, DLC1 peptide liposomes, DLC1 mutant expression systems, or a combination thereof represent a novel therapeutic target for the control of tamoxifen resistance and the hormone independence of hormone responsive reproductive cancers.

Figure 12:
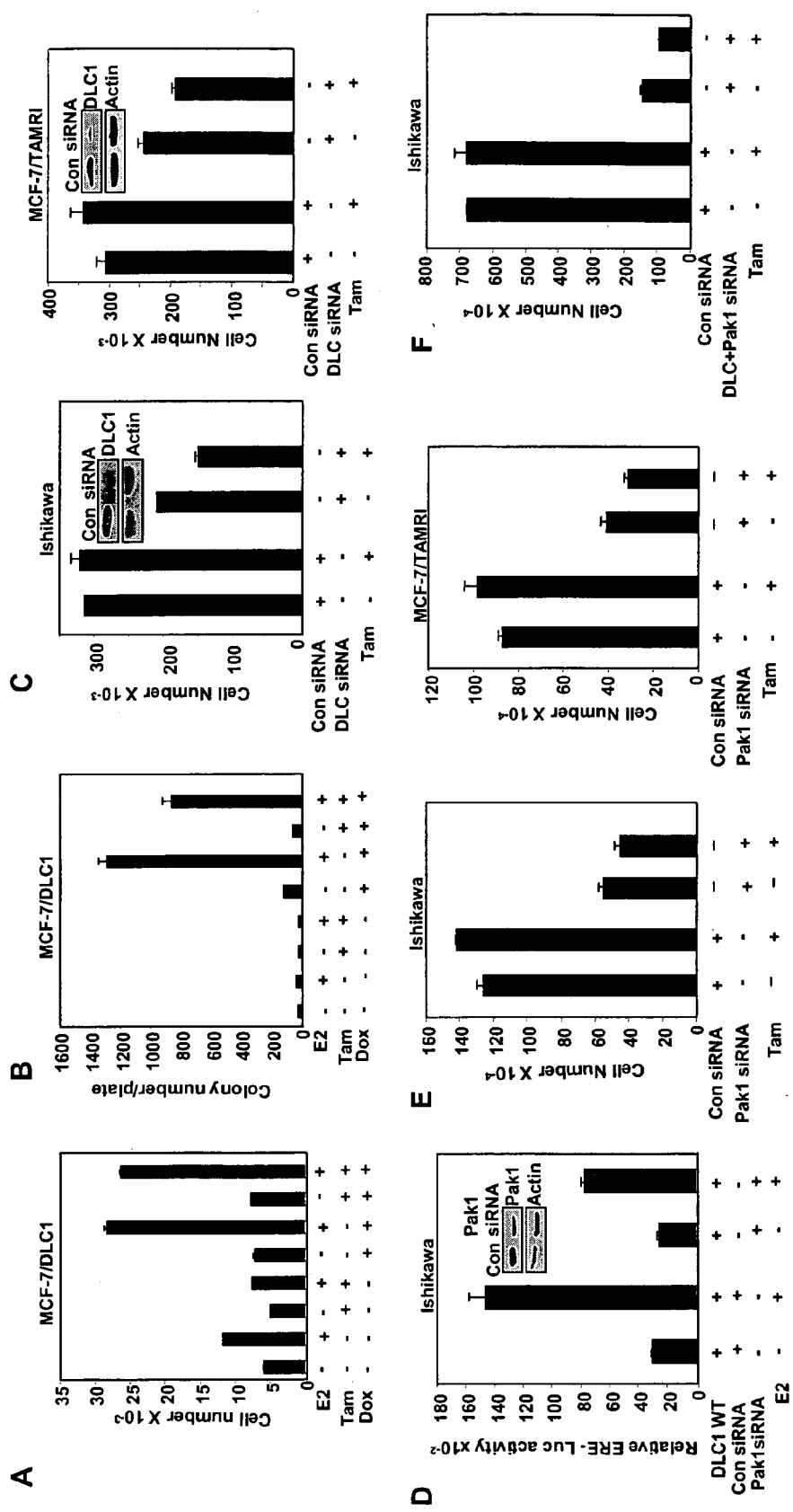
FIGS. 12A–12F—DLC1 deregulation potentiates ligand-induced growth and anchorage-independence

FIG. 12 illustrates that DLC1 deregulation potentiates ligand-induced growth and anchorage-independence. In FIG. 12A, DLC1 upregulation potentiates growth stimulation by E2 in a Tam-insensitive manner. MCF-7/DLC1 cells were treated with or without Dox and then with E2 ($10^{-9}$M) or Tam ($10^{-8}$M) for 5 days, and the cell number was determined. FIG. 12B shows that DLC1 upregulation promotes anchorage independence. MCF-7/DLC1 cells were plated in soft-agar, treated with or without Dox for 24 h and then with E2 ($10^{-9}$M) or Tam ($10^{-9}$M) for 21 days, and the colonies were counted. FIG. 12C demonstrates that DLC1 expression supports optimum growth of Tam-resistant cells. Ishikawa and MCF-7/TAMR1 cells were transfected with control or DLC siRNA for 48 h and then treated with or without Tam ($10^{-9}$M) for 96 h, and the cell number was determined.

FIG. 12D shows that DLC1-mediated potentiation of ER transactivation depends on the Pak1 status in Ishikawa and MCF-7/TAMR1 cell lines. Ishikawa and MCF-7/TAMR1 cells were transfected with control or Pak1 siRNA for 48 h and then with ERE-luc for 24 h and treated with E2 ($10^{-9}$M) for 24 h and ERE-luc activity was measured. In FIG. 12E, Pak1 expression level influences the growth of Tam resistant cells. Ishikawa and MCF-7/TAMR1 cells were treated with control or Pak1 siRNA for 48 h and treated with or without Tam ($10^{-8}$M) for 4 days, and cell number was determined. In FIG. 12F, co-downregulation of Pak1 and DLC1 in Tam-resistant cells restores Tam-sensitivity. Ishikawa cells were treated with control or and Pak1 and DLC siRNA for 48 h and then transfected with ERE-luc and treated with Tam ($10^{-8}$M) for 24 h and ERE-luc activity was measured.

These results indicate that DLC expression is deregulated in cancers (breast, endometrial and head and neck cancers) and that overexpression of DLC1 confers a growth advantage to cancer cells and co-operates with the growth factors and hormones. Thus, in a specific embodiment, DLC1 protein, DLC1 peptide, DLC1 peptide liposome, ominant-negative DLC1 mutants, or a combination thereof are used to interfere with cancer cell growth and motility.

Targeting DLC1 in Hormone-Independent Hormone-Responsive Cancers.

Tamoxifen is the most widely prescribed drug for estrogen receptor (ER) positive breast cancer patients. Unfortunately, 50% of the treated patients eventually become resistant to tamoxifen treatment. As described below, the present inventors found that tamoxifen induced the expression of DLC1 in tamoxifen-resistant breast and endometrial cancer cells but not in tamoxifen-sensitive cells. The deregulation of DLC1 hypersensitizes breast cancer cells to estrogen-mediated ER transactivation, growth stimulation, and anchorage-independent growth, and also conferred tamoxifen resistance. DLC1 regulation of ER transactivation and growth stimulation also required a functional Pak1.

Figure 13:
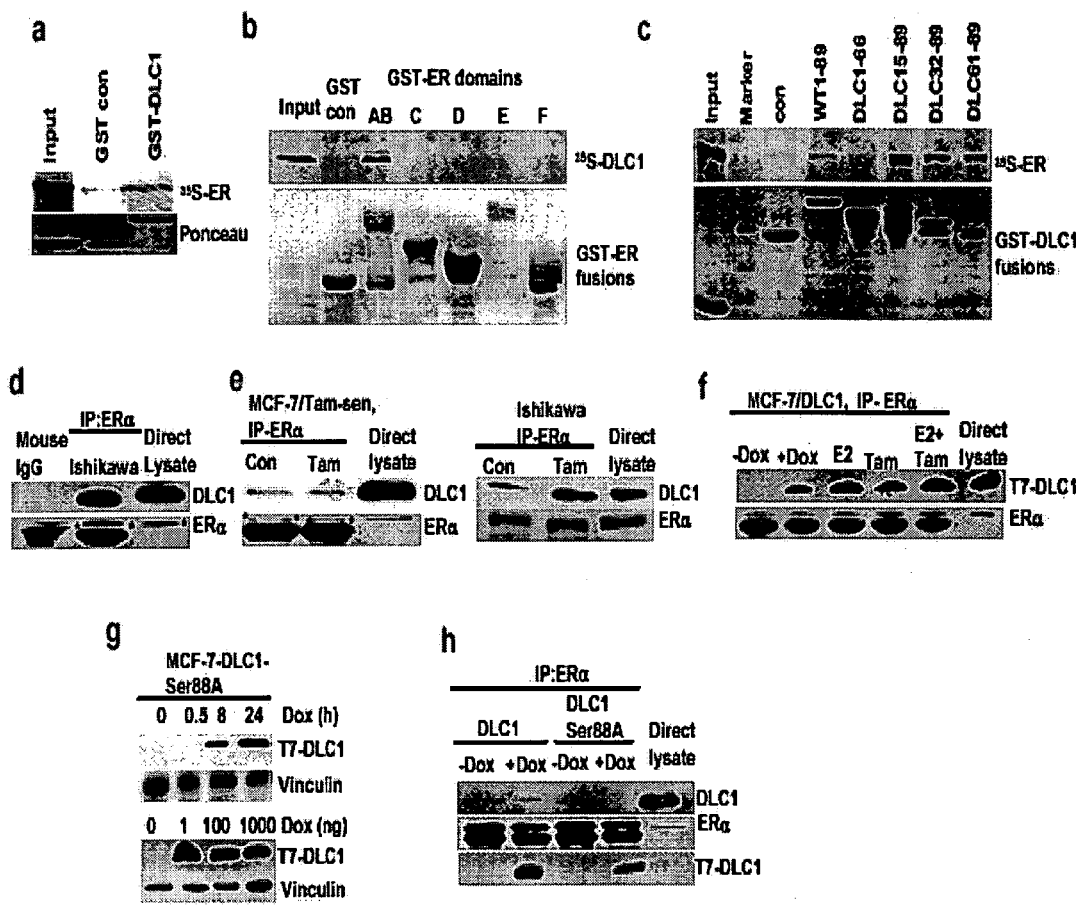
FIGS. 13A–13H—DLC1 interacts with Estrogen Receptor.

DLC1 interacts with estrogen receptor. FIG. 13A shows interaction of DLC1 with ERα. In vitro-translated $^{35}$S-ER were incubated with GST-DLC1, and analyzed by SDS-PAGE and autoradiography. In FIG. 13B, there is identification of ER domains that interact with DLC1. GST-ER fusion proteins containing different deletion constructs were incubated with in vitro-translated $^{35}$S-DLC1 (aa 1-89), and binding was analyzed by GST pull-down assay. FIG. 13C shows mapping of the ER-binding region in DLC1. GST-fusions of various DLC1 deletion constructs were incubated with in vitro-translated $^{35}$S-ER, and binding was analyzed by GST pull-down assay. In FIG. 13D, endogenous DLC1 and ER interaction. Cell lysates from Ishikawa cells was immunoprecipitated (IP) with anti-ERá mAb and immunoblotted with anti-DLC1 or ER Abs. In FIG. 13E, Tam increases DLC1-ER interaction in Tam-resistant cells. Cell lysates from MCF-7/TAM-sen or Ishikawa cells were treated with Tam ($10^{-9}$M) for 24 h, and IP with anti-ERá mAb and immunoblotted with anti-DLC1 or ER Abs. FIG. 13F shows that DLC1 deregulation increases DLC1-ER interaction. MCF-7/DLC1 cells were treated with or without Dox for 24 h and then treated with E2 ($10^{-9}$M) or Tam ($10^{-8}$M) for 24 h, and IP with anti-ERá mAb and immunoblotted with anti-DLC1 or ER Abs. FIG. 13G shows characterization of MCF-7 cells expressing T7-DLC1-Ser88A mutant under a tetracycline-inducible promoter. Time and dose-dependent Dox-mediated upregulation of T7-DLC1-Ser88A expression. In FIG. 13H, deregulation of DLC1 but not DLC1-Ser88A increases DLC1-ER interaction. MCF-7/DLC1 and MCF-7/DLC1-Ser88A cells were treated with or without Dox for 24 h and cell lysates were IP with anti-ERá mAb and blotted with anti-DLC1, ERá and T7 Abs.

Figure 14:
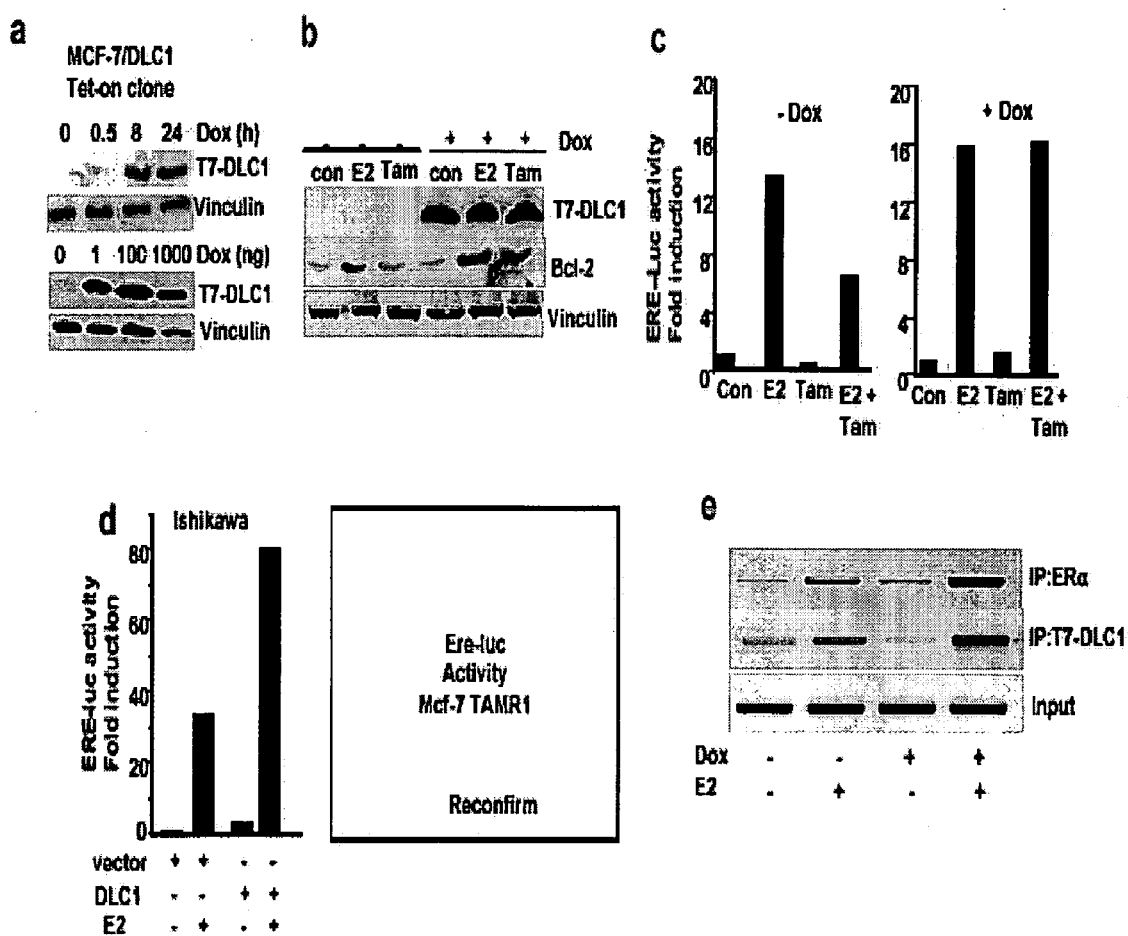
FIGS. 14A–14E—DLC1 deregulation leads to E2 hypersensitivity and tamoxifen resistance.

FIG. 14A shows characterization of MCF-7 cells expressing T7-DLC1 under a tet-inducible promoter. Time and dose dependent upregulation of Dox-mediated T7-DLC1 expression. FIG. 14B shows that DLC1 deregulation potentiates stimulation of Bcl-2 by E2 and by Tam. MCF-7/DLC1 cells were treated with or without Dox (1 μg/ml) for 24 h and treated with E2 or Tam for 24 h and cell lysates were immunoblotted with the indicated antibodies. In FIG. 14C, DLC1 upregulation suppresses Tam ability to inhibit E2-mediated ER transactivation. MCF-7/DLC1 cells were transfected with ERE-luc. After 24 h, the cells were treated with or without Dox for 24 h and then treated with E2 ($10^{-9}$M) or Tam ($10^{-8}$M), and ERE-luc activity was measured after 24 h. In FIG. 14D, DLC1 deregulation potentiated E2-mediated stimulation of ERE-luc activity in Ishikawa and MCF-7/TAMR1 cells. Ishikawa and MCF-7/TAMR1 cells were transfected with ERE-luc and then treated with E2 ($10^{-9}$M) for 24 h and luc activity was measured. FIG. 14E shows recruitment of DLC1 and ERá to the pS2 promoter chromatin. MCF-7/DLC1 cells were treated with or without Dox for 24 h and then with E2 ($10^{-9}$M) for 1 h. Chromatin lysates were immunoprecipitated with anti-ER-á or anti-T7 (to detect T7-DLC1) antibodies. Upper panels show the PCR analysis of 304 bp pS2 promoter fragment associated with ER or T7-DLC1. The lower panel shows the PCR analysis of the input DNA.

Thus, in a specific embodiment of the present invention, DLC1 protein, DLC1 peptide, DLC1 mutants, or a combination thereof interfere with ER interactions with DLC1, representing a useful drug for hormonal independence. DLC peptide/DLC1 liposomal formulation may be used as a therapeutic agent to treat hormonal resistant cancers.

DLC1 mutants and macropinocytosis. DLC1 is important for macropinocytosis function of both normal and cancer cells. Macropinocyitosis is important for motility, cell growth and for uptake of particles or medium by cells. The uptake molecules may be virus, pathogen, or any other type of bioparticle (including, for example, LDL). As shown below, DLC proteins lacking Pak1 binding and phosphorylation sites will interfere with DLC1 functions in a dominant negative manner.

The DLC1 1-66 peptide sequence is mcdrkavikn admseemqqd svecatqale kyniekdiaa hikkefdkky nptwhcivgr nfgsyv (SEQ ID NO:11). As shown below, expression of DLC1-66 peptide blocks macropinocytic functions in human breast cancer cell line SKBR3, and expression of DLC1-66 peptide blocks macropinocytic functions in human dendritic cells.

Figure 15:
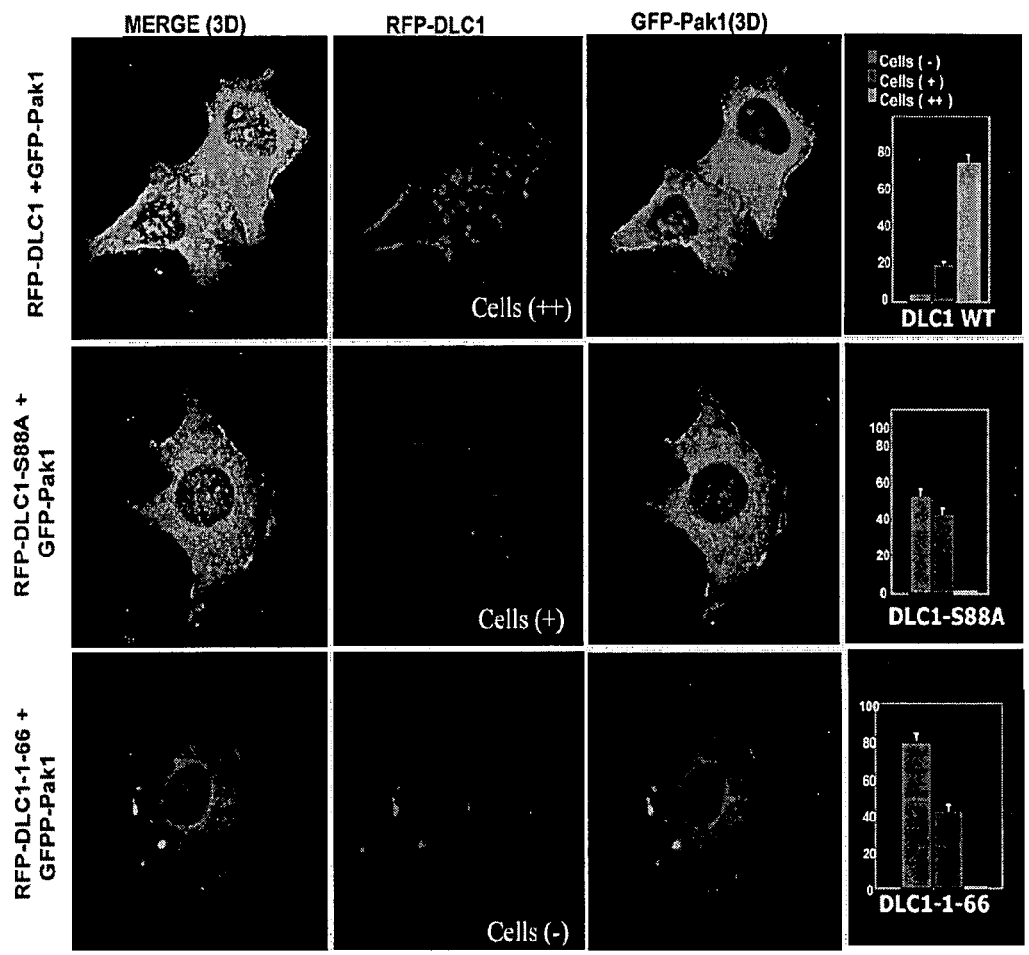
FIG. 15—Pak1 mediated macropinocytosis requires Pak1-DLC1 interactions. SK-BR3 cells were cotransfected with RFP-DLC1 and GFP-Pak1 (upper panel), RFP-DLC1-S88A and GFP-Pak1 (middle panel), and RFP-DLC$_{8-1}$-66 and GFP-Pak1 (bottom panel). Vesicle formation and localization of GFP and RFP proteins were analyzed by confocal microscopy. Ten randomly selected fields were analyzed for each condition. The experiment was repeated twice with similar results. Quantitation of vesicles formation was done using the folowing scoring system: −, cells containing 0–9 vesicles; +, cells containing 10–20 vesicles; and ++, cells containing >20 vesicles.

FIG. 15 shows thaat Pak1 mediated macropinocytosis requires Pak1-DLC1 interactions. SK-BR3 cells were cotransfected with RFP-DLC1 and GFP-Pak1 (upper panel), RFP-DLC1-S88A and GFP-Pak1 (middle panel), and RFP-DLC8-1-66 and GFP-Pak1 (bottom panel). Vesicle formation and localization of GFP and RFP proteins were analyzed by confocal microscopy. Ten randomly selected fields were analyzed for each condition. The experiment was repeated twice with similar results.

Figure 16:
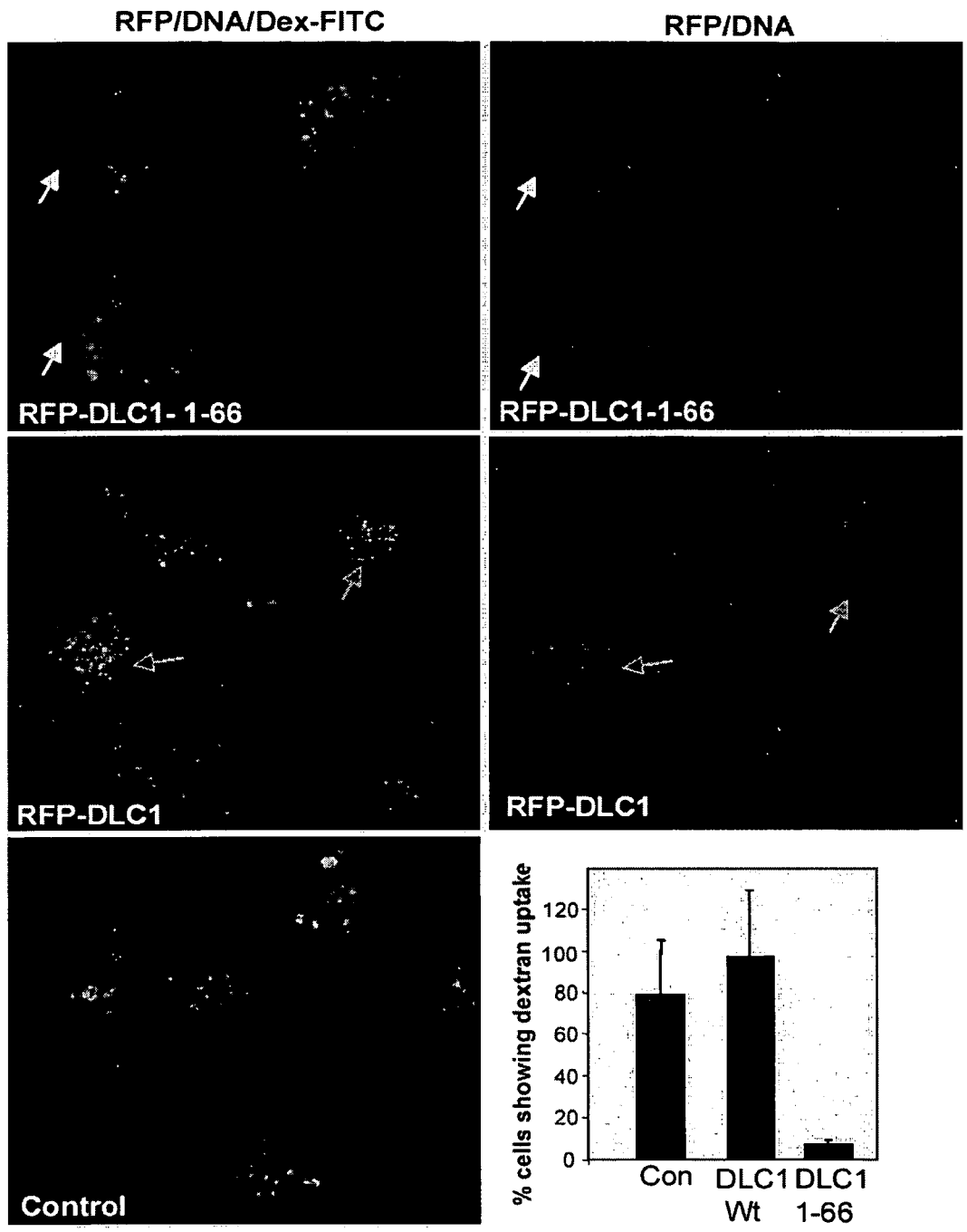
FIG. 16—DLC1 is required for macropinocytosis in dendritic cells. Human dendritic cells were plated on cover sips in 6-well tissue culture plates, transfected with RFP-DLC1 wild type or DLC1-1-66 mutant lacking Pak1 binding and phosphorylation sites. After 12 hours, FITC-dextran was added to the culture medium for 20 min and cells were fixed and stained with Topro-3 (a DNA dye) and analyzed by confocal microscopy for RFP-DLC1 (red) or RFP-DLC1-1-66 (red) and FITC-dextran (green). White arrows point to RFP-DLC1-1-66 transfected cells and red arrows point to cells transfected with RFP-DLC1.

FIG. 16 shows that DLC1 is required for macropinocytosis in dendritic cells. Human dendritic cells were plated on cover slips in 6-well tissue culture plates, transfected with RFP-DLC1 wild type or DLC1-1-66 mutant lacking Pak1 binding and phosphorylation sites. After 12 hours, FITC-dextran was added to the culture medium for 20 min and cells were fixed and stained with Topro-3 (a DNA dye) and analyzed by confocal microscopy for RFP-DLC1 (red) or RFP-DLC1-1-66 (red) and FITC-dextran (green). White arrows point to RFP-DLC1-1-66 transfected cells and red arrows point to cells transfected with RFP-DLC1.

Thus, in a specific embodiment of the present invention, DLC1 peptide containing 1-66 amino acid can be used as a potential drug to inhibit DLC1 functions.

DLC1 in regulation and sensitization of Apoptosis. As indicated below, Pak1 signaling via DLC1 also plays an important role as a guardian of survival by phosphorylation DLC-Bim (apoptosis inducer). Therefore, inappropriate expression of Pak1 that is seen in tumors may interfere with chemotherapy treatment due to enhanced cell survival signals. Similarly, knockdown of DLC or Pak1 promotes cell death upon UV irradiation. Therefore, blocking Pak1 pathway by DLC1/PIN peptide would enhance the sensitivity of UV treatment and may prevent chemo resistance.

Figure 17:
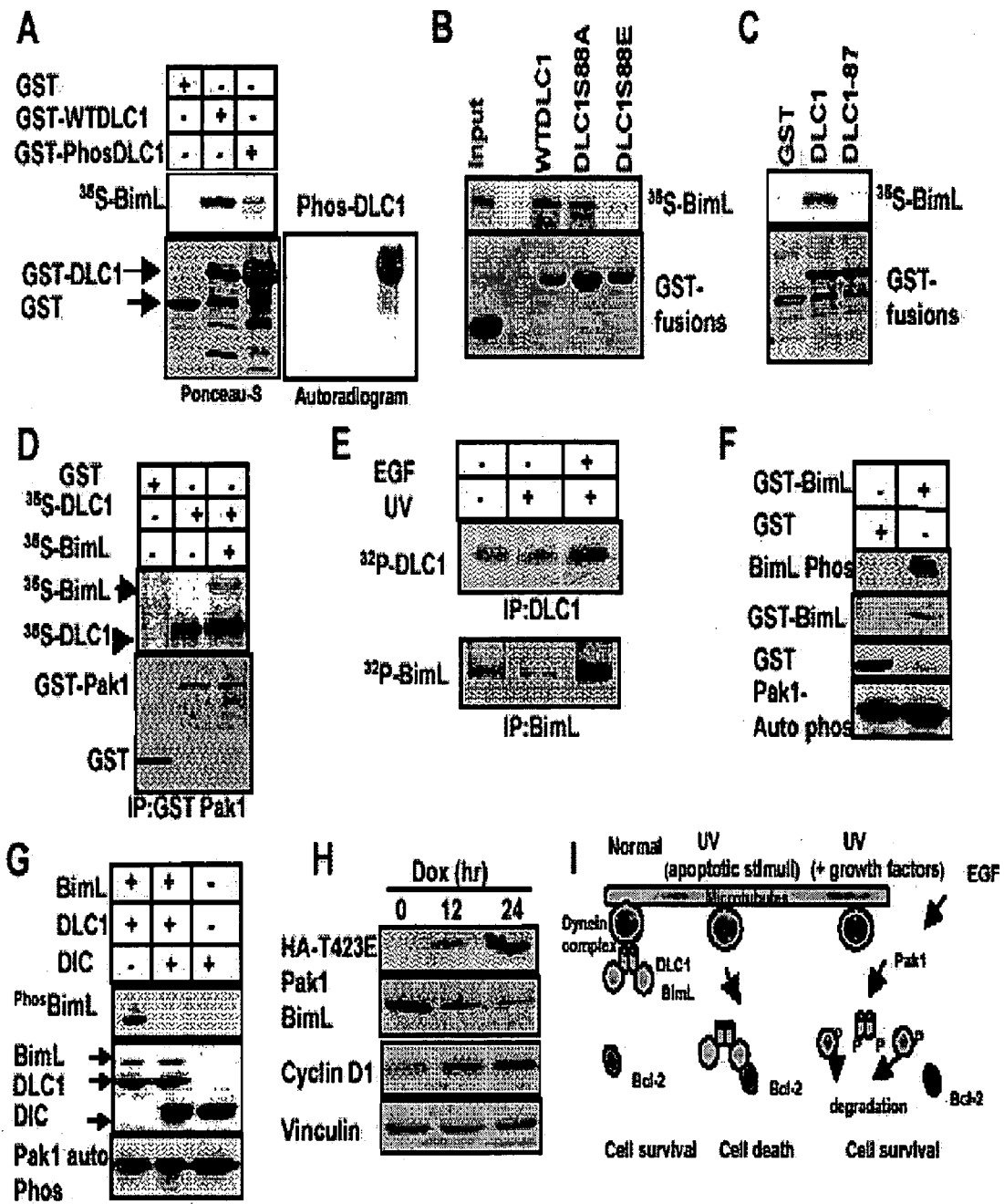
FIGS. 17A–17I—Pak1 phosphorylation regulates BimL and DLC1 interactions.

FIG. 17 demonstrates that Pak1 phosphorylation regulates BimL and DLC1 interactions. In FIG. 17A, there is the effect of Pak1 phosphorylation on the binding of DLC1 with BimL. GST-DLC1 was phosphorylated with Pak1 enzyme, and GST pull down assay was performed using phosphorylated GST-DLC1 or wild type GST-DLC1. Autoradiogram showing the phosphorylation of DLC1 is shown in the right panel. FIG. 17B shows ability of DLC1-Ser88A or DLC1-Ser88E mutants to interact with BimL in GST-pull down assay. In FIG. 17C, the ability of GST-DLC1-(aa1-87) to interact with BimL was analyzed by GST pull down assay. In FIG. 17D, the ability of Pak1 to interact with DLC1-BimL dimers was analyzed. $^{35}$S-labeled DLC1 and BimL were incubated with GST-Pak1 and GST pull down assay was performed. FIG. 17E shows that MCF-7 cells were labeled with $^{32}$P-orthophosphoric acid, and cells were treated with UV or pretreated with EGF (100 ng/ml) followed by UV treatment. Cell lysates were immunoprecipitated with antibodies against DLC1 or BimL, and the phosphorylation status of proteins was analyzed by autoradiography. In FIG. 17F, phosphorylation of GST-BimL by Pak1 in in vitro kinase assay is analyzed. In FIG. 17G, GST-BimL was incubated with purified beads bound GST-DLC1 along with or with GST-dynein intermediate chain. After 60 min of incubation, dimeric and trimericcomplexes were purified by GST-DLC1 pull down and used as a substrate in vitro Pak1 kinase assay. In FIG. 17H, downregulation of BimL levels by constitutively active Pak1 was analyzed. MCF-7 cells expressing T423E-Pak1 under the control of Tet-regulated promoter were treated with doxycycline for 12 or 24 h. Expression of BimL, cyclin D1, and HA-tagged T423E Pak1 was analyzed by western blotting. In FIG. 17I, there is a model for Pak1 regulation of DLC1 and BimL functions. Under physiological conditions, DLC1 sequesters BimL to the microtubules. Under apoptotic conditions, DLC1-BimL dimers are released and interact with Bcl-2. Survival factors activate Pak1, which in-turn phosphorylates DLC1-BimL dimers and, thus, prevents BimL interaction with Bcl-2.

Figure 18:
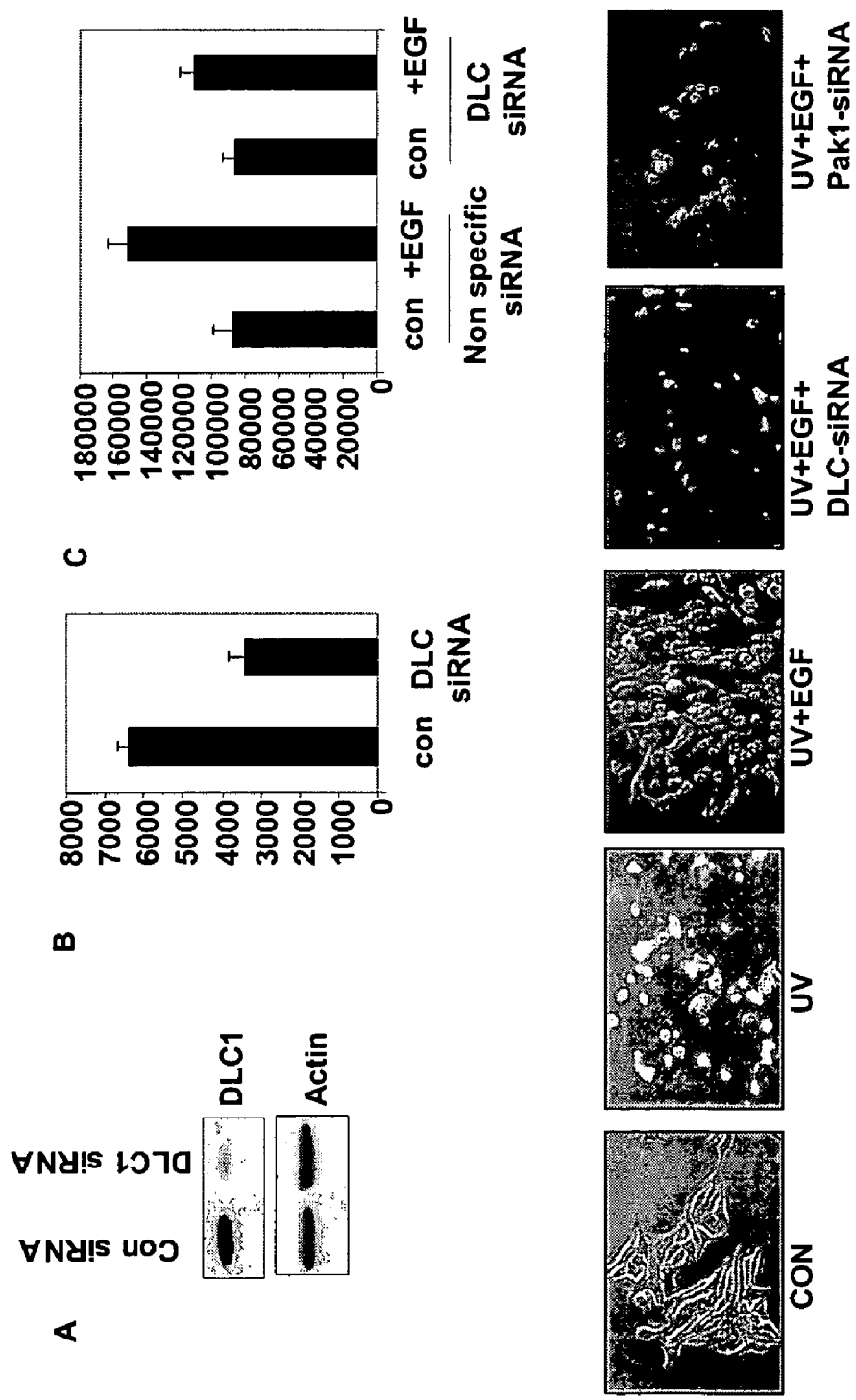
FIGS. 18A–18D—siRNA analysis with DLC1 or Pak1.

FIG. 18 demonstrates siRNA analysis with DLC1 or Pak1. FIG. 18A shows that MCF-7 cells were transfected with DLC-specific or control siRNA. After 48 hours, total cellular lysate was analyzed by western blotting using DLC1 antibody. Actin was used as a loading control. In FIG. 18B, MCF-7 cells were transfected with control or DLC specific siRNA. After 72 h, cells were trypsinized and counted using a coulter counter. In FIG. 18C, MCF-7 cells were serum starved and transfected with DLC siRNA and treated with or without EGF (100 ng/ml). After 72 hours, cells were trypsinized and counted using coulter counter. In FIG. 18D, MCF-7 cells were transfected with DLC-specific, Pak1-specific or control siRNA. Cells were serum starved for 24 h and pretreated for 30 min with EGF or with out EGF. Cells were then exposed to UV 100 J/m². After 12 h, cell morphology was documented using phase contrast microscope (10×).

Thus, in specific embodiments of the present invention, DLC1/PIN peptide may have a therapeutic role as an adjuvant therapy or pretreatment before chemotherapy. In addition, DLC1 peptide may induce apoptosis in cancer cells are dependent on PI3K-Pak1 pathway that is observed in ovarian cancer cells.

Pak1 and Cyclin D1 Expression in Breast Tumors.

Figure 19:
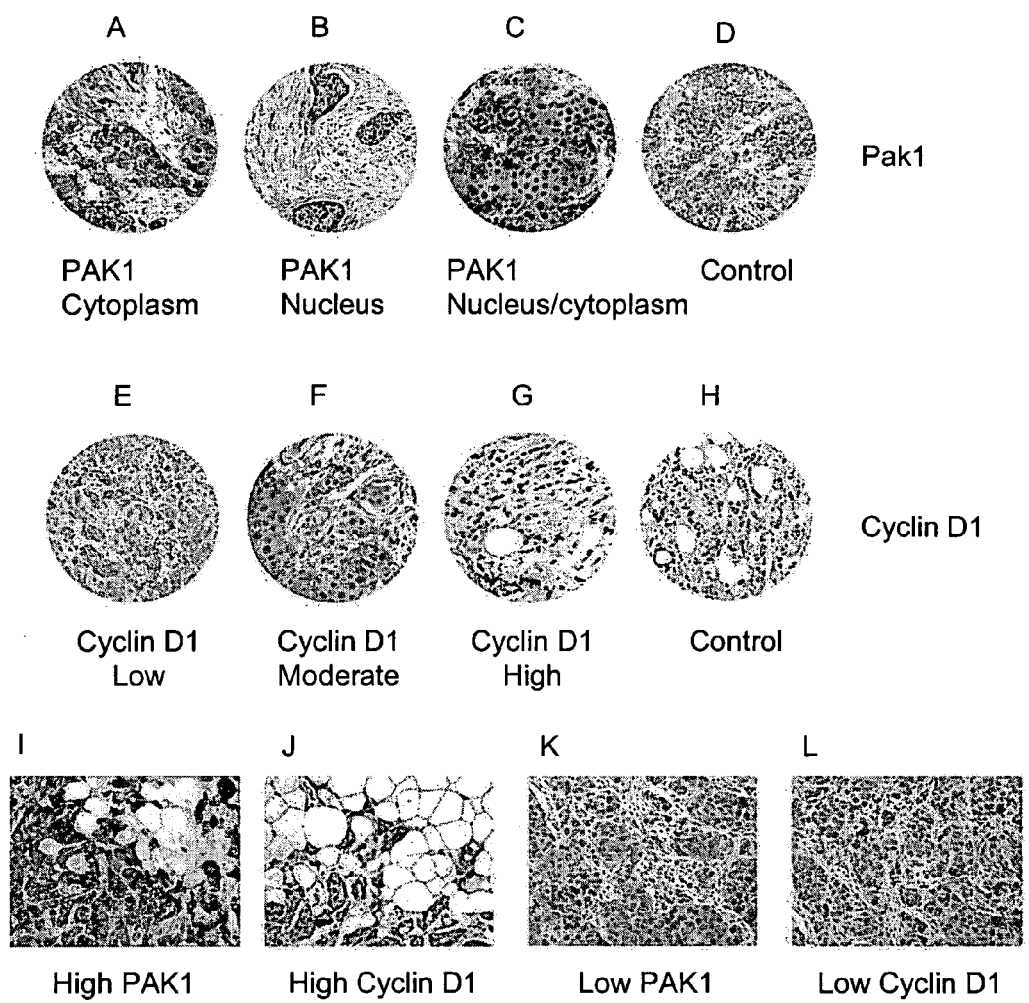
FIGS. 19A–19L—Pak1 and Cyclin D1 expression in breast tumors.

FIGS. 19A–19L illustrate Pak1 and Cyclin D1 expression in breast tumors utilizing standard immunohistochemical techniques in the art. Immunohistochemical analysis and localization of Pak1 is illustrated in FIGS. 19A–19C. Expression pattern of Cyclin D1 in breast tumor arrays is demonstrated in FIGS. 19E–19G. Correlation between Pak1 (FIGS. 19I and 19K) and Cyclin D1 expression (FIGS. 19J and 19L) is also demonstrated. In FIGS. 19D and 19H, negative controls are stained with corresponding IgG in place of the primary antibody.

Pak1 Hyperstimulation Leads to Tamoxifen Resistance

Figure 20:
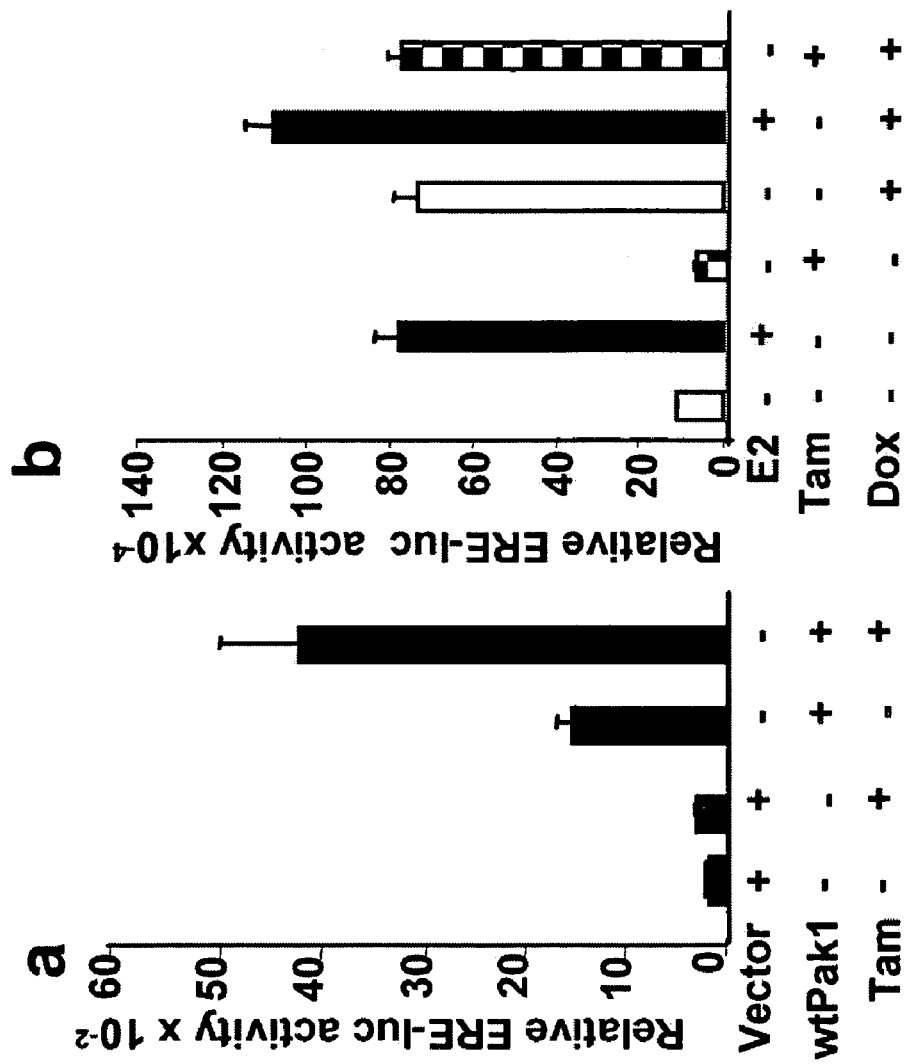
FIGS. 20A–20L—Pak1 activation confers tamoxifen-resistance.
Figure 20:
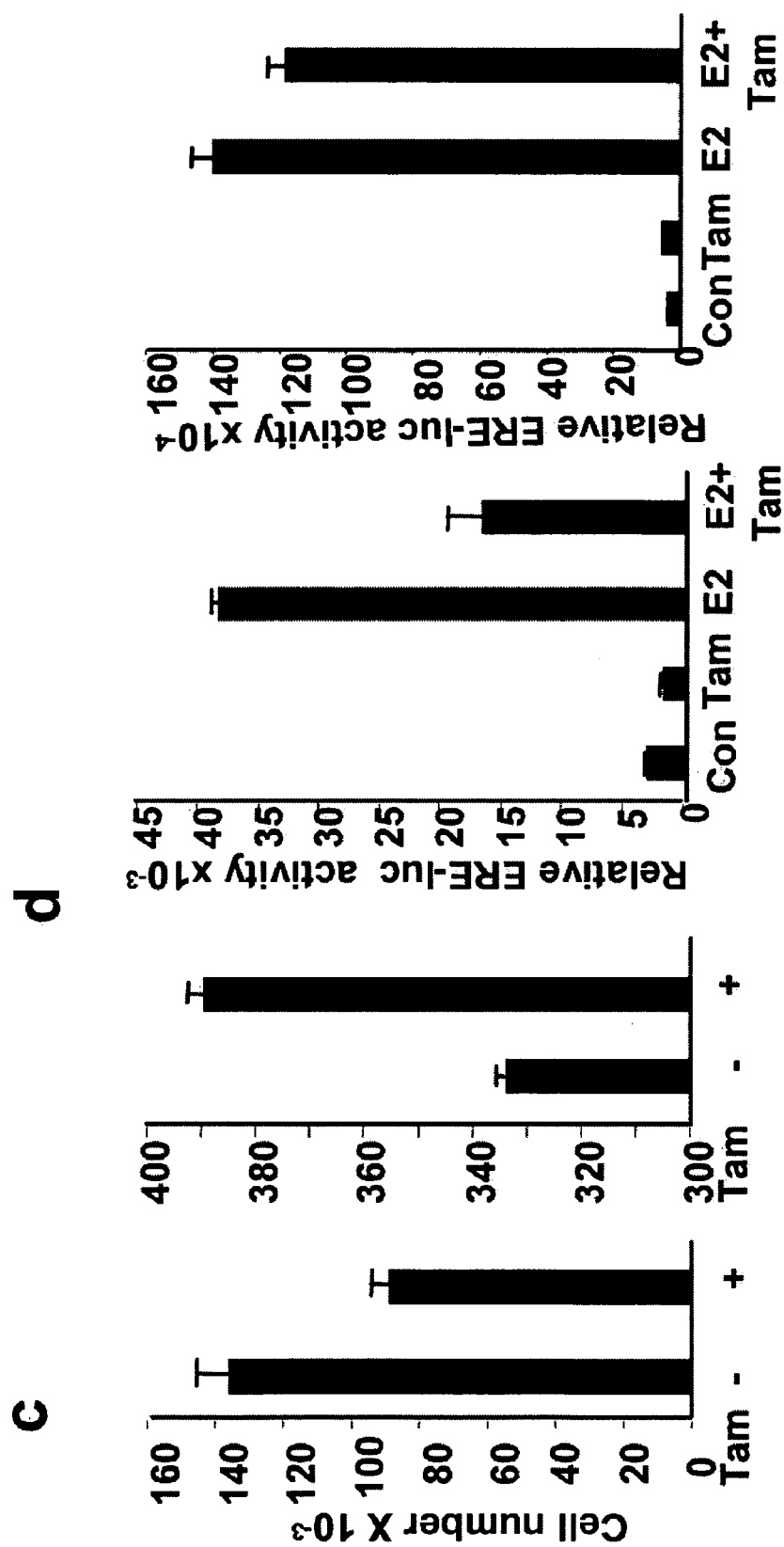
Figure 20:
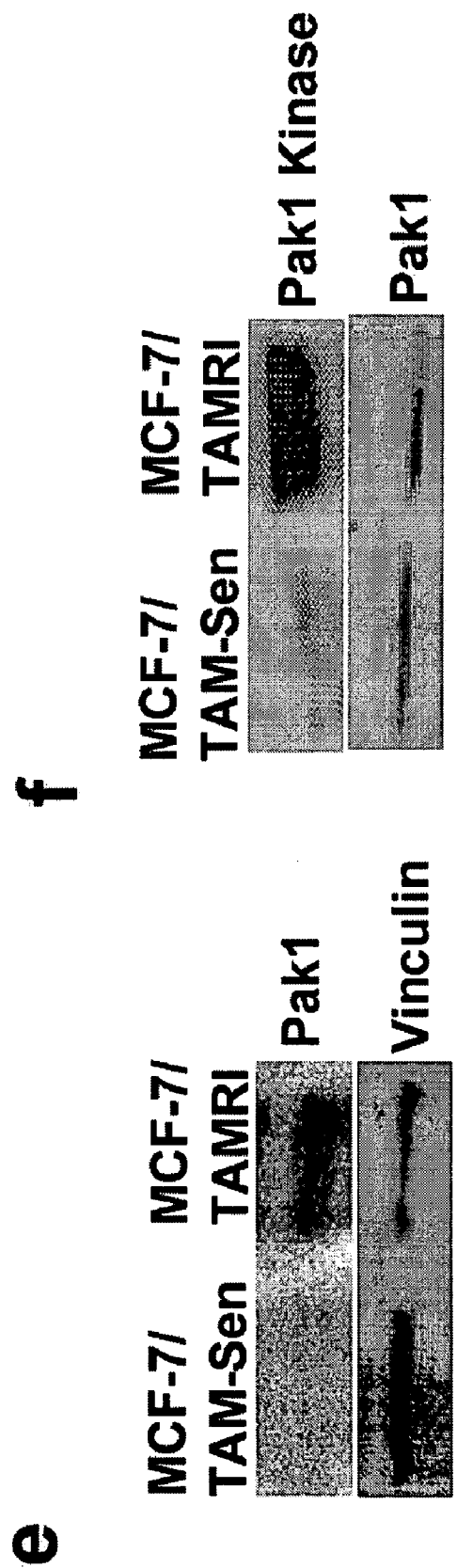
Figure 20:
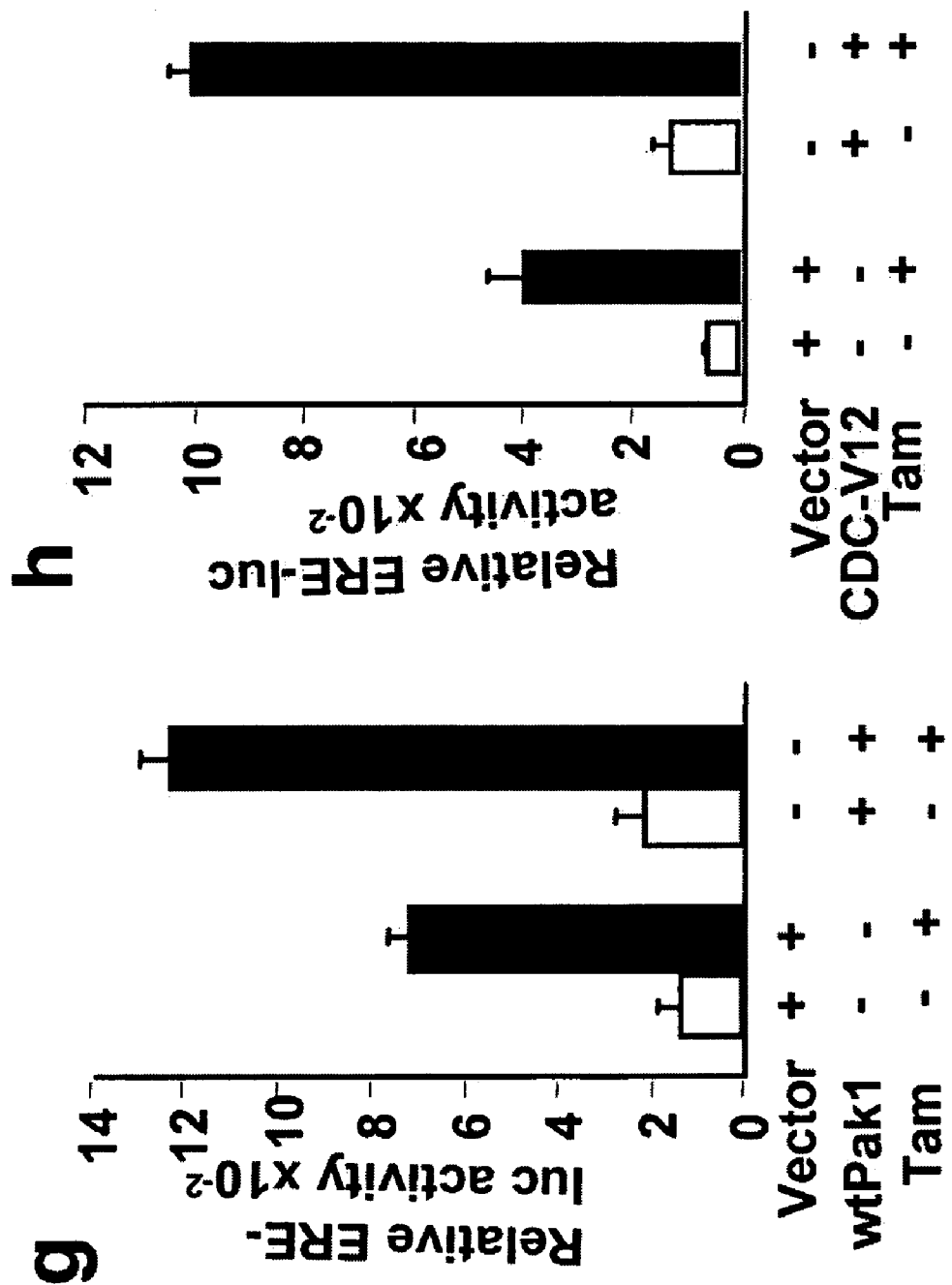
Figure 20:
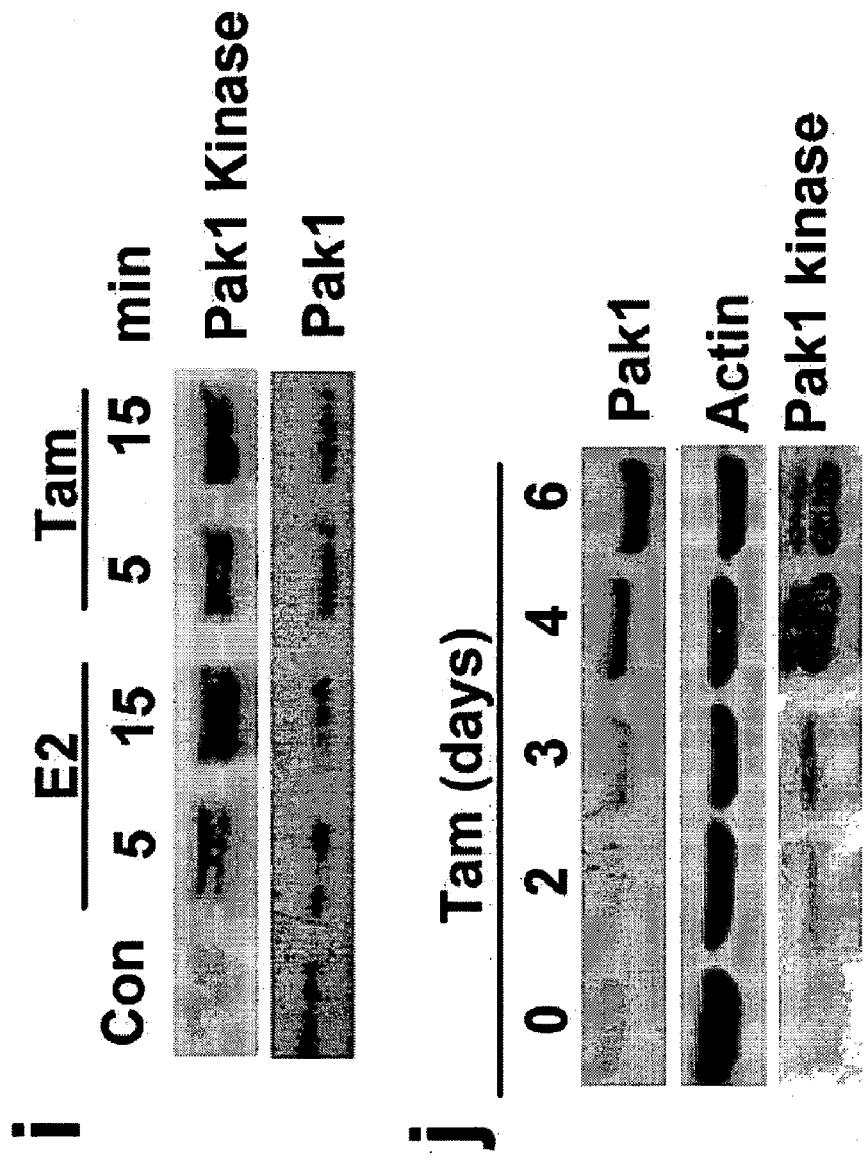
Figure 20:
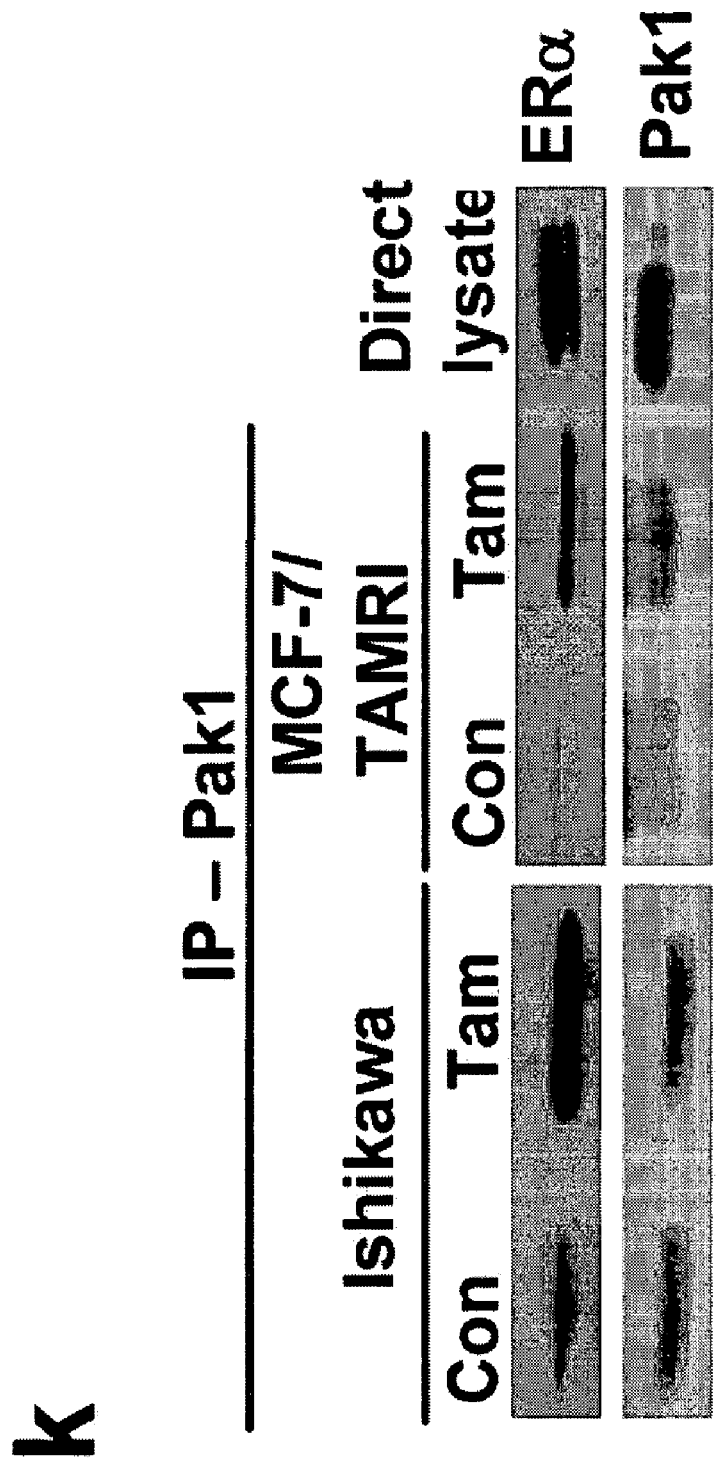
Figure 20:
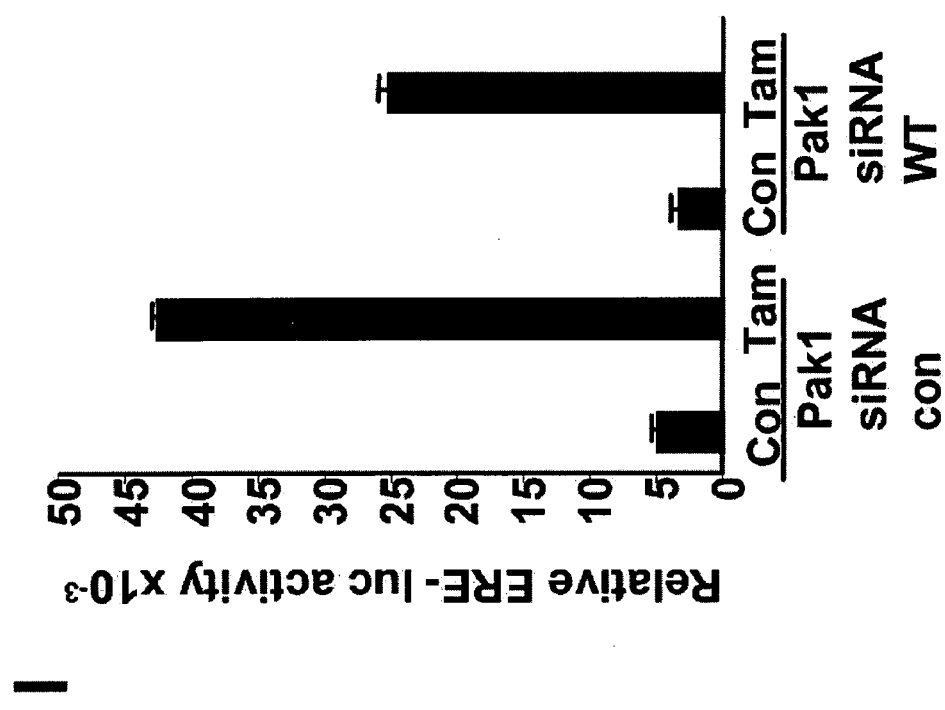

Wild-type Pak1 promotes ER-driven transactivation in breast cancer cells (Wang et al., 2002). To characterize the relationship between Pak1 deregulation and modification of tamoxifen sensitivity, the effect of Tam on the ability of Pak1 to stimulate estrogen response element (ERE) transactivation was examined. Deregulated Pak1 cooperated with tamoxifen in stimulating ERE-luc acivity in MCF-7 cells (FIG. 20A). To confirm Pak1 modulatation of tamoxifen sensitivity, a previously characterized MCF-7 clone (MCF-7/DA-Pak1) expressing catalytically active Pak1 under an inducible tetracycline (Tet)-promoter was utilized (Vadlamudi, 2000). This showed that Pak1-mediated ERE-stimulation was not inhibited by tamoxifen (FIG. 20B), suggesting that Pak1 stimulation is involved in tamoxifen resistance. To directly study this, the present inventors used recently generated MCF-7 clones (Hodges et al., 2003) that are either sensitive (MCF-7/TAM-sen) or resistant (MCF-7/TAMR1) to tamoxifen, as measured by the growth-rate (FIG. 20C) or ERE-transactivation assay (FIG. 20D). In addition, it was found that Pak1 expression (FIG. 20E) and activity (FIG. 20F) were both significantly upregulated in MCF-7/TAMR1 cells compared with the (MCF-7/TAM-sen) cells. The relationship between Pak1 activation and tamoxifen resistance was examined in human endometrial cancer Ishikawa cells, which are naturally resistant to tamoxifen (Shang and Brown, 2002). The transient expression of Pak1 in Ishikawa cells increased the ability of tamoxifen to stimulate ERE-dependent transactivation and cooperated with the tamoxifen in this process (FIG. 20G). This observed effect of Pak1 in Ishikawa cells was also mimicked by an activated form of its upstream regulator Cdc42 (FIG. 20H). These results therefore indicate that Pak1 activation constitutes an important target of tamoxifen in tamoxifen-resistant breast cancer cells and endometrial cancer cells.

Tamoxifen Promotes Pak1 Expression and Pak1-ER Interaction

Because tamoxifen acts as an agonist in Ishikawa endometrial cancer cells and both Pak1 and tamoxifen upregulate ER transactivation (FIG. 20A), the influence of tamoxifen on Pak1 activity was next studied. Unexpectedly, tamoxifen, like estrogen, also upregulated Pak1 kinase activity in Ishikawa cells (FIG. 20I). Because tamoxifen resistance is acquired over time, the long-term effect of tamoxifen on the Pak1 pathway in Ishikawa cells was studied. This showed that tamoxifen treatment of Ishikawa cells was accompanied by an increase in Pak1 protein expression and Pak1 kinase activity (FIG. 20J). As expected from a previous study (Mazumdar and Kumar, 2003) estrogen also upregulated Pak1 kinase activity in Ishikawa cells (FIG. 20J). There was no effect of tamoxifen on the levels of Pak1 protein in MCF-7 cells. These results indicate that tamoxifen-stimulated Pak1 expression leads to persistent Pak1 activity and, in some embodiments of the present invention, contributes tamoxifen-resistant phenotypes.

Because Pak1 interacts with and phosphorylates ERα at Ser305 and stimulates ER transactivation (Wang et al., 2002), the effect of tamoxifen on the interaction of Pak1 and ER was studied. Coimmunoprecipitation studies showed that tamoxifen promoted the interaction of Pak1 with ER in tamoxifen-resistant Ishikawa and MCF-7/TAMR1 cells (FIG. 20K), but not in MCF-7/TAM-Sen cells (see FIG. 13E).

To demonstrate a mechanistic role for Pak1 in the stimulation of ER transactivation by tamoxifen, Pak1 was knocked down using Pak1-specific siRNA (Wange et al., 2002). As shown in FIG. 20L, transient expression of siRNA(wt)-Pak1 reduced the ability of tamoxifen to stimulate ERE transactivation as compared to cells treated with control siRNA. Together, these findings imply that Pak1 is involved in the ER transactivation function of tamoxifen.

Pak1 Upregulates DLC1, a Common Target of Tamoxifen and Estrogen

Figure 21:
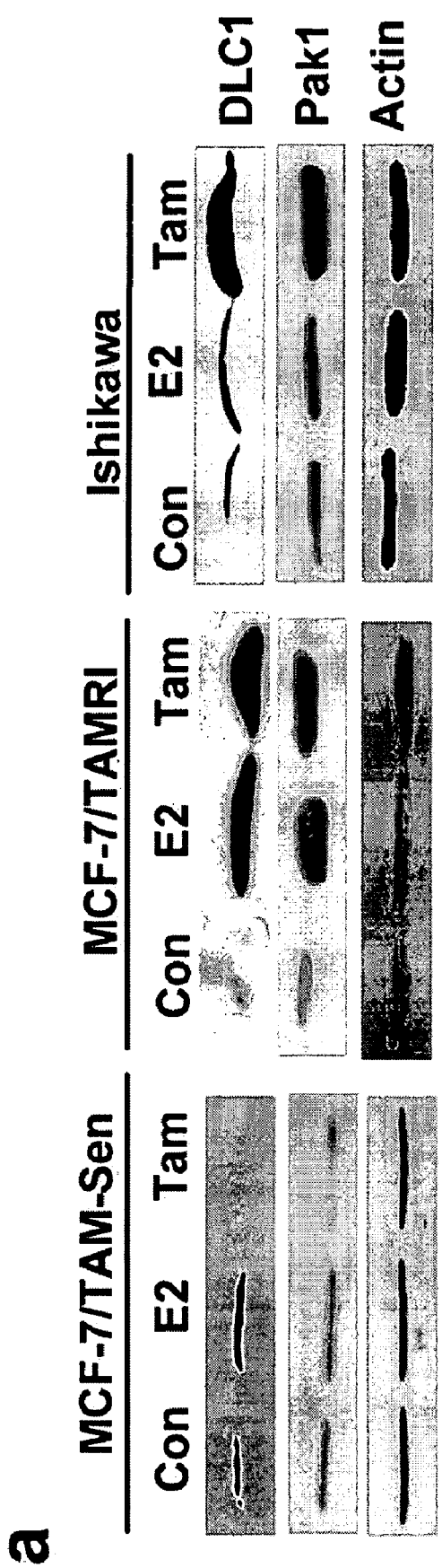
FIGS. 21A–21J—Estrogenic signals upregulate DLC1 expression via Pak1 pathway.
Figure 21:
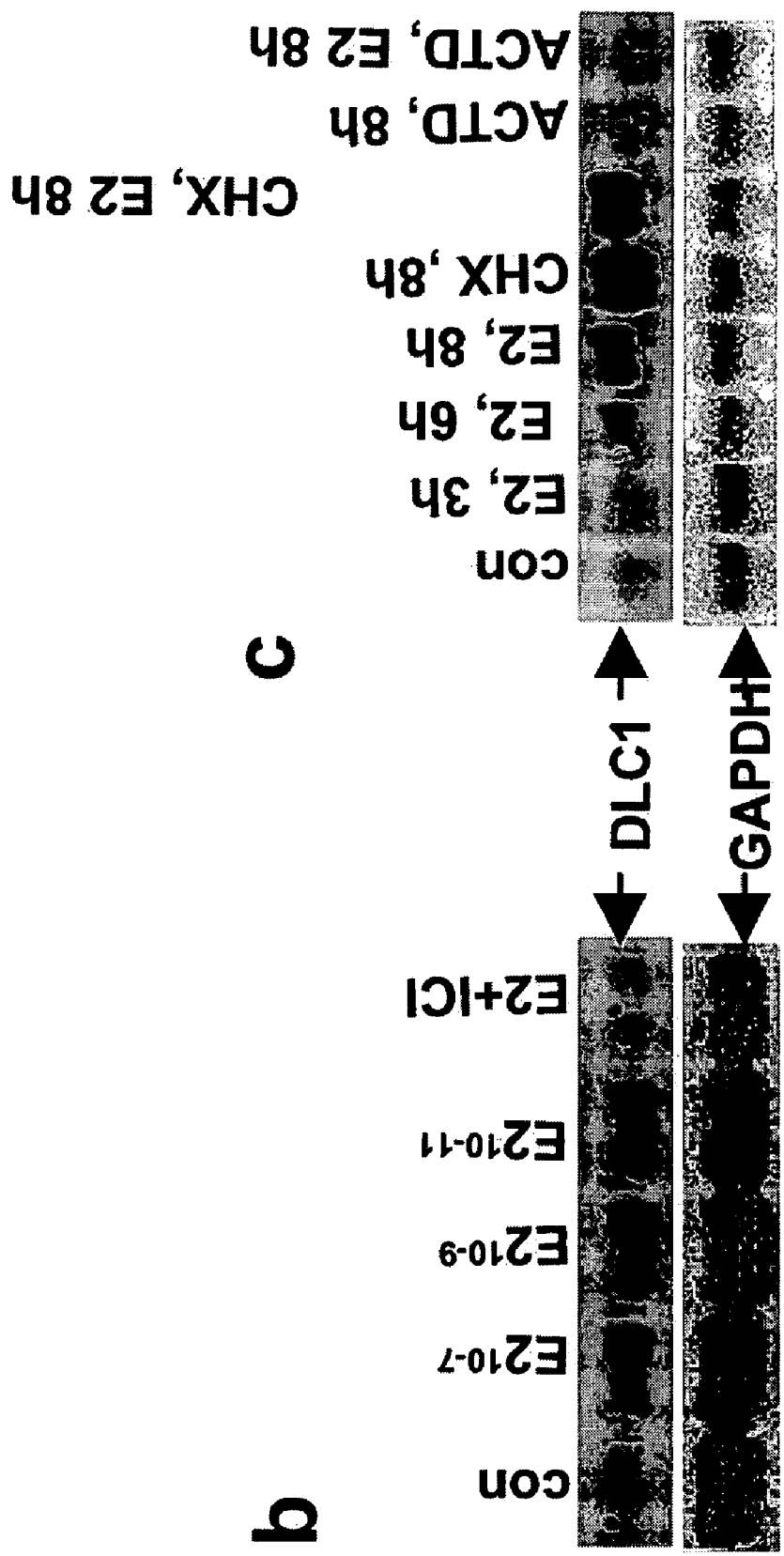
Figure 21:
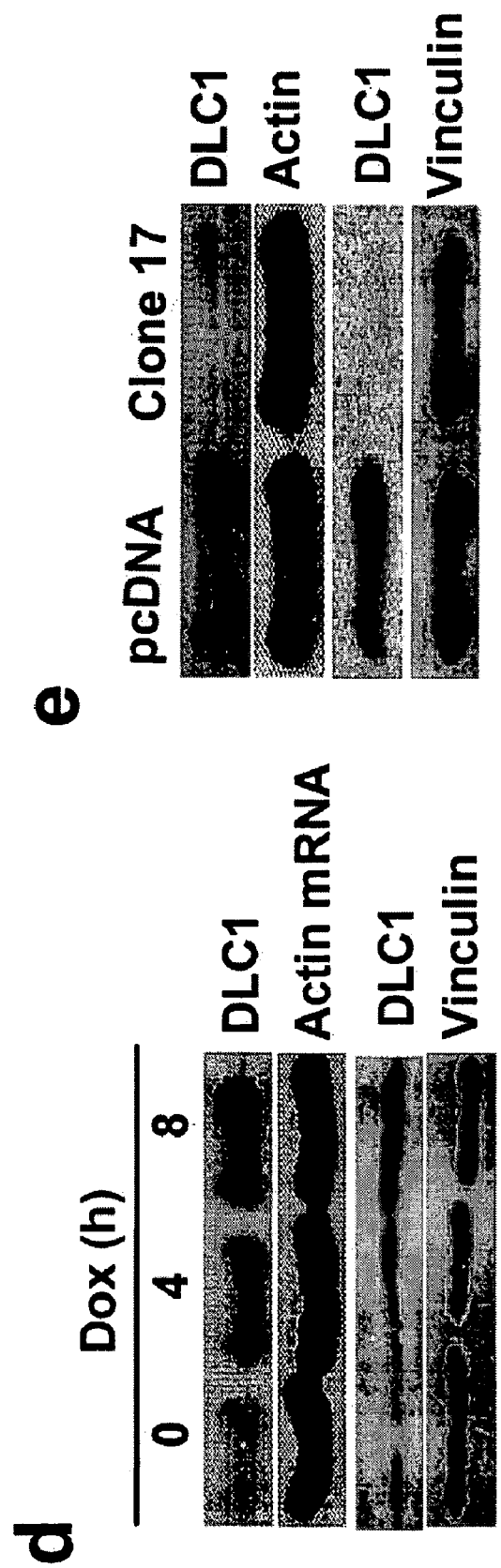
Figure 21:
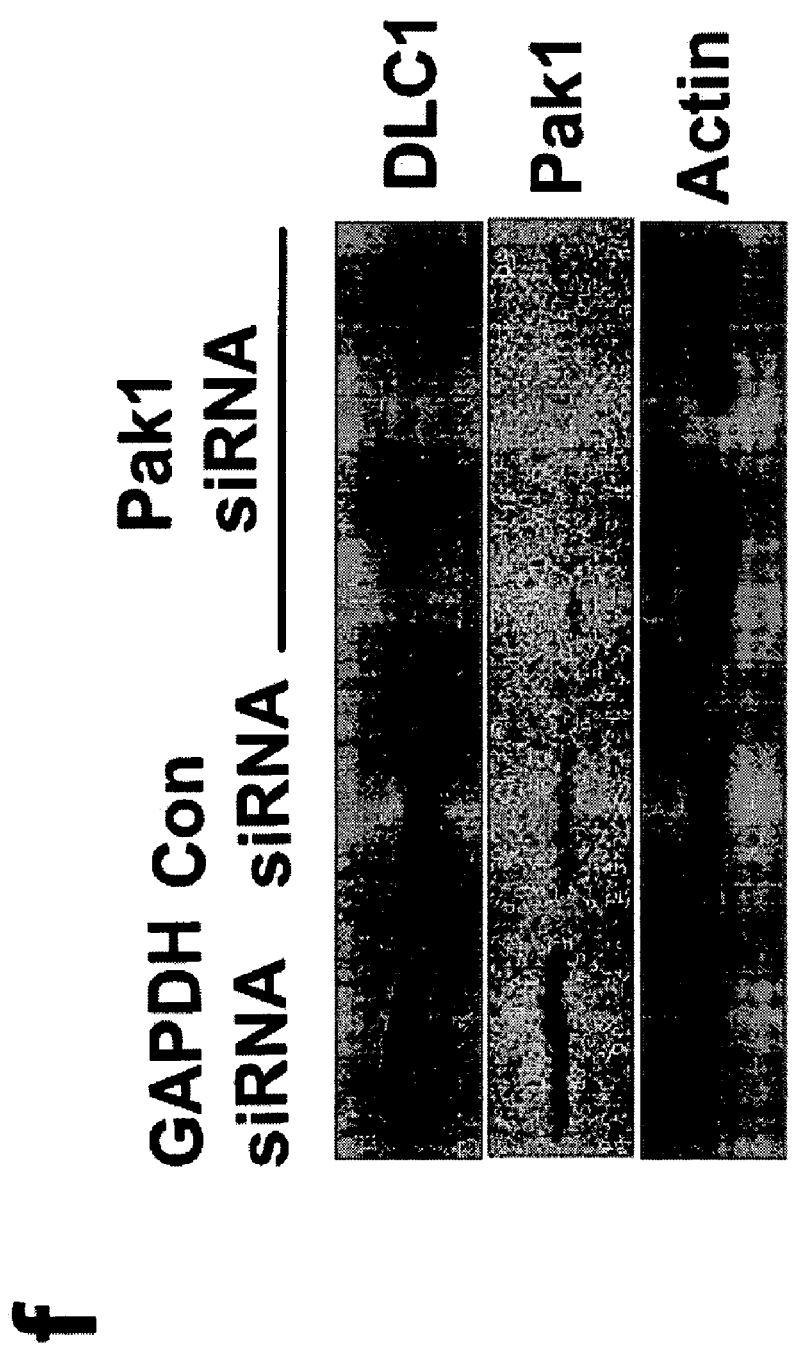
Figure 21:
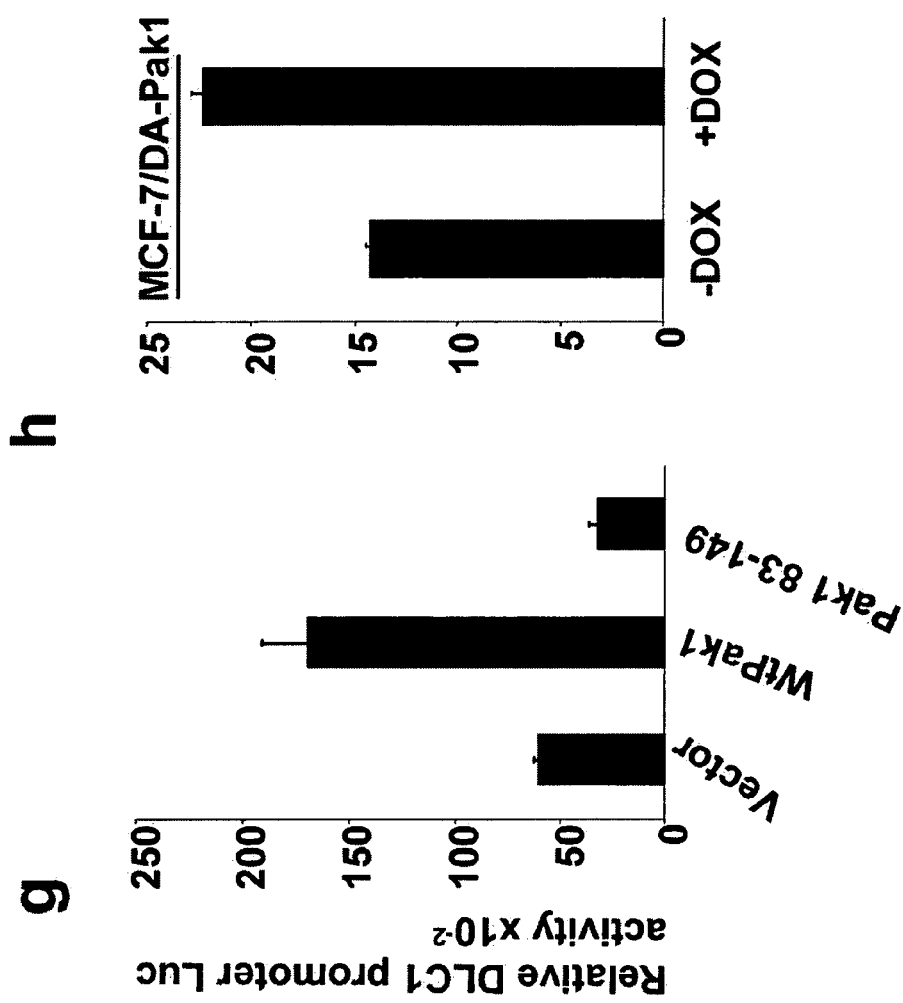
Figure 21:
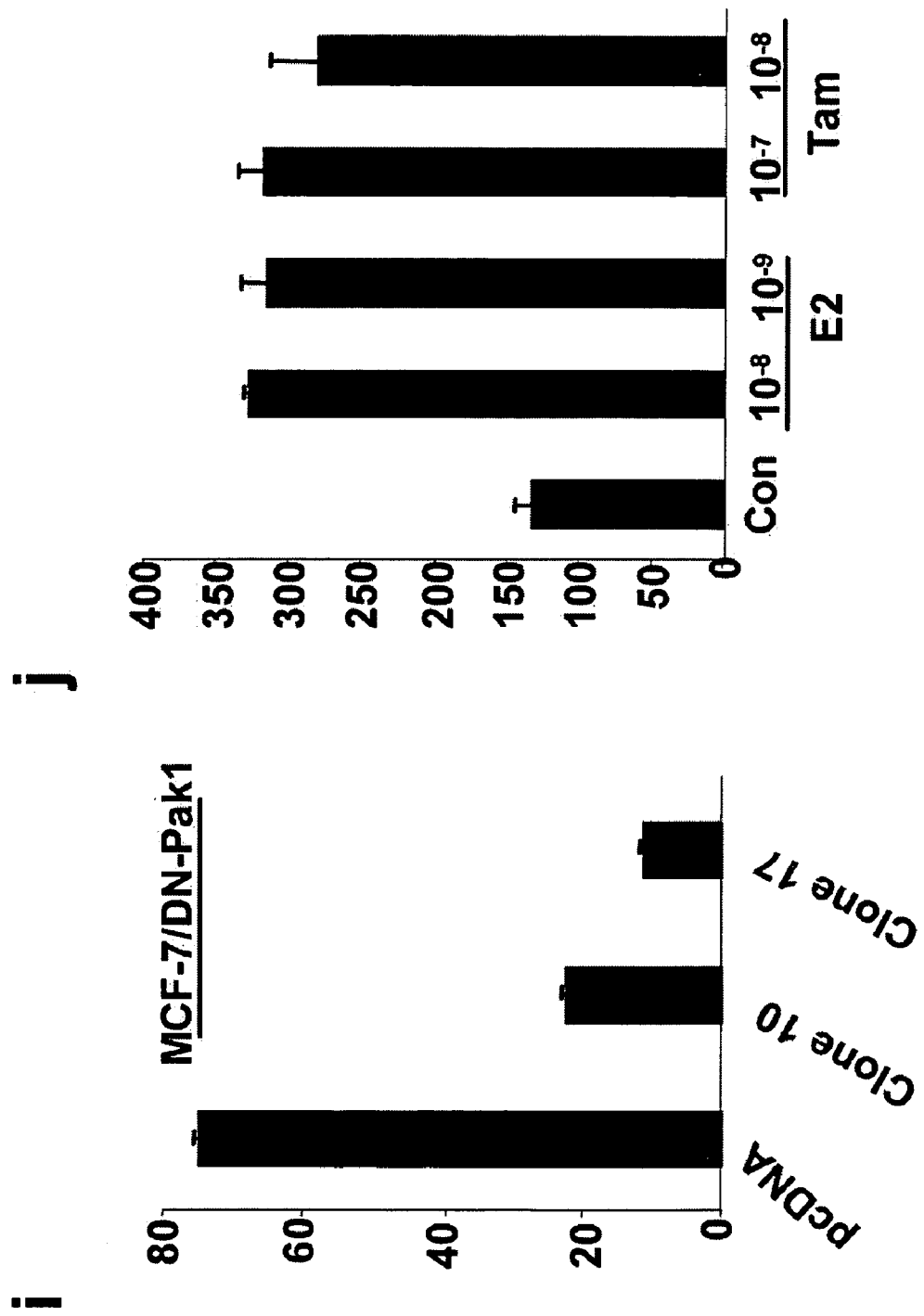

Because both tamoxifen and estrogen influence ER functions and stimulate Pak1, the present inventors considered the existence of at least a third protein that is differentially regulated by tamoxifen in sensitive but not resistant cells. In the meantime, a different gene array study identified DLC1 gene as a common target of tamoxifen and estrogen (Levenson et al., 2002). Therefore, the effect of tamoxifen and estrogen on DLC1 in MCF-7/TAM-Sen, MCF-7/TAMR1, and Ishikawa cells was characterized. Unexpectedly, it was found that tamoxifen robustly upregulated the expression of the DLC1 protein in MCF-7/TAMR1 and Ishikawa cells, but estrogen upregulated the expression of the DLC1 protein in MCF-7/TAM-Sen, MCF-7/TAMR1 and Ishikawa cells (FIG. 21A).

Next, the mechanism of DLC1 regulation by estrogen was further characterized. Estrogen induced DLC1 expression in a dose- and time-dependent manner, and this could be effectively blocked by pure antiestrogen ICI 182,780 and by the transcription inhibitor actinomycin D (FIGS. 21B and 21C). The effect of Pak1 signaling on the expression of DLC1 in MCF-7/DA-Pak1 cells or a previously characterized MCF-7 clone expressing the dominant-negative autoinhibitory Pak1 fragment amino acid 83–149 (MCF-7/DN-Pak1 cells) (Vadlamudi et al., 2002) was studied. The conditional expression of Pak1 upregulated DLC1 expression (FIG. 21D), and vice versa as Pak1 inactivation downregulated DLC1 expression (FIG. 21E). Consistent with these results, conditional knock down of Pak1 by Pak1-siRNA also resulted in the loss of DLC1 expression (FIG. 21F). These results indicated that the optimal expression of DLC1 depended on the presence of functional Pak1 pathway and that DLC1 is a common target of estrogen and antiestrogen. To determine whether the observed upregulation of DLC1 by Pak1, estrogen, and tamoxifen was transcriptional in nature, the sequence of the putative DLC1 promoter was analyzed (Genebank genomic sequence accession # NM 003746 using MatInspector software GmbH; Genomatix, München, Germany) to see if it contained ERE. This program did not reveal any consensus 13 bp ERE sites. However, the DLC1 promoter contained potential ERE half-sites (TGACC), each in the vicinity of AP1-binding sites. To study the function of these sites, the DLC1 promoter 2.4 kb fragment containing the ERE half-sites was cloned into a pGL3-luciferase (luc) reporter system. Wild-type Pak1 stimulated DLC1 promoter activity (FIGS. 21G and 21H) while expression of Pak1 inhibitor 83-149 suppressed DLC1 promoter activity (FIGS. 21G and 21I). In addition, both estrogen and tamoxifen stimulated DLC1 promoter activity in Ishikawa cells (FIG. 21J). Together, these findings showed that Pak1 signaling plays an important role in the regulation of DLC1 transcription.

DLC1 Deregulation Leads to Estrogen Hypersensitivity and Tamoxifen Resistance

To understand the significance of the differential regulation of DLC1 by tamoxifen in Tam-sensitive and -resistant cells, the present inventors next studied whether DLC1 deregulation is sufficient to modulate hormone response. For this purpose, MCF-7 cells expressing T7-DLC1 (MCF-7/DLC1 cells) under a tet-inducible promoter were generated (FIG. 14A). Surprisingly, MCF-7/DLC1 cells exhibited increased expression of ER-regulated cell survival Bcl-2 protein (FIG. 14B), indicating that DLC1 deregulation played a role in the enhanced responsiveness to hormones.

Conditional deregulation of DLC1 affects the ability of estrogen and or tamoxifen to influence ER transactivation and cell growth. Results showed that DLC1 deregulation in MCF-7 cells caused an increase in the ability of ligand to stimulate ERE-dependent transactivation as well as confer tamoxifen resistance (FIG. 14C). The observed ability of DLC1 to enhance ER transactivation function was also noticed in tamoxifen-resistant Ishikawa and MCF-7/TAMR1 cells (FIG. 14D).

DLC1 Interacts with ER-Target Gene Chromatin

To delineate the significance of the DLC1 in the modulation of ER transactivation, the effect of T7-DLC1 deregulation on the recruitment of ER to the ER-target pS2 gene promoter chromatin using a chromatin immunoprecipitation (ChIP) assay with anti-ERα or anti-T7 antibodies was examined. As expected, estrogen stimulation of the MCF-7/DLC1 (doxycycline-untreated) cells resulted in an increased recruitment of ER to the pS2 gene chromatin (FIG. 14E). Interestingly, DLC1 overexpression in MCF-7/DLC1 cells followed by treatment with tamoxifen led to any enhanced ER interaction with the pS2 gene chromatin (FIG. 14E). When the above ChIP studies were repeated using T7 antibody to isolate T7-DLC1, it was observed that both basal and ligand-activated DLC1 were also recruited to pS2 gene chromatin (FIG. 14E). There was an increased nuclear accumulation of DLC1 in MCF-7/DLC1 cells treated with Dox. Because tamoxifen upregulates DLC1 in tamoxifen-resistant cells and because DLC1 has been shown to have nuclear functions (Kaiser et al., 2003), the finding of the recruitment of DLC1-ER complex to pS2 gene chromatin indicates that DLC1 deregulation promotes ER-transactivation and, thus, contributes to the development of tamoxifen resistance.

DLC1 Deregulation Potentiates Ligand-Induced Growth and Anchorage-Independence

Figure 22:
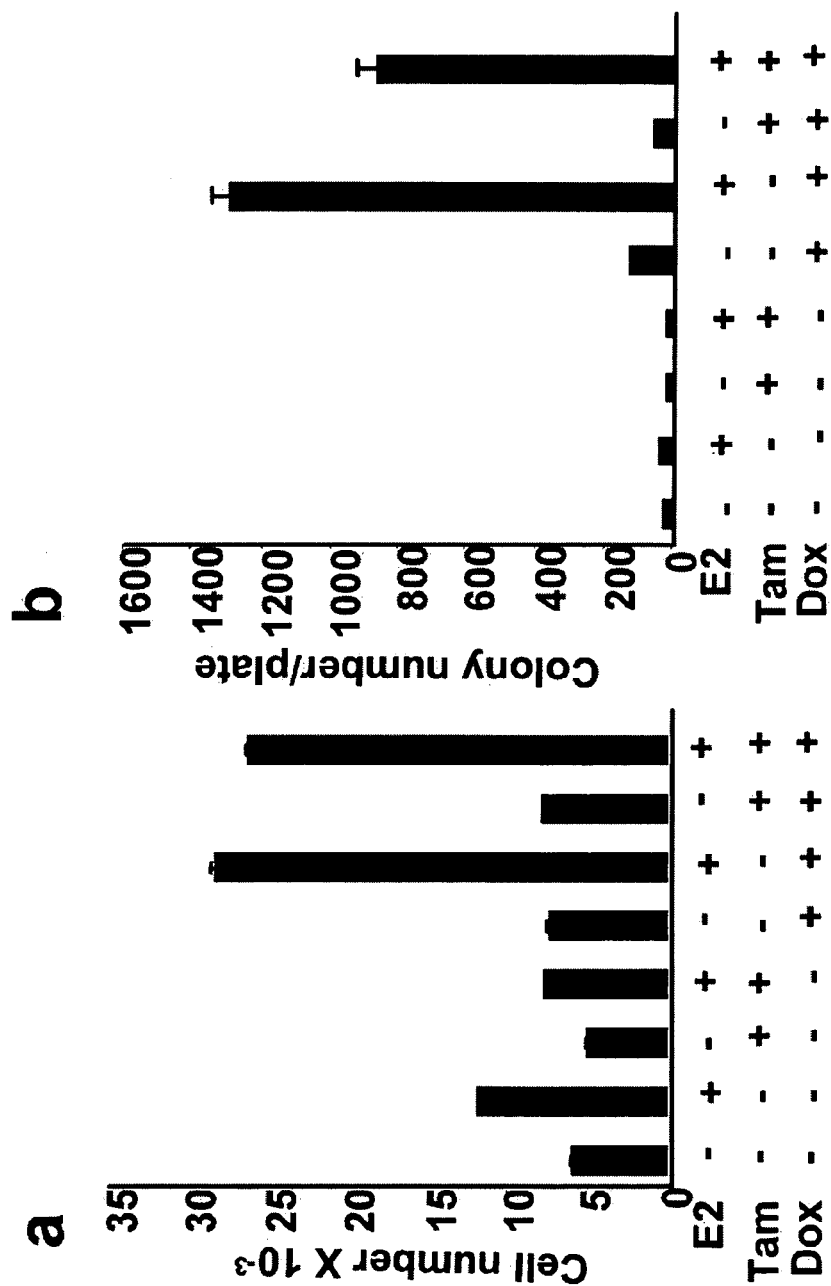
FIGS. 22A–22F—DLC1 deregulation potentiates ligand-induced growth and anchorage-independence.
Figure 22:
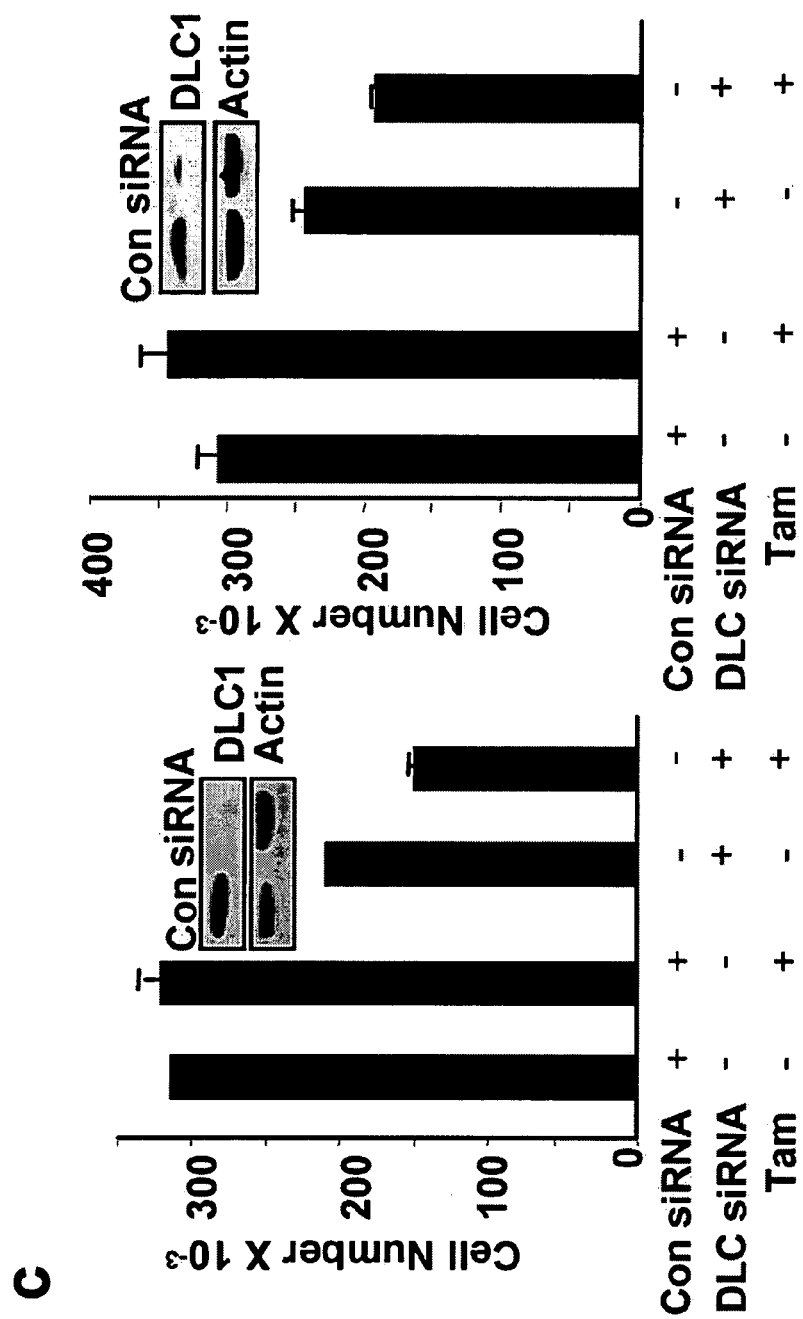
Figure 22:
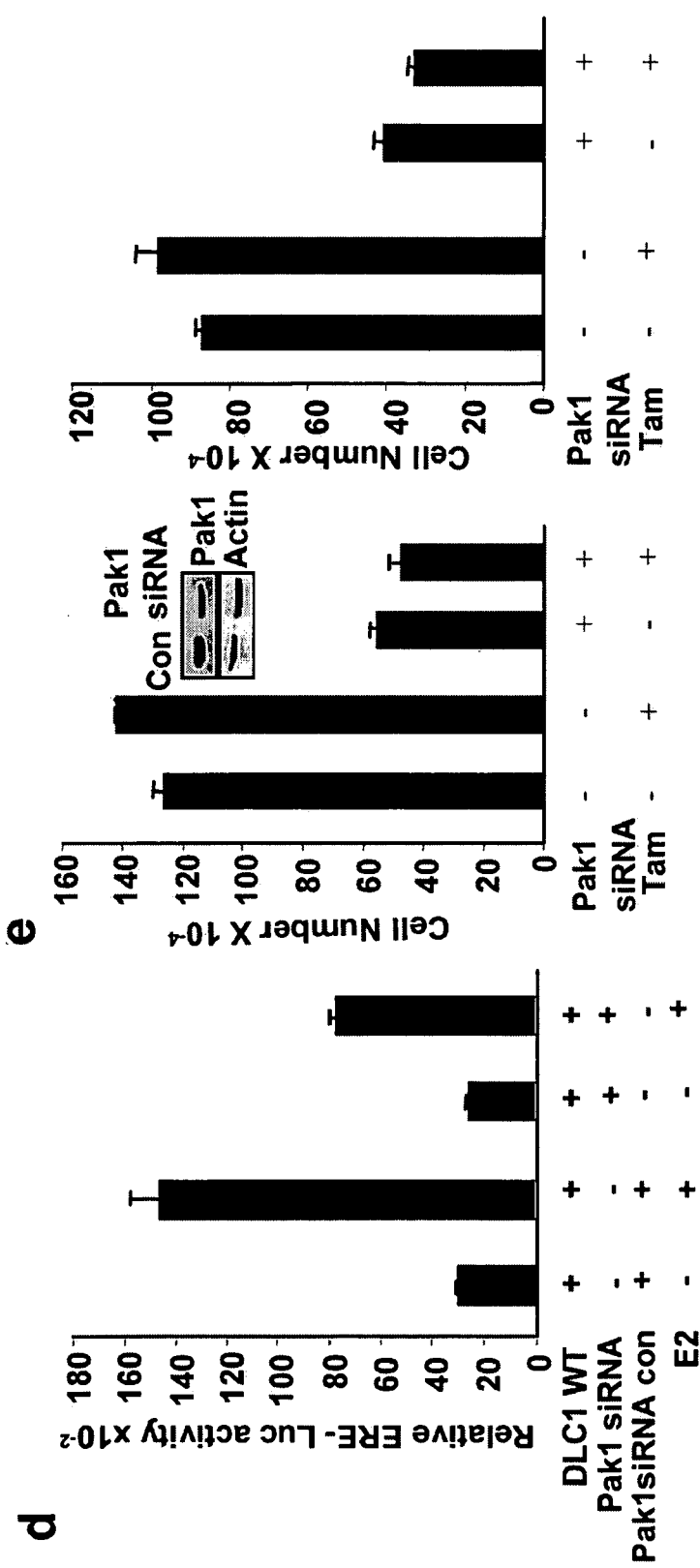
Figure 22:
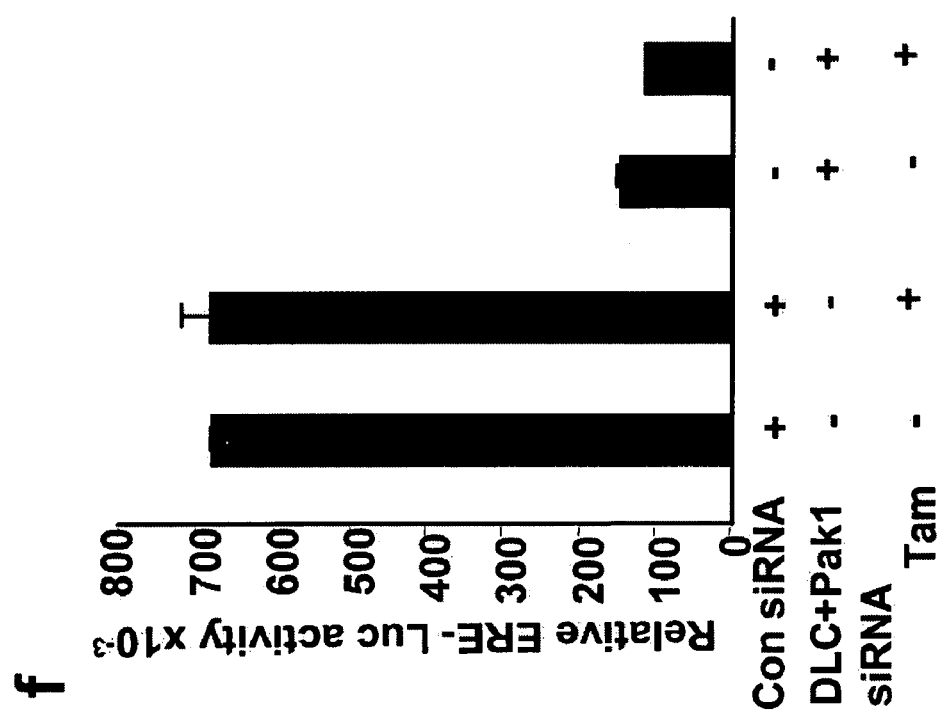

To examine the effect of DLC1 deregulation on the growth of breast cancer cells, it was explored whether conditional deregulation of DLC1 affects the ability of estrogen to promote the cell growth. Results showed that DLC1 deregulation in MCF-7 cells caused a significant increase in the ability of estrogen to stimulate the growth rate (FIG. 22A) as well as anchorage-independent growth in soft-agar (FIG. 22B). In addition, DLC1 deregulation was also observed to confer tamoxifen resistance in both of the assays (FIGS. 22A and 22B). To confirm the role of DLC1 in the regulation of cell growth, the endogenous DLC was downregulated using siRNA, which significantly reduced the growth of Ishikawa, and MCF-7/TAMR1 cells, and tamoxifen further reduced the growth of these cells (FIG. 22C).

Because the expression of DLC1 had proved to be under the control of Pak1 signaling (see FIG. 21), the present inventors reasoned that Pak1 played an upstream mechanistic role in the action of DLC1 in Ishikawa cells. To test this possibility, the present inventors selectively knocked down Pak1 by siRNA. Results showed that the selective downregulation of Pak1 by siRNA (wt) but not control siRNA prevented DLC1 from stimulating ERE transactivation (FIG. 22D). In addition, downregulation of the endogenous Pak1 in Ishikawa and MCF-7/TAMR1 cells also slowed the growth of these cells with no further significant effect of tamoxifen (FIG. 22E). To explain the noticed modest effect of tamoxifen in cells with knocked down DLC1 or Pak1, the present inventors reasoned that other Pak1 or DLC1-responsive pathways, respectively, has to play a role in tamoxifen resistance. Therefore, the present inventors next knocked down both DLC1 and Pak1 together, which restored the inhibitory effects of tamoxifen in Ishikawa cells (FIG. 22F). Together, these findings indicate that Pak1-DLC1 deregulation plays a role in both estrogen responsiveness and tamoxifen resistance.

DLC1, a Novel ER-interacting Protein

Because DLC1 deregulation induces both hypersensitivity to estrogen and tamoxifen resistance and because DLC1 contains two putative nuclear receptor binding motifs FXXFY (aa 74-78) and VXXLL (aa 81-85) (Hsu et al., 2003), it was studied whether tamoxifen resistance results from an interaction of DLC1 with ER. To test this possibility, the present inventors first evaluated the ability of in vitro-translated ER protein to bind to the DLC1-GST fusion protein. Indeed, the DLC1-GST-fusion protein, but not GST, efficiently interacted with 35S-labeled full-length ER protein (FIG. 13A). The DLC1 binding site in ER was mapped to the AB domain amino acid 1–180 of ER (FIG. 13B). Using a series of DLC1 deletion constructs, the minimal region of DLC1 required for it to interact with ER was identified. As shown in FIG. 13C (lanes 6–8), deletion of the N-terminal regions had no effect on ER binding, whereas deletion of the C-terminal's 22 amino acids in DLC1 (amino acids 67–89) containing the putative nuclear receptor binding motifs, completely abolished ER binding (FIG. 13C, lane 4).

The in vivo interaction of the endogenous DLC1 with ER was confirmed by the coimmunoprecipitation of ER and DLC1 from lysates from exponentially growing Ishikawa cells by an anti-ER-α monoclonal Ab but not by control IgG (FIG. 13D). To determine the effect of tamoxifen on the DLC1-ER interaction, the present inventors next immunoprecipitated ER from the cell lysates from MCF-7/TAM-Sen cells, and from Ishikawa cells, which are resistant to tamoxifen. This showed that tamoxifen substantially enhanced the DLC1-ER interaction in Ishikawa cells but not in MCF-7/TAM-Sen cells (FIG. 13E). To independently validate these findings, the present inventors treated MCF-7/DLC1 cells without or with doxycycline to induce the expression of T7-DLC1 and stimulated with estrogen or tamoxifen. Results showed that DLC1 deregulation was sufficient to promote the DLC1-ER interaction and that this interaction was modestly, but reproducibly, increased by estrogen or tamoxifen (FIG. 13F).

As stated elsewhere herein, DLC1 is a Pak1-interacting substrate, and Pak1 phosphorylates DLC1 on Ser88 and interacts with its C-terminal amino acid 67–89. Because DLC1 interacts with ER and because Pak1 phosphorylates DLC1 on Ser88, the influence of phosphorylated Ser88 in DLC1 on its ability to interact with ER was studied. To this end, MCF-7 cells expressing a T7-DLC1 mutant in which Ser88 and amino acid 89 were deleted under a tet-inducible promoter (MCF-7/DLC1-1-87 mutant) were generated (FIG. 13G). Coimmunoprecipitation studies failed to detect any interaction between ER and the T7-DLC1-1-87 mutant (FIG. 13H), suggesting that the Pak1 phosphorylation of DLC1 plays a role in an optimal DLC1-ER interaction and, presumably, that these interactions are enhanced in the setting of tamoxifen resistance. Further, expression of DLC1 1-68R mutant, lacking amino acids 67–89 and behaves as a dominant-negative, also reduced ERE-transactivation in the presence of tamoxifen compared to the wild type DLC1, suggesting that amino acids 67–89 of DLC1 is important for its ER transactivation function.

Because the binding sites for both Pak1 and ER (FIG. 13C) were mapped to an overlapping region of DLC1 amino acid 67–89, the present inventors next tested the relative interaction of Pak1 and DLC1 for the ER. Results from GST-AB domain pull-down studies using in vitro-translated $^{35}$S-labeled Pak1 and DLC1 proteins indicated that the GST-AB but not GST interacted with both DLC1 and Pak1, indicating a role of Pak1 regulation of DLC1 in the action of ER and tamoxifen resistance.

The Pak1-DLC1 Pathway is Upregulated in Endometrial Cancer

To characterize the physiological significance of the Pak1-DLC1 pathway in endometrial cancer, the levels of DLC1 and Pak1 in endometrial cancer, which is usually resistant to tamoxifen, were examined. Western blot analysis of seven tumor lysates revealed a 3- to 5-fold increase in the expression of DLC1 and 2 fold increase in Pak1 expression compared with the levels in normal endometrium (FIGS. 9A and 9B). The expression of DLC1 and Pak1 in a tumor array containing 54 endometrial cancer tissues was examined. Of the 54 specimens analyzed, 92% (49 of 54) showed about 3-fold increase in staining compared with normal endometrium and 8% (5 of 59) tumors showed undetectable DLC1 staining. Immunostaining of endometrial tumors showed an interesting change in the staining pattern (FIG. 9C). Many of the tumors showed strong nuclear staining for DLC1, unlike benign endometrial samples, which showed very weak staining. Pak1 expression was also upregulated in 38 out of 49 (77.6%) of endometrial tumors, and 11/49 (22.4%) tumors showed no positive staining. A secondary analysis of the samples (total 34 common spots on the array) scored positive for both DLC1 and Pak1 indicated that both DLC1 and Pak1 were upregulated in 30 out of 34 tumors. The expression and localization of DLC1 and Pak1 in the normal endometrium was also analyzed.

Because tamoxifen upregulates both Pak1 and DLC1, the present inventors reasoned that tamoxifen may activate Pak1 and DLC1 in endometrium, which might contribute to endometrial tumorigenesis. To assess this possibility, the status of Pak1 and DLC1 in a series of carefully selected endometrial tumors (n=2) from breast cancer patients treated with tamoxifen was examined. As a control, normal endometrium (n=9) was used from tamoxifen-treated breast cancer patients. The endometrial adenocarcinomas associated with tamoxifen use showed strong cytoplasmic Pak1 staining (FIG. 9D). Interestingly, many of these tumors also showed strong nuclear staining for DLC1 (FIG. 9D), which was not observed in the biopsy specimens of benign endometrium from breast cancer patients taking tamoxifen (FIG. 9D). Similarly, extension of these studies to a small number of breast cancer patients treated with tamoxifen also indicated that tamoxifen resistant breast tumors contain elevated DLC1 in the nuclear compartment as compared to the tamoxifen sensitive tumors with predominantly cytoplasmic DLC1. Strong cytoplasmic and nuclear staining of Pak1 was observed in tamoxifen resistant tumors compared to the tamoxifen sensitive tumors. Similarly, there was an enhancement in the levels of nuclear DLC1 in MCF-7/TAMR1 cells as compared to the levels in MCF-7/TAM-Sen cells. In a specific embodiment of the present invention, the expression of Pak1 and DLC1 is widely deregulated in the endometrial tumors, in endometrium of breast cancer patients treated with tamoxifen and in tamoxifen-resistant breast tumors (FIGS. 9C and 9D). Collectively, these data indicate an important role for Pak1 and DLC1 in the action of tamoxifen in endometrial tumorigenesis.

Thus, as described above, there is a role of the Pak1 pathway in modulating the responsiveness of the exemplary breast and endometrial cancer cells to estrogen and antiestrogens such as tamoxifen. The present inventors found that Pak1 activation was sufficient to stimulate ER transactivation, promote cell growth, and render cells insensitive to tamoxifen. There was also close linkage between the Pak1 level and hormone action that may have significant influence on the biology of breast cancer cells with acquired tamoxifen resistance and in endometrial cancer cells with natural tamoxifen resistance. Interestingly, tamoxifen induced steady-state levels of Pak1 under conditions of tamoxifen resistance, and thus promoted a persistent engagement of the putative downstream targets of Pak1, leading to prolonged stimulation of ER transactivation.

Consistent with the above notion, the present inventors unexpectedly found that tamoxifen selectively induced DLC1, a component of the dynein complex that predominantly exists in an uncomplexed form (Kaiser et al., 2003) in tamoxifen-resistant breast and endometrial cancer cells but not in tamoxifen-sensitive cells. The present inventors also discovered that the tamoxifen-mediated upregulation of DLC1 depended on a functional Pak1 pathway. Further supporting the mechanistic involvement of DLC1 in the action of estrogen was the finding that the conditional deregulation of DLC1 alone in tamoxifen-sensitive breast cancer cells led to estrogen hypersensitivity (as shown by ER transactivation, the growth rate, and anchorage-independent growth assays) and tamoxifen resistance. Interestingly, these phenotypic changes in cellular responsiveness to estrogen and tamoxifen were mimicked by the conditional deregulation of Pak1, an upstream regulator of DLC1 expression and function. From this it appears that breast cancer cells with deregulated DLC1 respond to estrogen and tamoxifen in a manner similar to Ishikawa endometrial cancer cells. Together, these findings revealed a new mechanistic role of Pak1 and DLC1 in tamoxifen resistance.

The observations that DLC1 directly interacted with ER and that the deregulation of DLC1 as well as tamoxifen, which enhances DLC1 expression, further promoted the DLC1-ER interaction are important because they indicate that the deregulation of DLC1 influences ER functions in tamoxifen-resistant cancer cells. Indeed, this study revealed that the deregulation of DLC1 potentiated ER transactivation only in the presence of an estrogenic signal, while there was no such effect from DLC1 upregulation and tamoxifen alone. Additional support for the role of the DLC1-ER interaction in the regulation of ER-inducible genes and mitogenic responses came from the fact that DLC1, in addition to ER, was also effectively recruited to ER target pS2 promoter chromatin only in the presence of an estrogenic signal, presumably due to the interaction of DLC1 with the activated ER. This finding, in turn, prompted the present inventors to determine the physiological significance of these findings and subsequently to discover the nuclear localization of DLC1 and the essential facilitating role of DLC1 in the nuclear accumulation of ER. This further led to their finding that the DLC1-ER complex influences the expression of ER-regulated genes. Because the levels of DLC1 were increased by both estrogen and tamoxifen in tamoxifen-resistant cells, it is conceivable that any upregulation of DLC1 leads to the increased nuclear localization of DLC1 as well as the upregulation of ER target gene products and ER-associated functions, as shown in the present study in tamoxifen-resistant breast and endometrial cancer cells. These findings are significant and physiologically relevant, as Pak1 and its effector DLC1 are widely deregulated in human endometrial cancer as compared with normal endometrium. In addition DLC1 was found to be predominantly localized in the nucleus in endometrial cancer cells from breast cancer patients treated with tamoxifen.

Besides the natural ligand estrogen, several growth factor signaling molecules, including Akt, protein kinase A, and pp90rsk1, can phosphorylate the AF1 domain of ER and thus, contributes to the transactivation function of ER in a ligand-independent manner (Osborne and Schiff, 2003). However, the transactivation function of the AF2 domain of ER has been shown to be regulated in both a ligand-dependent manner (Nilson and Gustafsson, 2002) and a ligand-independent manner by Pak1 (Wang et al., 2002). Because many of the growth factor signaling components converge at Pak1 and because DLC1 is downstream from Pak1, in some embodiments DLC1 acts as a broader-range effector of the previously shown growth factor-mediated development of tamoxifen resistance. In this context, the present inventors also found that epidermal growth factor stimulation promotes the interaction of DLC1 with ER in tamoxifen-resistant Ishikawa cells but not in tamoxifen-sensitive MCF-7 cells, providing evidence of the involvement of DLC1 in growth factor-associated tamoxifen resistance. Taken together, these findings establish a role for the DLC1 regulation of the AF1 domain of ER and its transactivation functions in tamoxifen resistance. Because inactivation of the Pak1 phosphorylation site in DLC1 prevents it from interacting with ER and because Pak1 phosphorylation of the AF2 domain at Ser305 also leads to the ligand-independent transactivation of ER18, it is contemplated that Pak1 promotes ER transactivation and function via both the AF2 and AF1 domains of ER.

DLC/PIN Peptide Affects LDL Stimulated Macropinocytosis

Figure 23:
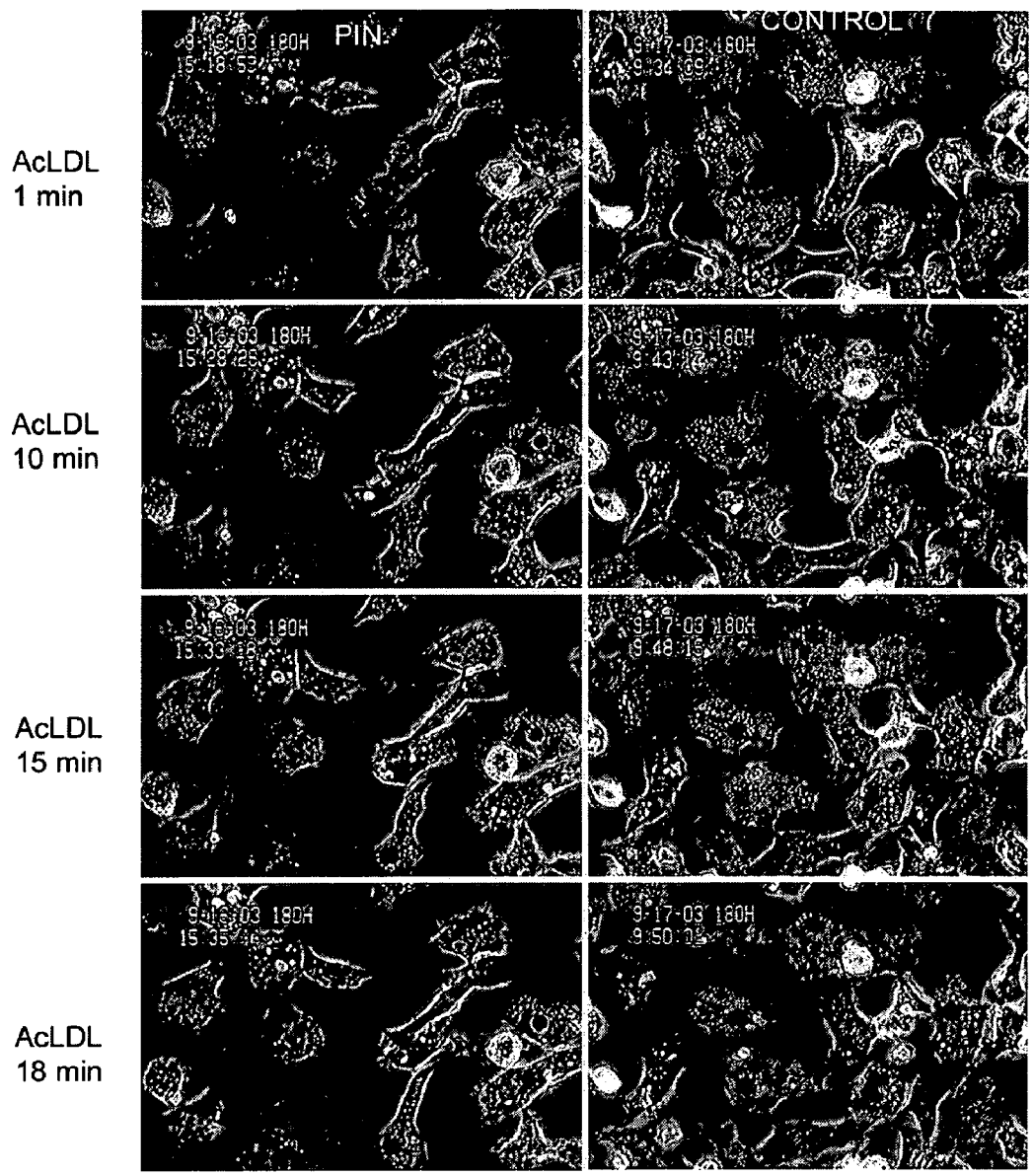
FIG. 23—DLC/PIN peptide effect on LDL-stimulated macropinocytosis. Macrophage cells grown on Petri dishes were given DLC1/PIN peptide or control peptide in presence of LDL and video images were taken using digital video camera. Time-lapse photos are provided at 1 min, 10 min, 15 min, and 18 min.

To study the effects of DLC1/PIN peptide on LDL and macropinocytosis, macrophage cells grown on Petri dishes were given DLC1/PIN peptide or control peptide in presence of LDL and video images were taken using digital video camera (FIG. 23).

LDL addition increased ruffling activity, an indication of increased macropinocytosis. Control peptide treatment did not stop higher membrane ruffling activity indicating no effect of control peptide on LDL mediated macropinocytosis. However, DLC1/PIN peptide treated cells have very little ruffling activity, suggesting DLC1/PIN peptide can interfere with LDL-induced macropinocytosis. Since LDL-mediated macropinocytosis is implicated in Foam cell formation and macrophage cholesterol accumulation in atherosclerosis, DLC1/PIN peptide or other DLC1 compositions are utilized for treating foam cell and atherosclerosis diseases, in some embodiments.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. patent Ser. No. 117,363
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,659,774
U.S. Pat. No. 4,682,195
U.S. Pat. No. 4,683,202
U.S. Pat. No. 4,797,368
U.S. Pat. No. 4,816,571
U.S. Pat. No. 4,938,948
U.S. Pat. No. 4,959,463
U.S. Pat. No. 5,021,235
U.S. Pat. No. 5,139,941
U.S. Pat. No. 5,141,813
U.S. Pat. No. 5,196,066
U.S. Pat. No. 5,214,136
U.S. Pat. No. 5,223,618
U.S. Pat. No. 5,264,566
U.S. Pat. No. 5,378,825
U.S. Pat. No. 5,428,148
U.S. Pat. No. 5,446,137
U.S. Pat. No. 5,466,786
U.S. Pat. No. 5,470,967
U.S. Pat. No. 5,539,082
U.S. Pat. No. 5,539,082
U.S. Pat. No. 5,554,744
U.S. Pat. No. 5,574,146
U.S. Pat. No. 5,602,240
U.S. Pat. No. 5,602,244
U.S. Pat. No. 5,610,289
U.S. Pat. No. 5,614,617
U.S. Pat. No. 5,623,070
U.S. Pat. No. 5,645,897
U.S. Pat. No. 5,652,099
U.S. Pat. No. 5,670,663
U.S. Pat. No. 5,672,344
U.S. Pat. No. 5,672,697
U.S. Pat. No. 5,681,947
U.S. Pat. No. 5,700,922
U.S. Pat. No. 5,708,154
U.S. Pat. No. 5,714,331
U.S. Pat. No. 5,714,331
U.S. Pat. No. 5,714,606
U.S. Pat. No. 5,719,262
U.S. Pat. No. 5,719,262
U.S. Pat. No. 5,736,336
U.S. Pat. No. 5,763,167
U.S. Pat. No. 5,766,855
U.S. Pat. No. 5,766,855
U.S. Pat. No. 5,773,571
U.S. Pat. No. 5,777,092
U.S. Pat. No. 5,786,461
U.S. Pat. No. 5,792,847
U.S. Pat. No. 5,858,988
U.S. Pat. No. 5,859,221
U.S. Pat. No. 5,872,232
U.S. Pat. No. 5,886,165
U.S. Pat. No. 5,891,625
U.S. Pat. No. 5,908,845
U.S. Pat. No. 5,925,565
U.S. Pat. No. 5,928,906
U.S. Pat. No. 5,935,819

Abbondanzo, *Ann Diagn Pathol*, 3(5):318–327, 1999.
Adam et al., *Canc. Res.* 61: 81–87, 2001.
Adam et al., *J. Biol. Chem.* 276: 28443–28450, 2001.
Aderem and Underhill, *Annu. Rev. Immunol.*, 17:593–623, 1999.
Aksentijevich et al., *Hum. Gene Ther.*, 7(9):1111–1122, 1996.
Allred et al., *Arch. Surg*, 125(1):107–113, 1990.
Angel et al., *Cell*, 49:729, 1987b.
Angel et al., *Mol. Cell. Biol.*, 7:2256, 1987a.
Antibodies, A Laboratory Manual, Cold Spring Harbor Laboratory, 1988.
Atchison and Perry, *Cell*, 46:253, 1986.
Atchison and Perry, *Cell*, 48:121, 1987.
Atherton et al., *Biol. Reprod.*, 32(1):155–171, 1985.
Bagheri et al., *J. Biol. Chem.*, 276:29403–29409, 2001.
Bagheri et al., *J. Pediatr. Ophthalmol. Strabismus*, 39(5):310–312, 2002.
Bagrodia and Cerione, *Trends Cell Biol.*, 9:350–355, 1999.
Banerjee et al., *Curr. Biol.*, 12:1233, 2002.
Banerji et al., *Cell*, 27(2 Pt 1):299–308, 1981.
Banerji et al., *Cell*, 33(3):729–740, 1983.
Batterson and Roizman, *J. Virol.*, 46(2):371–377, 1983.
Beckwith et al., *J. Cell Biol.*, 143:1239–47, 1998.
Benvenisty and Neshif, *Proc. Natl. Acad. Sci. USA*, 83(24):9551–9555, 1986.
Benz et al., *Brst. Canc. Res. Treat.*, 24:85–95, 1992.
Ben-Ze'ev, *Cell Biol.*, 9:99–108, 1997.
Berberian et al., *Science*, 261(5128):1588–1591, 1993.
Berkhout et al., *Cell*, 59:273–282, 1989.
Blanar et al., *EMBO J.*, 8:1139, 1989.
Bodine and Ley, *EMBO J.*, 6:2997, 1987.
Bokoch et al., *J. Biol. Chem.*, 271:25746–25749, 1996.
Bokoch et al., *J. Biol. Chem.*, 273:8137–8144, 1998.
Borg et al., *Cancer Lett.* 81:137–144, 1994.
Boshart et al., *Cell*, 41:521, 1985.
Bosze et al., *EMBO J.*, 5(7):1615–1623, 1986.
Boussif et al., *Proc. Natl. Acad. Sci. USA*, 92(16):7297–301, 1995.
Braddock et al., *Cell*, 58:269, 1989.
Brestscher, *Cell* 87:601–606, 1996
Bretscher and Aguado-Velasco, *Cell Biol.*, 10:537–541, 1998.
Brown et al., *Immunol. Ser.*, 53:69–82, 1990.
Bulla and Siddiqui, *J. Virol.*, 62:1437, 1986.
Butch et al., *Exp. Hematol.*, 29(1):85–92, 2001.
Caley et al., *J. Virology*, 71(4):3031–3038, 1997.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Carbonelli et al., *FEMS Microbiol. Lett.*, 177(1):75–82, 1999.
Carraway et al., *J. Biol. Chem.*, 270:7111–7116, 1995.
Cataldo et al., *Ann. Neurol.*, 50:661–665, 2001.

Celander and Haseltine, *J. Virology*, 61:269, 1987.
Celander et al., *J. Virology*, 62:1314, 1988.
Chandler et al., *Cell*, 33:489, 1983.
Chandler et al., *Proc. Natl. Acad. Sci. USA*, 94(8):3596–601, 1997.
Chang et al., *Hepatology*, 14:134A, 1991.
Chang et al., *Mol. Cell. Biol.*, 20:8571–8579, 2000.
Chang et al., *Mol. Cell. Biol.*, 9:2153, 1989.
Chen et al., *J. EMBO*, 21:6801–6810, 2002.
Chatterjee et al., *Proc Natl. Acad. Sci. U.S.A.*, 86:9114, 1989.
Chen and Okayama, *Mol. Cell Biol.*, 7(8):2745–2752, 1987.
Choi et al., *Cell*, 53:519, 1988.
Clark et al., *Hum. Gene Ther.*, 6(10):1329–1341, 1995.
Cleary et al., *J. Biol. Chem.*, 269(29):18747–18749, 1994.
Cocea, *Biotechniques*, 23(5):814–816, 1997.
Coffin, Retroviridae and Their Replication. In: *Virology*, Fields et al., (eds.), Raven Press, NY, 1437–1500, 1990.
Cohen et al., *J. Cell. Physiol.*, 5:75, 1987.
Costa et al., *Mol. Cell. Biol.*, 8:81, 1988.
Couch et al., *Am. Rev. Resp. Dis.*, 88:394–403, 1963.
Crepieux et al., *Mol. Cell Biol.*, 17:7375–7385, 1997.
Cripe et al, *EMBO J.*, 6:3745, 1987.
Culotta and Hamer, *Mol. Cell. Biol.*, 9:1376, 1989.
Dandolo et al., *J. Virology*, 47:55–64, 1983.
Daniels and Bokoch, *Trends Biochem. Sci.*, 24:350–355, 1999.
Davies et al., *J. Cell Physiol.*, 102:119–127, 1980.
Davis et al., *Curr. Biol.*, 6:146–148, 1996.
De Jager et al., *Semin. Nucl. Med.*, 23(2):165–179, 1993.
De Villiers et al., *Nature*, 312(5991):242–246, 1984.
DeLuca et al., *J. Virol.*, 56(2):558–570, 1985.
Derynck, *Adv. Canc. Res.* 58: 27–52, 1992.
Deschamps et al., *Science*, 230:1174–1177, 1985.
Dharmawardhane et al., *J. Cell Biol.*, 138:1265–1278, 1997.
Dharmawardhane et al, *Mol. Biol. Cell.* 11:3341–3352, 2000.
Dholakia et al., *J. Biol. Chem.*, 264(34):20638–20642, 1989.
Dick et al., *Molec. Cell. Biol.*, 16:1966–1977.
Doolittle and Ben-Zeev, *Methods Mol Biol*, 109:215–237, 1999.
Dowsett et al., *Cancer Research.* 61:8452–8458, 2001a.
Dowsett, *Endocrine-Related Cancer*, 8:191–195, 2001 b.
Dubensky et al., *Proc. Natl. Acad. Sci. USA*, 81:7529–7533, 1984.
Earp et al., *Brst Canc. Res. Treat.*, 35:115–132, 1995.
Edbrooke et al., *Mol. Cell. Biol.*, 9:1908, 1989.
Edlund et al., *Science*, 230:912–916, 1985.
Edwards and Gill, *J. Biol. Chem.*, 274:11352–11361, 1999.
Edwards et al., *Nature Cell Biology*, 1:253–259, 1999.
Elroy-Stein et al., *Proc. Natl. Acad. Sci. USA*, 86(16): 6126–30, 1989.
Espindola et al., 47:269–281, 2000.
European App. EP 01219
European App. EP 266,032
Fan et al., *J. Biol. Chem.*, 273:33472–33481, 1998.
Fan et al., *J. Mol. Biol.*, 306:97–108, 2001.
Fechheimer et al., *Proc. Natl. Acad. Sci. USA*, 84:8463–8467, 1987.
Feigner et al., *Proc. Natl. Acad. Sci. USA*, 84(21):7413–7417, 1987.
Feng and Holland, *Nature*, 334:6178, 1988.
Firak and Subramanian, *Mol. Cell. Biol.*, 6:3667, 1986.
Flotte et al., *Am. J. Respir. Cell Mol. Biol.*, 7(3):349–356, 1992.
Foecking and Hofstetter, *Gene*, 45(1):101–105, 1986.
Fraley et al., *Proc. Natl. Acad. Sci. USA*, 76:3348–3352, 1979.
Froehler et al., *Nucleic Acids Res.*, 14(13):5399–5407, 1986.
Frost et al., *J. Biol. Chem.*, 273:28191–28198, 1998.
Fujita et al., *Cell*, 49:357, 1987.
Gabizon et al., *Cancer Res*, 50(19):6371–8, 1996.
Ghosh and Bachhawat, In: *Liver Diseases, Targeted Diagnosis and Therapy Using Specific Receptors and Ligands*. Wu et al., eds., Marcel Dekker, NY, 87–104, 1991.
Ghosh-Choudhury et al., *EMBO J.*, 6:1733–1739, 1987.
Gilles et al., *Cell*, 33:717, 1983.
Glorioso et al., *Mol. Biotechnol.*, 4(1):87–99, 1995.
Gloss et al., *EMBO J.*, 6:3735, 1987.
Godbout et al., *Mol. Cell. Biol.*, 8:1169, 1988.
Gomez-Foix et al., *J. Biol. Chem.*, 267:25129–25134, 1992.
Goodbourn and Maniatis, *Proc. Nat'l Acad. Sci. USA*, 85:1447, 1988.
Goodbourn et al., *Cell*, 45:601, 1986.
Gopal, *Mol. Cell Biol.*, 5:1188–1190, 1985.
Graham and Prevec, In: *Methods in Molecular Biology: Gene Transfer and Expression Protocol*, Murray (Ed.), Humana Press, Clifton, N.J., 7:109–128, 1991.
Graham and van der Eb, *Virology*, 52:456–467, 1973.
Graham et al., "Characteristics of a human cell line transformed by DNA from human adenovirus type 5 DNA", *J. Gen. Virol.*, 36:59–72, 1977.
Greene et al., *Immunology Today*, 10:272, 1989
Grosschedl and Baltimore, *Cell*, 41:885, 1985.
Grunhaus et al., *Seminar in Virology*, 200(2):535–546, 1992.
Gulbis and Galand, *Hum Pathol*, 24(12):1271–85, 1993.
Haigler et al., *J. Cell Biol.*, 83(1):82–90, 1979.
Harland and Weintraub, *J. Cell Biol.*, 101:1094–1099, 1985.
Haslinger and Karin, *Proc. Nat'l Acad. Sci. USA*, 82:8572, 1985.
Hauber and Cullen, *J. Virology*, 62:673, 1988.
Hayden, *Cell. Motil. Cytoskeleton*, 10:255–262, 1988.
Hen et al., *Nature*, 321:249, 1986.
Hensel et al., *Lymphokine Res.*, 8:347, 1989.
Heppner et al., *Breast Cancer Res.*, 2:331–334, 2000.
Hermonat and Muzycska, *Proc. Natl. Acad. Sci. USA*, 81:6466–6470, 1984.
Herr and Clarke, *Cell*, 45:461, 1986.
Hersdorffer et al., *DNA Cell Biol.*, 9:713–723, 1990.
Herz and Gerard, *Proc. Natl. Acad. Sci. USA*, 90:2812–2816, 1993.
Hirochika et al., *J. Virol.*, 61:2599, 1987.
Hirokawa, *Science*, 279:519–526, 1998.
Hirsch et al., *Mol. Cell. Biol.*, 10:1959, 1990.
Hodges, L. C. et al. *Mol. Cancer. Res.* 1, 300–311 (2003).
Holbrook et al., *Virology*, 157:211, 1987.
Holland and Holland, *J. Biol Chem*, 255(6):2596–605, 1980.
Holzbaur and Vallee, *Annu. Rev. Cell Biol.*, 10:339–372, 1994.
Hones and Roizman, *J. Virol*, 16(5):1308–1326, 1975.
Hones and Roizman, *J. Virol.*, 14(1):8–19, 1974.
Horan et al., *J. Biol. Chem.*, 270:24604–24608, 1995.
Horlick and Benfield, *Mol. Cell. Biol.*, 9:2396, 1989.
Horwich et al., *Virol.*, 64:642–650, 1990.
Hsu, C-L. et al. *J. Biol. Chem.* 278, 23691–23698, 2003.
Huang et al., *Cell*, 27:245, 1981.
Hug et al., *Mol. Cell. Biol.*, 8:3065, 1988.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol*, 7:2558, 1987.
Imperiale and Nevins, *Mol. Cell. Biol.*, 4:875, 1984.

Jaffer and Chernoff, *Int. J. Biochem. Cell Biol.*, 34:713–717, 2002.
Jaffery and Snyder, *Science*, 274:774–777, 1996.
Jakobi et al., *J. Biol. Chem.*, 276:16624–16634, 2001.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Jones et al., *Arterioscler. Thromb. Vasc. Biol.*, 20:773–781, 2000.
Johnson et al., *Mol. Cell. Biol.*, 9:3393, 1989.
Jones and Shenk, *Cell*, 13:181–188, 1978.
Jordan, *Br. J. Pharm.*, 110:507–517, 1993.
Kadesch and Berg, *Mol. Cell. Biol.*, 6:2593, 1986.
Kaiser, F. J. et al. *Hum. Mol. Genet.* 12, 1349–1358, 2003.
Kaneda et al., *Science*, 243:375–378, 1989.
Kang et al., *Science*, 240(4855):1034–6, 1988.
Kaplitt et al., *Nat Genet.*, 8(2):148–54, 1994.
Karin et al., *Mol. Cell. Biol.*, 7:606, 1987.
Karin et al., *Mol. Cell. Biol.*, 7:606, 1987.
Karlsson et al., *EMBO J.*, 5:2377–2385, 1986.
Katinka et al., *Cell*, 20:393, 1980.
Kato et al., *J. Biol. Chem.*, 266:3361–3364, 1991.
Kawamoto et al., *Mol. Cell. Biol.*, 8:267, 1988.
Khatoon et al., *Ann. Neurol*, 26(2):210–5, 1989.
Kiledjian et al., *Mol. Cell. Biol.*, 8:145, 1988.
King et al., *J. Biol. Chem*, 264(17):10210–10218, 1989.
Klamut et al., *Mol. Cell. Biol.*, 10:193, 1990.
Klein et al., *Nature*, 327:70, 1987.
Koch et al., *Mol. Cell. Biol.*, 9:303, 1989.
Kohler et al., *Methods Enzymol*, 178:3–35, 1989.
Kornberg and Baker, In: *DNA Replication*, 2nd Ed., Freeman, San Francisco, 1992.
Kotin et al., *Proc. Natl. Acad. Sci. USA*, 87(6):2211–2215, 1990.
Kozma et al., *Mol. Cell. Biol.* 15: 1842–1952, 1995.
Kramarski et al., *J. Biol. Chem.*, 271: 19029–19032, 1996.
Kriegler and Botchan, In: *Eukaryotic Viral Vectors*, Gluzman (ed.), Cold Spring Harbor, Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kumar and Vadlamudi, *J. Cell. Physiol.*, 193:133–144, 2002.
Kumar et al. *J. Cell. Biochem.*, 62:102–112, 1995.
Kumar et al., *Clin. Can. Res.*, 2:1215–1219, 1996.
Kumar Mendelsohn, *Curr. Oncol.*, 3:70–75, 1991.
Kunz et al., *Nucl. Acids Res.*, 17:1121, 1989.
Kurokawa et al., *Canc. Res.*, 60:5887–5894, 2000.
LaFace et al., *Virology*, 162(2):483–486, 1988.
Lanzavecchia, *Curr. Immu.*, 8:348–354, 1996.
Larsen et al., *Proc Natl. Acad. Sci. USA*, 83:8283, 1986.
Laspia et al., *Cell*, 59:283, 1989.
Latimer et al., *Mol. Cell. Biol.*, 10:760, 1990.
Lauffenburger and Horwitz, *Cell.*, 84:359–369, 1996.
Laughlin et al., *J. Virol.*, 60(2):515–524, 1986.
Le Gal La Salle et al., *Science*, 259:988–990, 1993.
Lebkowski et al., *Mol. Cell. Biol.*, 8(10):3988–3996, 1988.
Lee et al., *Nature*, 294:228, 1981.
Lee et al., *Nucleic Acids Res.*, 12:4191–206, 1984.
Lemmon and Schlessinger, *Trends Biochem. Sch.*, 19:459–463, 1994.
Lenert et al., *Science*, 248(4963):1639–43, 1990.
Levenson et al., *Hum Gene Ther*, 9(8):1233–6, 1998.
Levenson, A. S. et al. *Cancer Res.* 62, 4419–4426 (2002).
Levinson et al., *Nature*, 295:79, 1982.
Levrero et al., *Gene*, 101:195–202, 1991.
Li et al., *EMBO Reports*, 3:767–773, 2002.
Li et al., *FEBS Lett.*, 524:49–53, 2002.
Li, Z. et al. *Cell* 114, 215–227, 2003.
Lian et al., *J. Immunol.*, 166:2643–2650, 2001.
Liana et al., *Canc. Res.*, 61:81–87, 2001.
Liang et al., *Nat. Struct. Biol.*, 6:735–740, 1999.
Lin et al., *Mol. Cell. Biol.*, 10:850, 1990.
Luria et al., *EMBO J.*, 6:3307, 1987.
Lusky and Botchan, *Proc Natl. Acad. Sci. USA*, 83:3609, 1986.
Lusky et al, *Mol. Cell. Biol.* 3:1108, 1983.
Macejak and Sarnow, *Nature*, 353:90–94, 1991.
Majors and Varmus, *Proc. Natl. Acad. Sci. USA*, 80:5866, 1983.
Mann et al., *Cell*, 33:153–159,1983.
Mann et al., *EMBO J.*, 10:1733–1739,1991.
Manser et al., *Molec. Cell Biol.*, 17:1129–1143, 1997.
Manser et al., *Nature*, 367:40–46, 1994.
Marechal et al., *J. Virol.*, 75(22):1116–11177, 2001.
Markowitz et al., *J. Virol.*, 62:1120–1124, 1988.
Marte et al., *Oncogene*, 10:167–175, 1995.
Mazumdar et al., *Canc. Res.* 61:400–405, 2001.
Mazumdar et al., *Nature Cell Biology.* 3:30–37, 2001.
Mazumdar, A. and Kumar, R. FEBS Lett. 535, 6–10 (2003).
McCarty et al., *J. Virol.*, 65(6):2936–45, 1991.
McLaughlin et al., *J. Virol.*, 62(6):1963–1973, 1988.
McLaughlin et al., *J. Virol.*, 62(6):1963–1973, 1988.
McManus et al., *J. Biol. Chem.*, 275:35328–35334, 2000.
McNeall et al., *Gene*, 76:81, 1989.
Medina, *Methods Canc. Res.*, 7:353–414, 1973.
Meier et al., *J. Cell Biol.*, 158(6):1119–1131,2002.
Menard et al., *J. Cell. Physiol.*, 182:150–162, 2000.
Miksicek et al., *Cell*, 46:203, 1986.
Mitchison and Cramer, *Cell*, 84:371–379, 1996.
Mordacq and Linzer, *Genes and Dev.*, 3:760, 1989.
Moreau et al., *Nuc. Acids Res.*, 9:6047, 1981.
Muesing et al., *Cell*, 48:691, 1987.
Muss et al., *New Eng. J. Med.*, 330:1260–1266, 1994.
Muzyczka, *Curr Top Microbiol Immunol*, 158:97–129, 1992.
Naisbitt et al., *J. Neurosci.*, 20:4524–4534, 2000.
Nakamura et al., In: *Handbook of Experimental Immunology* ($4^{th}$ Ed.), Weir et al., (eds), 1:27, Blackwell Scientific Publ., Oxford, 1987.
Naruiya et al., *FEBS Lett.*, 410:68–72, 1997.
Ng et al., *Nuc. Acids Res.*, 17:601, 1989.
Nicolas and Rubenstein, In: *Vectors: A survey of molecular cloning vectors and their uses*, Rodriguez and Denhardt (eds.), Stoneham: Butterworth, 493–513, 1988.
Nicolau and Sene, *Biochim. Biophys. Acta*, 721:185–190, 1982.
Nicolau et al., "Liposomes as carriers for in vivo gene transfer and expression," *Methods Enzymol.*, 149:157–176, 1987.
Nilson, S. & Gustafsson, J. A. *Crit. Rev. Eukaryot. Gene Expr.* 12, 237–257, 2002.
Nobes and Marsh, *Curr. Biol.*, 10(20):R739–741, 2000.
Nobles and Hall, *Cell*, 81:53–62, 1995.
Norton, *Seminars in Oncology*, 2410):3–10, 1997.
O'Shannessy et al., *Anal Biochem*, 163(1):204–209, 1987.
Ohi et al., *Gene*, 89(2):279–282, 1990.
Ondek et al., *EMBO J.*, 6:1017, 1987.
Omitz et al., *Mol. Cell. Biol.*, 7:3466, 1987.
Owens and Haley, *Biochem. Biophys. Res. Commun.*, 142 (3):964–71, 1987.
Palmiter et al., *Nature*, 300:611, 1982.

Paskind et al., *Virology*, 67:242–248, 1975.
Pazour et al., *J. Cell Biol.*, 141:979–992, 1998.
PCT App. WO 98/07408
PCT Appl. WO 84/03564
PCT Appl. WO 92/20702
Pech et al., *Mol. Cell. Biol.*, 9:396, 1989.
Peles et al., *Cell*, 69:205–216, 1992.
Pelletier and Sonenberg, *Nature*, 334(6180):320–325, 1988.
Perez-Stable and Constantini, *Mol. Cell. Biol.*, 10:1116, 1990.
Picard and Schaffner, *Nature*, 307:83, 1984.
Pietras et al., *Oncogene*, 10:2435–2446, 1995.
Pinkert et al., *Genes and Dev.*, 1:268, 1987.
Ponta et al., *Proc. Nat'l Acad. Sci. USA*, 82:1020, 1985.
Porton et al., *Mol. Cell. Biol.*, 10:1076, 1990.
Post et al., *Cell*, 24(2):555–65, 1981.
Potter and Haley, Methods Enzymol, 91:613–633, 1983.
Potter et al., *Proc. Natl. Acad. Sci. USA*, 81:7161–7165, 1984.
Puthalakath et al., *Mol. Cell*, 3:287–296, 1999.
Queen and Baltimore, *Cell*, 35:741, 1983.
Quinn et al., *Mol. Cell. Biol.*, 9:4713, 1989.
Racher et al., *Biotech. Tech.*, 9:169–174, 1995.
Ragot et al., *Nature*, 361:647–650, 1993.
Redondo et al., *Science*, 247:1225, 1990.
Reichmann, *Semin. Canc. Biol.*, 5:157–165, 1994.
Reisman and Rotter, *Mol. Cell. Biol.*, 9:3571, 1989.
Remington's Pharmaceutical Sciences, 15$^{th}$ ed., 1035–1038 and 1570–1580, Mack Publishing Company, Easton, Pa., 1980.
Renan, *Radiother. Oncol.*, 19:197–218, 1990.
Resendez Jr. et al., *Mol. Cell. Biol.*, 8:4579, 1988.
Rich et al., *Hum. Gene Ther.*, 4:461–476, 1993.
Ridley and Hall, *Cell*, 70:389–399, 1992.
Rigden et al., *Immunology*, 106(4):537–548, 2002.
Ripe et al., *Mol. Cell. Biol.*, 9:2224, 1989.
Rippe et al., *Mol. Cell Biol.*, 10:689–695, 1990.
Rittling et al., *Nuc. Acids Res.*, 17:1619, 1989.
Roig and Traugh, *J. Biol. Chem.*, 274:31119–31122, 1999.
Rosen et al., *Cell*, 41:813, 1988.
Rosenfeld et al., *Cell*, 68:143–155, 1992.
Rosenfeld et al., *Science*, 252:431–434, 1991.
Roux et al., *Proc. Natl. Acad. Sci. USA*, 86:9079–9083, 1989.
Sakai et al., *Genes and Dev.*, 2:1144, 1988.
Sambrook et al., In: *Molecular cloning*, Cold Spring Harbor Laboratory Press, Cold Spring Harbor, N.Y., 2001.
Samulski et al., *EMBO J.*, 10:3941–3950,1991.
Samulski et al., *J. Virol.* 63:3822–3828, 1989.
Santner et al., *Breast Cancer Res. Treat.*, 65:101–110, 2001.
Sasso et al., *J. Immunol.*, 142:2778–2783, 1989.
Satake et al., *J. Virology*, 62:970, 1988.
Schaffneretal., *J. Mol. Biol.*, 201:81, 1988.
Schnorrer et al., *Nat. Cell Biol.*, 2:185–190, 2000.
Schurmann et al., *Mol. Cell Biol.*, 20:453–461, 2000.
Searle et al., *Mol. Cell. Biol.*, 5:1480, 1985.
Sells and Chernoff, *J. Cell Biol.*, 151:1449–1458, 2000.
Sells et al., *Curr. Biol.*, 7:202–210, 1997.
Shang, Y. & Brown, M. *Science* 295, 2465–2468 (2002).
Sharp and Marciniak, *Cell*, 59:229, 1989.
Shaul and Ben-Levy, *EMBO J.*, 6:1913, 1987.
Shelling and Smith, *Gene Therapy*, 1: 165–169, 1994.
Sherman et al, *Mol. Cell. Biol.*, 9:50, 1989.
Shorki et al., *J. Immunol.*, 146:936–940, 1991.
Sieczkarski and Whittaker, *J. Gen. Virol.*, 83:1535–1545, 2002.
Silvermann et al., *J. Clin. Invest.*, 96:417–426, 1995.
Slamon et al., *Science*, 244:256–262, 1994.
Sleigh and Lockett, *J. EMBO*, 4:3831, 1985.
Smith and Moss, *Gene*, 25(1):21–8, 1983.
Solodin et al., *Biochemistry*, 34(41):13537–13544, 1995.
Soltoff et al., *Mol. Cell Biol.*, 14:3550–3558, 1994.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Steue et al., *Nature*, 345:266–268, 1990.
Stratford-Perricaudet and Perricaudet, In: *Human Gene Transfer*, Cohen-Haguenauer and Boiron (Eds.), John Libbey Eurotext, France, 51–61, 1991.
Stratford-Perricaudet et al., *Hum. Gene. Ther.*, 1:241–256, 1990.
Stuart et al., *Nature*, 317:828, 1985.
Sullivan and Peterlin, *Mol. Cell. Biol.*, 7:3315, 1987.
Swanson and Watts, *Trends Cell Biol.*, 5:424–428, 2002.
Swartzendruber and Lehman, *J. Cell. Physiology*, 85:179, 1975.
Takebe et al., *Mol. Cell. Biol.*, 8:466, 1988.
Talukder et al., *Oncogene*, 21:4289–4300, 2002.
Tang et al., *Canc. Res.*, 56: 3350–3358, 1996.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati (ed.), NY, Plenum Press, 149–188, 1986.
Thiel et al., *Curr. Biol.*, 12:1227, 2002.
Thierry et al., *Proc Natl. Acad. Sci. USA*, 92(21):9742–9746, 1995.
Thiesen et al., *J. Virol.*, 62:614, 1988.
Thompson and Bretscher, *Development*, 129:4185–4192, 2002.
Top et al., *J. Infect. Dis.*, 124:155–160, 1971.
Tratschin et al., *Mol. Cell. Biol.*, 4:2072–2081, 1984.
Tratschin et al., *Mol. Cell. Biol.*, 5:3258–3260, 1985.
Treisman, *Cell*, 42:889, 1985.
Tronche et al., *Mol. Biol. Med.*, 7:173, 1990.
Trudel and Constantini, *Genes and Dev.* 6:954, 1987.
Tsukamoto et al., *Nat. Genet.*, 9(3):243–248, 1995.
Tur-Kaspa et al., *Mol. Cell Biol.*, 6:716–718, 1986.
Turner et al., *J. Cell Biol.*, 145:851–863, 1999.
Tyndell et al., *Nuc. Acids. Res.*, 9:6231, 1981.
Ullrich and Schlessinger, *Cell.*, 61:203–212, 1990.
Vadlamudi et al., *J. Biol. Chem.*, 275:36238–36244, 2000a.
Vadlamudi et al., *Mol. Cell Biol.*, 20:9092–9101, 2000b.
Vadlamudi et al., *J. Cell Physiology*, 190:189–199, 2002.
Vadlamudi et al., *Nat. Cell Biol.*, 4:681–690, 2002.
Vaisberg et al., *J. Cell Biol.*, 123:849–58, 1993.
Vallee and Sheetz, *Science*, 271:1539–1544, 1996.
Vannice and Levinson, *J. Virology*, 62:1305, 1988.
Vasseur et al., *Proc Natl. Acad. Sci. U.S.A.*, 77:1068, 1980.
Wagner et al., *Science*, 260:1510–1513, 1993.
Walsh et al., *J. Clin. Invest*, 94:1440–1448, 1994.
Wang and Calame, *Cell*, 47:241, 1986.
Wang et al., *EMBO J.*, 21:5437–5447, 2002.
Watanabe et al., *Experimental Cell Research*, 230:76–83, 1997.
Weber et al., *Cell*, 36:983, 1984.
Wei et al., *Gene Therapy*, 1:261–268, 1994.
Weinberger et al. *Mol. Cell. Biol.*, 8:988, 1984.
Wen et al., *Cell*, 69:559–572, 1992.
West et al., *Curr. Biol.*, 10:839–848, 2000.
Winoto and Baltimore, *Cell* 59:649, 1989.
Wong et al., *Gene*, 10:87–94, 1980.

Wright et al., *Br. J. Cancer*, 65:118–121, 1992.
Wu and Wu, *J. Biol. Chem.*, 262:4429–4432, 1987.
Wu and Wu, *Biochemistry*, 27:887–892, 1988.
Yang and Huang, *Gene Therapy*, 4 (9):950–960, 1997.
Yang et al., *J. Virol.*, 68:4847–4856, 1994.
Yang et al., *Proc Natl. Acad. Sci. USA*, 87:9568–9572, 1990.
Yarmond et al., *J. Biol. Chem.*, 275:39451–39457, 2000.
Yoder et al., *Blood*, 82 (Supp.): 1:347A, 1994.

Yutzey et al. *Mol. Cell. Biol.*, 9:1397, 1989.
Zhao et al., *Mol. Cell Biol.*, 18:2153–2163, 1998.
Zhao, et al., *Mol. Cell Biol.*, 20:3906–3917, 2000.
Zhou et al., *Exp. Hematol*, 21:928–933, 1993.
Zhou et al., *J. Exp. Med.*, 179:1867–1875, 1994.
Zhu et al., *Science*, 261(5118):209–211, 1993.
Zwaka et al., *Circulation*, 103:1194–1197, 2001.

What is claimed is:

1. A purified composition comprising a dynein light chain-1/protein inhibitor of nitric oxide synthase (DLC1/PIN) polypeptide having a mutation in SEQ ID NO:2, wherein said polypeptide comprises activity that inhibits binding of DLC1/PIN to p21-activated protein kinase 1 (Pak1) and wherein said polypeptide comprises a DLC1/PIN polypeptide lacking serine 88 of DLC1/PIN, a DLC1/PIN polypeptide lacking the C-terminal 19 amino acids of DLC1/PIN, a DLC1/PIN polypeptide lacking the C-terminal 23 amino acids of DLC1/PIN, or a mixture thereof.

2. The composition of claim 1, further defined as a pharmaceutical composition.

3. The composition of claim 2, wherein said composition is dispersed in a pharmaceutically acceptable excipient.

4. A purified composition comprising a mutant dynein light chain-1/protein inhibitor of nitric oxide synthase (DLC1/PIN) polypeptide, wherein said mutant polypeptide comprises activity that inhibits binding of DLC1/PIN to p21-activated protein kinase 1 (Pak1) and wherein said mutant polypeptide comprises a DLC1/PIN polypeptide lacking seine 88 of DLC1/PIN, a DLC1/PIN polypeptide lacking the C-terminal 19 amino acids of DLC1/PIN, a DLC1/PIN polypeptide lacking the C-terminal 23 amino acids of DLC1/PIN, or a mixture thereof, wherein the DLC1/PIN polypeptide lacking seine 88 of DLC1/PIN comprises SEQ ID NO:4.

5. A purified composition comprising a mutant dynein light chain-1/protein inhibitor of nitric oxide synthase (DLC1/PIN) polypeptide, wherein said mutant polypeptide comprises activity that inhibits binding of DLC1/PIN to p21-activated protein kinase 1 (Pak1) and wherein said mutant polypeptide comprises a DLC1/PIN polypeptide lacking serine 88 of DLC1/PIN, a DLC1/PIN polypeptide lacking the C-terminal 19 amino acids of DLC1/PIN, a DLC1/PIN polypeptide lacking the C-terminal 23 amino acids of DLC1/PIN, or a mixture thereof, wherein the DLC1/PIN polypeptide lacking the C-terminal 19 amino acids of DLC1/PIN comprises SEQ ID NO:3.

6. A purified composition comprising a mutant dynein light chain-1/protein inhibitor of nitric oxide synthase (DLC1/PIN) polypeptide, wherein said mutant polypeptide comprises activity that inhibits binding of DLC1/PIN to p21-activated protein kinase 1 (Pak1) and wherein said mutant polypeptide comprises a DLC1/PIN polypeptide lacking seine 88 of DLC1/PIN, a DLC1/PIN polypeptide lacking the C-terminal 19 amino acids of DLC1/PIN, a DLC1/PIN polypeptide lacking the C-terminal 23 amino acids of DLC1/PIN, or a mixture thereof, wherein the DLC1/PIN polypeptide lacking the C-terminal 23 amino acids of DLC1/PIN comprises SEQ ID NO:11.

* * * * *

UNITED STATES PATENT AND TRADEMARK OFFICE
CERTIFICATE OF CORRECTION

PATENT NO. : 7,067,633 B2 Page 1 of 1
APPLICATION NO. : 10/787603
DATED : June 27, 2006
INVENTOR(S) : Kumar et al.

It is certified that error appears in the above-identified patent and that said Letters Patent is hereby corrected as shown below:

In column 116, line 57, change "seine" to --serine--.

Signed and Sealed this

Twelfth Day of September, 2006

JON W. DUDAS
*Director of the United States Patent and Trademark Office*

SEQUENCE LISTING

```
<160> NUMBER OF SEQ ID NOS: 11

<210> SEQ ID NO 1
<211> LENGTH: 643
<212> TYPE: DNA
<213> ORGANISM: Homo sapiens
<220> FEATURE:
<221> NAME/KEY: CDS
<222> LOCATION: (94)..(363)

<400> SEQUENCE: 1
ggtagcgacg gtagctctag ccgggcctga gctgtgctag cacctccccc aggagaccgt      60
tgcagtcggc cagccccctt ctccacggta acc atg tgc gac cga aag gcc gtg     114
                                    Met Cys Asp Arg Lys Ala Val
                                      1               5 atc aaa aat gcg gac atg tcg gaa gag atg caa cag gac tcg gtg gag     162
Ile Lys Asn Ala Asp Met Ser Glu Glu Met Gln Gln Asp Ser Val Glu
         10                  15                  20 tgc gct act cag gcg ctg gag aaa tac aac ata gag aag gac att gcg     210
Cys Ala Thr Gln Ala Leu Glu Lys Tyr Asn Ile Glu Lys Asp Ile Ala
     25                  30                  35 gct cat atc aag aag gaa ttt gac aag aag tac aat ccc acc tgg cat     258
Ala His Ile Lys Lys Glu Phe Asp Lys Lys Tyr Asn Pro Thr Trp His
 40                  45                  50                  55 tgc atc gtg ggg agg aac ttc ggt agt tat gtg aca cat gaa acc aaa     306
Cys Ile Val Gly Arg Asn Phe Gly Ser Tyr Val Thr His Glu Thr Lys
                 60                  65                  70 cac ttc atc tac ttc tac ctg ggc caa gtg gcc att ctt ctg ttc aaa     354
His Phe Ile Tyr Phe Tyr Leu Gly Gln Val Ala Ile Leu Leu Phe Lys
             75                  80                  85 tct ggt taa aagcatggac tgtgccacac acccagtgat ccatccagaa             403
Ser Gly
     90 acaaggactg cagcctaaat tccaaatacc agagactgaa attttcagcc ttgctaaggg    463 aacatctcga tgtttgaacc tttgttgtgt tttgtacagg gcattctctg tactagtttg    523 tcgtggttat aaaacaatta gcagaatagc ctacatttgt atttattttc tattccatac    583 ttctgcccac gttgttttct ctcaaaatcc attcctttaa aaaataaatc tgatgcaccg    643

<210> SEQ ID NO 2
<211> LENGTH: 89
<212> TYPE: PRT
<213> ORGANISM: Homo sapiens

<400> SEQUENCE: 2

Met Cys Asp Arg Lys Ala Val Ile Lys Asn Ala Asp Met Ser Glu Glu
  1               5                  10                  15

Met Gln Gln Asp Ser Val Glu Cys Ala Thr Gln Ala Leu Glu Lys Tyr
             20                  25                  30
```

Asn Ile Glu Lys Asp Ile Ala Ala His Ile Lys Lys Glu Phe Asp Lys
            35                  40                  45

Lys Tyr Asn Pro Thr Trp His Cys Ile Val Gly Arg Asn Phe Gly Ser
        50                  55                  60

Tyr Val Thr His Glu Thr Lys His Phe Ile Tyr Phe Tyr Leu Gly Gln
65                  70                  75                  80

Val Ala Ile Leu Leu Phe Lys Ser Gly
                85

<210> SEQ ID NO 3
<211> LENGTH: 70
<212> TYPE: PRT
<213> ORGANISM: Artificial Sequence
<220> FEATURE:
<223> OTHER INFORMATION: Description of Artificial Sequence: Symthetic
      Peptide

<400> SEQUENCE: 3

Met Cys Asp Arg Lys Ala Val Ile Lys Asn Ala Asp Met Ser Glu Glu
1               5                   10                  15

Met Gln Gln Asp Ser Val Glu Cys Ala Thr Gln Ala Leu Glu Lys Tyr
            20                  25                  30

Asn Ile Glu Lys Asp Ile Ala Ala His Ile Lys Lys Glu Phe Asp Lys
            35                  40                  45

Lys Tyr Asn Pro Thr Trp His Cys Ile Val Gly Arg Asn Phe Gly Ser
        50                  55                  60

Tyr Val Thr His Glu Thr
65                  70

<210> SEQ ID NO 4
<211> LENGTH: 87
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Met Cys Asp Arg Lys Ala Val Ile Lys Asn Ala Asp Met Ser Glu Glu
1               5                   10                  15

Met Gln Gln Asp Ser Val Glu Cys Ala Thr Gln Ala Leu Glu Lys Tyr
            20                  25                  30

Asn Ile Glu Lys Asp Ile Ala Ala His Ile Lys Lys Glu Phe Asp Lys
            35                  40                  45

Lys Tyr Asn Pro Thr Trp His Cys Ile Val Gly Arg Asn Phe Gly Ser
        50                  55                  60

Tyr Val Thr His Glu Thr Lys His Phe Ile Tyr Phe Tyr Leu Gly Gln
65                  70                  75                  80

Val Ala Ile Leu Leu Phe Lys
                85

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: SYnthetic
      Peptide

<400> SEQUENCE: 5

```
Lys His Phe Ile Tyr Phe Tyr Leu Gly Gln Val Ala Ile Leu Leu Phe
 1               5                  10                  15

Lys Ser Gly

<210> SEQ ID NO 6
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Tyr Gly Arg Lys Lys Arg Gln Arg Arg Gly Lys His Phe Ile
 1               5                  10                  15

Tyr Phe Tyr Leu Gly Gln Val Ala Ile Leu Leu Phe Lys Ser Gly
             20                  25                  30

<210> SEQ ID NO 7
<211> LENGTH: 2318
<212> TYPE: DNA
<213> ORGANISM: Homo sapiens
<220> FEATURE:
<221> NAME/KEY: CDS
<222> LOCATION: (394)..(2031)

<400> SEQUENCE: 7
gccacgaagg ccacagacgc cttcccctt ggactctcat tcccttttcc acggagcccc      60
gcgctttcgt gagcccctc gaggaacctg gtctccgcat ccagttacca cctcctgcct    120
cagaggccat ctgagccctt cgcacctcgc ccctcagtcc cccttgccc cccgcggag     180 atcgcctcgc tccctcccgc cccccatca tcccttccct cgcagttccc ctgtcctgag    240
gggagccccg ccacggcagc gacagcgggc aggagggaga agtgaaggt tgggcgacac    300 ttggcctcac tcccggctag cgcacccac ggggaggaga ggaggagccg agagagctga    360
gcagcgcgga agtagctgct gctggtggtg aca atg tca aat aac ggc cta gac   414
                                    Met Ser Asn Asn Gly Leu Asp
                                     1               5 att caa gac aaa ccc cca gcc cct ccg atg aga aat acc agc act atg    462
Ile Gln Asp Lys Pro Pro Ala Pro Pro Met Arg Asn Thr Ser Thr Met
        10                  15                  20 att gga gtc ggc agc aaa gat gct gga acc cta aac cat ggt tct aaa    510
Ile Gly Val Gly Ser Lys Asp Ala Gly Thr Leu Asn His Gly Ser Lys
    25                  30                  35 cct ctg cct cca aac cca gag gag aag aaa aag aag gac cga ttt tac    558
Pro Leu Pro Pro Asn Pro Glu Glu Lys Lys Lys Lys Asp Arg Phe Tyr
 40                  45                  50                  55 cga tcc att tta cct gga gat aaa aca aat aaa aag aaa gag aaa gag    606
Arg Ser Ile Leu Pro Gly Asp Lys Thr Asn Lys Lys Lys Glu Lys Glu
                 60                  65                  70 cgg cca gag att tct ctc cct tca gat ttt gaa cac aca att cat gtc    654
Arg Pro Glu Ile Ser Leu Pro Ser Asp Phe Glu His Thr Ile His Val
             75                  80                  85 ggt ttt gat gct gtc aca ggg gag ttt acg gga atg cca gag cag tgg    702
Gly Phe Asp Ala Val Thr Gly Glu Phe Thr Gly Met Pro Glu Gln Trp
         90                  95                 100 gcc cgc ttg ctt cag aca tca aat atc act aag tcg gag cag aag aaa    750
Ala Arg Leu Leu Gln Thr Ser Asn Ile Thr Lys Ser Glu Gln Lys Lys
    105                 110                 115 aac ccg cag gct gtt ctg gat gtg ttg gag ttt tac aac tcg aag aag    798
Asn Pro Gln Ala Val Leu Asp Val Leu Glu Phe Tyr Asn Ser Lys Lys
```

```
                                                    -continued
     120                 125                 130                 135
aca tcc aac agc cag aaa tac atg agc ttt aca gat aag tca gct gag       846
Thr Ser Asn Ser Gln Lys Tyr Met Ser Phe Thr Asp Lys Ser Ala Glu
                    140                 145                 150 gat tac aat tct tct aat gcc ttg aat gtg aag gct gtg tct gag act       894
Asp Tyr Asn Ser Ser Asn Ala Leu Asn Val Lys Ala Val Ser Glu Thr
            155                 160                 165 cct gca gtg cca cca gtt tca gaa gat gag gat gat gat gat gat gat       942
Pro Ala Val Pro Pro Val Ser Glu Asp Glu Asp Asp Asp Asp Asp Asp
        170                 175                 180 gct acc cca cca cca gtg att gct cca cgc cca gag cac aca aaa tct       990
Ala Thr Pro Pro Pro Val Ile Ala Pro Arg Pro Glu His Thr Lys Ser
    185                 190                 195 gta tac aca cgg tct gtg att gaa cca ctt cct gtc act cca act cgg      1038
Val Tyr Thr Arg Ser Val Ile Glu Pro Leu Pro Val Thr Pro Thr Arg
200                 205                 210                 215 gac gtg gct aca tct ccc att tca cct act gaa aat aac acc act cca      1086
Asp Val Ala Thr Ser Pro Ile Ser Pro Thr Glu Asn Asn Thr Thr Pro
                220                 225                 230 cca gat gct ttg acc cgg aat act gag aag cag aag aag aag cct aaa      1134
Pro Asp Ala Leu Thr Arg Asn Thr Glu Lys Gln Lys Lys Lys Pro Lys
            235                 240                 245 atg tct gat gag gag atc ttg gag aaa tta cga agc ata gtg agt gtg      1182
Met Ser Asp Glu Glu Ile Leu Glu Lys Leu Arg Ser Ile Val Ser Val
        250                 255                 260 ggc gat cct aag aag aaa tat aca cgg ttt gag aag att gga caa ggt      1230
Gly Asp Pro Lys Lys Lys Tyr Thr Arg Phe Glu Lys Ile Gly Gln Gly
    265                 270                 275 gct tca ggc acc gtg tac aca gca atg gat gtg gcc aca gga cag gag      1278
Ala Ser Gly Thr Val Tyr Thr Ala Met Asp Val Ala Thr Gly Gln Glu
280                 285                 290                 295 gtg gcc att aag cag atg aat ctt cag cag cag ccc aag aaa gag ctg      1326
Val Ala Ile Lys Gln Met Asn Leu Gln Gln Gln Pro Lys Lys Glu Leu
                300                 305                 310 att att aat gag atc ctg gtc atg agg gaa aac aag aac cca aac att      1374
Ile Ile Asn Glu Ile Leu Val Met Arg Glu Asn Lys Asn Pro Asn Ile
            315                 320                 325 gtg aat tac ttg gac agt tac ctc gtg gga gat gag ctg tgg gtt gtt      1422
Val Asn Tyr Leu Asp Ser Tyr Leu Val Gly Asp Glu Leu Trp Val Val
        330                 335                 340 atg gaa tac ttg gct gga ggc tcc ttg aca gat gtg gtg aca gaa act      1470
Met Glu Tyr Leu Ala Gly Gly Ser Leu Thr Asp Val Val Thr Glu Thr
    345                 350                 355 tgc atg gat gaa ggc caa att gca gct gtg tgc cgt gag tgt ctg cag      1518
Cys Met Asp Glu Gly Gln Ile Ala Ala Val Cys Arg Glu Cys Leu Gln
360                 365                 370                 375 gct ctg gag ttc ttg cat tcg aac cag gtc att cac aga gac atc aag      1566
Ala Leu Glu Phe Leu His Ser Asn Gln Val Ile His Arg Asp Ile Lys
                380                 385                 390 agt gac aat att ctg ttg gga atg gat ggc tct gtc aag cta act gac      1614
Ser Asp Asn Ile Leu Leu Gly Met Asp Gly Ser Val Lys Leu Thr Asp
            395                 400                 405 ttt gga ttc tgt gca cag ata acc cca gag cag agc aaa cgg agc acc      1662
Phe Gly Phe Cys Ala Gln Ile Thr Pro Glu Gln Ser Lys Arg Ser Thr
        410                 415                 420 atg gta gga acc cca tac tgg atg gca cca gag gtt gtg aca cga aag      1710
Met Val Gly Thr Pro Tyr Trp Met Ala Pro Glu Val Val Thr Arg Lys
    425                 430                 435 gcc tat ggg ccc aag gtt gac atc tgg tcc ctg ggc atc atg gcc atc      1758
```

```
Ala Tyr Gly Pro Lys Val Asp Ile Trp Ser Leu Gly Ile Met Ala Ile
440                 445                 450                 455 gaa atg att gaa ggg gag cct cca tac ctc aat gaa aac cct ctg aga      1806
Glu Met Ile Glu Gly Glu Pro Pro Tyr Leu Asn Glu Asn Pro Leu Arg
                460                 465                 470 gcc ttg tac ctc att gcc acc aat ggg acc cca gaa ctt cag aac cca      1854
Ala Leu Tyr Leu Ile Ala Thr Asn Gly Thr Pro Glu Leu Gln Asn Pro
            475                 480                 485 gag aag ctg tca gct atc ttc cgg gac ttt ctg aac cgc tgt ctc gat      1902
Glu Lys Leu Ser Ala Ile Phe Arg Asp Phe Leu Asn Arg Cys Leu Asp
        490                 495                 500 atg gat gtg gag aag aga ggt tca gct aaa gag ctg cta cag cat caa      1950
Met Asp Val Glu Lys Arg Gly Ser Ala Lys Glu Leu Leu Gln His Gln
    505                 510                 515 ttc ctg aag att gcc aag ccc ctc tcc agc ctc act cca ctg att gct      1998
Phe Leu Lys Ile Ala Lys Pro Leu Ser Ser Leu Thr Pro Leu Ile Ala
520                 525                 530                 535 gca gct aag gag gca aca aag aac aat cac taa aaccacactc accccagcct    2051
Ala Ala Lys Glu Ala Thr Lys Asn Asn His
                540                 545 cattgtgcca agctctgtga gataaatgca catttcagaa attccaactc ctgatgccct    2111
cttctccttg ccttgcttct cccatttcct gatctagcac tcctcaagac tttgatcctt   2171
ggaaaccgtg tgtccagcat tgaagagaac tgcaactgaa tgactaatca gatgatggcc   2231
atttctaaat aaggaatttc ctcccaattc atggatatga gggtggttta tgattaaggg   2291
tttatataaa taaatgtttc tagtctt                                       2318

<210> SEQ ID NO 8
<211> LENGTH: 545
<212> TYPE: PRT
<213> ORGANISM: Homo sapiens

<400> SEQUENCE: 8

Met Ser Asn Asn Gly Leu Asp Ile Gln Asp Lys Pro Pro Ala Pro Pro
1               5                   10                  15

Met Arg Asn Thr Ser Thr Met Ile Gly Val Gly Ser Lys Asp Ala Gly
            20                  25                  30

Thr Leu Asn His Gly Ser Lys Pro Leu Pro Pro Asn Pro Glu Glu Lys
        35                  40                  45

Lys Lys Lys Asp Arg Phe Tyr Arg Ser Ile Leu Pro Gly Asp Lys Thr
    50                  55                  60

Asn Lys Lys Lys Glu Lys Glu Arg Pro Glu Ile Ser Leu Pro Ser Asp
65                  70                  75                  80

Phe Glu His Thr Ile His Val Gly Phe Asp Ala Val Thr Gly Glu Phe
                85                  90                  95

Thr Gly Met Pro Glu Gln Trp Ala Arg Leu Leu Gln Thr Ser Asn Ile
            100                 105                 110

Thr Lys Ser Glu Gln Lys Lys Asn Pro Gln Ala Val Leu Asp Val Leu
        115                 120                 125

Glu Phe Tyr Asn Ser Lys Lys Thr Ser Asn Ser Gln Lys Tyr Met Ser
    130                 135                 140

Phe Thr Asp Lys Ser Ala Glu Asp Tyr Asn Ser Ser Asn Ala Leu Asn
145                 150                 155                 160

Val Lys Ala Val Ser Glu Thr Pro Ala Val Pro Pro Val Ser Glu Asp
                165                 170                 175

Glu Asp Asp Asp Asp Asp Ala Thr Pro Pro Pro Val Ile Ala Pro
```

-continued

```
                180                 185                 190
Arg Pro Glu His Thr Lys Ser Val Tyr Thr Arg Ser Val Ile Glu Pro
        195                 200                 205
Leu Pro Val Thr Pro Thr Arg Asp Val Ala Thr Ser Pro Ile Ser Pro
        210                 215                 220
Thr Glu Asn Asn Thr Thr Pro Pro Asp Ala Leu Thr Arg Asn Thr Glu
225                 230                 235                 240
Lys Gln Lys Lys Lys Pro Lys Met Ser Asp Glu Ile Leu Glu Lys
                245                 250                 255
Leu Arg Ser Ile Val Ser Val Gly Asp Pro Lys Lys Tyr Thr Arg
        260                 265                 270
Phe Glu Lys Ile Gly Gln Gly Ala Ser Gly Thr Val Tyr Thr Ala Met
        275                 280                 285
Asp Val Ala Thr Gly Gln Glu Val Ala Ile Lys Gln Met Asn Leu Gln
        290                 295                 300
Gln Gln Pro Lys Lys Glu Leu Ile Ile Asn Glu Ile Leu Val Met Arg
305                 310                 315                 320
Glu Asn Lys Asn Pro Asn Ile Val Asn Tyr Leu Asp Ser Tyr Leu Val
                325                 330                 335
Gly Asp Glu Leu Trp Val Val Met Glu Tyr Leu Ala Gly Gly Ser Leu
                340                 345                 350
Thr Asp Val Val Thr Glu Thr Cys Met Asp Glu Gly Gln Ile Ala Ala
        355                 360                 365
Val Cys Arg Glu Cys Leu Gln Ala Leu Glu Phe Leu His Ser Asn Gln
        370                 375                 380
Val Ile His Arg Asp Ile Lys Ser Asp Asn Ile Leu Leu Gly Met Asp
385                 390                 395                 400
Gly Ser Val Lys Leu Thr Asp Phe Gly Phe Cys Ala Gln Ile Thr Pro
                405                 410                 415
Glu Gln Ser Lys Arg Ser Thr Met Val Gly Thr Pro Tyr Trp Met Ala
                420                 425                 430
Pro Glu Val Val Thr Arg Lys Ala Tyr Gly Pro Lys Val Asp Ile Trp
        435                 440                 445
Ser Leu Gly Ile Met Ala Ile Glu Met Ile Glu Gly Glu Pro Pro Tyr
        450                 455                 460
Leu Asn Glu Asn Pro Leu Arg Ala Leu Tyr Leu Ile Ala Thr Asn Gly
465                 470                 475                 480
Thr Pro Glu Leu Gln Asn Pro Glu Lys Leu Ser Ala Ile Phe Arg Asp
                485                 490                 495
Phe Leu Asn Arg Cys Leu Asp Met Asp Val Glu Lys Arg Gly Ser Ala
                500                 505                 510
Lys Glu Leu Leu Gln His Gln Phe Leu Lys Ile Ala Lys Pro Leu Ser
        515                 520                 525
Ser Leu Thr Pro Leu Ile Ala Ala Lys Glu Ala Thr Lys Asn Asn
        530                 535                 540
His
545

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 9
ctgctggtgg aattccaatg tcaaataac                                          29

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 10
tccaatcttc tcgagccgtg tata                                               24

<210> SEQ ID NO 11
<211> LENGTH: 66
<212> TYPE: PRT
<213> ORGANISM: Homo sapiens

<400> SEQUENCE: 11

Met Cys Asp Arg Lys Ala Val Ile Lys Asn Ala Asp Met Ser Glu Glu
 1               5                  10                  15

Met Gln Gln Asp Ser Val Glu Cys Ala Thr Gln Ala Leu Glu Lys Tyr
             20                  25                  30

Asn Ile Glu Lys Asp Ile Ala Ala His Ile Lys Lys Glu Phe Asp Lys
         35                  40                  45

Lys Tyr Asn Pro Thr Trp His Cys Ile Val Gly Arg Asn Phe Gly Ser
     50                  55                  60

Tyr Val
 65
```